(12) United States Patent
Samain et al.

(10) Patent No.: US 11,980,277 B2
(45) Date of Patent: *May 14, 2024

(54) SYSTEM FOR DISPENSING A COSMETIC PRODUCT

(71) Applicant: L'OREAL, Paris (FR)

(72) Inventors: Henri Samain, Chevilly Larue (FR); Franck Giron, Chevilly Larue (FR); Guillaume Kergosien, Chevilly Larue (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/666,760

(22) Filed: Feb. 8, 2022

(65) Prior Publication Data

US 2022/0160105 A1     May 26, 2022

Related U.S. Application Data

(63) Continuation of application No. 16/306,408, filed as application No. PCT/EP2017/063508 on Jun. 2, 2017, now Pat. No. 11,291,287.

(30) Foreign Application Priority Data

Jun. 2, 2016  (FR) ...................... 1655053

(51) Int. Cl.
| | |
|---|---|
| A45D 40/24 | (2006.01) |
| A45D 34/00 | (2006.01) |
| A45D 34/04 | (2006.01) |
| A45D 44/00 | (2006.01) |
| A61K 8/19 | (2006.01) |
| A61K 8/73 | (2006.01) |
| A61K 8/81 | (2006.01) |
| A61Q 1/02 | (2006.01) |
| A61Q 19/00 | (2006.01) |

(52) U.S. Cl.
CPC ............. *A45D 40/24* (2013.01); *A45D 34/04* (2013.01); *A45D 44/005* (2013.01); *A61K 8/19* (2013.01); *A61K 8/731* (2013.01); *A61K 8/81* (2013.01); *A61Q 1/02* (2013.01); *A61Q 19/00* (2013.01); *A45D 2034/005* (2013.01); *A45D 2200/058* (2013.01); *A61K 2800/10* (2013.01); *A61K 2800/48* (2013.01); *A61K 2800/882* (2013.01)

(58) Field of Classification Search
None
See application file for complete search history.

(56) References Cited

U.S. PATENT DOCUMENTS

| | | |
|---|---|---|
| 4,578,266 A | 3/1986 | Tietjen et al. |
| 5,051,305 A | 9/1991 | Whitaker, Sr. |
| 5,622,692 A | 4/1997 | Rigg et al. |
| 5,785,960 A | 7/1998 | Rigg et al. |
| 5,903,465 A | 5/1999 | Brown |
| 6,117,433 A | 9/2000 | Edens et al. |
| 6,402,364 B1 | 6/2002 | Esclar et al. |
| 6,464,107 B1 | 10/2002 | Brugger |
| 6,516,245 B1 | 2/2003 | Dirksing et al. |
| 6,517,816 B1 | 2/2003 | Gonzalez et al. |
| 6,986,442 B2 | 1/2006 | Engel et al. |
| 8,593,634 B1 | 11/2013 | Igarashi |
| 2001/0015936 A1 | 8/2001 | Heusser et al. |
| 2003/0062385 A1 | 4/2003 | Engel et al. |
| 2003/0069667 A1 | 4/2003 | Dirksing et al. |
| 2004/0164096 A1 | 8/2004 | Engel et al. |
| 2005/0199254 A1 | 9/2005 | Kang |
| 2006/0108247 A1 | 5/2006 | Liechty et al. |
| 2008/0014164 A1 | 1/2008 | Jacquier |
| 2016/0022010 A1 | 1/2016 | Rabe et al. |
| 2016/0052007 A1 | 2/2016 | Fuller et al. |
| 2017/0340087 A1 | 11/2017 | Samain et al. |
| 2017/0360178 A1 | 12/2017 | Samain et al. |
| 2017/0367462 A1 | 12/2017 | Samain et al. |
| 2017/0369229 A1 | 12/2017 | Samain et al. |
| 2018/0042361 A1 | 2/2018 | Giron et al. |

FOREIGN PATENT DOCUMENTS

| | | |
|---|---|---|
| EP | 0 847 752 A1 | 6/1998 |
| EP | 1 040 773 A1 | 10/2000 |
| EP | 1 142 564 A1 | 10/2001 |

(Continued)

OTHER PUBLICATIONS

Korean Office Action dated Dec. 28, 2021 in Korean Patent Application No. 10-2020-7032089 (submitting unedited computer generated English translation only), citing documents 15 through 17 therein, 9 pages.

(Continued)

*Primary Examiner* — Robert A Wax
*Assistant Examiner* — Quanglong N Truong
(74) *Attorney, Agent, or Firm* — Oblon, McClelland, Maier & Neustadt, L.L.P.

(57) ABSTRACT

The invention relates to a system (10) for dispensing a product, comprising a dispenser that can house at least two cartridges, each of which includes a reservoir containing a base product, a first base product comprising at least 0.1 wt.-% particles having a density differential relative to the medium containing same, preferably of at least 0.5 g/cm3, in particular particles having a density greater than or equal to 2 g/cm3, and a thickening agent. The dispenser allows at least two base products to be dispensed in adjustable proportions, the viscosity of the first base product being preferably greater than 2 Pa·s and more preferably greater than or equal to 4 Pa·s.

12 Claims, 27 Drawing Sheets

(56) References Cited

FOREIGN PATENT DOCUMENTS

Figure 1:
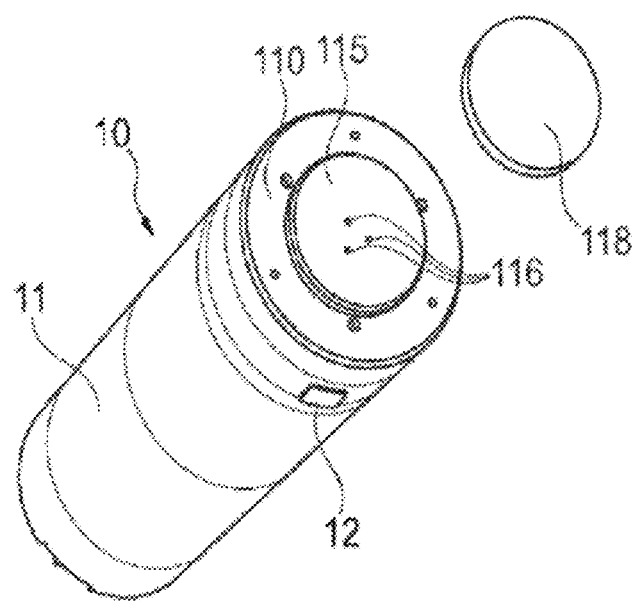

| EP | 1 516 613 A1 | 3/2005 |
|---|---|---|
| FR | 2 232 303 A1 | 6/1974 |
| FR | 2 818 101 A1 | 6/2002 |
| FR | 2 877 819 A1 | 5/2006 |
| FR | 2 970 403 A1 | 7/2012 |
| JP | 2000-191789 A | 7/2000 |
| JP | 2002-522187 A | 7/2002 |
| JP | 2003-128788 A | 5/2003 |
| JP | 2005-505505 A | 2/2005 |
| JP | 2013-40106 A | 2/2013 |
| KR | 2001-0078375 A | 8/2001 |
| KR | 10-2007-0120898 A | 12/2007 |
| KR | 10-2014-0023539 A | 2/2014 |
| WO | WO 02/094423 A1 | 11/2002 |
| WO | WO 2014/037967 A1 | 3/2014 |
| WO | WO 2016/057294 A1 | 4/2016 |

OTHER PUBLICATIONS

Japanese Office Action dated Oct. 4, 2021 in Japanese Patent Application No. 2020-117021 (submitting unedited computer generated English translation only), citing documents 4, 18 and 19 therein, 5 pages.
International Search Report dated Jul. 26, 2017 in PCT/EP2017/063531, 10 pages.
International Search Report dated Sep. 22, 2017 in PCT/EP2017/063508, 4 pages.
French Preliminary Search Report dated Feb. 10, 2017 in Patent Application No. FR 1655053 (with English translation of categories of cited documents), 5 pages.
"Phil V, Amazing Airbrush Changes Colors By Turning A Dial! The Transformation Station!" Retrieved from the Internet: URL: https://www.youtube.com/watch?v=_iuvMWhhu3l, XP054975957, May 28, 2013, 2 pages.
Doerschner et al. (EP1516613A1) Machine English Translation (Year: 2005).

| Area No. | Name | A | B | C | D | Date | Time of year | Age | Event |
|---|---|---|---|---|---|---|---|---|---|
| Z1 | Forehead | | | | | | | | |
| Z2 | Nose | | | | | | | | |
| Z3 | Cheeks | | | | | | | | |
| Z4 | Eyelids | | | | | | | | |
| Z5 | Chin | | | | | | | | |
| | | | | | | | | | |

SYSTEM FOR DISPENSING A COSMETIC PRODUCT

CROSS-REFERENCE TO RELATED APPLICATIONS

The present application is a continuation of and claims the benefit of priority to U.S. application Ser. No. 16/306,408, filed Nov. 30, 2018, which is the National Stage of the International Patent Application No. PCT/EP2017/063508, filed Jun. 2, 2017, which is based on and claims the benefits of priority to French Application No. 1655053, filed on Jun. 2, 2016. The entire contents of these applications are incorporated herein by reference.

The present invention relates to methods and systems for dispensing a cosmetic product, notably a makeup product, a coloring product, an antisun product, a care product or a perfume.

A) Blender System that can Work with Compositions Comprising Dense Particles

Many people wish to make themselves up in order to enhance their appearance, particularly their face.

There are two types of reason why these people may wish to do this:

to conceal certain imperfections, such as blemishes, wrinkles or pores, to enhance the look of the face by changes of color.

In these different cases, the operation involves supplying a colored substance and covering the skin or an area of skin therewith.

In order to obtain an attractive effect, the person needs to make the correct choice of colored substance.

In the first of the cases given above, the operation may be complicated because the face comprises a whole range of colors.

Thus, if the person wishes to cover only a few areas of the face, by attempting to make the color added coincide with the natural color of the surrounding skin, he or she needs to find the color suited to each area of the face, a task rendered all the more difficult by the fact that the coverage of the product and the thickness of the layer applied, together with the color and surface condition of the underlying skin or the greasiness thereof may influence the result.

Bearing these difficulties in mind, people seeking to conceal imperfections on their face adopt the habit of covering the entire face. This then gets around the problem of choosing the colored substance depending on the area of the face.

However, because of the uniformity it brings, the result detracts from the natural appearance of the face.

In the second case, the operation is not simple either because it is difficult to find a colored substance which best suits the appearance of the face. In particular, it is difficult to find the color of one's complexion, particularly if looking for a bold color different from one's natural coloring. Some people would like to choose sun-kissed colors or other shades of different coloring, but do not do so out of fear that the color will not suit them. And if they do, they often give up, disappointed. When not disappointed by the result, they no longer dare change color.

The same goes for makeup applied to the lips, cheeks and eyelids.

There are very few solutions for solving these problems.

A first approach is to purchase numerous products and try them all out. This approach is costly and often gives rise to waste insofar as only a small number of the colored substances tried are generally kept.

A second approach is to test out various products in store. That is not always suitable, because it is very difficult to get a feeling for the results in just a few moments and at a location missing the usual landmarks. In particular, in order to fully assess the makeup effect in store, it would be necessary to be able to have the same lighting as will be found in future conditions of use, and this is something that is rarely possible. In general, it is only by testing out makeup over the course of a day that one can determine whether or not it is suitable. In addition, while certain stores have advisers and allow testing, this is not the case for a large number of other sales outlets and Internet sales.

Another approach has been tested but not developed. This consists in creating one's products by hand by mixing several colored products. This may prove relatively difficult to do because it is not very easy to reproduce the same mixture exactly a number of times over, and it is awkward to quickly create the mixtures one needs at the moment of applying the makeup.

Dispensers for dispensing a cosmetic composition of variable color are also known.

The application US2003069667 relates to methods and devices that allow the cosmetic products used by a consumer to be customized. The consumer provides selection criteria and a cosmetic product formulation is derived therefrom. The base ingredients are blended in accordance with the formulation and a customized cosmetic product is dispensed onto an intermediate surface for later application.

The U.S. Pat. No. 5,785,960 discloses a method for obtaining foundations which are able to cover imperfections of the human skin. The steps of the method include using spectophotometry to measure a normal client skin in order to obtain values for the brightness, red and yellow in the skin color, these being respectively denoted as the L, a and b values. These values are then converted by calculation into modified values determined by an L, a and b correction program. A foundation is formulated on the basis of these modified values. A remote-formulation machine converts the instructions received and meters out and blends a series of base products. The mixture delivered by the machine is packaged and sent to the client.

The application FR2970403 discloses a device for dispensing a cosmetic product, notably a perfume, having at least one reservoir containing a product to be dispensed, notably several reservoirs, and a rinsing device. The device may be operated using a microcomputer or the like. A man-machine interface, for example a keyboard or a screen, notably a touch screen, allows the user to command the dispensing of a formulation of his or her choice. The device may be designed to communicate with a server or other similar devices to exchange recipes or allow the user to receive advice. A memory of an electronic circuit of the device may record the best formulations so that these can be reproduced on demand and exchanged. The device may also be used to produce mixtures of colored cosmetic products. A certain quantity, for example one drop, of colored composition is then produced by the device and used for makeup application or is intended to be blended with a foundation cream or any other colored or uncolored base. The device allows easy generation of the color desired by the user, who may, for example, create several different color mixtures in just a few moments.

The patent application FR2818101 relates to a device for spraying a cosmetic product, notably a foundation. It is possible to create an extemporaneous mixture on the substrate treated.

The application FR 2877819 describes a dispenser that allows the relative proportions of different base products that are dispensed to be varied. It is thus possible to adjust the color. The base products come from different reservoirs and are dispensed via separate passages which open out side by side at one end of the dispenser. One drawback of this is that the user has to do the mixing on the skin or on an intermediate support. In addition, if the quantity dispensed is excessive, it is lost.

U.S. Pat. Nos. 5,622,692 and 5,903,465 describe other examples of dispensers for dispensing a customized cosmetic composition.

Of the tests that have been able to be attempted for automating the manufacture of a customized cosmetic composition, many are those in which the proposed solutions allow mixtures to be created in quantities of around 100 g or sometimes less, but not in the very small proportions generally needed by a person applying makeup, namely in the region of one gram or much less.

In order to illustrate this problem, consider the case of somebody wishing to hide two imperfections in the region of one cm$^2$ on her face. For the first area, she needs to find the corresponding mixture, then deliver a very small quantity, for example around 10 mg, thereof. For the second, she needs to change the setting of the dispenser, then, once again, deliver a very small quantity.

Therefore, for a great many people, choosing the colored substances that will yield the best results remains a difficult matter.

There is therefore a need to make searching for a makeup product that meets the expectations of a consumer and that allows this consumer to create mixtures under reliable conditions and in very small quantities easier.

Therefore, according to certain aspects, the invention seeks to make it easier to make up the face, and notably to find the products best suited to the various areas thereof.

There is also a need to improve the dispensing systems for delivering products of variable color, in order notably to make these easier to use and improve the quality of the makeup.

Certain aspects of the invention rely upon a dispensing system that allows mixtures to be generated from base products. These base products may be of different colors, such that the color of the mixture can be varied. The base products may even make it possible to vary the coverage of the mixture, such that the color resulting from applying the mixture to human keratin materials varies, being fairly close to that of said materials. Thus, the idea of color is to be understood in a broad sense and encompasses mixtures of which the color varies after application as a result of variations in their level of coverage and in the color of the underlying skin.

The precision of the color obtained only matters if the color remains constant throughout the use of the system. This is all the more essential when the manufacturer bases the attractiveness of the system on the makeup results allowed thereby. Thus, in the first scenario, if a particular color has been identified for an area of the face, it is necessary that the system be capable of reproducing this identified color each time it is used. The same goes in the second scenario, in which the treatment for adjustment purposes has to be very faithful to the color that has been chosen.

The concealing effects are based on the use of particles (pigments, filler). As is known, the particles can separate out naturally. In the process, this phenomenon can bring about a difference in concentration of particles throughout the use of the system, and this can produce marked variations in the makeup effect. In order to understand the phenomenon of variation, it should be recalled that, usually (outside the invention), a variation in pigment concentration causes especially variations in coverage, but little in the way of color variation. Moreover, if a separating phenomenon occurs, the user can identify the problem by seeing:

1) that the system is delivering a product without particles, characteristic of phase separation, i.e. an aqueous or oily product,
2) or that the system is delivering a product very full of particles, i.e. one that is thick and difficult to spread.

In a dispensing system with multiple reservoirs, in which compositions of different colors are delivered in order to create a mixture, a variation in particle concentration in one or more of the reservoirs risks not being noticed since the other products delivered by the other reservoirs dilute the mixture. It follows that the user cannot identify the problem from the appearance of the mixture and in this way applies a mixture with a color different from that which is expected.

It may be conceivable that, with the separating phenomena being equivalent in each of the reservoirs, they compensate one another and limit the variations in color. However, the user may very easily use his or her system such that the reservoirs empty at different speeds. Thus, since the compartments are used at different rates, there is a risk of the separating phenomena being very different from one compartment to the other. This is especially the case when a reservoir may remain in the system for a very long time if it is used little.

There is a problem when it is desired to use products containing particles of high density (ranging from 2 g/cm$^3$ to sometimes more than 8 g/cm$^3$), such as those chosen from
Bismuth oxychloride: 7.7 g/cm$^3$
Cerium oxide: 7.6 g/cm$^3$
Chromium oxide: 5.7 g/cm$^3$
Zirconium oxide: 5.6 g/cm$^3$
Iron oxide: 5.2 g/cm$^3$
Titanium oxide: 4.3 g/cm$^3$
Talc (hydroxylated magnesium silicate): 2.7 g/cm$^3$
Calcium carbonate: 2.7 g/cm$^3$
Silica: 2.6 g/cm$^3$
Boron nitride: 2.1 g/cm$^3$
or even more than 8 g/cm$^3$, such as tungsten carbide (15 g/cm$^3$).

One possibility would be to use agitation systems, but these are complicated in particular if small doses are required. In particular, the agitation processes require a minimum time, which is difficult to limit to less than a few seconds. However, in order for the system to work, in particular when small doses are produced, the reaction time has to be very short, typically less than one second, in order that the user does not have to wait too long.

Furthermore, the agitation systems act especially on the mass in direct contact therewith. Thus, if a stirring blade is used, for example, it is especially the part in contact with the blade that will be agitated. Any product situated in other parts such as tubes will not be agitated. However, the latter have to have a uniform particle density.

The agitation systems also have other limits such as energy consumption, noise, and also:
The difficulty of homogenizing certain compositions (shear-thickening compositions)
The difficulty of placing a homogenizing system in a reservoir if the latter has a variable volume and is intended to change volume (the case of compartments pushed by a piston)

The risks of forming aggregates, in particular when the products contain fibers, for example Finally, the manufacturer may intentionally wish to impose a gradient of particles or other non-particulate ingredient in one or more reservoirs, for example, in order to create a variation in an effect over time, such as an anti-acne effect that decreases from application to application. In this case, he will fill the reservoir with a gradient that he wishes to retain throughout the use. Homogenization would thus hinder this application.

According to a first aspect, the invention seeks to make it possible to treat one or more areas of the face and to obtain mixtures that are very precise in terms of color faithfulness. Hereinbelow, the term "area" is used to denote a defined part of the face, fairly small in surface area, covering between 1 cm$^2$ and 100 cm$^2$, better still ranging from 2 cm$^2$ to 50 cm$^2$.

The invention achieves this aim by virtue of a system for dispensing a product, having a dispenser that receives at least two cartridges that each have a reservoir (also known as compartment) containing a base product, a first base product comprising at least 0.1% by mass of particles exhibiting a difference in density of at least 0.5 g/cm$^3$ with the medium which contains them, particles having a density greater than or equal to 2 g/cm$^3$, and a thickener, the dispenser making it possible to deliver at least two base products in adjustable proportions.

The first base product comprises at least 0.1% by mass, relative to the total mass of the first base product, of particles exhibiting a difference in density of at least 0.5 g/cm$^3$ with the medium which contains them.

Preferably, the first base product is contained in one of the at least two cartridges, and the at least two base products delivered by the dispenser in adjustable proportions are the first base product and a second base product, contained in the other of the at least two cartridges.

The invention may have one or more of the following features, considered in isolation or in combination:
- the first base product comprises at least 1% by mass, relative to the total mass of the first base product, better still at least 2% by mass, relative to the total mass of the first base product, even better still between 3% and 10% by mass, relative to the total mass of the first base product, even more preferably between 4% and 7% by mass, relative to the total mass of the first base product, of particles exhibiting a difference in density of at least 0.5 g/cm$^3$, better still of at least 1 g/cm$^3$, even better still between 2 g/cm$^3$ and 10 g/cm$^3$, even more preferably between 4 g/cm$^3$ and 8 g/cm$^3$, with the medium which contains them.
- the viscosity of the first base product is greater than or equal to 2 Pa·s and preferably greater than or equal to 4 Pa·s, more preferably between 4 Pa·s and 10 Pa·s, even more preferably between 5 Pa·s and 8 Pa·s, the viscosity being measured at 1 atm and 25° C. with a CONTRAVES TV rotary viscometer fitted with an MS-r3 or MS-r4 measuring bar at a frequency of 60 Hz after 10 minutes of rotation of the measuring bar.
- the second base product has a viscosity less than that of the first base product.
- the second base product has a viscosity less than or equal to 2 Pa·s, preferably less than or equal to 1 Pa·s, more preferably less than or equal to 0.8 Pa·s, even more preferably between 0.6 Pa·s and 0.2 Pa·s.
- the density of said particles is greater than or equal to 5 g/cm$^3$, better still greater than or equal to 6 g/cm$^3$, even better still between 6 g/cm$^3$ and 10 g/cm$^3$, preferably between 7 g/cm$^3$ and 8 g/cm$^3$.
- the particles comprise at least one of the materials chosen from the following list: bismuth oxychloride, cerium oxide, chromium oxide, zirconium oxide, iron oxide, titanium oxide, talc, calcium carbonate, silica, boron nitride, tungsten carbide, preferably being chosen from bismuth oxychloride and cerium oxide.
- the second product does not have any particles with a density greater than or equal to 7 g/cm$^3$, better still with a density greater than or equal to 6 g/cm$^3$, even better still with a density greater than or equal to 5 g/cm$^3$, preferably with a density greater than or equal to 2 g/cm$^3$.
- the thickener of the first base product is chosen from saccharide compounds of the rubber type, such as gum arabic, acacia gum, guar gum, gellan gum, karaya gum, carrageenan gum, cellulose-based compounds such as CMC, HMC, HPMC, synthetic polymers such as polyacrylic or polymethacrylic acids such as carbomers (Carbopol), or polyurethanes, polyvinyl acetate, polyvinyl alcohol, inverse or direct thick emulsions, combinations of non-aqueous solvents with thickening agents for oil, clays such as bentonite, attapulgite, organochelators, proteins such as casein or collagen, shear-thinning or thixotropic rheology agents, preferably being chosen from saccharide compounds of the rubber type, such as gum arabic, acacia gum, guar gum, gellan gum, karaya gum, carrageenan gum.
- the thickener of the first base product is chosen from saccharide compounds of the rubber type, and its mass content in the first base product is between 0.1% and 5% relative to the total mass of the first base product, better still between 0.8% and 2.5% relative to the total mass of the first base product, even better still between 1.5% and 2.3% relative to the total mass of the first base product.
- the system comprises a third cartridge with a third base product.
- the third base product comprises a thickener identical to or different than that of the first base product, preferably identical to that of the first base product.
- the thickener of the third base product that is different from the thickener of the first base product is chosen from the same list as the thickener of the first base product, preferably being chosen from saccharide compounds of the rubber type, such as gum arabic, acacia gum, guar gum, gellan gum, karaya gum, carrageenan gum.
- the cartridges are received in a removable manner in the dispenser.
- each product leaves the cartridge through an outlet passage of the cartridge, the outlet passage being defined by a dispensing end piece of the cartridge, said end piece being driven in rotation relative to a body of the cartridge by a drive mechanism of the dispenser in order to dispense the base product contained in the cartridge.
- the system comprises a mechanism for homogenizing the first base product, notably a vibrating mechanism; this mechanism may be incorporated into the cartridge, if necessary.

Dispensing System

The dispensing system may consist of a single device operating autonomously, preferably able to be manipulated in one hand, or of a device that operates in interaction with other components or devices. It may for example entail various outlet interfaces which are mounted on the dispenser depending on the type of makeup to be created, as will be specified below. It may also entail a computer system which exchanges information with the dispenser in order to operate the latter, this computer system comprising, for example, a portable terminal such as a smartphone, a camera phone, a tablet, a laptop computer or a dedicated terminal.

Preferably, the dispenser is designed to pressurize one or more compartments containing the base product(s), via volumetric metering devices, preferably a motor causing a piston to move in the corresponding compartment.

The dispenser may be formed of a housing and of at least two or three compartments, and preferably an identical number of motors. For example, the rotation of the motors drives endless screws which push the pistons of each compartment. The advancing movement of the pistons is, for example, controlled by the number of command pulses sent to the motors and/or by the length of time for which the latter are operating. The motors may be powered in sequence or preferably simultaneously.

For example, the motors are powered during an elementary operating cycle for a short duration one after the other or at the same time as one another, so as to dispense corresponding microdoses.

The elementary cycles are repeated, possibly with a pause between them, giving the base products time to flow out of the compartments.

The compartments may be defined by cartridges, which are removed when they become empty. As an alternative, the compartments are permanently present and refilled once they become empty.

Each cartridge may be closed by a stopper that can be removed to allow the cartridge to be cleaned.

Preferably, the housing of the dispenser is of elongate shape along a longitudinal axis, making it easier to handle, and the cartridges are disposed about this axis, inside the housing.

Preferably, the cartridges are inserted from the rear and the mixture is delivered from the front. The cartridges may be inserted individually or, as an alternative, the cartridges constitute a one-piece assembly as they are inserted.

The cartridges may each have a volumetric metering mechanism comprising a piston moved by a drive mechanism of the dispenser in a direction accompanied by a reduction in the internal volume containing the base product and the expulsion of some product. It may be advantageous for the cartridges to have at least a region of their wall that is transparent so that the color of the product contained therein can be seen.

The drive mechanism may have a motorization system formed of motors coupled to gearboxes, of elongate shape parallel to the longitudinal axis of the dispenser, and positioned between the cartridges. Positioning the motors and cartridges in this way makes the dispenser particularly compact.

The base product can leave the corresponding cartridge in a sealed manner, then flow along a passage provided for this purpose in the housing of the dispenser, before leaving the latter.

The cartridges advantageously end in an end piece produced in such a way that, once the cartridge has been inserted into the housing of the dispenser, the end of the end piece terminates flush with the housing. As an alternative, the end piece is long enough to protrude beyond the housing and thus connect various outlet interfaces that can be attached to the housing of the dispenser.

By virtue of the drive mechanism having motors for causing the pistons to advance, it is possible to precisely deliver mixtures in very small quantities. Thus, the drive mechanism can deliver the base products with a minimum flow rate less than or equal to 50 µL/s, better still less than or equal to 20 µL/s, even better still less than or equal to 10 µL/s. Preferably, the drive mechanism delivers flow rates of between 20 and 100 µL/s, better still between 40 µL/s and 60 µL/s. It is thus possible to easily create a mixture of around 10 mg. Such a dispensing system is therefore ideal for achieving small touches of makeup, for covering an area of 1 $cm^2$, better still an area of 0.5 $cm^2$, for example.

It is also possible to create larger quantities of mixture such as the quantities needed to make up a cheek or a face. These quantities remain relatively low, however, for example a quantity of between 100 and 500 mg, better still between 150 and 250 mg.

The dispensing system may thus comprise a dispenser having a housing, and at least one cartridge received in the housing of the dispenser, this cartridge having a body and a piston that is able to move in the body, the housing having a motorized drive mechanism for moving the piston of the cartridge.

Preferably, the cartridge has a dispensing end piece through which the product exits, and this dispensing end piece is driven in rotation by the drive mechanism for moving the piston. The end piece may have at least one rotation-proofing relief, better still two diametrically opposed rotation-proofing studs.

The end piece may bear a seal, notably an O-ring seal. Thus, when changing the cartridge, the seal is also changed, making it possible to get around the problem of seal wear.

The dispenser may have an electronic board for controlling the motorized drive mechanism, this electronic board having the end piece(s) passing through it. This may make it possible to produce a board extending across substantially the entire cross section of the dispenser so that all the electronic components of the dispenser can be grouped together on a single board, thus improving compactness and reliability. The board may extend substantially perpendicularly to the longitudinal axis of the housing. The board may bear a switch for controlling operation of the dispenser.

The dispensing system may be designed to operate in at least two dispensing modes.

In a first mode, referred to as "continuous", the mixture is dispensed as long as pressure is applied to the control switch.

In a second mode, referred to as "dose", a predefined quantity of the mixture is dispensed for each press of the switch.

The end piece(s) may terminate at one end of the housing. This may make it possible to reduce the dead volume, as will be explained in detail below.

The end piece(s) may have at their end a shutoff system for preventing the products from drying out in the duct, for example a self-healing membrane.

The cartridge may have a hollow screw onto which the piston is screwed, the piston being able to move axially along the screw as the latter turns; the piston is prevented from turning in the body of the cartridge. For example, the friction of the piston against the body of the cartridge may be enough to prevent it from turning when the screw turns.

Preferably, rotation is rendered impossible with a cartridge body of non-circular cross section and a piston that is not deformable.

The torque of the motors may be determined electronically depending on the current drawn, and may be used for example to detect that the piston has reached the end of its travel. Information regarding the torque may be transmitted remotely to a computer system that has a man-machine interface, in order that correct operation of the dispenser can be monitored.

In order to adjust the shade, the dispensing system according to the invention has to allow the user to vary the volume delivered from each compartment.

Preferably, the dispenser is operated by a computer system built into the dispenser or external thereto, the dispenser then being able to exchange information with the computer system using a wireless or wired protocol.

The dispenser may thus be operated so as to allow the shade to be adjusted by controlled simultaneous or sequential dispensing of several base products of different colors.

The dispensing of the base products may be continuous; in such a case, the volumes of each of the base products are dispensed in a single shot, simultaneously or in succession.

In the case of simultaneous dispensing, it is beneficial to be able to adjust the respective flow rates of the various base products in order for the dispensed mixture to correspond to the desired mixture at all times. Such a dispensing mode may be suitable in particular when dispensing the mixture by spraying, using an airbrush. To adjust the flow rates it is possible, for example, to alter the speed at which the pistons move, for example in the case where the pistons are driven by an endless screw, by varying the rotational speed of the motors that drive the screw. The products may also be dispensed in a pulsed manner with a dispensing time and a pause in each cycle. By altering the duty cycle it is possible to alter the flow rate.

All the products may be delivered simultaneously during the dispensing time; as an alternative, the cycles of the various products are phase-shifted such that one product is dispensed while the other products are paused.

In one particular embodiment of the invention, the mixture is delivered into a cavity of a container which may close hermetically or not, for example in the form of a cup, into which an applicator, particularly a stylus or a brush may be slipped. Such a dispensing system is especially suited to liners, glosses and other formulations applied without direct contact with the hands. This container may be removable.

For example, it is used as a lip-color dispenser and has a dispensing system, for example using a screw. When it is not removable, the container may be produced with the body of the dispenser. When it is removable, it may constitute one output interface among others that can be mounted on the dispenser.

The compartments, and in particular the cartridges, may contain all or part of the drive mechanism and, for example, the motorizing system or, better still, part of the motorizing system, the purpose of this being to reduce the number of moving parts in the body of the dispenser outside the cartridges. For example, the cartridges contain the rotor of the motor. Once the cartridges have been installed in the body of the dispenser, the rotors are made to interact with the stators.

The dispensing system is advantageously arranged in such a way as to allow the running of preprogrammed sequences in which the mixture delivered by the system is modified continuously or discontinuously. A "graduated" mode makes it possible for example to progress gradually from a mixture A to a mixture B. In the case where the application is by spraying, notably using an airbrush, this makes it possible for graduations to be achieved simply. An "alternate" mode makes it possible for example to switch quickly from a mixture A to a mixture B several times in succession. In the case of application by spraying, a multilayer application can thus be achieved, with different formulations for two superposed adjacent coats. Another mode makes it possible for example to offer several preprogrammed successive mixtures, the computer system each time indicating to the user how these should be used, for example by display on a screen.

In the case of manual application, the mixtures are dispensed for example into a cup. The person applies the makeup to the recommended place with a corresponding mixture taken from the cup, then, if necessary, cleans out the cup and commands delivery of a new mixture; the operation is repeated as many times as necessary until the person is fully made up.

The mixtures dispensed can be homogenized in various ways depending on the type of use. In the case of manual application, it can be done directly on the application area at the time of application or in the cup before the mixture is picked up; in the case of an airbrush application, the pipe of the airbrush is used as a mixing chamber; if the mixture is dispensed into a container for later use, homogenization can be performed by hand or by passing the dispensed products through a mixing chamber situated between the dispenser and the container or incorporated directly into the container, as described in detail below.

The product may be delivered by the dispensing system and used extemporaneously. As an alternative, the product delivered by the dispensing system is packaged and used later, for example on several occasions, with, for example, at least one day's interval between two uses.

Particles

The density of the medium which contains the particles may be between 0.7 g/cm$^3$ and 1.3 g/cm$^3$, better still between 0.8 g/cm$^3$ and 1.2 g/cm$^3$, even better still between 0.9 g/cm$^3$ and 1.1 g/cm$^3$.

One or more compartments comprise particles with a density greater than or equal to 2 g/cm$^3$, better still greater than or equal to 5 g/cm$^3$, better still greater than or equal to 6 g/cm$^3$, even better still between 6 g/cm$^3$ and 10 g/cm$^3$, preferably between 7 g/cm$^3$ and 8 g/cm$^3$ in a content of at least 0.1% by mass relative to the mass of the base product containing said particles, better still at least 1% by mass relative to the mass of the base product containing said particles, even better still at least 2% by mass relative to the mass of the base product containing said particles, preferably in a content of between 2% and 10% by mass relative to the mass of the base product containing said particles, more preferably in a content of between 4% and 7% by mass relative to the mass of the base product containing said particles.

The particles may contain metal atoms, such as atoms of titanium, iron, chromium, cobalt, lead, mercury, cerium, bismuth, zinc or copper. They may be of all shapes and sizes.

The invention also relates to the products containing particles that are lighter than the medium in which they are present and therefore risk collecting at the top. In particular, the particles of the invention may be mineral or organic particles containing air or a gas such as silica aerogels or expanded polymer particles, such as polystyrene expanded by light alkanes. The density of such particles may be less than or equal to 0.5 g/cm$^3$, better still less than or equal to 0.2 g/cm$^3$, even better still between 0.05 and 0.2 g/cm$^3$.

The particles may be intended to impart color or coverage or other optical effects (reflection, mattness, photoprotection) (main object of the invention) or other advantages, such as a softening effect or absorption of sebum, moisture or pollution.

Viscosity and Viscosity Agents

The viscosity of the products is measured at 1 atm and 25° C. with a CONTRAVES TV rotary viscometer fitted with an MS-r3 or MS-r4 measuring bar at a frequency of 60 Hz after 10 minutes of rotation of the measuring bar.

The rheologies are newtonian or non-newtonian. In particular, preference is given to thickeners that confer a shear-thinning rheology, meaning that the viscosity thereof is not proportional to the stress applied, with or without a thixotropic nature, meaning that the viscosity thereof decreases over time. They are typically produced from mineral compounds such as bentonite or organic compounds such as hyaluronic acid.

The thickeners of the invention may be gelling compounds, for instance natural ingredients such as saccharides for instance gum arabics, acacia gum, guar gum, gellan gum, karaya gum, etc., synthetic polymers such as polyacrylic or polymethacrylic acids such as carbomers (Carbopol), inverse or direct thick emulsions, or combinations of non-aqueous solvents with thickening agents for oil.

In the case of saccharide compounds of the "rubber" type, its mass content in the first base product is between 0.1% and 5% relative to the total mass of the base product, better still between 0.8% and 2.5% relative to the total mass of the base product, even better still between 1% and 2% relative to the total mass of the base product.

The gelling compounds that can be used may be natural or artificial, such as starches (E441), pectins (E440), agar (E406), alginic acid (E400), sodium alginate (E401), potassium alginate (E402), ammonium alginate (E403), calcium alginate (E404), carrageenan (E407) or ingredients originating from animals (gelatin such as E441).

For solvent-rich formulations, use may be made of an organogelator. These are typically organic liquids, a mineral oil or a vegetable oil, trapped in a three-dimensional network resulting from the supramolecular self-assembly of small organic molecules (known as organogelators) forming microscopic or nanoscopic structures. They are used in an amount of 1 to 10% and may be for example derivatives of 4-tert-butyl-1-arylcyclohexanols, polymeric derivatives such as polyethylene glycols, polyesters, polyalkylenes, derivatives of N-lauroyl-L-lysine ethyl ester, derivatives of peptides, small fatty acids.

When a thickener of shear-thinning rheology is used, products of which the viscosity exceeds 50 Pa·s, better still exceeds 100 Pa·s, even better still is between 10 and 100 Pa·s, may be used. This shear-thinning rheology is defined such that the viscosity drops at least by a factor of 2 when the stress is increased by a factor of 10. (passage from 1 to 10 $s^{-1}$)

In order to measure this viscosity, a test is carried out as is described in the thesis by Clément Saidou HAL Id: tel-00870761: https://tel.archives-ouvertes.fr/tel-00870761/document More specifically, an ARG2 type imposed-stress rheometer distributed by TA may be used. The tests are carried out in a geometry of the rotary module of the Couette type made of plexiglass, with an air gap e=1 mm. The torque is applied to around 30 ml of product through the use of a shear cell into which the sample is filled. This torque brought about by electromechanical stress is then monitored by means of a sensor fixed to the moving part of the rheometer. Then, the corresponding shear stress and the speed of deformation (or speed gradient) generated are determined as a characteristic function of the Couette used, making it possible to link the apparent viscosity (in Pa·s) to the shear rate (in $s^{-1}$).

Compliance with the Rheological Rules Over the Set of Compartments

If the dispensing system only comprises a single base product containing dense particles, it preferably complies with the rheological rules defined above.

If the system comprises two or more base products containing dense particles:
- at least one base product containing dense particles may comply with the rheological rules defined above.
- preferably, all the base products containing dense particles comply with the rheological rules defined above.

Preferably, if the dispensing system comprises at least one compartment without dense particles, at least one base product that does not contain dense particles has a viscosity less than or equal to 2 Pa·s, better still less than or equal to 1 Pa·s, more preferably less than or equal to 0.8 Pa·s, even more preferably between 0.6 Pa·s and 0.2 Pa·s.

Use of a Base Product for Reducing the Viscosity

As just mentioned above, the low viscosity of the particle-free compartment makes it possible, by dilution, to limit the viscosity of the mixture dispensed.

However, if this compartment is used in minor proportions, for example less than 33% by mass of the final composition obtained in the case of a three-compartment dispensing system, this dilution effect is relatively small. Thus, it is possible to add to this base product without dense particles a viscosity-limiting agent, such as ethanol.

Optional Use of a Homogenizing Means

The dispensing system may include a homogenizing means such as a vibrating part or some other system that sets the base product in movement in the corresponding compartment.

The dispensing system may also be intended to be placed on a vibrating stand, for example vibrating at between 10 000 Hz and 1 Hz, better still between 1000 and 5 Hz, even better still between 400 and 100 Hz.

This homogenizing system may be triggered by the user, or may be triggered as part of a sequence triggered by the user. For example, when the user starts up the device, homogenization is initiated. Or, when the system senses a movement (an acceleration), the system produces a homogenizing action.

The homogenizing system may be triggered regularly, even when the system is not being used.

Use for Making Up One or More Precise Areas of the Skin

The dispensing system allows makeup to be applied, day after day, with only the areas that need to be hidden being treated. To this end, small doses of makeup are delivered, and are applied specifically and sequentially to the corresponding areas. Each small dose is created using the mixture suited to the area.

In one preferred embodiment of the invention, the dispensing system waits for information regarding which area is to be treated and then delivers the corresponding mixture. It may use a preprogrammed look-up table for that purpose, this table being the result for example of a learning process as defined below. As an alternative, the dispensing system informs the person, when delivering a mixture, of the area to which the person is to apply the mixture. Thus, the dispensing system may follow an application program in which it delivers, in a given order, the various mixtures that are to be applied.

In one particular embodiment of the invention, the dispensing system is informed as to the quantities to be delivered. For that, it memorizes the relationship between the color, the area of the face and the quantity needed, thereby making it possible to reduce costs and wastage of product, and to cover the skin only lightly, thus avoiding occlusion effects. In so doing, it is possible to use products that have a high covering capability and provide too much cover to be applied to the whole of the face. Thus, it is possible to obtain makeup of natural or even undetectable appearance.

The dispensing system may also make it possible, by facilitating the dispensing of small quantities and rapid use thereof, to reduce the time for which the products are kept, thus making it possible to reduce the risks of the products changing and/or to reduce the amounts of preservative to be used.

The dispensing system is suited to treating the areas that are to be concealed, without having to conceal the entire face.

When the user is looking for the color to apply to an area of the face, it is advantageous to memorize the color best suited to each area, and the dispensing system is thus advantageously designed to memorize this color and the corresponding area. Thus, by using the memorized information, on each use, the same mixture can be delivered for each area or, if several areas are being treated, the same series of mixtures can be delivered for the same series of areas.

The dispensing system may also be designed to allow an area to be treated by varying the colors application after application. Thus, the person may make up her lips using different colors that she chooses on a day-by-day basis to suit her tastes. This approach is also suitable for the eyelids or eyelashes, and for face makeup because the person may fancy a change of foundation color. For example, on weekdays, the person applies a pale colored foundation, with a more tanned foundation color at the weekends, or may have eye makeup in one color one day and another color another day.

The dispensing system may be designed to allow the user to change color to suit her tastes according to the day, the time, what she is wearing, and the weather. Thus, a system to assist with decision making is advantageously provided to guide the user in her choices of color.

An assistance system may also be provided for balancing the colors on the same face and to contribute toward a successful overall makeup look.

It may be desirable for several people in the same group, for example a family, to be able to use the dispensing system, thus reducing costs and minimizing the space taken up. This solution is particularly suited to travel or hotels, campsites, airplanes, campervans, boutiques, schools, etc. For that, provision may be made for the dispensing system to be able to be informed as to which person is using it, so as to access pre-stored personal data.

Continuous Use for Graduated Makeup

It is possible to ensure that the dispensing system changes the formulation of the mixture while it is delivering the product. It is possible to move the outlet for the base products or for the mixture relative to a container or a support defining an application surface. In one particular embodiment of the invention, the dispensing system is designed to calculate the way in which the mixture evolves as a function of the color C1 of one area to be treated and of the color C2 of another area to be treated. For example, with the knowledge that the chin requires a color C1 and that the cheek requires a color C2, the dispensing system may vary the formulation of the mixture while it is delivering it in order to graduate the color between these two colors. This makes it possible for example to better conceal imperfections of the face while ensuring that the end result is realistic, or allows color to be graduated for beautifying purposes.

The dispensing system may also be designed such that the user can command a variation in color of the mixture dispensed without the start and/or end colors having been set beforehand. To do that, the dispensing system may possess a location or auto-location system and deduce from a look-up table the colors C1 and C2 that it has to create and therefore the changes in the mixture that it has to make.

The dispensing system may have an outlet head, in particular in the case of an airbrush, which is mobile and steered. This option then makes it possible to achieve graduated effects without moving the rest of the dispensing system. For example, the dispensing system is located near to the cheek, then a control system is triggered that will automatically steer the variation in formulation of the mixture and the movement of the outlet head so as, for example, to make the center of the cheek redder than the periphery thereof, with a graduation between the two.

The dispensing system may even be used to create tailor-made products that are kept for several applications.

It is also possible to produce solid or semi-solid products.

Manufacture of "Bespoke" Compacts or Other Solid or Semi-Solid Products

The dispensing system may be designed to allow a mixture to be chosen and delivered to a container such as a cup. The mixture preferably comprises compounds which are such that the mixture can set solid.

More preferably, use is made of compounds that make the setting especially rapid. These compounds are either deposited in the container before or after it is filled with the other ingredients, or are provided in the compartments of the dispenser with the other constituents of the base products, or are contained in the dispenser in a compartment especially designed to contain them.

Specific compositions which may harden quickly by chemical, biochemical or physicochemical reaction after discharge may thus be dispensed.

These compositions are especially designed for the creation of compacts, namely they:
set solid,
yield a material that can crumble if rubbed, and are preferably colored.

Preferably, these compositions are very rich in solid particles, with for example more than 10% by mass of solid particles relative to the total mass of the composition, better still more than 20% by mass of solid particles relative to the total mass of the composition, even better still more than 30% by mass of solid particles relative to the total mass of the composition, preferably between 10 and 40% by mass of solid particles relative to the total mass of the composition.

These compositions may contain absorbent particles or reactive compounds, such as those that react in contact with the air, for example cyanoacrylate or alpha-silanes or those which react to light, notably UV.

The container into which the mixture is dispensed may contain a compound A and the dispensed compositions may contain a compound B, A and B being chosen to react with one another and solidify the mixture.

In one particular embodiment of the invention, the dispensing system incorporates a heating means, for example with an electrical resistor, to create lipsticks or other waxy products. In that case, the base products are heated before being delivered.

The dispensing system may also comprise a means for supplying heat and/or light energy, after the mixture has been dispensed into a container, for example an electrical resistor or an LED, notably UV. This energy may accelerate the setting-solid of the dispensed mixture.

Preferably, the mixture is homogenized before it sets solid, and thus homogenized after being delivered.

Creation of Color Palettes

The dispensing system may have a support, having several regions, and may be designed to automatically generate several mixtures deposited in said regions, for example a series of colors suited to various parts of the face.

The support may define several cavities to receive the mixtures or may bear several containers, for example in the form of cups, potentially cups that are separable from the support.

In one particular case, the support adopts the shape of a face with regions for receiving the mixtures for targeted application areas.

The support may be able to move, notably to rotate, with respect to the body of the dispenser and, for example, may be driven in its movement by the dispenser so that various spaces or containers can be filled in succession.

Cup-Type Dispenser

There is a benefit to having a dispensing system capable of delivering a mixture that the user can easily pick up. Moreover, in cases in which the base products delivered by the dispensing system are not already blended, there is a need to allow the user to perform the mixing easily.

The dispensing system may thus have a cup and a dispenser for filling the cup with at least one product, the cup being secured to the dispenser at least while it is being filled.

The cup is sometimes also known as a "crucible" and that term should be understood in its broadest sense.

A "cup secured to the dispenser" should be understood as meaning that the cup is held, notably immobilized, at least temporarily, on the dispenser, being for example fixed to the latter by screws, magnetic attraction, clip-fastening, bayonet locking, clamping, or produced with a part of the dispenser body by material molding. When it is secured to the dispenser, the cup allows the latter to be manipulated in one hand, the cup remaining in place on the dispenser while the latter is being moved around.

The dispenser may be offered to the user with the cup already in place.

As an alternative, the cup is installed by the user the first time the dispensing system is used.

The cup is preferably less deep than it is wide, making access to it easier and allowing the product, notably the mixture, to be picked up with an applicator or a finger.

Preferably, the cup is separable from the dispenser and constitutes one outlet interface that can be chosen from a collection of outlet interfaces that can be mounted on the dispenser, at the choice of the user and according to the making up to be performed, as described in detail below.

Preferably, the dispensing system comprises several filling orifices for filling with different base products, opening into the cup. Thus, the mixing of these products may take place in the cup.

The cup preferably has a bottom that is concave toward the outside, making it easier for the user to clean it between two uses.

In addition, this may make the product easier for the user to pick up and the base products easier to mix.

Preferably, the dispenser allows at least two base products to be delivered into the cup, in adjustable proportions, and better still at least three products.

In one exemplary embodiment, the dispensing system has at least two cups that can be selectively fed by the dispenser. This may allow the user to fill these two cups quickly with mixtures with different characteristics. This may facilitate the testing of colored substances and/or allow the preparation of several different color mixtures intended for making up respective areas of the face. The cups may be associated with identifiers that remind the user of the area of the face for which a mixture contained in a given cup is intended.

The cups may be able to move relative to the dispenser, being for example borne by a mobile support such as a turret that is rotatable with respect to the dispenser or by a slide capable of translational movement with respect to the dispenser.

The dispensing system may comprise a lid for closing the cup. This closure lid is preferably transparent so that the user can see the color of the mixture contained inside.

When the cup is separable from the dispenser it may if necessary be introduced into a housing that allows it to be transported more easily, this housing being able, if necessary, to contain a mirror and/or an applicator. The lid of the housing may in this case act as a lid for the cup.

The volume of the cup may be between 2 and 1000 mm$^3$, better still between 100 and 1000 mm$^3$, even better still between 250 and 750 mm$^3$.

The base product(s) delivered into the cup are preferably foundations, but as an alternative may be makeup products for the lips or eyelids.

The cup preferably has a shape that exhibits symmetry of revolution. As an alternative, it has a polygonal or some other contour. Its largest inside diameter, or that of the inscribed circle in the case of a noncircular contour, is preferably between 2 and 100 mm, preferentially between 5 and 40 mm. Its depth is preferably between 1 and 10 mm, better still between 3 and 8 mm. Preferably, the size and shape of the cup either allow direct application of the mixture to the skin or allow the mixture to be picked up on a finger or using an applicator. The cup may be made of an elastically deformable material, making it possible for example to turn the concavity of the bottom of the cup inside out and empty it more easily or use it to apply the product.

The cup may have no blender; in that case, the base products may arrive in the cup from the dispenser in the unmixed state, via distinct respective dispensing orifices. As an alternative, the dispenser incorporates a blender and the base products arrive in the cup already blended.

The cup may also incorporate a static blender as described in detail below, which is fed via distinct filling orifices of the dispenser and which preferably delivers the mixture into a cavity of the cup situated above the blender.

A further subject of the invention is a method for preparing a makeup product, comprising the step of filling a cup of a dispensing system as defined above with at least one base product from the dispenser.

Several products may be delivered into the bottom of the cup, then blended using a finger or an applicator, or a static blender incorporated into the cup.

The cup is preferably filled from beneath. Dispensing systems using a sonotrode have been proposed in the past.

The cup according to the invention is not intended to vibrate in order to dispense the product(s) conveyed by the feed passage(s) supplying it. It differs from a sonotrode.

Preferably, the cup is made of plastic.

Blender Incorporated into the Outlet Interface

There is a benefit in having a dispensing system capable of delivering a mixture that can easily be used, notably picked up by the user, without the need for an additional mixing action on the part of the user.

The dispensing system may thus have a dispenser having outlet passages for base products and an outlet interface that is separable from the dispenser, this interface having a static blender that preferably delivers the mixture into a cavity where it can be picked up.

The static blender may be situated under the abovementioned cavity. The dispensing system is then particularly suited to the creation of compacts, using cups with an in-built static blender as outlet interfaces. In that case, the cavity of the cup is filled with product from beneath. After passing into the static blender, the blended base products cover the blender.

It is possible to use several outlet interfaces and to fill them with different respective mixtures, without the need to purge the blender, thereby reducing losses of product. The outlet interface may be a single-use interface, if necessary.

Preferably, the static blender has a central chamber communicating with base product intake ducts. This central chamber may communicate with a peripheral chamber having a series of partitions which act as deflectors for the mixture and create shearing thereof.

The peripheral chamber may have a perforated annular partition defining perforations through which the mixture passes as it circulates in the peripheral chamber. The central and peripheral chambers may be closed at the top by a wall which defines the end wall of the cavity receiving the mixture.

The end wall of the peripheral chamber may be of helical shape about the axis of the cup and of a height that decreases in the direction toward the outlet. The latter may open ahead of a connecting ramp connecting the end wall of the peripheral chamber and the top wall of the blender, this connecting ramp preferably being a portion of a helix extending the helix formed by the end wall of the peripheral chamber.

Preferably, the peripheral chamber comprises the abovementioned annular partition and radial partitions that force the mixture to circulate alternately between upper and lower regions of the peripheral chamber and between radially inner and outer regions, the mixture circulating for example from an upper and radially outer region to a lower and radially outer region by passing through the abovementioned annular partition.

The blender may have an outer body in which a component forming the core of the blender is housed, the outer body radially closing the peripheral chamber on the outside and comprising an upright that separates the central and peripheral chambers.

The outer body of the blender and the core of the blender may each be produced as a single piece by injection molding.

Reduced Dead Volume

There is benefit to be had in reducing the losses of product when changing the formulation of the mixture and in allowing the color of the mixture to be varied as quickly as possible during application, particularly when the dispenser is coupled to an airbrush.

In one of its aspects, independently of or in combination with the other aspects thereof, and notably with the foregoing, one subject of the invention is a system for dispensing a makeup product, having a dispenser that receives at least two cartridges that each have a reservoir containing a base product, the latter leaving the cartridge through an outlet passage of the cartridge, this outlet passage opening to outside of the dispenser or near the external surface thereof.

The outlet passage may notably open into an area in which the mixture is picked up or close to this area, notably less than 5 mm away, better still less than 3 mm away, better still less than 1 mm away, or even better still flush therewith.

The cross section of the outlet passage is, for example, between 1 and 3 mm$^2$.

Thus, each base product coming from a cartridge can leave the dispenser without mixing with a base product from another cartridge and the dead volume that cannot be picked up and is likely to increase the inertia of the system is minimized. The product is more quickly available without having to circulate through special passages in the housing of the dispenser, thereby avoiding a painstaking purging step in the event of a cartridge change.

The outside of the dispenser may be the product pickup area, notably when the dispenser is produced with a cup that is not designed to be removed, into which the mixture is dispensed, or a dispensing area intended for the mounting of a removable outlet interface, which defines the pickup area. This outlet interface may have a cup as defined above. This mounting area corresponds for example to the end of the housing of the dispenser in the absence of the outlet interface. The mounting area may be substantially planar and perpendicular to the longitudinal axis of the dispenser housing.

The dispenser may have three cartridges of base products.

The dispenser may have housings for receiving the cartridges, which are preferably received removably in the dispenser. The latter may comprise passages for ducts for the cartridges defining the outlet passages.

The length of these ducts is preferably such that the ducts are set back slightly from the end or lie flush with the cavity used for picking up the product or, as an alternative, are set back slightly from or lie flush with the end face of the housing of the dispenser that defines the mounting area.

These ducts of the cartridges may be end pieces used for causing the pistons to move within the cartridges, as described in detail above.

Multiple Outlet Interfaces

There is a need to be able, using the same dispensing system, to achieve different makeup looks easily and be able, if so desired, to make up areas as different as the skin, the lips, the eyelashes or eyebrows.

The dispensing system may thus comprise an assembly having a dispenser of at least one cosmetic product, in particular makeup, and at least two outlet interfaces, each of which can be mounted removably on the dispenser, these outlet interfaces being able to receive the product(s) delivered by the dispenser, preferably being chosen from the following:
  an outlet interface having a container, notably a cup, allowing the product to be picked up using a finger or using an applicator,
  an outlet interface allowing the product to be delivered to a spray system, notably an airbrush,
  an outlet interface having several regions for receiving the product, which can move relative to the dispenser,
  an outlet interface that allows the product to be delivered to a dispensing end piece.

Preferably, the assembly comprises at least three of said outlet interfaces, or better still the four outlet interfaces.

The dispenser may comprise at least two different base products and allow these to be delivered in variable proportions and, preferably, the dispenser comprises three different base products and allows these to be delivered in variable proportions.

Each outlet interface may have a base allowing it to be fixed to the dispenser. This fixing may be done using screws for example, but preferably the base is designed to allow an outlet interface to be removed and replaced without the need for tools. It is, for example, a quarter-turn fixing or a fixing using an external locking ring.

The outlet interface and/or the housing of the dispenser may comprise seals allowing sealed communication between the housing of the dispenser and the outlet interface. If appropriate, the dispenser is designed to recognize the outlet interface mounted above, for example by virtue of the outlet interface having identifiers in the form of specific reliefs which are detected by the dispenser, or in the form of an electronic chip that the dispenser recognizes. That may allow the operation of the dispenser to be adapted to the outlet interface mounted above. The dispenser may communicate information about the outlet interface it is bearing to a computer system, and the computer system may, on the basis of this information, display a specific screen and/or run a specific program for controlling the operating parameters of the dispenser so as, for example, to adapt the dose dispensed and/or the flow rate to the type of outlet interface.

The user may be initially offered several outlet interfaces with a common dispenser within one and the same package, for example a case or a cardboard box.

A further subject of the invention is a makeup method involving the step of selecting an outlet interface, mounting it on the dispenser, and delivering the product(s) contained in the dispenser to the interface.

Mapping and Learning

The term "mapping" should be understood here as meaning a process of indexing a color with an area, with recording.

The mapping may relate to applications to areas smaller than 1 cm$^2$. However, the naked eye then has difficulty in discerning whether the result obtained is adequate, and it is preferable to substitute an instrumented evaluation with magnification for evaluation by the naked eye. Small quantities of colored substance may be applied with a finger, using conventional tools such as brushes, or using specialist applicators.

The map may be generated during a learning period in which the user carries out tests with mixtures on different areas of the face; once created, the map can then be used for everyday makeup.

Specific graphic interfaces can be used during the learning period and during the period of use of the map.

In particular, the dispensing system may be used with a graphic interface in which the operator sees the face, which is for example a schematic, figurative or accurate representation such as a photograph or a 3D simulation. In that case, the operator can point at part of the face on the screen to show and/or deliver the appropriate color.

The graphic interface may also show the other areas of the face where use of that same color is appropriate.

To create the map, the operator applies a color, then makes an assessment.

The areas of the face can be treated one after the other; for example, the exercise is carried out on part of the cheek, then on the nose, etc.

Another option is to create a given mixture and apply this same mixture to several areas. The operator then needs to look for the area of the face to which the color is suited. The mixture is then indexed in the computer system which attributes it to the area(s) of the face for which it is suitable.

In one of its aspects, independently of or in combination with the other aspects thereof, and notably with the foregoing, one subject of the invention is a learning process for a dispensing system comprising a dispenser for dispensing a mixture of variable color, and a computer system for selecting a color and for storing data, comprising the steps of:

a) selecting at least one color with the aid of an interface of the computer system,
b) delivering, with the aid of the dispenser, at least one mixture of the selected color,
c) evaluating the mixture(s) dispensed following the application thereof to at least one area of the face,
d) memorizing the characteristics of at least one mixture, notably a mixture that the user wishes to be able to recall, and of at least one area on which it has been tested.

This memorizing can be carried out notably with a view to subsequent dispensing of this mixture for making up said area.

Preferably, the computer system is designed to allow the user to indicate whether or not the result of the test is satisfactory, or even to inform same of the comparison with a test carried out earlier.

It is also possible to create a given mixture and to look for the area of the face for which it is suitable. The mixture is then recorded, being attributed to the area(s) of the face for which it is suitable, in a look-up table that will be used subsequently in order to deduce which mixture to use on the basis of an area of the skin.

The same procedure can be adopted with other mixtures in order to create a map of the entire face and thus have a complete look-up table for the face.

It is also possible to create a given mixture, apply it to a given area, and then vary the mixture until the most suitable mixture is obtained. The mixture is then recorded, being attributed to the area(s) of the face for which it is suitable, in a look-up table that will be used subsequently in order to deduce which mixture to use on the basis of an area of the skin.

Preferably, the computer system evaluates and memorizes the quantities used area by area. Such a method, which uses "test patches" makes it possible to identify the product(s) required by the person wishing to apply makeup. Thus, the dispensing system can be used at sales outlets to advise people wishing to apply makeup or at home in order to define correctly which products to order.

The interface of the computer system preferably has a touch screen displaying the color of the mixture when it is selected.

The interface may display a face and allow the computer system to be informed by selecting the area on the face displayed.

The computer system is preferably designed to allow an area, mixture reconstruction parameters, and the date of the test and/or any other identifier of the mixture to be associated with one another.

The computer system is preferably also designed to allow at least one of the following data: the name of the area, the period of the year, the name of an event, a user identifier and the age of the user, to additionally be associated with said area, with the mixture reconstruction parameters, and with the date or identifier of the mixture.

Steps a) to c) may be repeated at least once before the characteristics of the mixture are memorized in step d).

The computer system may be designed to search a database for a reference of a commercial product on the basis of the characteristics of the mixture identified as being suitable for at least one given area, and to relay this information to the user.

The selection in step a) may be carried out using an expert system, which may or may not be external to the computer system.

The expert system may analyze an image of the user in order to propose a mixture color at least on the basis of the image analyzed.

Step a) may be preceded by the computer system proposing to the user a color and an area to be tested with a mixture of this color.

The computer system may be designed to allow the user to inform same of his or her assessment of the result of the test in step c) and to generate a proposal to modify the mixture to be selected upon return to step a).

The computer system may be designed to propose at least one color of mixture in step a) depending on an application area of which it has been informed by the user.

The computer system may be designed to propose at least one application area in step a), on the basis of a color of which it has been informed by the user.

The dispenser may deliver, in step b), at least two mixtures of different colors, preferably separate, so that they can be applied simultaneously to the test area.

This may allow time to be saved and make it easier to compare the results.

A further subject of the invention is a method of making up using a dispensing system according to the invention, in which:
  a) the user sends the computer system a request regarding a need for makeup,
  b) in return, the computer system generates a proposed color for making up an associated zone, on the basis of the learning performed beforehand, and
  c) the computer system operates the dispenser to produce the mixture of the proposed color, notably if this is validated by the user.

Such a method may use a map previously established with the user.

A further subject of the invention is a computer program product containing code instructions which, when run in a computer system, allow the computer system to be made to:
  allow the user to select at least one color and/or one application area, notably using an interface such as a touch screen,
  operate a dispenser in such a way as to deliver a mixture of the color selected by the user,
  allow the user to trigger the memorizing of the color of the mixture and of an associated application area, notably with a view to subsequently dispensing the same mixture, notably on the same area.

The computer program product may comprise code instructions which, when run in a computer system, allow the computer system to be made to:
  receive a request from the user regarding a need for makeup, notably using an interface such as a touch screen,
  propose, on the basis at least of data generated by the learning process as defined above, at least one color and/or one application area,
  operate a dispenser to produce the mixture of the proposed color, notably if this is validated by the user.

Remote Assistance

It is desirable to be able to assist the user in applying makeup, notably in choosing the correct colorings.

In one of its aspects, independently of or in combination with the other aspects thereof, and notably with the foregoing, one subject of the invention is thus a method of applying makeup involving the steps of:
  allowing a video link to be established, for example over the Internet, between a camera on a first site and a second site,
  allowing the second site to directly or indirectly operate a dispenser present at the first site, this dispenser making it possible to vary the color of a mixture dispensed,
  allowing a person present at the first site to apply the mixture dispensed and to send a corresponding image to the second site, so as to receive in return information relating to the makeup result.

The second site may notably have a viewing screen which allows an adviser sitting at this screen to see the makeup result with the product dispensed by the dispenser and advise the person who has applied the makeup. This adviser may in return influence the dispenser to alter the color of the mixture and adapt it to best suit the face of the person present at the first site. Thus, this person controls the mixture delivered by the dispenser. The first person may make herself up under the gaze of the second. The second person sees the result of the test on their screen and can thus correct the mixture that this second person will control remotely until the ideal makeup is obtained.

If appropriate, the video acquisition can be calibrated using a test pattern or with the mixture dispensed by the dispenser onto a reference surface. That then allows a more faithful display of the makeup applied at the first site.

Preferably, the video link between the two sites is a two-way link.

The first site may receive a tutorial from the second site, if appropriate.

Identifiers of the base products may be communicated to the second site; this may make it possible to precisely determine the color of each of the base products.

The method may involve memorizing the dispenser setting parameters once a given mixture is considered to be satisfactory. Preferably, this memory storage may be commanded from the second site. The memory storage may be in the computer system present at the first site and/or on an external server.

One alternative may be to have one person working to help several apply makeup. This embodiment makes it possible to develop makeup artists and their work, either within an institute or over the Internet. It also allows people with limited capabilities, such as people with poor eyesight, or people who have difficulty discerning colors, or the elderly, or those lacking in self-confidence to apply makeup.

Operation Via Touch-Sensitive Interface

There is a need to make it easier to control the dispensing system and notably the choice of the color of the mixture dispensed.

The dispensing system may thus have a dispenser and a computer system for operating the dispenser, this computer system having a touch screen on which the color of the mixture can be displayed, and a selection means movable on the screen, in order to vary the color of the dispensed mixture.

Preferably, the screen displays end-point colors between which the color of the mixture can be selected by moving the selection means between these end-point colors.

The screen may display a scale of colors between at least two colors, or an area, notably of triangular outline, within which the selection means can be moved. This area may locally show the color of the mixture depending for example on the distance from each of the vertices, each one embodying a pure base product.

The computer system may perform some of the calculations necessary to determine the fractions of each of the base products that lead to a mixture of the desired color.

The computer system may be a smartphone, a camera phone, a tablet, or a personal computer. As an alternative, it is incorporated into the housing of the dispenser.

The computer system may have a camera. The latter can be used notably for capturing an image of the user and/or of the mixture.

The computer system may be designed to display an image of a face, in order to make it easier to identify the areas to which the mixture is to be applied.

Coupling of the Dispensing System to a Spray Means

The dispensing system may have or be connected to a means of spraying the mixture, preferably an airbrush.

The dispensing system may have a spray system, preferably an airbrush, the assembly having:
- a spray means, preferably an airbrush having a pickup chamber subjected to a stream of entrainment air,
- a dispenser having at least two compartments containing different base products, the products being delivered to the spray means preferably via distinct distribution orifices.

The dispenser may have three cartridges containing makeup products of different colors.

The airbrush may have a stylus defining the pickup chamber, the stylus being fixed to the dispenser or to an outlet interface fixed to the dispenser, or forming an integral part of this outlet interface.

The dispensing system may have a circuit controlling operation of the dispenser, allowing the proportion of base products delivered to the pickup chamber to be varied while the airbrush is in operation. The proportions may be modified depending on the movement of the airbrush relative to the surface onto which the mixture is sprayed. This movement may be mechanized, if appropriate.

This control circuit may have or be constituted by a computer system as defined above.

The housing of the dispenser may act as a hand grip when the assembly is being handled for delivering the mixture.

The dispenser may have a camera and/or one or more sensors such as accelerometers so as to automatically locate the area to which the mixture is applied, and so as to be able to automatically regulate the color depending on the position, if appropriate.

A further subject of the invention is a method for applying makeup using an assembly as defined above, in which a mixture is sprayed onto the skin using the spray means, notably the airbrush.

The composition of the mixture can be modified as the airbrush is moved relative to the skin. A graduated effect can be achieved.

This aspect of the invention is based on the observation that the dispenser can be used to supply the spray system, notably the airbrush, while at the same time allowing the dispensing system to be responsive enough to allow a change in the color of the mixture dispensed while the face is being made up, notably as the area to be made up changes.

It may be advantageous for the dispensing of products to be performed iteratively, notably with dispensing times that are not phase-shifted between the various products.

This may make it easier to vary the composition of the mixture dispensed over time.

The mixture may be created directly in the airbrush, with practically no troublesome dead volume, thus allowing the mixture sprayed to be changed in real time.

The depression created in the pickup chamber is strong enough to entrain the base products without in any way impeding the metering.

The depression which prevails in the pickup chamber is for example between 10 mbar and 200 mbar, better still between 50 and 150 mbar, even better still between 75 and 125 mbar.

The cross section of the passages along which the base products arrive in the chamber is, for example, between 1 and 3 $mm^2$, better still between 2 and 3 $mm^2$.

The product is preferably supplied continuously.

It is also possible to apply immiscible or reactive base products, such as an aqueous gel and an oily gel, simultaneously, and these will be deposited directly onto the skin in a pixelated manner, producing a kind of gel/gel in situ, reactive silicones, or colorants that react with one another.

The ratios of base products can be adjusted depending on the particular result desired. For example, in the case of aqueous gels and oily gels, the ratio corresponding to the volume of the first base product to the volume of the second base product could be varied between 10/1 and 1/10, better still between 5/1 and 1/5.

Location or Auto-Location System

The dispensing system according to the invention may have a location or auto-location system.

A location system is the name given to a means via which the person inputs the area that she is to treat. This can be performed notably using systems that leave at least one hand free. Thus, an interface of a computer system such as a touch screen, a joystick, or voice recognition system can be used.

An auto-location system is the name given to a means for inputting the area that is to be treated without intervention on the part of the person. This can be achieved using one or more accelerometers which deduce, from the movements, the directions targeted by the person or by a camera and an image recognition system.

Figure 2:
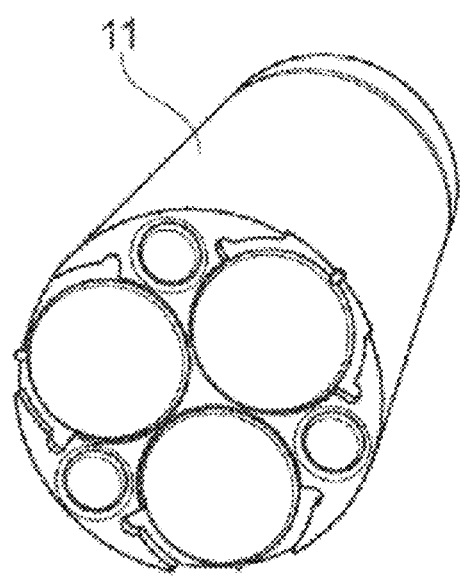
Figure 3:
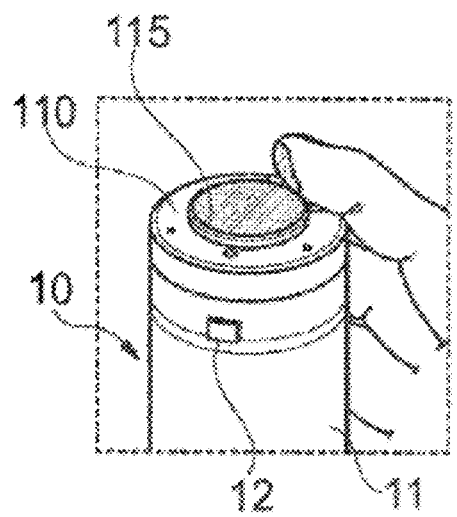
Figure 4:
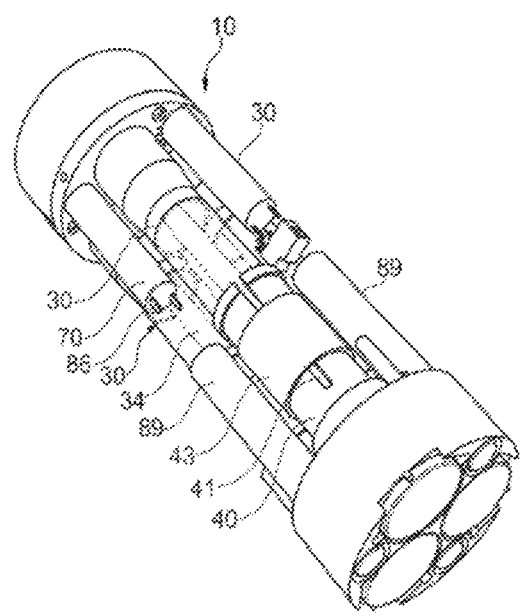
Figure 5:
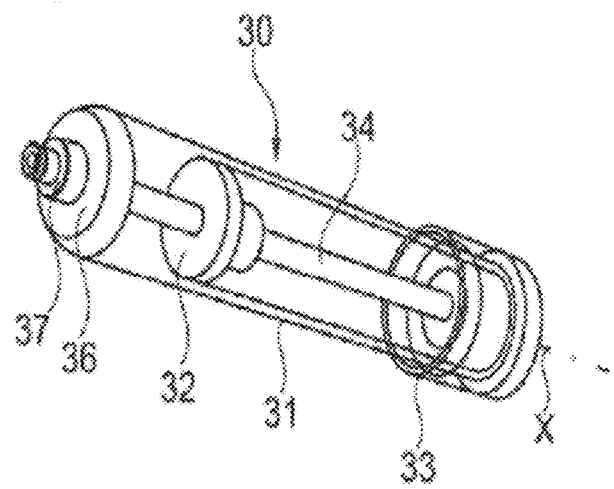
Figure 6:
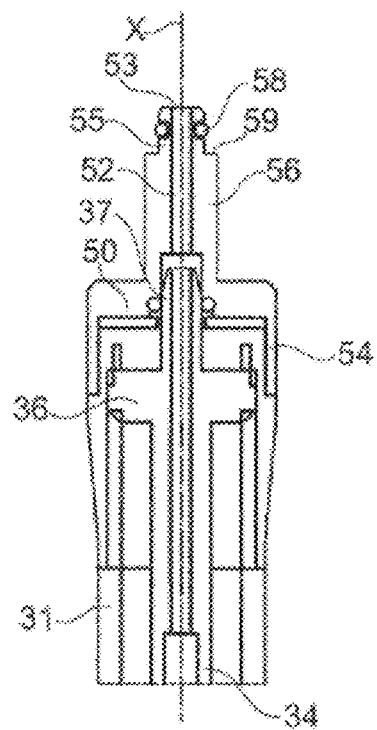
Figure 7:
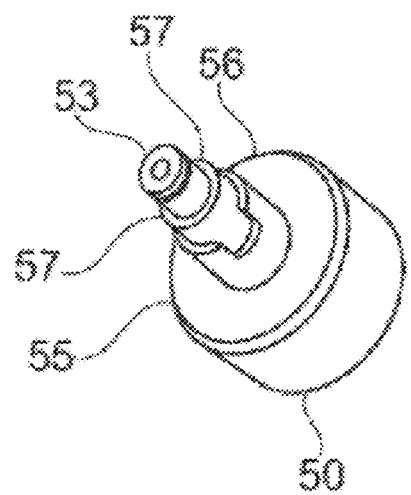
Figure 8:
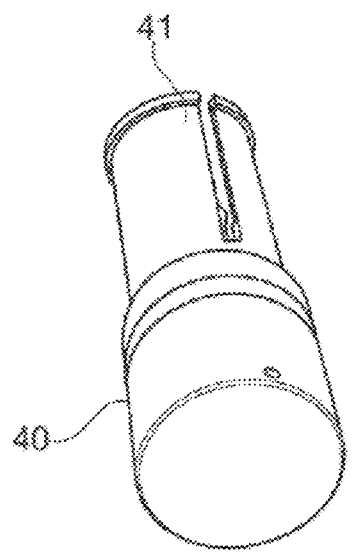
Figure 9:
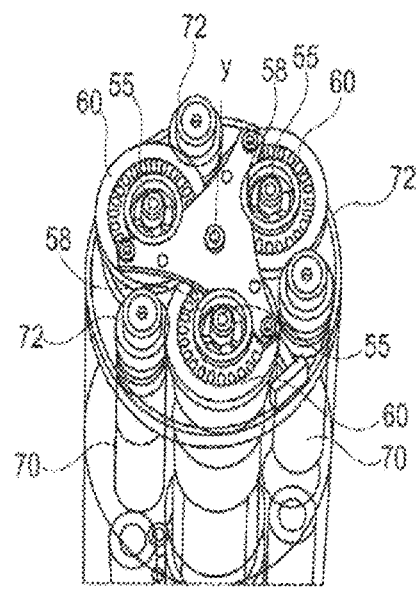
Figure 10:
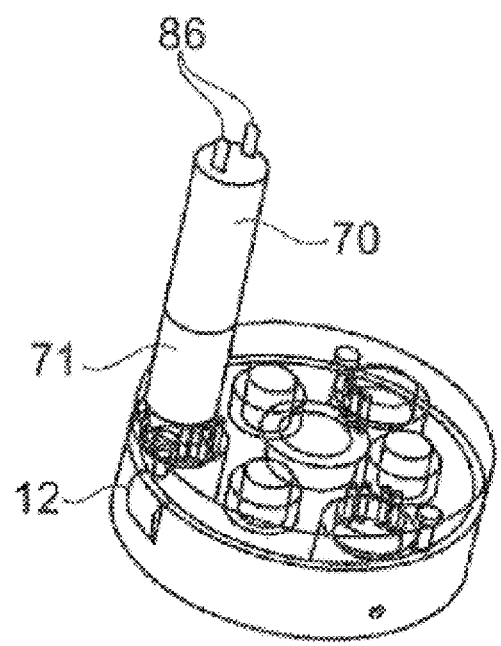
Figure 11:
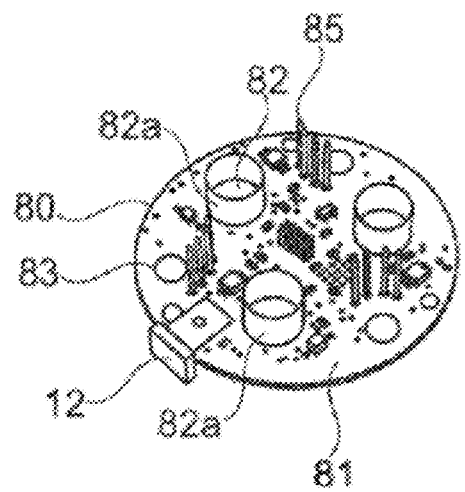
Figure 12:
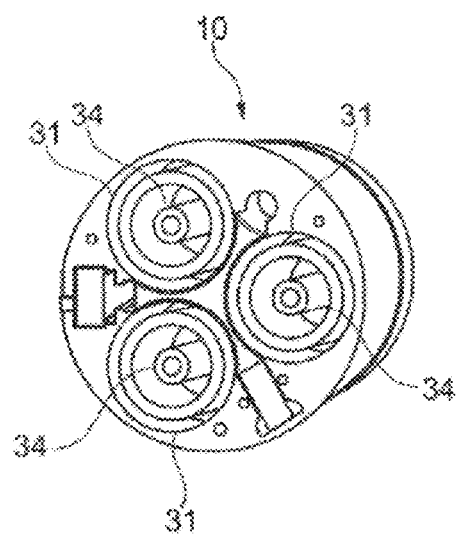
Figure 13:
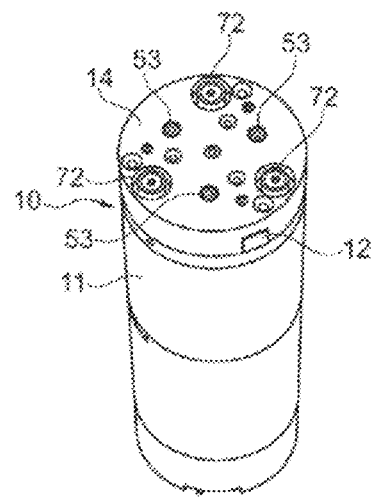
Figure 14:
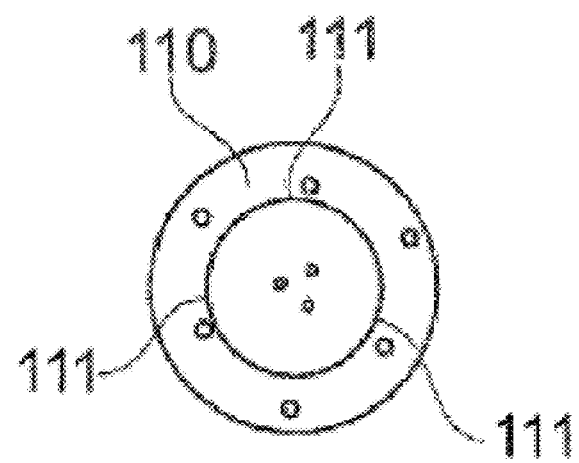
Figure 15:
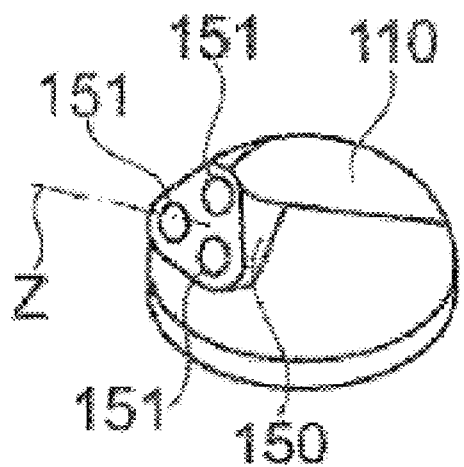
Figure 15A:
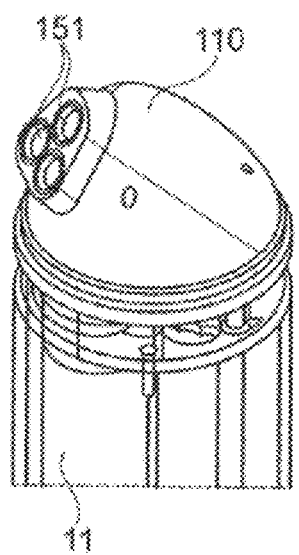
Figure 16:
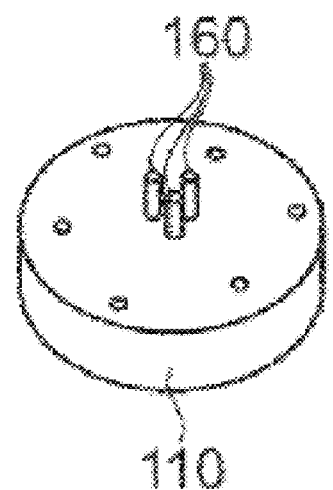
Figure 16A:
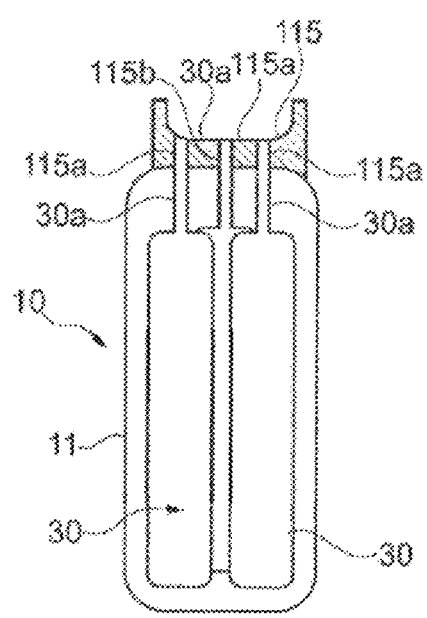
Figure 17:
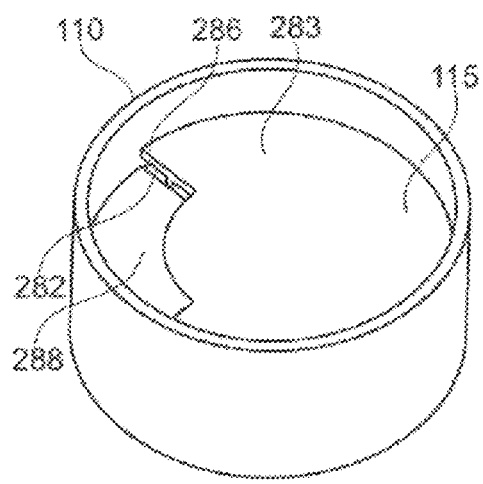
Figure 18:
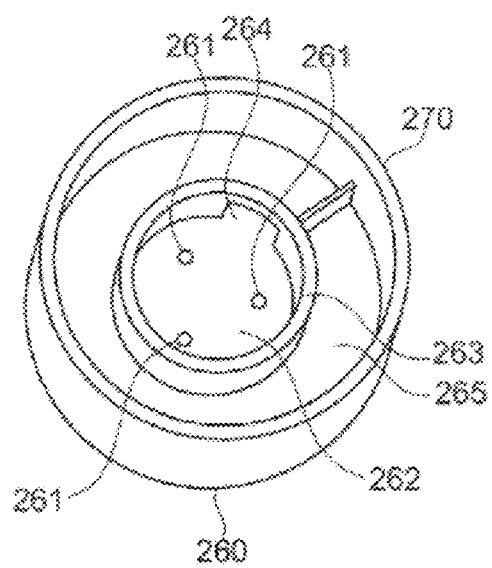
Figure 19:
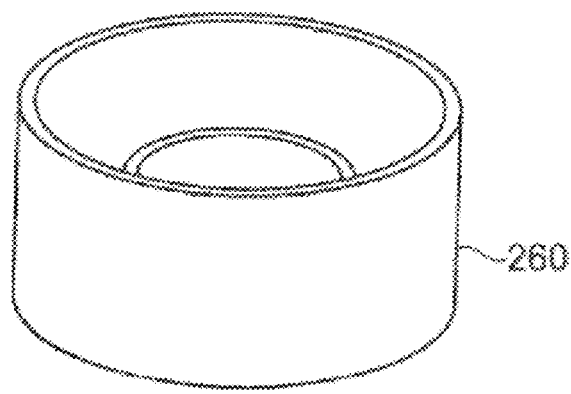
Figure 20:
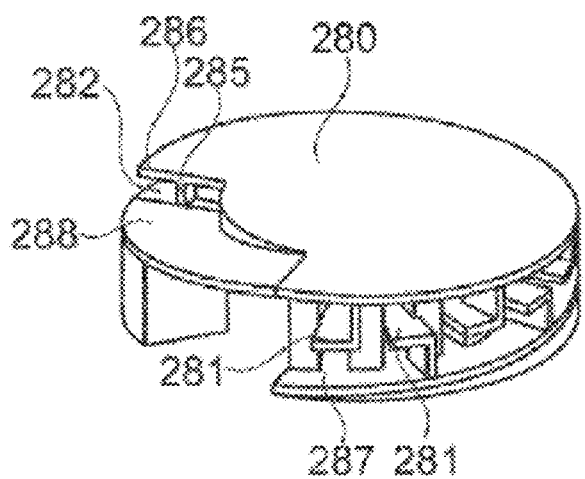
Figure 21:
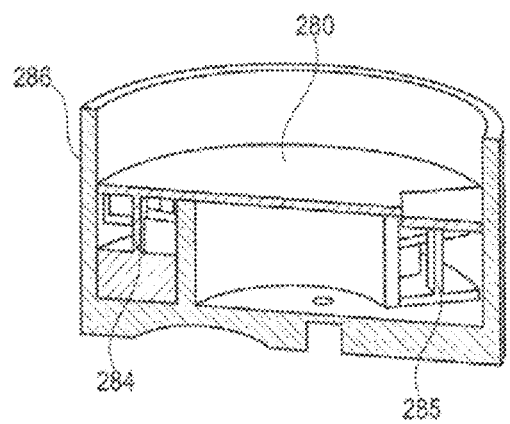
Figure 22:
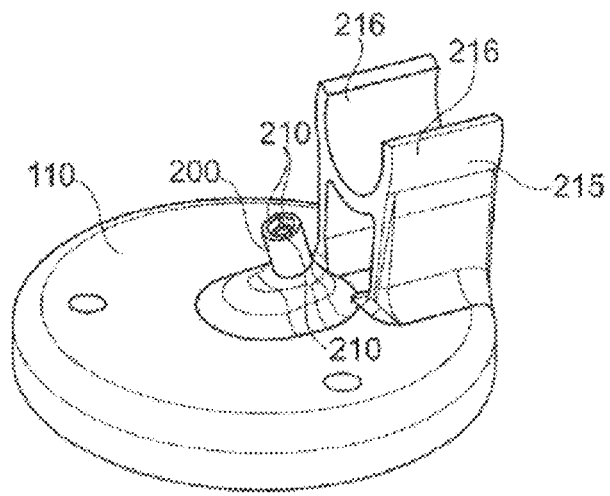
Figure 23:
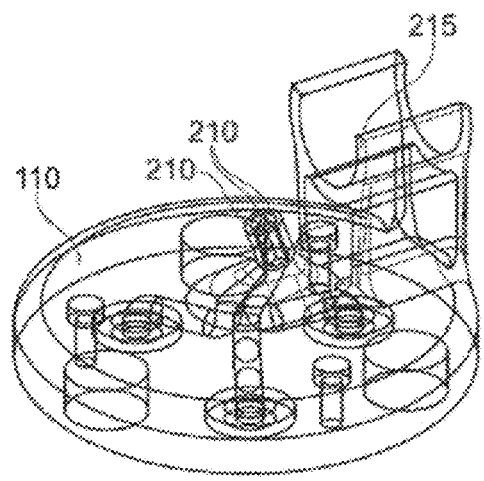
Figure 24:
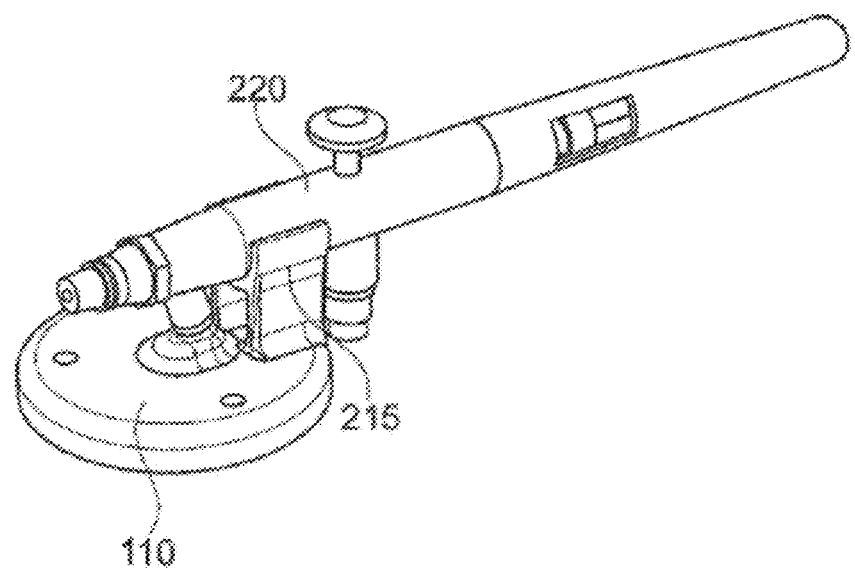
Figure 27:
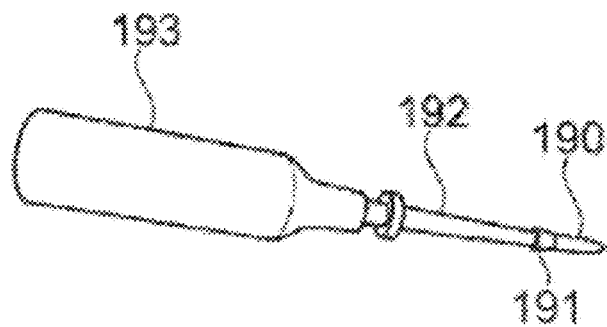
Figure 28:
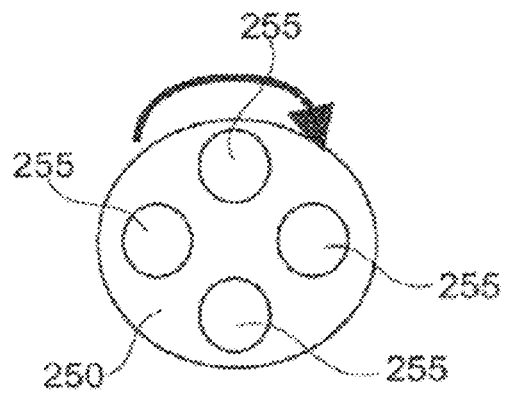
Figure 28A:
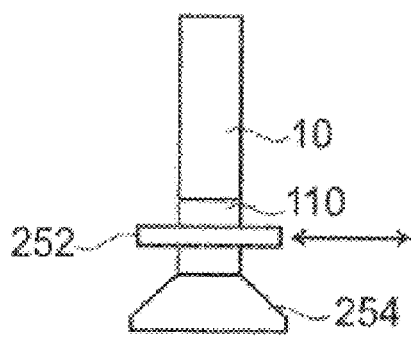
Figure 28B:
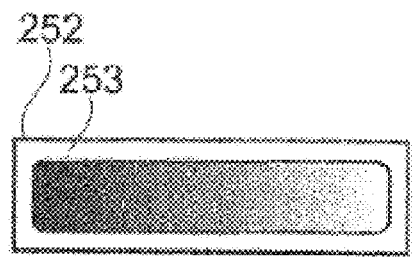
Figure 28C:
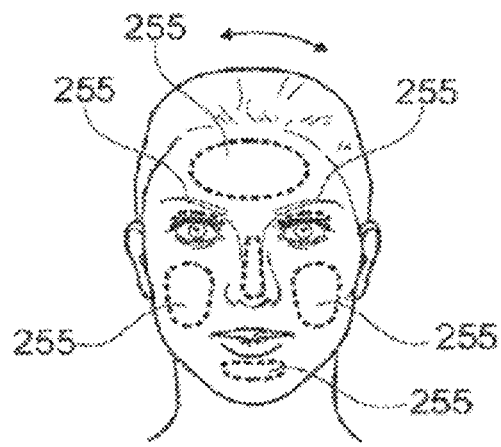
Figure 29:
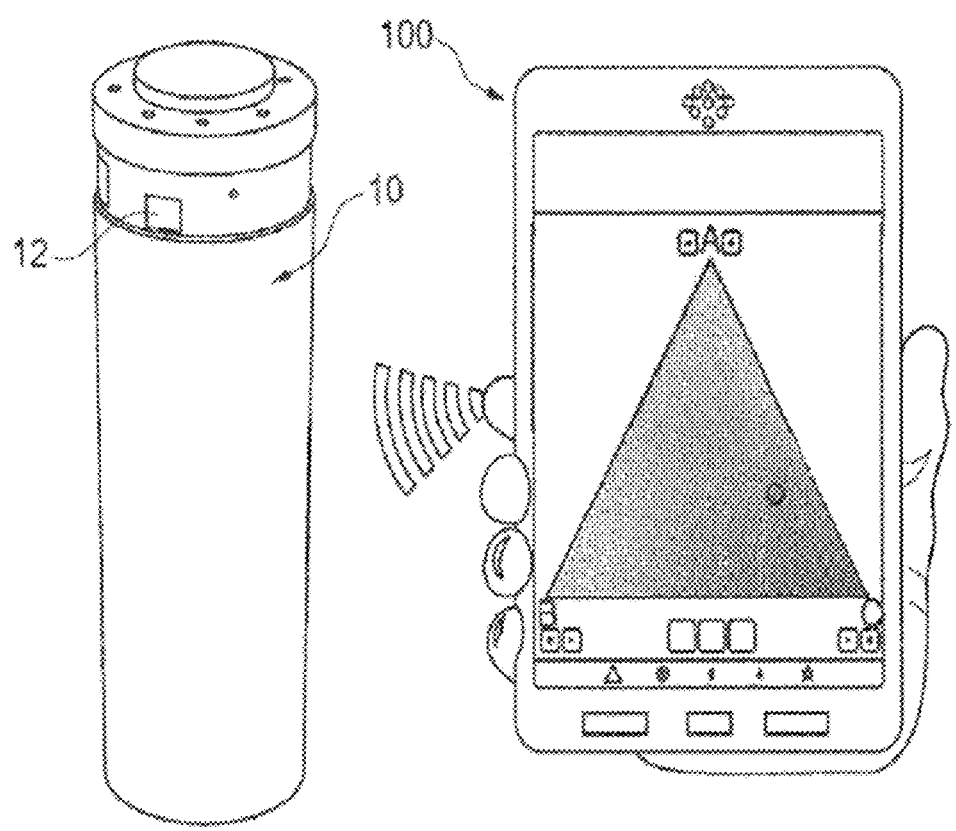
Figure 30:
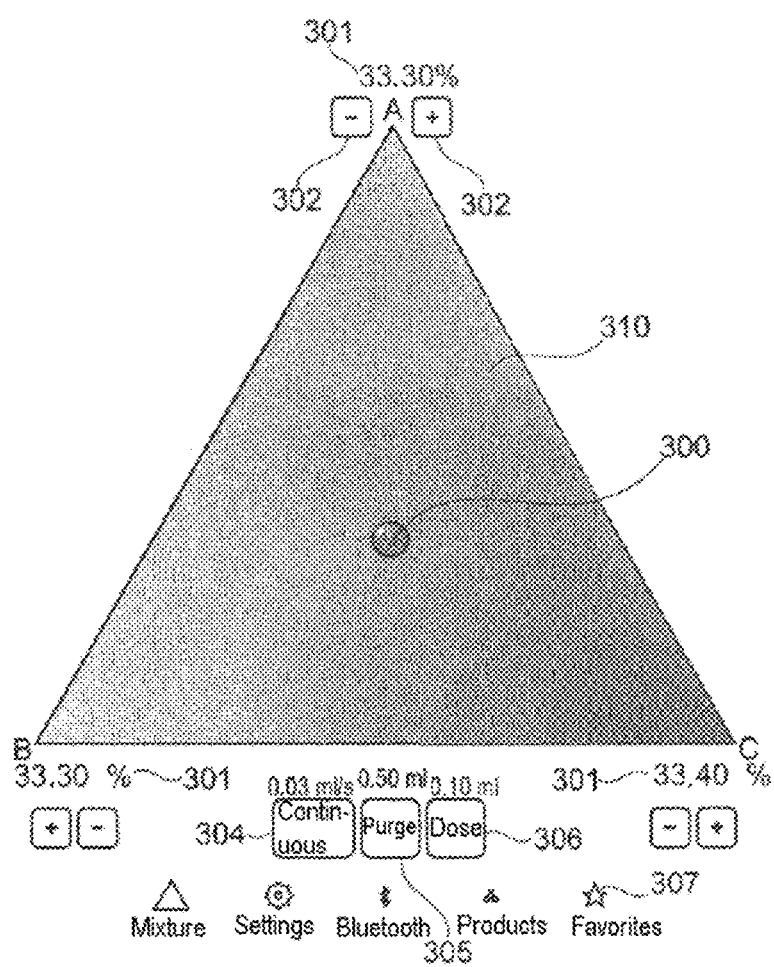
Figure 31:
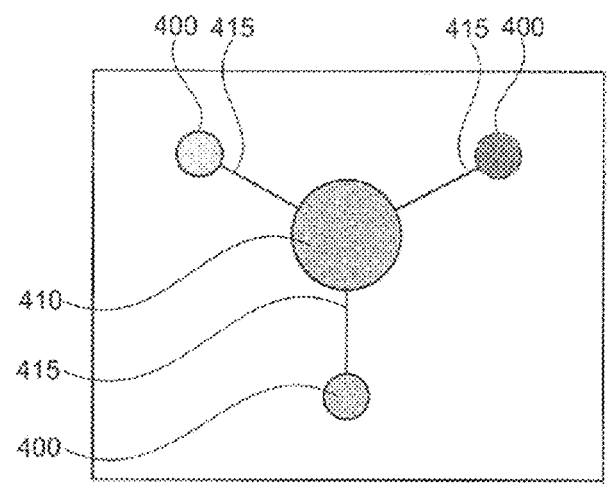
Figure 32:
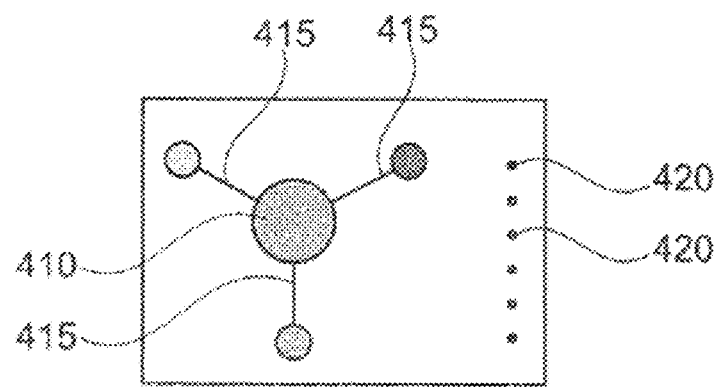
Figure 33:
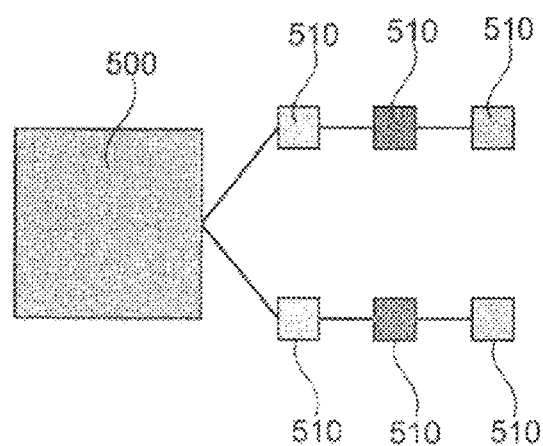
Figure 34:
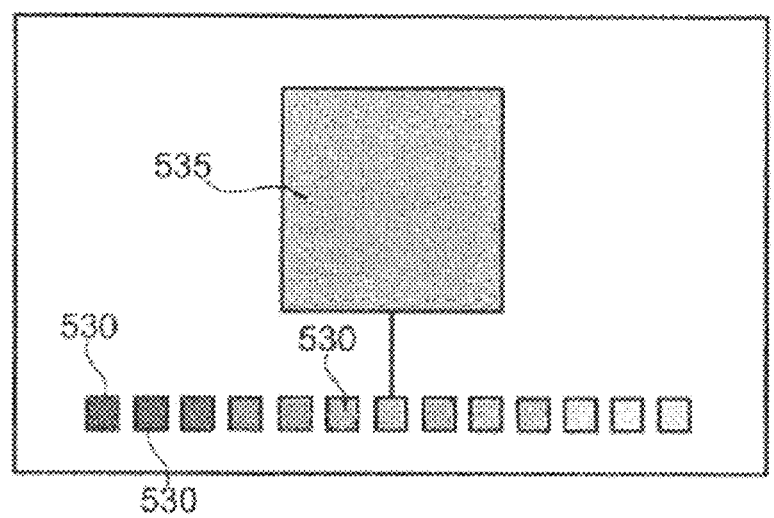
Figure 35:
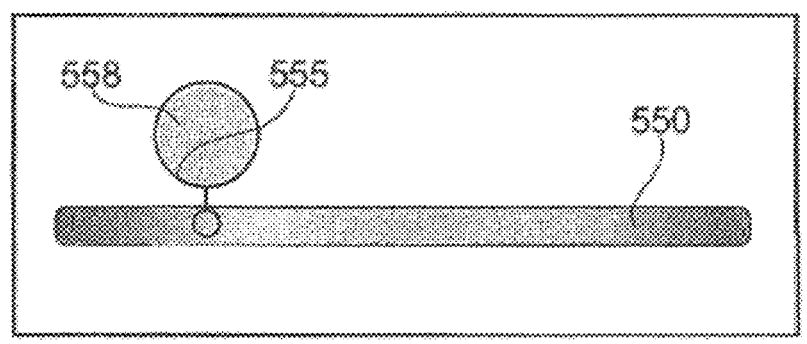
Figure 36:
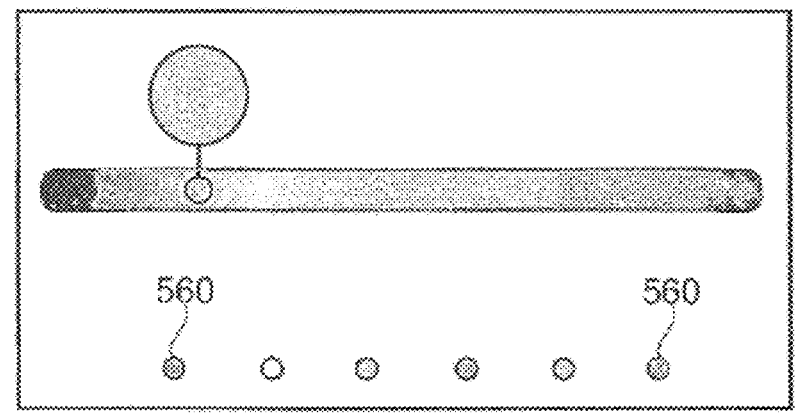
Figures 37, 38:
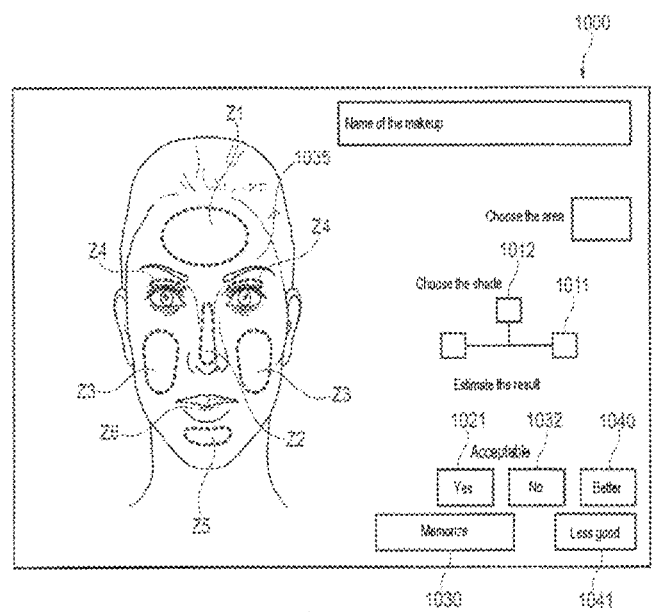
Figure 39:
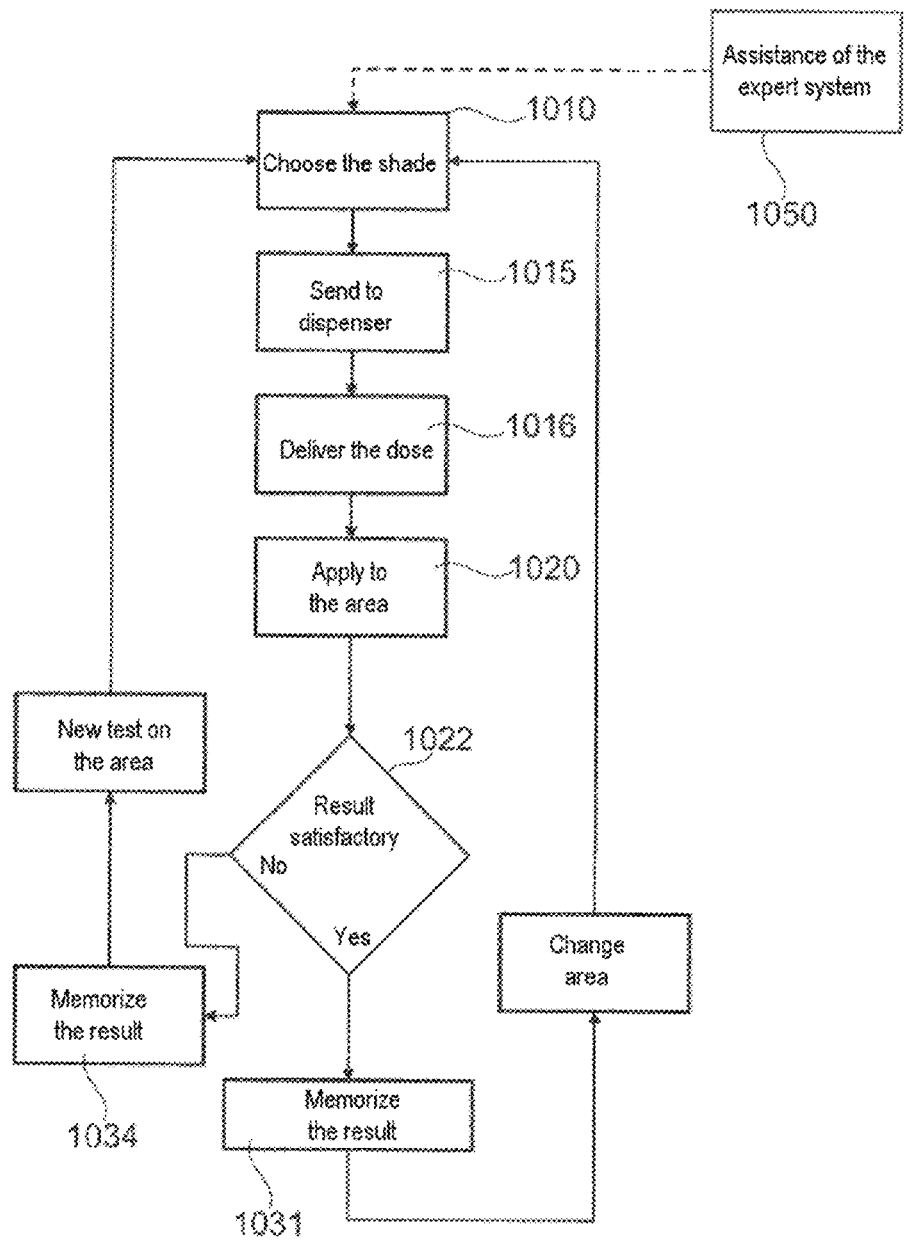
Figure 42:
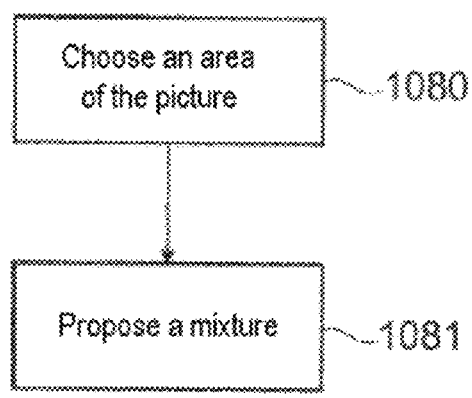
Figure 43:
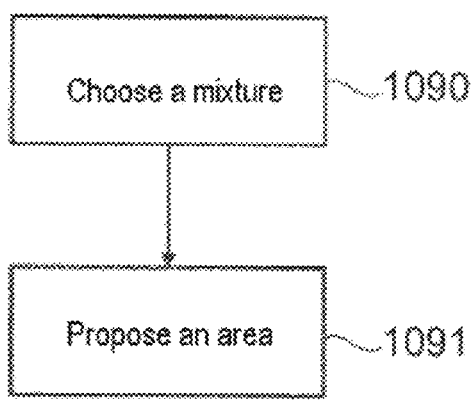
Figure 44:
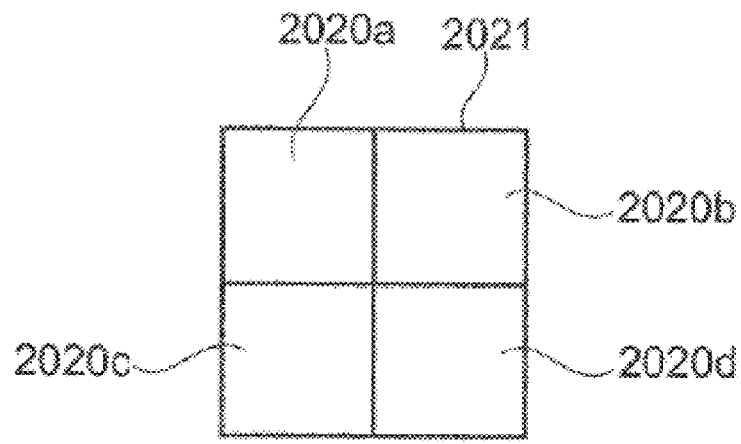
Figure 45:
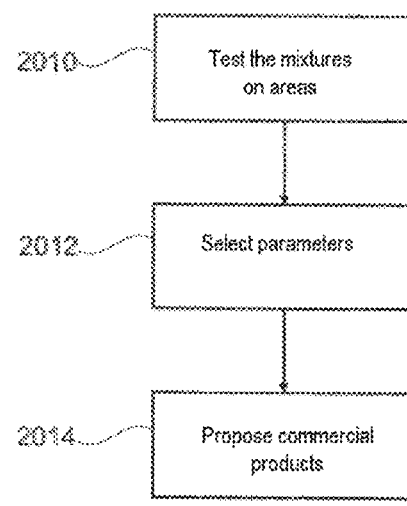

The invention may be understood better from reading the following detailed description of nonlimiting exemplary embodiments thereof and from studying the appended drawing, in which:

FIG. 1 is a schematic perspective view of an example of a dispensing system according to the invention, FIG. 2 is a rear view of the dispensing system in FIG. 1, FIG. 3 illustrates the picking up of product delivered by the dispensing system, FIG. 4 is a schematic perspective view, with certain components removed, of the dispensing system in FIG. 1, FIG. 5 separately and partially shows a cartridge of base product for the dispenser, FIG. 6 shows the top of the cartridge with the drive piece, FIG. 7 separately shows the drive piece, in perspective, FIG. 8 separately shows a support for the cartridge, FIG. 9 shows the dispenser drive mechanism, FIG. 10 shows one of the motors separately, coupled to the rest of the drive mechanism, FIG. 11 shows an electronic board for controlling the motors, FIG. 12 is a cross section of the dispenser, FIG. 13 shows the housing of the dispenser without the outlet interface, FIG. 14 separately shows a first example of an outlet interface, viewed from above, FIGS. 15, 15A, 16, 16A and 17 show other examples of outlet interfaces, FIGS. 18 and 19 are two other views of the outlet interface in FIG. 17, FIG. 20 separately shows the static blender, FIG. 21 is an axial section of the outlet interface in FIG. 17, FIG. 22 shows another outlet interface intended to cooperate with an airbrush, FIG. 23 shows, with hidden detail, the various passages of the outlet interface in FIG. 22, FIG. 24 illustrates the outlet interface in FIGS. 22 and 23 connected to an airbrush, FIGS. 25, 26 to 28, 28A, 28B and 28C show other examples of outlet interfaces, FIG. 29 illustrates the operation of the dispenser using a portable terminal, FIG. 30 shows one example of a graphic interface allowing the dispenser to be operated, FIG. 31 shows another example of a graphic interface, FIG. 32 illustrates an example of how the graphic interface in FIG. 32 evolves as the device is being used, FIG. 33 shows another example of a graphic interface, FIGS. 34 and 35 show other examples of graphic interfaces, FIG. 36 illustrates how the interface in FIG. 36 evolves while the device is being used, FIG. 37 shows a graphic interface of an example of a computer system according to the invention, FIG. 38 shows an example of a look-up table, FIG. 39 is a block diagram illustrating steps of an example of a method according to the invention, FIGS. 40 to 43 are views similar to FIG. 39 of other examples of methods, FIG. 44 shows an example of a support allowing the application of several different colored compositions, FIG. 45 shows a view similar to firgure 39 of other examples of methods.

Figure 46:
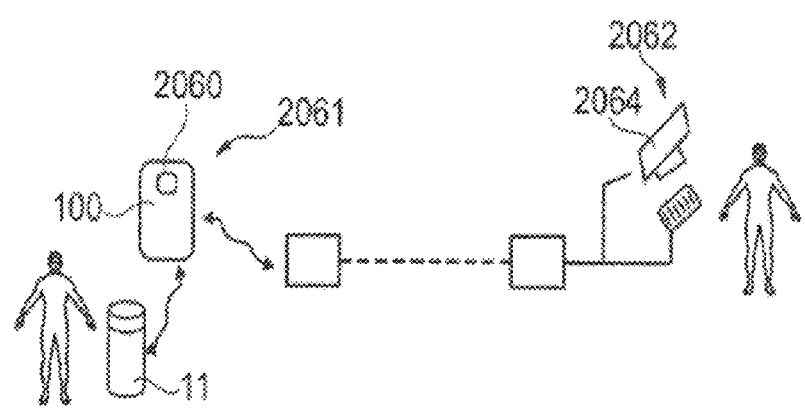
Figure 47:
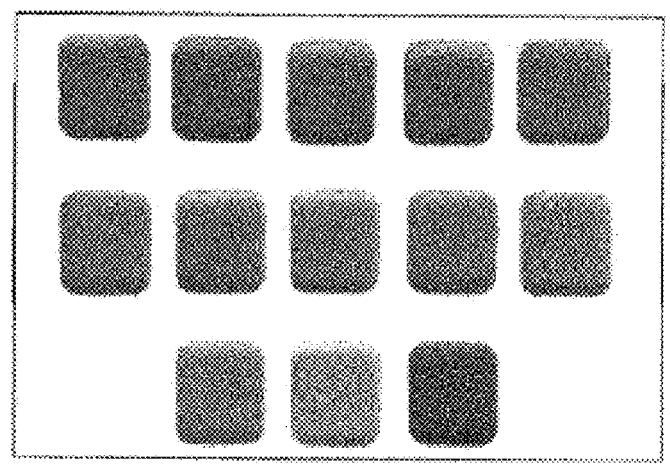

FIG. 46 illustrates a system allowing exchange of information with a remote adviser, and FIG. 47 illustrates a support having a plurality of spaces containing different mixtures.

An example of a dispensing system 10 that may be suitable for the invention is shown in FIGS. 1 and 2 and has a dispenser 11 which is provided in its upper part with an outlet interface 110 via which a cosmetic product of customized formulation is dispensed.

The dispenser 11 can be manipulated by one hand. Its length, excluding the outlet interface, is, for example, between 140 and 160 mm and its diameter is between 40 and 60 mm.

The dispensing system 10 may, as illustrated, have an actuating means for controlling the dispensing, for example a push-button 12.

When the user presses the push-button 12, the dispenser 11 delivers the product on the basis of information communicated to it beforehand by a computer system, for example using a wireless transmission, as will be described in detail below. The operation of the push-button 12 may be programmed from an interface of the computer system, so as to deliver the mixture continuously for as long as pressure is applied, or to deliver only a predefined dose, irrespective of the length of time for which the user presses the push-button.

As can be seen notably in FIG. 4, the dispenser 11 houses several cartridges 30 that each contain a base product, the dispenser 11 allowing the quantity of each of the base products that is dispensed to be metered so that after the dispensed doses have been blended, a product is obtained that has the desired properties.

Each of the cartridges 30 can be introduced into the housing of the dispenser 11 from the rear, as illustrated in FIG. 2. In the example in question, the dispenser 11 receives three cartridges 30, but the invention also extends to instances in which the number of cartridges 30 is different.

A cartridge 30 has been shown separately in FIG. 5. This cartridge has a body 31 in which a piston 32 can move along the longitudinal axis X of the cartridge so as to reduce the volume of a reservoir 33 that is situated under the piston 32 and contains the corresponding base product. The volume of the reservoir is preferably between 2 and 5 mL, being for example in the region of 3 mL.

The piston 32 is driven along the axis X by an externally threaded hollow rod 34 that engages with a corresponding screw thread passing through the piston 32.

The rod 34 defines a passage via which the product contained in the reservoir 33 can circulate when the piston 32 moves in the body 31 in the direction of a reduction in volume of the reservoir 33.

The rod 34 is rotated about the axis X by a head 36 which can turn relative to the body 31, and communicates with a nozzle 37. Each cartridge 30 is mounted in the dispenser 11 with a support piece 40 which has been shown separately in FIG. 8 and comprises an axially slit clamping sleeve 41 along which a locking ring 43, visible in FIG. 4, can slide.

When a cartridge 30 is fitted, the support piece 40 is engaged over it, on the opposite side to the nozzle 37, and the locking ring 43 is moved along the sleeve 41 to clamp the support piece 40 on the body 31. The support piece 40 allows the cartridge 30 to be immobilized in the housing of the dispenser 11.

The head 36 of the cartridge 30, which has the nozzle 37, is capped by a drive piece 50, shown separately in FIG. 7, which grips the head 36 so as to be able to rotate about the axis X therewith.

When the drive piece 50 is rotated about the axis X, its rotation is transmitted to the head 36, which can turn relative to the body 31 and drive the rod 34 in rotation therewith.

The friction force of the piston 30 against the inner surface of the body 31 is enough to prevent the piston 32 from turning relative to the body 31, such that the relative rotation of the rod 34 and of the piston 32 causes the latter to move along the axis X. This movement is accompanied by a reduction in the volume of the reservoir 33 and by base product contained in the cartridge 30 rising up through the rod 34 and then into the nozzle 37.

The drive piece 50 has an internal passage 52 which is fed by the nozzle 37 and which opens to the outside via a dispensing orifice 53. This passage 52 is formed by an end piece 36. The drive piece 50 has a mounting skirt 54 which axially covers the head 36 of the cartridge 30. This mounting skirt 54 is connected to the end piece 56 via a transverse wall 55.

The end piece 56 has reliefs 57 allowing it to be coupled for rotation to a toothed wheel 60, visible notably in FIG. 9, belonging to a drive mechanism of the housing of the dispenser 11.

In the example in question, the reliefs 57 are in the form of two diametrically opposed studs that project from the end piece 56 at the base thereof and engage in corresponding cutouts in the toothed wheel 60.

The end piece 56 has a narrowed portion which comprises a groove accommodating an O-ring seal 58. The narrowed portion is connected to the rest of the end piece via a shoulder 59.

The head 36 of the cartridge 30 may bear an O-ring seal which ensures sealed coupling between the nozzle 37 and the drive piece 50.

The drive mechanism comprises electric motors 70 equipped with reduction gears 71, visible notably in FIG. 10. The output shaft of these reduction gears is coupled to a driving wheel 72 which meshes with the toothed wheel 60.

In the example in question, the longitudinal axes X of each of the cartridges are arranged at 120° to one another about the longitudinal axis Y of the housing of the dispenser 11.

The motors 70 are disposed between the cartridges 30, the axes of rotation of the motors likewise being arranged at 120° to one another about the axis Y of the dispenser 11.

This then makes for a compact design of the dispenser 11.

The geared motor units advantageously have a torque in excess of 70 nN·m. For example, use is made of a Maxon 118392 motor combined with a Maxon 218418 planetary reduction gear set. Such a motor has a diameter of 10 mm, a power of 1.5 W, a nominal voltage of 3 V, an idling speed of 1300 rev/min and a maximum torque of 1.5 mNm. The reduction gear has a diameter of 10 mm, an absolute reduction ratio of 256/1 and a torque of 0.2 Nm.

An electronic circuit 81, shown separately in FIG. 11, is present near the top end of the housing of the dispenser 1. This electronic circuit 81 has a board 80 through which passages 83 for the output shafts of the reduction gears 71 pass, and openings 82 for the narrowed parts 55 of the driving end pieces 56.

Sleeves 82a may be fixed to the board 80 to act as barriers against any leaks of product toward the board 80. The end pieces 56 pass through the sleeves 82a, preferably with a small clearance.

The board 80 bears the abovementioned push-button 12 and supports a certain number of output pins 86 used for powering the motors 70.

The electronic circuit 81 comprises a microcontroller or the like so that the various motors 70 can be operated with a view to dispensing the desired quantity of each of the base products. The resolution of the delivery of the base products is for example between 0.001 and 0.003 mL, being, for example, in the region of 0.0025 mL.

The housing of the dispenser 11 also houses a battery, the cells 89 of which are advantageously set out as can be seen in FIG. 4, each in the continuation of a motor 70.

Preferably, as illustrated in FIG. 30, the dispenser 11 is operated via a computer system 100 such as a portable terminal, for example a smartphone, a tablet, for example of the "iPad" make, or a laptop computer.

The operating information of the dispenser 11 is transmitted preferably wirelessly by the terminal 100, for example by a Bluetooth link.

In one particular example, the electronic board 81 allows control over the following:
calculation of the volume of each product to be delivered depending on the volumetric fraction instruction for each product, the mode of operation (continuous, dose or purge), the value of the flow rate or of the volume,
measurement of the currents powering the motors 70,
Bluetooth communication with the computer system 100,
management of the button 12 for the delivery of products,
management of the on/off switch,
management of the display of the LED(s),
charging of the battery.

The board 80 has for example the following components:
a Texas Instruments CC2541 microcontroller,
a blue CMS LED to provide the user with status information,
a thermal cutout fuse,
a 32 MHz quartz oscillator,
an on/off switch.

The Texas Instruments CC2541 microcontroller incorporates a programmable flash memory with 256 kB of RAM and numerous functionalities. This microcontroller may be programmed in C, in the IAR Embedded Workbench environment.

The outlet orifices 53 of the cartridges 30 open out substantially at the top end of the housing of the dispenser 11, as may be seen notably in FIG. 13. The upper face 14 of the housing of the dispenser 11 defines a mounting surface for mounting an outlet interface which channels the products coming from the cartridges toward a pickup or dispensing area.

In the example in FIG. 1, this outlet interface 110 is in the form of an added component that has been shown separately in FIG. 14 and which has at its periphery, as illustrated, passages 111 for screws used for fixing it to the housing of the dispenser 11.

In this example, the outlet interface 110 defines a cup 115 into the bottom of which the supply orifices 116 open, each orifice being in communication with a respective outlet orifice 53 via an internal duct at the outlet interface 110.

Thus, in the example in question, the base products contained in the cartridges 30 can be dispensed into the cup 115 without mixing with each other.

When using the dispenser 11, the user can fill the cup 115 with predefined proportions of each of the base products, as illustrated in FIG. 3, then pick up the product present in the cup 115 with a view to applying it. This pickup may be performed for example using a finger, as illustrated, or using any suitable cosmetic applicator. The cup 115 is preferably fairly shallow, making it easier to clean, and has a diameter large enough not to hamper access to the product. The depth p of the cup 115 is thus preferably between 1 and 5 mm and its diameter d or that of the circle circumscribing it when the contour of the crucible is not circular, is preferably between 20 and 50 mm. Preferably, $4>=d/p<=50$.

The supply orifices 116 preferably have a diameter smaller than 3 mm, for example in the region of 1 mm.

The outlet interface 110 may receive a lid 118 for closing the cup 115, to prevent the product from drying out or being exposed to dirt when not in use. This lid 118 is preferably made of a transparent plastic and may be fixed to the upstand of the cup 115, or more generally to any suitable point of the outlet interface 110, by friction, screwing or clip-fastening.

The maximum capacity of the cup 115 is preferably between 0.02 and 0.25 ml. Preferably, the volume defined by the volume of the internal passages of the outlet interface 110 between the inlet thereto from the supply orifices 53 to the supply orifices 116 is less than or equal to 0.4 ml.

The housing of the dispenser 11, in the configuration thereof illustrated in FIG. 13, i.e. without the outlet interface 110 described above, has the advantage that it can be coupled to various forms of other outlet interfaces, depending on the making-up that is to be performed and/or on the area to be treated.

Thus, FIG. 15 shows a variant outlet interface 110 having a dispensing end piece 150 oriented generally along an axis Z which extends obliquely with respect to the longitudinal axis Y of the dispenser 11. Three internal passages communicate respectively with the outlet orifices 53 of the various cartridges 30 and open onto the end of the end piece 150. The outlet interface 110 can be fitted at one end of the housing of the dispenser 11, as illustrated in FIG. 15A.

In the variant in FIG. 16, the outlet interface 110 has three nozzles 160 which communicate respectively with the outlet orifices 53. These nozzles 160 are grouped together at the center of the outlet interface 110, thereby allowing an end piece 170, for example, for applying product to the eyelashes, as illustrated in FIG. 25, a porous end piece 180 for application to the lips, as illustrated in FIG. 27, or a flocked end piece 190 such as a felt tip, as illustrated in FIG. 28, to be mounted on them.

Figure 25:
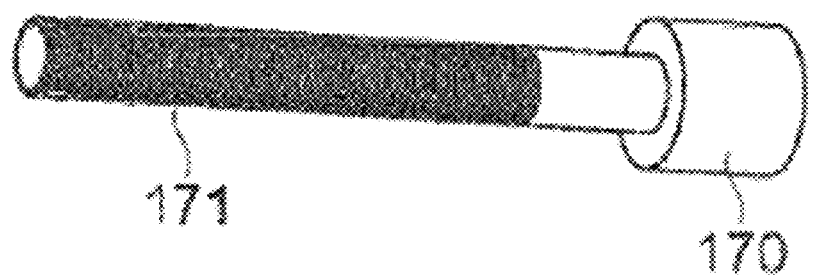
Figure 26:
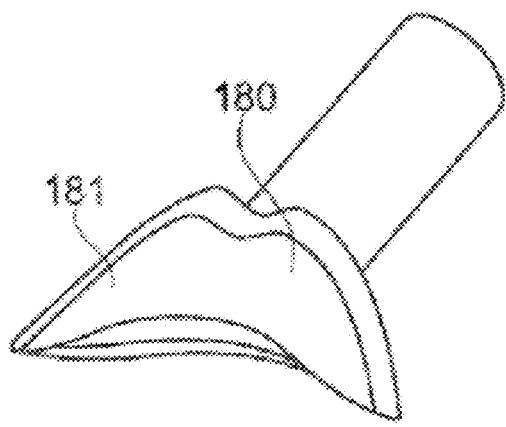

In the case of the end piece 170 in FIG. 25, this has, for example, as illustrated, transverse striations 171 between which the product supply orifices open out. The mixing of the various base products may take place within the end piece 170, by virtue of an in-built static blender, for example.

The end piece 180 has for example a part made of open-cell foam, in the shape of the lips. The base products may be mixed within an internal duct of the end piece 180.

The end piece 190 may have a porous application member 191, at the end of a stem 192, which is connected to a base 193 used for mounting on the rest of the outlet interface in FIG. 16.

FIG. 16A schematically illustrates the possibility of having, as outlet interface 110, a cup 115 with passages 115a for outlet ducts 30a of the cartridges, even when these ducts are used for rotating the threaded rods for moving the pistons. The length of the ducts 30a is such that they open into the bottom 115b of the cup or near to the bottom thereof, without protruding into it.

Preferably, the internal section of the ducts 30a is small, in order to minimize the dead volume.

In the example in FIGS. 22 to 24, the outlet interface 110 has an end piece 200 which is oriented generally obliquely with respect to the longitudinal axis Y of the dispenser. This end piece 200 has internal passages 210 running through it, these communicating respectively with the outlet orifices 53 for the base products coming from the cartridges 30.

The outlet interface 110 has a mounting part 215 which allows an airbrush 220 to be fixed to the outlet interface 110, as illustrated in FIG. 24.

The end piece 200 is fixed in place of the usual reservoir of the airbrush and the passages 210 open into the spray nozzle of the airbrush where they are subjected to the depression created by the speed of the stream of entrainment air.

A clip is formed by two uprights 216 to receive the body of the stylus of the airbrush 220 and hold it in place by clip-fastening.

Preferably, the orientation of the end piece 200 is such that it allows the spray axis to be oriented substantially perpendicularly to the longitudinal axis of the housing of the dispenser 11. This housing can then be used as a handle for manipulating the airbrush.

The outlet orifices 210 are advantageously very close together, being separated by fine internal partitions of the end piece 200.

Preferably, the cross section of each of the outlet orifices is less than or equal to 3 mm$^2$ over a length of at least 5 mm.

The housing of the dispenser 11 may also be equipped in its upper part with a support that is movable with respect to the housing, for example in the form of a turret 250, as illustrated in FIG. 29.

This turret 250 turns for example about an axis of rotation that coincides with the longitudinal axis Y of the dispenser.

The turret 250 may have several spaces 255 that are each able to accommodate the products delivered by the dispenser 11 in a corresponding filling position. In order to fill the various spaces in succession, the turret 250 is made to rotate, for example by a quarter-turn each time. The presence of several spaces 255 may allow products of different formulations, made from different base products, to be dispensed for example so as to vary the shade of the products present in the various spaces 255.

FIG. 29C illustrates a support having spaces disposed thereon substantially in the manner of the different areas of a face; each space may contain a mixture, the color of which is suited to the corresponding part of the face. Thus it is easy for the user to know where to apply the mixture picked up from a given space.

The dispenser 11 can be used to deliver a mixture, the formulation of which changes over time, and to collect the mixture in a container that is movable with respect to the dispenser, such that the mixture is deposited in a location of the container that varies over time, in order to achieve a graduated effect.

For example, as illustrated in FIGS. 29A and 29B, the dispensing system has an outlet interface 110 having a part that is fixed relative to the dispenser and a moving part 252 that has a space 253 for receiving the mixture.

For example, the dispenser 11 is arranged in this case with the outlet orifices of the cartridges downward and is equipped with a blender such that the mixture falls into the space 253 under its own weight. A motor may move the moving part of the outlet interface relative to the dispenser, in a manner that is synchronized with the variation in characteristics of the mixture, such that a graduated effect is obtained all along the space 253, as illustrated in FIG. 29B.

The dispensing system may have a stand 254 which keeps the dispenser head down.

The outlet interface 110, notably when it comprises a cup, may have a static blender which mixes the base products.

FIGS. 17 to 21 show an outlet interface 110 having such a static blender.

This outlet interface 110 may have an exterior body 260 which is fixed to the housing of the dispenser 11 and has an exterior tubular upright 270.

The body 260 has passages 261 for admitting the various base products. These passages 261 open into a central chamber 262 delimited by an interior tubular upright 263.

This upright 263 has an opening 264 passing through it, which opens into an annular space 265 between the interior upright 263 and the exterior upright 270.

A static blender core 280, shown separately in FIG. 20, is disposed inside this space 265.

The central chamber 262 may communicate with a peripheral chamber comprising a series of partitions which are formed by the core of the blender and which act as deflectors for the mixture and create shear therein.

The peripheral chamber may have a perforated annular partition 284 defining perforations 285, one of which is visible in FIG. 21, through which the mixture passes as it circulates through the peripheral chamber. The central and peripheral chambers may be closed at the top by a wall 286 which defines the end wall of the cavity receiving the mixture.

The end wall 287 of the peripheral chamber may be of helical shape and of a height that decreases toward the outlet. The latter may open out ahead of a connecting ramp 288 between the end wall 287 of the peripheral chamber and the top wall 286 of the blender, this connecting ramp preferably being a portion of a helix extending the helix formed by the end wall of the peripheral chamber.

Preferably, the peripheral chamber has the abovementioned annular partition and radial partitions 281 which force the mixture to circulate alternately between upper and lower regions of the peripheral chamber and between radially inner and outer regions, the mixture circulating for example from an upper and radially outer region to a lower and radially outer region by passing through the abovementioned annular partition.

The body 260 radially closes the peripheral chamber on the outside.

The outer body 260 of the blender and the core 280 of the blender may each be produced as a single piece by injection molding.

The product reaches the core 280 of the static blender via the passage 264, then circulates between the uprights 263 and 270 around practically a full circumference until it reaches the outlet 282.

The numerous chicanes imposed by the partitions 281 cause intimate mixing of the components introduced into the outlet interface 110. The mixture obtained can be picked up by the user from the space 283, above the static blender.

As indicated above, the dispensing system 10 according to the invention preferably has a man-machine interface that allows the user to easily and intuitively operate the dispenser 11. This interface may form part of a computer system 100 which communicates with the dispenser 11.

FIGS. 31 to 37 show various examples of touch-sensitive interfaces that may allow the user to select the color of the mixture resulting from the metered dispensing of the various base products.

This interface may have, as illustrated in FIG. 31, a color selection area, for example in the form of a triangle, the vertices of which correspond to the colors of each of the base products contained in the cartridges.

The user can move a cursor 300, for example in the form of a ball, relative to the vertices A, B and C of the triangle.

The closer he brings the cursor 300 to one of the vertices, the larger the fraction of the corresponding base product relative to the total quantity of the various products dispensed.

The fraction of each product relative to the total quantity may be indicated at 301 by a numerical value on the interface.

The interface may allow the user to increment or decrease the quantity of each of the products, for example by operating control buttons 302, which allow precise adjustment of the quantity of each of the base products.

The surface of the triangle 310 may have a color that varies locally so as to be indicative at each point of the color of the mixture that results from the weighting of the various base products in the proportions corresponding to the relative coordinates at this point.

The interface may have a button 305 providing access to a specific menu for adjusting the volume of product dispensed for purging the dispenser.

The interface may also advantageously allow the flow rate of product to be adjusted using buttons 304 and 306 returning to a specific menu for adjusting the flow rate.

In the example in question, the interface affords the choice between a continuous dispensing mode, using the button 304, in which the products are dispensed for as long as the user is pressing the control button 12.

The corresponding dose can be transmitted to the interface and displayed.

The button 306 allows selection of a dose mode of operation, during which even a brief press of the button 12 triggers the dispensing of a predefined dose.

In order to vary the flow rate, the dispenser acts, for example, on the
 operating duty cycle of the motors.

The interface may be designed to allow the user to program or memorize the settings he or she prefers, using a menu 307 providing access to favorites.

The touch-sensitive interface illustrated in FIG. 32 shows on the screen three colored areas 400, each one corresponding to the color of one of the base products contained in the dispenser 10, and a central area 410 which shows the color of the resulting mixture.

The relative quantity of each of the base products can be adjusted using cursors 415 which move for example along lines joining each of the areas 400 to the central area 410.

During use of the interface, the latter may memorize a given setting and cause a button 420 of the color of the mixture to appear on the screen. The user can then, simply by pressing this button 420, dispense a mixture of the corresponding color.

In the example in FIG. 34, the interface displays, in an area 500, a given shade and offers the user, by virtue of control buttons 510 that are each in the color of the corresponding base product, the opportunity to increase or decrease the proportion of this base product in the final mixture. The color of the area 500 is recalculated depending on the actions on the control buttons 510.

In the variant in FIG. 35, the interface shows a color chart having several areas 530, each one corresponding to a particular proportion of the various base products.

The user may select one of these areas, for example by pressing it with his or her finger.

The interface may be designed to display the selected color to a larger scale in an area 535. The programming of the dispenser 11 to dispense this color is triggered for example by pressing the area.

In the example in FIG. 36, the user may move a cursor 555 over a continuous color chart 550, causing the selected color to be displayed in an area 558.

The user can then, for example by pressing the area 556, trigger the sending to the dispenser 11 of the necessary instructions for the dispenser to dispense a product in the selected color.

It is apparent from FIG. 37 that the interface can memorize the various shades selected and then display them on the screen so as to allow the user, by pressing corresponding buttons 560, very easily to again select a shade that has already been chosen.

FIG. 38 shows an example of a user interface 1000 of a dispensing system comprising a dispenser, preferably as described above, and a computer system 100 to which the interface belongs.

The computer system comprises here, for example, a device such as a laptop computer, a tablet or a smartphone, that operates autonomously or is connected to a remote server.

In the example in question, the interface 1000 is defined by the touch screen of such a device. In a variant that has not been illustrated, the dispenser incorporates a touch screen or any other type of man-machine interface, and can be used without connection to another device.

The device runs an application, for example which has been downloaded beforehand and which displays on the screen a face 1035 and a series of buttons allowing the user to input information.

The face may comprise several areas Z1 to Z6 that can be selected by touch, for example the forehead, the nose, the cheeks, the eyelids, the chin, and the lips.

The buttons present on the screen may make it possible for example to input the name of the makeup or of the user, to display the selected area, to choose the color, and to inform the computer system as to whether or not the result of the test carried out is acceptable, or even, as illustrated, to provide information regarding the assessment of the result relative to a test carried out previously, namely, for example, better or "not as good". The screen may also display a button allowing the choice of a color and an area to be memorized after a test has been carried out with this color on the area in question.

The choice of color is made for example with a color scale similar to the one described with reference to FIG. 36.

The computer system is designed to memorize the data in the form of a look-up table for example, so as to associate an area of the face with the parameters that allow the mixture dispensed during the test to be reproduced. These parameters include, for example, the relative contents of each of the base products of the dispenser in the mixture, the quantity Q dispensed, and additional data such as, for example, the name of the area, the date the mixture was dispensed and/or any other mixture identifier, identifiers of the base products, the period of the year, notably the season, the age of the user, his or her sex, his or her given or family name, the name of an event associated with the makeup, for example a birthday, amongst other data, and the quantity of product suitable for the area. The ancillary data may allow the user to reproduce more easily a makeup look considered suitable for a time of year or recalling a life event, or to give a rejuvenating effect.

These data may be memorized in the computer system 100, for example in the abovementioned device and/or on a remote server with which the device is in communication, or alternatively in an electronic memory incorporated into the dispenser 11.

Thus, according to the invention, the user may make the dispenser deliver a first colored substance, and apply it to a first area of the face, then judge whether or not it is suitable. If the result is satisfactory, the user may record it, indexing it to the area; if the result is unsatisfactory, the user may command a new color in order to repeat the above operations.

The computer system can be used in this context in various ways.

Figure 40:
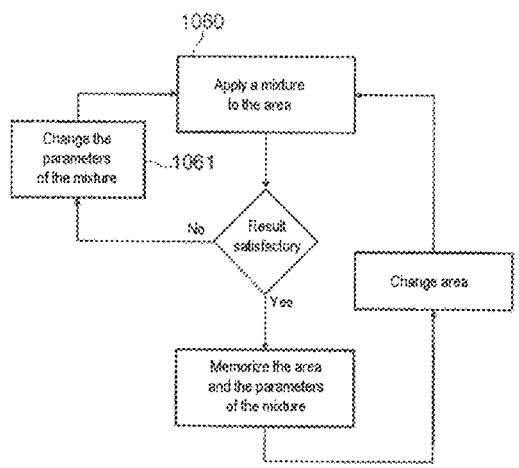

For example, as illustrated in FIG. 40, in a step 1010, the user has selected a color to test, using for example the color scale 1011 displayed on the screen, by moving the adjusting button 1012.

Next, the choice of color is transmitted to the dispenser 11, in step 1015.

For example, the device transmits the quantities of each of the base products to be dispensed and the electronic circuit 81 takes charge of operating the motors accordingly.

In step 1016, the user presses the control button 12 of the dispenser 11, this causing, for example, a dose of the mixture, in the color selected by the user, to be dispensed.

The mixture is, for example, dispensed into the cup 115 then picked up and applied by the user to the cheeks or any other area instructed on the interface, in step 1020.

In variants, the product is applied using an airbrush or by any other means as described above.

The user then, in step 1022, informs the computer system of the result using the buttons 1021.

If the user indicates that the result is satisfactory, the system suggests for example that he/she validate the parameters of the test using a button so as to memorize these parameters in step 1031.

If the user does not consider the result to be satisfactory and makes this known using the button 1032, the result can nevertheless be automatically saved in step 1034.

Thus, each area can be indexed not only with the suitable color(s), but also with the color(s) that is/are not at all suited to this area.

The user can then perform a further test on the same area by returning to step 1010.

If the user is satisfied with the result, he or she may also wish to carry out a further test, for example on a different area of the face.

If appropriate, if the user is not satisfied, the interface may suggest that the user indicate whether the result is considered better than or not as good as the previous test, using corresponding buttons 1040 and 1041.

In that case, the computer system may be designed to determine whether, in light of the information input by the user, a proposal can be automatically made as to what color to test next.

If appropriate, a questionnaire may be displayed to assist the computer system in proposing a color in light of the tests carried out and the way in which the user or a professional assisting the user has assessed these tests.

For example, if the color is considered "unsuitable", the system may receive from the user additional information, for example "too light", which will assist the system in proposing a new color better suited to the user's expectations.

It may be advantageous for the computer system to be able to receive information comparing the result against the previous tests, for example "it's better" or "it's not as good" and, from there, for the system to be capable of deducing what new color to propose.

Another option is for the computer system to be able to receive comparison information regarding a comparison against a target, for example "it's almost ideal" and, from there, for the system to be capable of automatically adjusting its color modifications.

In this particular instance, if it receives the information that the desired result has almost been achieved, the system can adopt small levels of color change and revise the colorimetric scale of adjustment accordingly.

If the dispensing system itself proposes the colored mixtures to be tested, these may be based on preprogrammed test scenarios and the system may alter how the scenario is followed through according to the successes or failures of the assessment. Thus, for example if, from the third application of product, it receives information that the color is almost ideal for the user, the dispensing system may exit the program and thereafter allow itself to be guided by instructions from the operator.

In general, the user may be assisted by an expert system in the choice of colors to test.

This expert system is, for example, a program run on the device with which the dispenser communicates or on the dispenser itself, and which is based on the answers to a questionnaire and/or on measurements, for example of the color of the skin, taken by a specific sensor or by a camera. The user can thus get assistance from an instrumented evaluation, for example a color sensor. The expert system can even be implemented on a remote server with which the device or the dispenser exchanges information. The operator may even send an image of his or her face to a specialist, who can preprogram the starting color choice. In another exemplary embodiment, the user presents the computer system with a photo of his or her face, and the computer system is designed to analyze this and create a program defining the areas to be tested and the first products to be delivered, both in terms of color and in terms of quantity. For example, the computer system may be designed to automatically select the colors of makeup to propose to the user by capturing a photograph in step 1070, as illustrated in FIG. 42. For example, the device which communicates with the dispenser 11 is equipped with a camera, and the user takes a photograph of his or her face. The image is then analyzed in step 1071, and colors are proposed for each area of the face in step 1072, for example in accordance with predefined color combination rules.

The dispensing system may be oriented by the user to decide on the color and also on the quantity of product to be delivered. For example, the user may indicate "nose" or "blemish" and the dispensing system is designed to adapt the dose dispensed according to a memorized map of doses to be dispensed depending on the areas to be treated.

The computer system may guide the user in the choice of colors in the mixture to be tested, so as to limit the number of tests needed until the user obtains a result that pleases him or her.

Figure 41:
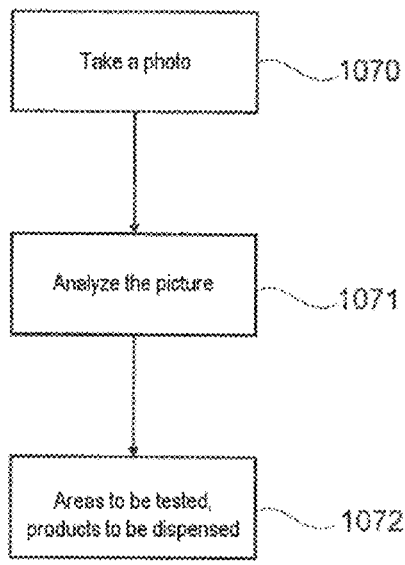

It is thus possible, as illustrated in FIG. 41, that after a mixture dispensed by the dispenser has been applied to a given area of the face in step 1060, the computer system will ask the user whether or not the result is satisfactory and will, of its own accord, if the result is considered to be unsatisfactory, make a change 1061 to the dispenser parameters in order to modify the mixture dispensed.

The user then only has to perform a new test with the modified mixture.

When a mixture is indicated as being satisfactory, the computer system can memorize the corresponding parameters so as to allow the mixture to be recreated at a later date.

The system can then begin the above steps afresh for a new application area.

During the successive tests, the operator does not need to treat the entire face. He or she may for example choose between 3 and 8, for example 5, small areas. The dispensing system is then advantageously designed to interpolate and/or extrapolate the data regarding the colors considered to be suitable, so as to calculate the colors that ought to be considered suitable for areas for which the exercise has not been conducted.

At the end of the learning stage, the system may generate a display of the suitable colors on the various areas, tested or calculated.

The dispensing system may be designed to indicate whether certain colors appear to be incorrect, doing so on the strength of a comparison against standard maps it has in memory. Thus, it may propose that the user repeat all or some of the mapping exercise.

Once the computer system has completed its learning, i.e. once the colors of mixtures have been identified as being agreeable to the user for making-up certain areas, the user wishing to apply makeup only has to call up the area that is to be made up, in step 1080 of FIG. 43, and the system will be able to automatically propose a suitable mixture color to the user in step 1081.

In the variant illustrated in FIG. 44, the user selects a color in step 1090 and the computer system proposes, in step 1091, an area in which to apply a mixture of this color, on the basis of information previously collected on the basis of the tests performed.

The area proposed is, for example, the area in which an identical or very similar color has already been applied and the result considered acceptable by the user.

FIG. 46 illustrates an example of an implementation of the invention in which, having carried out tests on various zones in step 2010, the user informs the system of the mixture(s) he or she considers to afford the best result, this allowing the system to know the corresponding parameters in step 2012. Next, in step 2014, the system may propose to the user references of commercial products that have the same properties or very similar properties.

In one variant, the system sends the parameters to a remote manufacturing center so that a composition that has the same formulation or the same properties as that of the mixture that the user has tested and found to be satisfactory can be produced.

FIG. 45 illustrates the possibility of using the dispenser to dispense several doses 2020a to 2020d of different mixtures, next to one another on a support 2021, so as to allow these to be applied to adjacent distinct regions of the same area.

The user can, in a single hit, apply a series of colors in order rapidly to home in on the appropriate color. The colored substances present on the support 2021 may have been chosen by the operator him- or herself or proposed by the dispensing system.

The support 2021 is, for example, movable with respect to the housing of the dispenser and is moved sequentially to deposit the corresponding mixtures in the various areas 2020a to 2020d, being for example similar to the supports described with reference to FIG. 29 or 29A. The user can thus easily compare the results between the various regions and inform the system of which mixture produces the best effect.

FIG. 47 illustrates a system that assists the user in applying makeup, notably in choosing the correct colorings.

This system makes it possible to establish a video link, for example over the Internet, between a camera 2060 at a first site 2061 and a second site 2062.

The camera 2060 is, for example, built into a tablet or a smartphone that constitutes the computer system 100.

The second site 2062 is allowed to operate the dispenser 11 present at the first site 2061 either directly or indirectly.

Thus, the person present at the first site can apply the mixture dispensed and send to the second site 2062 a corresponding image, and in return receive information relating to the makeup result.

The second site 2062 may have a display screen 2064 that allows an adviser sitting at this screen to see the result of the makeup with the mixture dispensed by the dispenser and advise the person who has applied the makeup. This adviser may in return influence the dispenser 11 to modify the color of the mixture and better suit it to the face of the person present at the first site. The protocol for the exchange of data between the two sites thus allows command instructions to be sent to the dispenser 11, either directly or via the computer system 100 present at the first site. Thus, the person present at the second site controls the mixture delivered by the dispenser 11. The first person may make herself up under the gaze of the second. The second person sees the result of the test on the screen and can thus correct the mixture that this second person will control remotely until the ideal makeup is obtained.

Preferably, the video link between the two sites is a two-way link, such that the user present at the first site can see an image of the adviser on the screen of the computer system. This adviser can send the user present at the first site a tutorial if need be.

The memorizing of the setting parameters of the dispenser 11, once a given mixture has been considered satisfactory, may be commanded from the second site.

Advantageously, the dispensing system 10 is designed to be able to modify all the colors esthetically for each area if the person wishes to change the color of his or her face. The dispensing system may be designed in such a way that the user only has to modify a single color in one area for the system to modify all the others. To this end, the dispensing system can use translations, for example by recording the color saturation or shifting the shade.

The dispensing system may be designed to receive the map of somebody else, real or virtual. It may also combine the map of the person with the map of another, in order to sublimate the makeup without losing the inherent characteristics.

The interface may be used to define makeup programs in which the order of the areas to make up or the order of the colors to propose is defined.

EXAMPLES

A dispenser 11 like that illustrated in FIG. 3 is created. The dispenser is designed to communicate with a tablet 100 such as an iPad. This computer system runs an application known as "µMix" developed in the specific Apple environment (XCode 4 and iOS simulator) in the Objective C language.

It uses Foundation, UIKit and CoreGraphics basic frameworks which supply the tools for manipulating the data structures, computation tools and functionalities associated with the user graphics interface.

The application also uses the CoreBluetooth framework providing access to the Bluetooth 4 Low Energy peripherals, with the following main tasks:
  looking for Bluetooth 4.0 Low Energy peripherals,
  connection/disconnection and management of connection parameters,
  communication in read and/or write mode based on the GATT (Generic Attribute Profile) architecture.

The application proposes the following functionalities:
  definition of the fractions of base products,
  choice of mode of operation when pressing the control button 12, namely continuous, purge or dose,
  display of a triangle of volumetric fraction as illustrated in FIG. 30 with management of the volumetric fraction by tactile touch on the triangle or using the +/−buttons associated with each product,
  Bluetooth connection/disconnection and real-time transfer of instructions to the dispenser,
  settings of flow rates in continuous mode, and of quantities in dose mode,
  calculation, display and transfer to the dispenser of the volumetric fractions of products in real time, depending on the instruction, with the sum of the fractions always equal to 100%,
  collection and display of the torques of the three motors in real time, and
  saving of the key parameters in a configuration file.

The continuous mode is a dispensing mode in which the mixture of the three base products is dispensed for as long as the user presses the dispensing button 12. The product is dispensed at a flow rate, an estimate of which is displayed above the "Continuous" button 304.

The choice of flow rate is made in a "Settings" menu.

The "dose" mode is a mode of dispensing the mixture in doses, in which the dose is delivered after the user presses the dispensing button 12. One press is enough and the user can then release the button. The overall dose of product dispensed is that indicated above the "Dose" button 306, for example 0.1 ml. This volume can be altered in the "Settings" menu.

The "purge" mode is a dispensing mode in which a dose of mixture with equal volumetric fractions (33%) is delivered as soon as the user has pressed the dispensing button 12, as in the "dose" mode. One press is enough and the user can then release the button. When the dose has been dispensed in full, the button may be released. If the button is released before the end, dispensing stops, even if the specified volume has not been achieved. The overall dose of product dispensed is that indicated above a "Purge" button 305, for example 3 ml. This volume can be altered in the Settings menu.

The user determines the desired color with the application which is run on the tablet and which calculates the fractions of the various products. The tablet communicates this value to the dispenser by a Bluetooth connection.

The electronics built into the dispenser 11 collects the information and automatically adjusts the flow rates of the three cartridges so as to obtain a mixture of the desired color.

When the user wishes to use the product, he or she presses the button 12 of the dispenser in order to cause the product to be expelled. He or she presses for as long as he or she wants product, in "continuous" mode. In "dose" mode, the user presses the button 12 once and the predefined dose is delivered.

Dispensing may be performed continuously, namely with the motors operating continuously, the entire volume being dispensed in one hit, or iteratively, the motors then operating in a pulsed fashion; in that case, the time interval between two pulses makes it possible to vary the flow rate. Small volumes are delivered one after another in several stages.

The pulses may be separated for example by intervals of 50 ms, 100 ms or 200 ms. The duration of a pulse during which the motor is turning will be from 50 to 150 ms, for example.

The main page of the "µMix" application comprises in this example the following elements, as can be seen notably in FIG. 31:
  status bar at the top of the screen: indicates the status of the Bluetooth connection or µMix if there is no Bluetooth connection;
  thumbnails at the bottom of the screen: for selecting the active page: main page, Settings, Bluetooth, Products and Favorites;
  Continuous button 304 for selecting the mode in which products are dispensed continuously;
  Purge button 305 for selecting the Purge mode;
  Dose button 306 for selecting the mode in which dispensing is in doses with the volume of the dose associated with the Dose button;
  a blue ball 300 that the user can move around inside the volumetric triangle either by dragging it or using a double tap;
  "−" buttons 302 for each product A, B and C: reduces the fraction of product selected when moving along the straight line connecting the point to the vertex of the product selected;
  "+" buttons 302 for each product A, B and C: increases the fraction of product selected when moving along the straight line connecting the point to the vertex of the product selected;
  volumetric fraction of each product as a percentage: modifiable by the user and updated in real time according to the instruction from the + and − buttons 302 and the position of the ball 300.

While the volumetric fractions are being modified by moving the ball or using the + and − buttons, the values of the volumetric fractions of the products A, B and C are updated automatically. When the volumetric fractions are modified using the + and − buttons, the ball 300 is moved automatically into the corresponding position in the triangle.

When the application run on the tablet is started up, it automatically connects to the dispenser 11 if it is detected. When the dispenser is switched off or the Bluetooth connection is broken, the tablet disconnects. When the user moves the cursors that adjust the proportions of the products A and B, the values are transmitted in real time to the dispenser 11.

The Settings page of the application contains the following elements:
- status bar at the top of the screen: indicates the status of the Bluetooth connection or µMix if there is no Bluetooth connection;
- thumbnails at the bottom of the screen: for selecting the active page:
- main page, Settings, Bluetooth, or Info;
- "Volumes" part with a text field to be filled in by the user to define the volume of the dose, in ml (2 ml for example), and a field for the purge volume, in ml (3 ml for example). The minimum doses in this example are 0.023 ml and the maximum doses are 9.90 ml (3×3.3 ml);
- "Flow rate" part with selection of the flow rate: fast (»0.03 ml/s), medium (»0.02 ml/s) or slow (»0.01 ml/s);
- "Dose" part with iterative choice of the mixture, for dispensing a mixture of products with small volumes delivered one after another in several stages;

In the contrary case, the total volume of each product is dispensed in one hit;
- "Triangle image" part for selecting the image of the triangle that will be displayed on the main page in order to be able to display a triangle with the colors delivered by the dispenser 11. By using a "Choose image" button on the "Settings" page, an album can be accessed.

The "Products" page of the application has, in the example in question, the following elements:
- a choice of the value of each product in code step units from 0 to 1414.

Each unit corresponds to a delivered product volume of 2.33 µl, which is the smallest quantity that the dispenser in this example can deliver; when this page is displayed, it is the values of products on this page that are transmitted in real time to the dispenser. As soon as the page is no longer displayed, the values sent to the dispenser are those of the main page with the triangle;
- display of the motor torques for A, B and C in real time refreshed every 45 values.

The mode in which the products are delivered is the iterative or direct dose mode, according to the option chosen on the Settings page.

The "Favorites" page allows configurations to be saved in a file. It provides access in the example in question to 10 files, namely "Configuration 1" to "Configuration 10" in addition to the default file. These files record for example the following parameters:
- fractions of products A, B and C,
- Purge volume,
- Dose volume,
- fast, medium or slow flow rate,
- Dose, Purge or Continuous mode,
- continuous or iterative dispensing.

Example 1 (First Aspect of the Invention)

Several base products are created with what is known as a high-density pigment and a low-density pigment.

The base products "A", "B" and "C" are intended for respective cartridges. Certain base products have a high level of thickening (A1, B1, C1), others do not (A2, B2, C2).

| ormulation | Bismuth oxychloride (Kolortec co) 7.7 g/cm3 | Silica aerogel (DOW CORNING VM-2260 AEROGEL BEADS) Density = 0.09 g/c m3 | Jaguar HP 60 (Solvay Novecare) | Red40 (Emerald Performance material) | Glycerol | water |
|---|---|---|---|---|---|---|
| A1 | 5% | | 2% | | % | qs 100% |
| A2 | 5% | | 0.2% | | % | qs 100% |
| B1 | | 0.5% | 2% | | % | qs 100% |
| B2 | | 0.5% | 0.2% | | % | qs 100% |
| C1 | | | 2% | 0.05% | % | qs 100% |
| C2 | | | 0.2% | 0.05% | % | qs 100% |

The densities of the formulations are measured (at 1 atm and 25° C. with a CONTRAVES TV rotary viscometer fitted with an MS-r4 measuring bar at a frequency of 60 Hz after 10 minutes of rotation of the measuring bar)

A1: 2.6 Pa·s
A2: 0.55 Pa·s
B1: 2.4 Pa·s
B2: 0.4 Pa·s
C1: 2.6 Pa·s
C2: 0.6 Pa·s

Test 1 (According to the Invention)

The system was tested with:
A1,
B1,
C1

By virtue of the system for dispensing, a mixture with the following volumetric proportions in the final mixture A: 25%, B: 25%, C: 50% is defined.

The system is used at t0 to deliver 200 mg of product. The mixture is then spread.

The same operation is carried out for several days (20 days).

By comparing the results, it is apparent that they are constant.

Test 2 (not According to the Invention)

The system was tested with:
A2,
B2,
C1

As in the case of test 1, a mixture with the following volumetric proportions A: 25%, B: 25%, C: 50% is dispensed.

The same test as in test 1 is carried out.

By comparing the results, it is apparent that the colors obtained vary from one day to another.

Test 3
The system was tested with:
A1,
B2,
C1

As in the case of test 1, a mixture with the volumetric proportions A: 25%, B: 25%, C: 50% is created.

The same test as in test 1 is carried out.

By comparing the results, it is apparent that the colors obtained vary from one day to another, but less than in test 2.

Test 4
The system was tested with:
A1,
B1,
C2

As in the case of test 1, a mixture A: 25%, B: 25%, C: 50% is created.

The same test as in test 1 is carried out.

By comparing the results, it is apparent that the colors obtained remain constant. This configuration is preferred in the case of test 1 since it is easier to apply.

Example 2 (First Aspect of the Invention)

The same base products are created but the glycerol and some of the water are replaced with ethanol in the formulation without dense particles.

| Formulation | Bismuth oxychloride (Kolortec co) 7.7 g/cm3 | Silica aerogel (DOW CORNING VM-2260 AEROGEL BEADS) Density = 0.09 g/cm3 | Jaguar HP 60 (Solvay Novecare) | Ethanol | Glycerol | water |
|---|---|---|---|---|---|---|
| A1 | 5% | | 2% | | 16% | qs 100% |
| B1 | | 0.5% | 2% | | 16% | qs 100% |
| C1 | | | 1% | 40% | | qs 100% |

Test 1
The system was tested with:
A1,
B1,
C1

By virtue of the system, a mixture A: 40%, B: 40%, C: 20% is defined.

The system is used at t0 to deliver 200 mg of product. The mixture is then spread.

The same operation is carried out for several days (20 days).

By comparing the results, it is apparent that they are constant.

In spite of the high rheology of the base products in compartments A and B, a mixture that is easy to apply is obtained.

B) System for Dispensing a Product, Comprising a Dispenser Receiving at Least Two Cartridges that Each have a Reservoir Containing a Base Product, a First Base Product Comprising a Thickener, a Second Base Product Comprising an Agent for Modulating the Viscosity of the Thickening Agent The precision of the color obtained is a very important factor for obtaining a quality result. However, it is also necessary, in order to obtain the most attractive results, that the product have the best possible applicability.

This is particularly true in the case of concealing areas with imperfections, this requiring local application in order to avoid the spreading reflex.

Several other points of view should be considered.

Verticality/Horizontality: For example, in vertical areas, such as the forehead, there is a risk of the products running (compared with horizontal areas such as the under-eye area).

Skin grain: The areas with an "open" skin grain (dilated pores, fine lines) cause different application problems compared with smoother areas, notably in order to avoid "marking" of the defects.

Coverage: It is known that certain colored areas require significant thicknesses. It is thus necessary that applicability allows this. Idem with the opposite meaning in the case of low coverage to leave the face with a natural appearance, with the skin visible through the makeup.

Bilayer: In some cases, two products are made to react or interact in the form of two layers (for example for visual effects). In these cases, it is important to respect the ratio of applied quantities of products. Here too, it is necessary that the quantity of each layer produced be well controlled.

Finally, it is possible for the user to be disappointed with the applicability of the products, finding it not very suitable for his or her particular case. Thus, it is advantageous for him or her to be able to modify the applicability of the products generated with his or her system after certain tests.

This is all the more essential when the manufacturer bases the attractiveness of the system on the makeup results allowed thereby. It is not readily conceivable that users will buy several systems to cover the different scenarios or will use the system replacing the compartments depending on these scenarios. The other possibility, consisting in providing a very large number of compartments, is not easy to implement, either.

According to a second of its aspects, the subject of the present invention is a system for dispensing a product, comprising a dispenser that receives at least two cartridges that each have a reservoir containing a base product, a first base product comprising a thickener, a second base product comprising an agent for modulating the viscosity of the thickening agent, the dispenser making it possible to deliver at least these two base products in adjustable proportions.

According to this second aspect, the invention may have one or more of the following features:

First implementation: The first base product has a viscosity greater than or equal to 2 Pa·s, and preferably greater than or equal to 4 Pa·s, more preferably between 4 Pa·s and 10 Pa·s, even more preferably between 5 Pa·s and 8 Pa·s, with a pH-sensitive thickening active agent, and the second base product contains an acid agent that modifies the viscosity of the active agent of the first product upon contact between the two products. The thickening active agent of the first product is notably a gelling agent based on acrylate or methacrylate polymer or copolymer, such as a Carbomer, used between 0.8 and 2.5% by mass relative to the mass of the first product, better still between 1 and 2.3% by mass relative to the mass of the first product, even better still between 1.5 and 2.2% by mass relative to the mass of the first product, and the acidifying agent is notably a mineral or organic acid such as citric acid or lactic acid, used between 0.2 and 10% by mass relative to the mass of the second product, better still between 2 and 10% by mass relative to the mass of the second product, even better still between 5 and 8% by mass relative to the mass of the second product. The first product may contain other thickeners (not pH-sensitive), for example polyose thickening agents. The viscosity of the second product may be less than or greater than or equal to the viscosity of the first product and be brought about by a polyose gelling agent. Preferably, the viscosity of the second product is between 1 and 3 Pa·s. The pH of the first product is greater than or equal to 6, preferably greater than or equal to 7, more preferably greater than or equal to 8. The pH of the second product is less than or equal to 6, better still less than or equal to 5, preferably between 2 and 5, more preferably between 3 and 5. Preferably, the acidifying agent of the second product is combined with a basifying agent such that the pH of the second product is not less than 2. In this combination, the basifying agent and the acidifying agent are regulated with an alkaline/acid normality ratio less than or equal to 1, preferably less than or equal to, such that the pH of the second product is less than or equal to 7 and preferably greater than or equal to 2. Preferably, the alkaline agent is mineral, such as sodium hydroxide, and the acidifying agent is organic, such as a carboxylic acid such as citric acid or lactic acid.

Second implementation: The first base product has a viscosity greater than or equal to 2 Pa·s, and preferably greater than or equal to 4 Pa·s, more preferably between 4 Pa·s and 10 Pa·s, even more preferably between 5 Pa·s and 8 Pa·s, and the second base product has a viscosity of between 0.01 and 2 Pa·s, better still between 0.05 and 1 Pa·s, preferably between 0.1 and 0.5 Pa·s. The first product and the second product contain notably a gelling agent based on acrylate or methacrylate polymer or copolymer, such as a Carbomer, or a polyose-based gelling agent, with concentrations of gelling agent (all the gelling agents) for the first of between 0.8 and 2.5% by mass relative to the mass of the first product, better still between 1 and 2.3% by mass relative to the mass of the first product, even better still between 1.5 and 2.2% by mass relative to the mass of the first product, and for the second product of between 0 and 2.5% by mass relative to the mass of the second product, better still between 0 and 2% by mass relative to the mass of the second product, even better still between 0 and 1% by mass relative to the mass of the second product, preferably between 0 and 0.5% by mass relative to the mass of the second product. In one particular case, the first and the second product contain a pH-sensitive gelling active agent. In this case, the two base products may contain this thickening agent in different or similar concentrations. In the second case (similar concentrations), the pH values may be different, such as greater than or equal to 6, preferably greater than or equal to 7, more preferably greater than or equal to 8 for the first product, and such as less than 6, preferably less than 5 for the second base product.

Third implementation: The first base product has a viscosity less than or equal to 2 Pa·s, and better still less than or equal to 1 Pa·s, and contains a pH-sensitive thickening active agent, and the second base product contains an alkaline agent that modifies the viscosity of the active agent of the first product upon contact between the two products. The thickening active agent of the first product is notably a thickening agent based on acrylate or methacrylate polymer or copolymer, such as a Carbomer, and the second product is a basifying agent, such as a mineral or organic base such as an amine or aqueous ammonia. The viscosity of the second product may be less than or greater than or equal to the viscosity of the first product. Preferably, the viscosity of the second product is between 1 and 3 Pa·s. The concentration of thickening agent in the first product may vary from 0.8 to 5% by mass relative to the mass of the first product, better still between 1 and 2.3% by mass relative to the mass of the first product, even better still between 1.5 and 2.2% by mass relative to the mass of the first product. The pH of the first product is less than 6 and preferably less than 5. The pH of the second product is greater than 6, better still greater than 7, even better still greater than or equal to 8. Preferably, the basifying agent of the second product is combined with an acidifying agent such that the pH of the second product is less than or equal to 10. In this combination, the basifying agent and the acidifying agent are regulated with an alkaline/acid normality ratio greater than or equal to 1, such that the pH is greater than or equal to 7, preferably less than or equal to 10. Preferably, the alkaline agent is organic, such as an organic amine, and the alkaline agent is mineral, such as hydrochloric acid.

the second base product may comprise a quantity of anionic surfactants less than or equal to 5%. Such a quantity of anionic surfactants makes it possible to confer additional characteristics on the second product, such as a foaming effect, a detergent effect or a makeup removal effect, without there being any thickening effect in the second base product, the thickening effect arising only upon mixing of the first and the second base product. The anionic surfactant is chosen for example from sodium laureth sulfate, oxyethylenated sodium laureth sulfate, surfactants comprising sulfonic functions such as sodium lauroyl sarcosinate.

the dispensing system may comprise a third cartridge with a third base product, the third base product may comprise a thickener, notably with a different concentration than that of the first base product, the thickener of the third base product is chosen from saccharide compounds of the rubber type, such as gum arabic, acacia gum, guar gum, gellan gum, karaya gum, carrageenan gum, cellulose-based compounds such as CMC, HMC, HPMC, synthetic polymers such as polyacrylic or polymethacrylic acids such as carbomers (Carbopol), or polyurethanes, polyvinyl acetate, polyvinyl alcohol, inverse or direct thick emulsions, combinations of non-aqueous solvents with thickening agents for oil, clays such as bentonite, attapulgite, organochelators, proteins such as casein or collagen, shear-thinning or thixotropic rheology agents, preferably chosen from synthetic polymers such as polyacrylic or polymethacrylic acids partially crosslinked for example by erythritol allyl ether, or sucrose allyl ether or propylene allyl ether groups, such as carbomers (Carbopol), the thickener may be a Carbopol gel, preferably in a neutral or alkaline medium, notably with a content of between 0.1 and 2.5% by mass relative to the total mass of the third base product, better still between 0.8% and 2.5% relative to the total mass of the first base product, even better still between 1.5% and 2.3% relative to the total mass of the first base product, the cartridges may be received in a removable manner in the dispenser, each product may leave the cartridge through an outlet passage of the cartridge, the outlet passage being defined by a dispensing end piece of the cartridge, said end piece being driven in rotation relative to a body of the cartridge by a drive mechanism of the dispenser in order to dispense the base product contained in the cartridge, the system may have a mechanism for homogenizing the first base product, notably a vibrating mechanism.

This aspect of the invention also relates to a method for applying a cosmetic, makeup and/or care, product to human keratin materials, comprising the setting of the dispenser depending on the area to be treated, and the dispensing of the product by base products being picked up from the cartridges in the proportions corresponding to the setting of the dispenser.

Setting may be carried out so as to have the greatest viscosity, application being carried out on skin blemishes.

Setting may be carried out so as to have an intermediate viscosity between the end-point viscosities that can be obtained, application being carried out on skin blemishes or in the under-eye area.

Thus, according to this second aspect of the invention, the dispensing system comprises at least two compartments:

One compartment 1 comprises a thickening agent E

Another compartment 2 comprises a regulating agent R for the thickening effect of the thickening agent.

The other compartments (3, 4, etc.) that may be present comprise other agents for the makeup M or for skincare (pigments, biological active agents, protective active agents, colorants, etc.).

E is typically a thickener that is modulable by a pH agent

R is typically a pH agent

Or:

E is a thickener

R is a diluent

Agents M can be placed in compartment 1 and compartment 2, with a degree of logic.

According to this second aspect, the invention makes it possible to treat one or more areas of the face and to obtain mixtures that are very precise in terms of color faithfulness and suitable applicability for obtaining particularly effective effects. Hereinbelow, the term "area" is used to denote a defined part of the face, fairly small in surface area, covering between 1 cm$^2$ and 100 cm$^2$, better still ranging from 2 cm$^2$ to 50 cm$^2$.

The dispensing system preferably has a dispenser as defined above. The dispensing system may thus consist of a single device operating autonomously, preferably able to be manipulated in one hand, or of a device that operates in interaction with other components or devices. It may for example entail various outlet interfaces which are mounted on the dispenser depending on the type of makeup to be created, as will be specified below. It may also entail a computer system which exchanges information with the dispenser in order to operate the latter, this computer system comprising, for example, a portable terminal such as a smartphone, a camera phone, a tablet, a laptop computer or a dedicated terminal.

Preferably, the dispenser is designed to pressurize one or more compartments containing the base product(s), via volumetric metering devices, preferably a motor causing a piston to move in the corresponding compartment.

The dispenser may be formed of a housing and of at least two or three compartments, and preferably an identical number of motors. For example, the rotation of the motors drives endless screws which push the pistons of each compartment. The advancing movement of the pistons is, for example, controlled by the number of command pulses sent to the motors and/or by the length of time for which the latter are operating. The motors may be powered in sequence or preferably simultaneously.

For example, the motors are powered during an elementary operating cycle for a short duration one after the other or at the same time as one another, so as to dispense corresponding microdoses.

The elementary cycles are repeated, possibly with a pause between them, giving the base products time to flow out of the compartments.

The compartments may be defined by cartridges, which are removed when they become empty. As an alternative, the compartments are permanently present and refilled once they become empty.

Each cartridge may be closed by a stopper that can be removed to allow the cartridge to be cleaned.

Preferably, the housing of the dispenser is of elongate shape along a longitudinal axis, making it easier to handle, and the cartridges are disposed about this axis, inside the housing.

Preferably, the cartridges are inserted from the rear and the mixture is delivered from the front. The cartridges may be inserted individually or, as an alternative, the cartridges constitute a one-piece assembly as they are inserted.

The cartridges may each have a volumetric metering mechanism comprising a piston moved by a drive mechanism of the dispenser in a direction accompanied by a reduction in the internal volume containing the base product and the expulsion of some product. It may be advantageous for the cartridges to have at least a region of their wall that is transparent so that the color of the product contained therein can be seen.

The drive mechanism may have a motorization system formed of motors coupled to gearboxes, of elongate shape parallel to the longitudinal axis of the dispenser, and positioned between the cartridges. Positioning the motors and cartridges in this way makes the dispenser particularly compact.

The base product can leave the corresponding cartridge in a sealed manner, then flow along a passage provided for this purpose in the housing of the dispenser, before leaving the latter.

The cartridges advantageously end in an end piece produced in such a way that, once the cartridge has been inserted into the housing of the dispenser, the end of the end piece terminates flush with the housing. As an alternative, the end piece is long enough to protrude beyond the housing and thus connect various outlet interfaces that can be attached to the housing of the dispenser.

By virtue of the drive mechanism having motors for causing the pistons to advance, it is possible to precisely deliver mixtures in very small quantities. Thus, the drive mechanism can deliver the base products with a minimum flow rate less than or equal to 50 L/s, better still less than or equal to 20 μL/s, even better still less than or equal to 10 μL/s. Preferably, the drive mechanism delivers flow rates of between 20 and 100 L/s, better still between 40 μL/s and 60 μL/s. It is thus possible to easily create a mixture of around 10 mg. Such a dispensing system is therefore ideal for achieving small touches of makeup, for covering an area of 1 $cm^2$, better still an area of 0.5 $cm^2$, for example.

It is also possible to create larger quantities of mixture such as the quantities needed to make up a cheek or a face. These quantities remain relatively low, however, for example a quantity of between 100 and 500 mg, better still between 150 and 250 mg.

Thus, one subject of the invention, according to one aspect thereof, is a dispensing system comprising a dispenser having a housing, and at least one cartridge received in the housing of the dispenser, this cartridge having a body and a piston capable of moving in the body, the housing comprising a motorized drive mechanism for moving the piston of the cartridge.

Preferably, the cartridge has a dispensing end piece through which the product exits, and this dispensing end piece is driven in rotation by the drive mechanism for moving the piston. The end piece may have at least one rotation-proofing relief, better still two diametrically opposed rotation-proofing studs.

The end piece may bear a seal, notably an O-ring seal. Thus, when changing the cartridge, the seal is also changed, making it possible to get around the problem of seal wear.

The dispenser may have an electronic board for controlling the motorized drive mechanism, this electronic board having the end piece(s) passing through it. This may make it possible to produce a board extending across substantially the entire cross section of the dispenser so that all the electronic components of the dispenser can be grouped together on a single board, thus improving compactness and reliability. The board may extend substantially perpendicularly to the longitudinal axis of the housing. The board may bear a switch for controlling operation of the dispenser.

The dispensing system may be designed to operate in at least two dispensing modes.

In a first mode, referred to as "continuous", the mixture is dispensed as long as pressure is applied to the control switch.

In a second mode, referred to as "dose", a predefined quantity of the mixture is dispensed for each press of the switch.

The end piece(s) may terminate at one end of the housing. This may make it possible to reduce the dead volume, as will be explained in detail below.

The end piece(s) may have at their end a shutoff system for preventing the products from drying out in the duct, for example a self-healing membrane.

The cartridge may have a hollow screw onto which the piston is screwed, the piston being able to move axially along the screw as the latter turns; the piston is prevented from turning in the body of the cartridge. For example, the friction of the piston against the body of the cartridge may be enough to prevent it from turning when the screw turns.

Preferably, rotation is rendered impossible with a cartridge body of non-circular cross section and a piston that is not deformable.

The torque of the motors may be determined electronically depending on the current drawn, and may be used for example to detect that the piston has reached the end of its travel. Information regarding the torque may be transmitted remotely to a computer system that has a man-machine interface, in order that correct operation of the dispenser can be monitored.

In order to adjust the shade, the dispensing system according to the invention has to allow the user to vary the volume delivered from each compartment.

Preferably, the dispenser is operated by a computer system built into the dispenser or external thereto, the dispenser then being able to exchange information with the computer system using a wireless or wired protocol.

The dispenser may thus be operated so as to allow the shade to be adjusted by controlled simultaneous or sequential dispensing of several base products of different colors.

The dispensing of the base products may be continuous; in such a case, the volumes of each of the base products are dispensed in a single shot, simultaneously or in succession.

In the case of simultaneous dispensing, it is beneficial to be able to adjust the respective flow rates of the various base products in order for the dispensed mixture to correspond to the desired mixture at all times. Such a dispensing mode may be suitable in particular when dispensing the mixture by spraying, using an airbrush. To adjust the flow rates it is possible, to alter the speed at which the pistons move, for example in the case where the pistons are driven by an endless screw, by varying the rotational speed of the motors that drive the screw. The products may also be dispensed in a pulsed manner with a dispensing time and a pause in each cycle. By altering the duty cycle it is possible to alter the flow rate.

All the products may be delivered simultaneously during the dispensing time or, as an alternative, the cycles of the various products are phase-shifted from one another so that one product is being dispensed while the other products are paused.

In one particular embodiment, the mixture is delivered into a cavity of a container which may close hermetically or not, for example in the form of a cup, into which an applicator, particularly a stylus or a brush may be slipped. Such a dispensing system is especially suited to liners, glosses and other formulations applied without direct contact with the hands. This container may be removable.

For example, it is used as a lip-color dispenser and has a dispensing system, for example using a screw. When not removable, the container may be produced with the body of the dispenser. When it is removable, it may constitute one output interface among others that can be mounted on the dispenser.

The compartments, and in particular the cartridges, may contain all or part of the drive mechanism and, for example, the motorizing system or, better still, part of the motorizing system, the purpose of this being to reduce the number of moving parts in the body of the dispenser outside the cartridges. For example, the cartridges contain the rotor of the motor. Once the cartridges have been installed in the body of the dispenser, the rotors are made to interact with the stators.

The dispensing system is advantageously arranged in such a way as to allow the running of preprogrammed sequences in which the mixture delivered by the system is modified continuously or discontinuously. A "graduated" mode makes it possible for example to progress gradually from a mixture A to a mixture B. In the case where the application is by spraying, notably using an airbrush, this makes it possible for graduations to be achieved simply. An "alternate" mode makes it possible for example to switch quickly from a mixture A to a mixture B several times in succession. In the case of application by spraying, a multilayer application can thus be achieved, with different formulations for two superposed adjacent coats. Another mode makes it possible for example to offer several preprogrammed successive mixtures, the computer system each time indicating to the user how these should be used, for example by display on a screen.

In the case of manual application, the mixtures are dispensed for example into a cup. The person applies the makeup to the recommended place with a corresponding mixture taken from the cup, then, if necessary, cleans out the cup and commands delivery of a new mixture; the operation is repeated as many times as necessary until the person is fully made up.

The mixtures dispensed can be homogenized in various ways depending on the type of use. In the case of manual application, it can be done directly on the application area at the time of application or in the cup before the mixture is picked up; in the case of an airbrush application, the pipe of the airbrush is used as a mixing chamber; if the mixture is dispensed into a container for later use, homogenization can be performed by hand or by passing the dispensed products through a mixing chamber situated between the dispenser and the container or incorporated directly into the container, as described in detail below.

The product may be delivered by the dispensing system and used extemporaneously. As an alternative, the product delivered by the dispensing system is packaged and used later, for example on several occasions, with, for example, at least one day's interval between two uses.

Adjustment of Applicability

According to one exemplary embodiment of the invention, compartment 1 contains a composition of viscosity R1 and compartment 2 contains a composition intended to modify the viscosity R1 of the product in compartment 1 upon contact.

Scenario a: Compartment 2 may contain an agent that is capable, upon contact with the product in compartment 1, to modify the viscosity of the product in the latter. By deciding on the ratios of products to be delivered, it is thus possible to modify and adjust the final viscosity to its correct value.

Scenario b: Compartment 2 may contain a composition of viscosity R2, less than or greater than R1. In this case, upon contact, the resultant viscosity will be modified. By deciding on the ratios of products to be delivered, it is thus possible to modify and adjust the final viscosity to its correct value.

Scenario c: In a particular and advantageous case, compartment 2 may contain a composition of viscosity close (or equal) to R1, provided that contact modifies the viscosity of the product in compartment 1.

In order to implement all of these scenarios, it is possible to use various thickening agents E and regulating agents R.

The thickeners "E" are typically gelling compounds, for instance natural ingredients such as saccharides for instance gum arabics, acacia gum, guar gum, gellan gum, karaya gum, etc., synthetic polymers such as polyacrylic or polymethacrylic acids such as carbomers (Carbopol), inverse or direct thick emulsions, or combinations of non-aqueous solvents with thickening agents for oil.

In the case of saccharide compounds of the "rubber" type, they are used at between 0.2% and 5% by mass relative to the mass of the base product comprising them, better still between 0.8% and 2.5% by mass relative to the mass of the base product comprising them, even better still between 1.5% and 2.3% by mass relative to the mass of the base product comprising them.

The gelling compounds that can be used may be natural or artificial, such as starches (E441), pectins (E440), agar (E406), alginic acid (E400), sodium alginate (E401), potassium alginate (E402), ammonium alginate (E403), calcium alginate (E404), carrageenan (E407) or ingredients originating from animals (gelatin such as E441).

For solvent-rich formulations, use may be made of an organogelator. These are typically organic liquids, a mineral oil or a vegetable oil, trapped in a three-dimensional network resulting from the supramolecular self-assembly of small organic molecules (also known as organogelators) forming microscopic or nanoscopic structures. They are used in an amount of 1 to 10% by mass relative to the mass of the base product comprising them, and may be for example derivatives of 4-tert-butyl-1-arylcyclohexanols, polymeric derivatives such as polyethylene glycols, polyesters, polyalkylenes, derivatives of N-lauroyl-L-lysine ethyl ester, derivatives of peptides, small fatty acids.

The agents R are:
In particular for scenario a, solvents such as water, ethanol or oil, pH agents, such as aqueous ammonia, amine or sodium hydroxide, salts such as NaCl,
In particular for scenario b, thickening compounds. The thickening compound may:
be different than the compound E,
or be the same at a different concentration,
or be the same at an identical concentration but under conditions
in which its thickening expression is different.
In the particular case of scenario c, the product in compartment 2 contains a thickener in order to come close to the viscosity R1 and a second agent that is able to modify the viscosity of the product in compartment 1.

Examples illustrating scenario a:
A 100% neutralized (aqueous ammonia) 1% Carbopol gel is placed in compartment 1. A 4% acidifying agent (citric acid) is placed in compartment 2.
A 10% neutralized (aqueous ammonia) 1% Carbopol gel is placed in compartment 1. An alkaline agent (10% aqueous ammonia) is placed in compartment 2.
An anionic surfactant solution (5% LES) is placed in compartment 1. A 10% saline agent (NaCl) is placed in compartment 2.

Examples illustrating scenario b:
A 100% neutralized (aqueous ammonia) 1% Carbopol gel is placed in compartment 1. A diluted (0.2%) guar gum (jaguar HP 60) is placed in compartment 2.

Example illustrating scenario c:
A 100% neutralized (aqueous ammonia) 1% Carbopol gel is placed in compartment 1. A 50% neutralized 2% Carbopol gel is placed in compartment 2.

Optimization

It is very advantageous to have as few compartments as possible.

Thus, if a color adjustment is desired, it would be necessary to provide two compartments in addition to the two that are intended to control the viscosity.

If the system only comprises a single product containing dense particles, it will have to comply with the rheological rules defined above.

It is possible to place the active agents M in compartments 1 or 2 or 1 and 2.

For example, the active agents M are placed in compartments 1 and 2 at two different concentrations.

If the product in compartment 2 is considered to increase the viscosity in compartment 1, it is advantageous to place less active agent M in compartment 2 than in compartment 1. Specifically, by putting the product in compartment 2 into contact with the product in compartment 1, the concentration of active agent M is reduced in the mixture, but by increasing the thickening of the mixture, the thickness of the layer produced is increased, thereby realizing a compensation effect.

It is possible to place an active agent M1 in a compartment 1 and an active agent M2 in compartment 2. For example, M1 is a covering component and M2 is an anti-acne active agent. Thus, the more the user decides to put the product in compartment 2 into contact with the product in compartment 1, the more he will reduce the concentration of active agent M1 in the mixture and the more he will increase the concentration of active agent M2 in the mixture. This configuration is especially advantageous for treating acneic skin. In an embodiment rich in product in compartment 1, the product is applied to the entire face. In an embodiment rich in product in compartment 2, the product is thick and applied well to the buttons: (when there is not necessarily a need for a high concentration of covering active agent M1 or when there is a need for a high concentration of anti-acne active agent M2).

It is possible to place the active agents M in a compartment 3. Thus, it is possible to regulate the concentration of active agents M and to regulate the viscosity and thus the applicability.

Use for Making Up One or More Precise Areas of the Skin

The dispensing system allows makeup to be applied, day after day, with only the areas that need to be hidden being treated. To this end, small doses of makeup are delivered, and are applied specifically and sequentially to the corresponding areas. Each small dose is created using the mixture suited to the area.

In one preferred embodiment of the invention, the dispensing system waits for information regarding which area is to be treated and then delivers the corresponding mixture. It may use a preprogrammed look-up table for that purpose, this table being the result for example of a learning process as defined below.

In one particularly advantageous embodiment, the programming takes into account the viscosity to be achieved in order to obtain optimum results. As an alternative, the dispensing system informs the person, when delivering a mixture, of the area to which the person is to apply the mixture. Thus, the dispensing system may follow an application program in which it delivers, in a given order, the various mixtures that are to be applied.

In one particular embodiment of the invention, the dispensing system is informed as to the quantities to be delivered. For that, it memorizes the relationship between the color, the area of the face and the quantity needed, thereby making it possible to reduce costs and wastage of product, and to cover the skin only lightly, thus avoiding occlusion effects. In so doing, it is possible to use products that have a high covering capability and provide too much cover to be applied to the whole of the face. Thus, it is possible to obtain makeup of natural or even undetectable appearance.

The dispensing system may also make it possible, by facilitating the dispensing of small quantities and rapid use thereof, to reduce the time for which the products are kept, thus making it possible to reduce the risks of the products changing and/or to reduce the amounts of preservative to be used.

The dispensing system is suited to treating the areas that are to be concealed, without having to conceal the entire face.

When the user is looking for the color to apply to an area of the face, it is advantageous to memorize the color best suited to each area, and the dispensing system is thus advantageously designed to memorize this color and the corresponding area. Thus, by using the memorized information, on each use, the same mixture can be delivered for each area or, if several areas are being treated, the same series of mixtures can be delivered for the same series of areas.

The dispensing system may also be designed to allow an area to be treated by varying the colors application after application. Thus, the person may make up her lips using different colors that she chooses on a day-by-day basis to suit her tastes. This approach is also suitable for the eyelids or eyelashes, and for face makeup because the person may fancy a change of foundation color. For example, on weekdays, the person applies a pale colored foundation, with a more tanned foundation color at the weekends, or may have eye makeup in one color one day and another color another day.

The dispensing system may be designed to allow the user to change color to suit her tastes according to the day, the time, what she is wearing, and the weather. Thus, a system to assist with decision making is advantageously provided to guide the user in her choices of color.

An assistance system may also be provided for balancing the colors on the same face and contribute toward a successful overall makeup look.

It may be desirable for several people in the same group, for example a family, to be able to use the dispensing system, thus reducing costs and minimizing the space taken up. This solution is particularly suited to travel or hotels, campsites, airplanes, campervans, boutiques, schools, etc. For that, provision may be made for the dispensing system to be able to be informed as to which person is using it, so as to access pre-stored personal data.

The invention may make it possible to achieve a graduated effect, in the same way as described above.

Continuous Use for Graduated Makeup

In this application, the dispensing system changes the formulation of the mixture while it is delivering the product. In addition, the outlet for the base products or for the mixture is moved relative to a container or a support defining an application surface. In one particular embodiment of the invention, the dispensing system is designed to calculate the way in which the mixture evolves as a function of the color C1 of one area to be treated and of the color C2 of another area to be treated. For example, with the knowledge that the chin requires a color C1 and that the cheek requires a color C2, the dispensing system may vary the formulation of the mixture while it is delivering it in order to graduate the color between these two colors. This makes it possible for example to better conceal imperfections of the face while ensuring that the end result is realistic, or allows color to be graduated for beautifying purposes. The dispensing system may also be designed such that the user can command a variation in color of the mixture dispensed without the start and/or end colors having been set beforehand. To do that, the dispensing system may possess a location or auto-location system and deduce from a look-up table the colors C1 and C2 that it has to create and therefore the changes in the mixture that it has to make.

The dispensing system may have an outlet head, in particular in the case of an airbrush, which is mobile and steered. This option then makes it possible to achieve graduated effects without moving the rest of the dispensing system. For example, the dispensing system is located near to the cheek, then a control system is triggered that will automatically steer the variation in formulation of the mixture and the movement of the outlet head so as, for example, to make the center of the cheek redder than the periphery thereof, with a graduation between the two.

The dispensing system may even be used to create tailor-made products that are kept for several applications.

It is also possible to produce solid or semi-solid products.

Manufacture of "Bespoke" Compacts or Other Solid or Semi-Solid Products

The dispensing system may be designed to allow a mixture to be chosen and delivered to a container such as a cup. The mixture preferably comprises compounds which are such that the mixture can set solid.

More preferably, use is made of compounds that make the setting especially rapid. These compounds are either deposited in the container before or after it is filled with the other ingredients, or are provided in the compartments of the dispenser with the other constituents of the base products, or are contained in the dispenser in a compartment especially designed to contain them.

Specific compositions which may harden quickly by chemical, biochemical or physicochemical reaction after discharge may thus be dispensed.

These compositions are especially designed for the creation of compacts, namely they:

set solid, yield a material that can crumble if rubbed, and are preferably colored.

Preferably, these compositions are very rich in solid particles, with for example more than 10% by mass of solid particles relative to the total mass of the composition, better still more than 20% by mass of solid particles relative to the total mass of the composition, even better still more than 30% by mass of solid particles relative to the total mass of the composition, preferably between 10 and 40% by mass of solid particles relative to the total mass of the composition.

These compositions may contain absorbent particles or reactive compounds, such as those that react in contact with the air, for example cyanoacrylate or alpha-silanes or those which react to light, notably UV.

The container into which the mixture is dispensed may contain a compound A and the dispensed compositions may contain a compound B, A and B being chosen to react with one another and solidify the mixture.

In one particular embodiment of the invention, the dispensing system incorporates a heating means, for example with an electrical resistor, to create lipsticks or other waxy products. In that case, the base products are heated before being delivered.

The dispensing system may also comprise a means for supplying heat and/or light energy, after the mixture has been dispensed into a container, for example an electrical resistor or an LED, notably UV. This energy may accelerate the setting-solid of the dispensed mixture.

The use of the agents E and R makes it possible to regulate the rheological performance of the solid or semi-solid product.

Preferably, the mixture is homogenized before it sets solid.

Creation of Color Palettes

The dispensing system may have a support, having several regions, and may be designed to automatically generate several mixtures deposited in said regions, for example a series of colors suited to various parts of the face.

The support may define several cavities to receive the mixtures or may bear several containers, for example in the form of cups, potentially cups that are separable from the support.

In one particular case, the support adopts the shape of a face with regions for receiving the mixtures for targeted application areas.

The support may be able to move, notably to rotate, with respect to the body of the dispenser and, for example, may be driven in its movement by the dispenser so that various spaces or containers can be filled in succession.

Cup-Type Dispenser

There is a benefit to having a dispensing system capable of delivering a mixture that the user can easily pick up. Moreover, in cases in which the base products delivered by the dispensing system are not already blended, there is a need to allow the user to perform the mixing easily.

The dispensing system may have a cup and a dispenser for filling the cup with at least one product, the cup being secured to the dispenser at least while it is being filled.

The cup is sometimes also known as a "crucible" and that term should be understood in its broadest sense.

A "cup secured to the dispenser" should be understood as meaning that the cup is held, notably immobilized, at least temporarily, on the dispenser, being for example fixed to the latter by screws, magnetic attraction, clip-fastening, bayonet locking, clamping, or produced with a part of the dispenser body by material molding. When it is secured to the dispenser, the cup allows the latter to be manipulated in one hand, the cup remaining in place on the dispenser while the latter is being moved around.

The dispenser may be offered to the user with the cup already in place.

As an alternative, the cup is installed by the user the first time the dispensing system is used.

The cup is preferably less deep than it is wide, making access to it easier and allowing the product, notably the mixture, to be picked up with an applicator or a finger.

Preferably, the cup is separable from the dispenser and constitutes one outlet interface that can be chosen from a collection of outlet interfaces that can be mounted on the dispenser, at the choice of the user and according to the making up to be performed, as described in detail below.

Preferably, the dispensing system comprises several filling orifices for filling with different base products, opening into the cup. Thus, the mixing of these products may take place in the cup.

The cup preferably has a bottom that is concave toward the outside, making it easier for the user to clean it between two uses.

In addition, this may make the product easier for the user to pick up and the base products easier to mix.

Preferably, the dispenser allows at least two base products to be delivered into the cup, in adjustable proportions, and better still at least three products.

In one exemplary embodiment, the dispensing system has at least two cups that can be selectively fed by the dispenser. This may allow the user to fill these two cups quickly with mixtures with different characteristics. This may facilitate the testing of colored substances and/or allow the preparation of several different color mixtures intended for making up respective areas of the face. The cups may be associated with identifiers that remind the user of the area of the face for which a mixture contained in a given cup is intended.

The cups may be able to move relative to the dispenser, being for example borne by a mobile support such as a turret that is rotatable with respect to the dispenser or by a slide capable of translational movement with respect to the dispenser.

The dispensing system may comprise a lid for closing the cup. This closure lid is preferably transparent so that the user can see the color of the mixture contained inside.

When the cup is separable from the dispenser it may if necessary be introduced into a housing that allows it to be transported more easily, this housing being able, if necessary, to contain a mirror and/or an applicator. The lid of the housing may in this case act as a lid for the cup.

The volume of the cup may be between 2 and 1000 mm$^3$, better still between 100 and 1000 mm$^3$, even better still between 250 and 750 mm$^3$.

The base product(s) delivered into the cup are preferably foundations, but as an alternative may be makeup products for the lips or eyelids.

The cup preferably has a shape that exhibits symmetry of revolution. As an alternative, it has a polygonal or some other contour. Its largest inside diameter, or that of the inscribed circle in the case of a noncircular contour, is preferably between 2 and 100 mm, preferentially between 5 and 40 mm. Its depth is preferably between 1 and 10 mm, better still between 3 and 8 mm. Its depth is preferably between 1 and 10 mm. Preferably, the size and shape of the cup either allow direct application of the mixture to the skin or allow the mixture to be picked up on a finger or using an applicator. The cup may be made of an elastically deformable material, making it possible for example to turn the concavity of the bottom of the cup inside out and empty it more easily or use it to apply the product.

The cup may have no blender; in that case, the base products may arrive in the cup from the dispenser in the unmixed state, via distinct respective dispensing orifices. As an alternative, the dispenser incorporates a blender and the base products arrive in the cup already blended.

The cup may also incorporate a static blender as described in detail below, which is fed via distinct filling orifices of the dispenser and which preferably delivers the mixture into a cavity of the cup situated above the blender.

A further subject of the invention is a method for preparing a makeup product, comprising the step of filling a cup of a dispensing system as defined above with at least one base product from the dispenser.

Several products may be delivered into the bottom of the cup, then blended using a finger or an applicator, or a static blender incorporated into the cup.

The cup is preferably filled from beneath. Dispensing systems using a sonotrode have been proposed in the past.

The cup according to the invention is not intended to vibrate in order to dispense the product(s) conveyed by the feed passage(s) supplying it. It differs from a sonotrode.

Preferably, the cup is made of plastic.

Blender Incorporated into the Outlet Interface

There is a benefit in having a dispensing system capable of delivering a mixture that can easily be used, notably picked up by the user, without the need for an additional mixing action on the part of the user.

The dispensing system preferably has a dispenser having outlet passages for base products and an outlet interface that is separable from the dispenser, this interface having a static blender that preferably delivers the mixture into the cavity where it can be picked up.

The static blender may be situated under the abovementioned cavity. The dispensing system is then particularly suited to the creation of compacts, using cups with an in-built static blender as outlet interfaces. In that case, the cavity of the cup is filled with product from beneath. After passing into the static blender, the blended base products cover the blender.

It is possible to use several outlet interfaces and to fill them with different respective mixtures, without the need to purge the blender, thereby reducing losses of product.

The outlet interface may be a single-use interface, if necessary.

Preferably, the static blender has a central chamber communicating with base product intake ducts. This central chamber may communicate with a peripheral chamber having a series of partitions which act as deflectors for the mixture and create shearing thereof.

The peripheral chamber may have a perforated annular partition defining perforations through which the mixture passes as it circulates in the peripheral chamber. The central and peripheral chambers may be closed at the top by a wall which defines the end wall of the cavity receiving the mixture.

The end wall of the peripheral chamber may be of helical shape about the axis of the cup and of a height that decreases in the direction toward the outlet. The latter may open ahead of a connecting ramp connecting the end wall of the peripheral chamber and the top wall of the blender, this connecting ramp preferably being a portion of a helix extending the helix formed by the end wall of the peripheral chamber.

Preferably, the peripheral chamber comprises the abovementioned annular partition and radial partitions that force the mixture to circulate alternately between upper and lower regions of the peripheral chamber and between radially inner and outer regions, the mixture circulating for example from an upper and radially outer region to a lower and radially outer region by passing through the abovementioned annular partition.

The blender may have an outer body in which a component forming the core of the blender is housed, the outer body radially closing the peripheral chamber on the outside and comprising an upright that separates the central and peripheral chambers.

The outer body of the blender and the core of the blender may each be produced as a single piece by injection molding.

Reduced Dead Volume

There is benefit to be had in reducing the losses of product when changing the formulation of the mixture and in allowing the color of the mixture to be varied as quickly as possible during application, particularly when the dispenser is coupled to an airbrush.

Since the dispenser receives at least two cartridges that each have a reservoir containing a base product, the latter can leave the cartridge through an outlet passage of the cartridge, this outlet passage opening out at the outside of the dispenser or near the external surface thereof.

The outlet passage may notably open into an area in which the mixture is picked up or close to this area, notably less than 5 mm away, better still less than 3 mm away, better still less than 1 mm away, or even better still flush therewith.

The cross section of the outlet passage is, for example, between 1 and 3 mm$^2$.

Thus, each base product coming from a cartridge can leave the dispenser without mixing with a base product from another cartridge and the dead volume that cannot be picked up and is likely to increase the inertia of the system is minimized. The product is more quickly available without having to circulate through special passages in the housing of the dispenser, thereby avoiding a painstaking purging step in the event of a cartridge change.

The outside of the dispenser may be the product pickup area, notably when the dispenser is produced with a cup that is not designed to be removed, into which the mixture is dispensed, or a dispensing area intended for the mounting of a removable outlet interface, which defines the pickup area. This outlet interface may have a cup as defined above. This mounting area corresponds for example to the end of the housing of the dispenser in the absence of an outlet interface. The mounting area may be substantially planar and perpendicular to the longitudinal axis of the dispenser housing.

The dispenser may have three cartridges of base products.

The dispenser may have housings for receiving the cartridges, which are preferably received removably in the dispenser. The latter may comprise passages for ducts for the cartridges defining the outlet passages.

The length of these ducts is preferably such that the ducts are set back slightly from the end or lie flush with the cavity used for picking up the product or, as an alternative, are set back slightly from or lie flush with the end face of the housing of the dispenser that defines the mounting area.

These ducts of the cartridges may be end pieces used for causing the pistons to move within the cartridges, as described in detail above.

Multiple Outlet Interfaces

There is a need to be able, using the same dispensing system, to achieve different makeup looks easily and be able, if so desired, to make up areas as different as the skin, the lips, the eyelashes or eyebrows.

In one of its aspects, independently of or in combination with the other aspects thereof, and notably with the foregoing, one subject of the invention is a dispensing system comprising an assembly comprising a dispenser of at least one cosmetic, notably makeup, product and at least two outlet interfaces, each of which can be mounted removably on the dispenser, these outlet interfaces which are able to receive the product or products delivered by the dispenser preferably being chosen from among the following:
- an outlet interface having a container, notably a cup, allowing the product to be picked up using a finger or using an applicator,
- an outlet interface allowing the product to be delivered to a spray system, notably an airbrush,
- an outlet interface having several regions for receiving the product, which can move relative to the dispenser,
- an outlet interface that allows the product to be delivered to a dispensing end piece.

Preferably, the assembly comprises at least three of said outlet interfaces, or better still the four outlet interfaces.

The dispenser may comprise at least two different base products and allow these to be delivered in variable proportions and, preferably, the dispenser comprises three different base products and allows these to be delivered in variable proportions.

Each outlet interface may have a base allowing it to be fixed to the dispenser. This fixing may be done using screws for example, but preferably the base is designed to allow an outlet interface to be removed and replaced without the need for tools. It is, for example, a quarter-turn fixing or a fixing using an external locking ring.

The outlet interface and/or the housing of the dispenser may comprise seals allowing sealed communication between the housing of the dispenser and the outlet interface. If appropriate, the dispenser is designed to recognize the outlet interface mounted above, for example by virtue of the outlet interface having identifiers in the form of specific reliefs which are detected by the dispenser, or in the form of an electronic chip that the dispenser recognizes. That may allow the operation of the dispenser to be adapted to the outlet interface mounted above. The dispenser may communicate information about the outlet interface it is bearing to a computer system, and the computer system may, on the basis of this information, display a specific screen and/or run a specific program for controlling the operating parameters of the dispenser so as, for example, to adapt the dose dispensed and/or the flow rate to the type of outlet interface.

The user may be initially offered several outlet interfaces with a common dispenser within one and the same package, for example a case or a cardboard box.

A further subject of the invention is a makeup method involving the step of selecting an outlet interface, mounting it on the dispenser, and delivering the product(s) contained in the dispenser to the interface.

Mapping and Learning

The term "mapping" should be understood here as meaning a process of indexing a color with an area, with recording.

The mapping may relate to applications to areas smaller than 1 cm². However, the naked eye then has difficulty in discerning whether the result obtained is adequate, and it is preferable to substitute an instrumented evaluation with magnification for evaluation by the naked eye. Small quantities of colored substance may be applied with a finger, using conventional tools such as brushes, or using specialist applicators.

The map may be generated during a learning period in which the user carries out tests with mixtures on different areas of the face; once created, the map can then be used for everyday makeup. This learning period may take account of the viscosity. In the process, the user tests several rheologies and inputs the best adjustment obtained.

Specific graphic interfaces can be used during the learning period and during the period of use of the map.

In particular, the dispensing system may be used with a graphic interface in which the operator sees the face, which is for example a schematic, figurative or accurate representation such as a photograph or a 3D simulation. In that case, the operator can point at part of the face on the screen to show and/or deliver the appropriate color.

The graphic interface may also show the other areas of the face where use of that same color is appropriate.

To create the map, the operator applies a color, then makes an assessment.

The areas of the face can be treated one after the other; for example, the exercise is carried out on part of the cheek, then on the nose, etc.

Another option is to create a given mixture and apply this same mixture to several areas. The operator then needs to look for the area of the face to which the color is suited. The mixture is then indexed in the computer system which attributes it to the area(s) of the face for which it is suitable.

In one of its aspects, independently of or in combination with the other aspects thereof, and notably with the foregoing, one subject of the invention is a learning process for a dispensing system comprising a dispenser for dispensing a mixture of variable color, and a computer system for selecting a color and for storing data, comprising the steps of:
a) selecting at least one color with the aid of an interface of the computer system,
b) delivering, with the aid of the dispenser, at least one mixture of the selected color,
c) evaluating the mixture(s) dispensed following the application thereof to at least one area of the face, d) memorizing the characteristics of at least one mixture, notably a mixture that the user wishes to be able to recall, and of at least one area on which it has been tested.

This memorizing can be carried out notably with a view to subsequent dispensing of this mixture for making up said area.

Preferably, the computer system is designed to allow the user to indicate whether or not the result of the test is satisfactory, or even to inform same of the comparison with a test carried out earlier.

It is also possible to create a given mixture and to look for the area of the face for which it is suitable. The mixture is then recorded, being attributed to the area(s) of the face for which it is suitable, in a look-up table that will be used subsequently in order to deduce which mixture to use on the basis of an area of the skin.

The same procedure can be adopted with other mixtures in order to create a map of the entire face and thus have a complete look-up table for the face.

It is also possible to create a given mixture, apply it to a given area, and then vary the mixture until the most suitable mixture is obtained. The mixture is then recorded, being attributed to the area(s) of the face for which it is suitable, in a look-up table that will be used subsequently in order to deduce which mixture to use on the basis of an area of the skin.

Preferably, the computer system evaluates and memorizes the quantities used area by area. Such a method, which uses "test patches" makes it possible to identify the product(s) required by the person wishing to apply makeup. Thus, the dispensing system can be used at sales outlets to advise people wishing to apply makeup or at home in order to define correctly which products to order.

The interface of the computer system preferably has a touch screen displaying the color of the mixture when it is selected.

The interface may display a face and allow the computer system to be informed by selecting the area on the face displayed.

The computer system is preferably designed to allow an area, mixture reconstruction parameters, and the date of the test and/or any other identifier of the mixture to be associated with one another.

The computer system is preferably also designed to allow at least one of the following data: the name of the area, the period of the year, the name of an event, a user identifier and the age of the user, to additionally be associated with said area, with the mixture reconstruction parameters, and with the date or identifier of the mixture.

Steps a) to c) may be repeated at least once before the characteristics of the mixture are memorized in step d).

The computer system may be designed to search a database for the reference of a commercial product on the basis of the characteristics of the mixture identified as being suitable for at least one given area, and to relay this information to the user.

The selection in step a) may be carried out using an expert system, which may or may not be external to the computer system.

The expert system may analyze an image of the user in order to propose a mixture color at least on the basis of the image analyzed.

Step a) may be preceded by the computer system proposing to the user a color and an area to be tested with a mixture of this color.

The computer system may be designed to allow the user to inform same of his or her assessment of the result of the test in step c) and to generate a proposal to modify the mixture to be selected upon return to step a).

The computer system may be designed to propose at least one color of mixture in step a) depending on an application area of which it has been informed by the user.

The computer system may be designed to propose at least one application area in step a), on the basis of a color of which it has been informed by the user.

The dispenser may deliver, in step b), at least two mixtures of different colors, preferably separate, so that they can be applied simultaneously to the test area.

This may allow time to be saved and make it easier to compare the results.

A further subject of the invention is a method of making up using a dispensing system according to the invention, in which:
a) the user sends the computer system a request regarding a need for makeup,
b) in return, the computer system generates a proposed color for making up an associated area, on the basis of the learning performed beforehand, and
c) the computer system operates the dispenser to produce the mixture of the proposed color, notably if this is validated by the user.

Such a method may use a map previously established with the user.

A further subject of the invention is a computer program product containing code instructions which, when run in a computer system, allow the computer system to be made to:
allow the user to select at least one color and/or one application area, notably using an interface such as a touch screen,
operate a dispenser in such a way as to deliver a mixture of the color selected by the user,
allow the user to trigger the memorizing of the color of the mixture and of an associated application area, notably with a view to subsequently dispensing the same mixture, notably on the same area.

The computer program product may comprise code instructions which, when run in a computer system, allow the computer system to be made to:
receive a request from the user regarding a need for makeup, notably using an interface such as a touch screen,
propose, on the basis at least of data generated by the learning process as defined above, at least one color and/or one application area,
operate a dispenser to produce the mixture of the proposed color, notably if this is validated by the user.

Remote Assistance

It is desirable to be able to assist the user in applying makeup, notably in choosing the correct colorings.

In one of its aspects, independently of or in combination with the other aspects thereof, and notably with the foregoing, one subject of the invention is thus a method of applying makeup involving the steps of:
allowing a video link to be established, for example over the Internet, between a camera on a first site and a second site,
allowing the second site to directly or indirectly operate a dispenser present at the first site, this dispenser making it possible to vary the color of a mixture dispensed,
allowing a person present at the first site to apply the mixture dispensed and to send a corresponding image to the second site, so as to receive in return information relating to the makeup result.

The second site may notably have a viewing screen which allows an adviser sitting at this screen to see the makeup result with the product dispensed by the dispenser and advise the person who has applied the makeup. This adviser may in return influence the dispenser to alter the color of the mixture and adapt it to best suit the face of the person present at the first site. Thus, this person controls the mixture delivered by the dispenser. The first person may make herself up under the gaze of the second. The second person sees the result of the test on the screen and can thus correct the mixture that this second person will control remotely until the ideal makeup is obtained.

If appropriate, the video acquisition can be calibrated using a test pattern or with the mixture dispensed by the dispenser onto a reference surface. That then allows a more faithful display of the makeup applied at the first site.

Preferably, the video link between the two sites is a two-way link.

The first site may receive a tutorial from the second site, if appropriate.

Identifiers of the base products may be communicated to the second site; this may make it possible to precisely determine the color of each of the base products.

The method may involve memorizing the dispenser setting parameters once a given mixture is considered to be satisfactory. Preferably, this memory storage may be commanded from the second site. The memory storage may be in the computer system present at the first site and/or on an external server.

One alternative may be to have one person working to help several apply makeup. This embodiment makes it possible to develop makeup artists and their work, either within an institute or over the Internet. It also allows people with limited capabilities, such as people with poor eyesight, or people who have difficulty discerning colors, or the elderly, or those lacking in self-confidence to apply makeup.

Operation Via Touch-Sensitive Interface

There is a need to make it easier to control the dispensing system and notably the choice of the color of the mixture dispensed.

According to another of its aspects, independently of or in combination with the other aspects thereof, and notably with the foregoing, one subject of the invention is thus a dispensing system comprising a dispenser and a computer system for operating the dispenser, this computer system comprising a touch screen on which the color of the mixture may be displayed and a selection means that can be moved over the screen in order to vary the color of the mixture dispensed.

Preferably, the screen displays end-point colors between which the color of the mixture can be selected by moving the selection means between these end-point colors.

The screen may display a scale of colors between at least two colors, or an area, notably of triangular outline, within which the selection means can be moved. This area may locally show the color of the mixture depending for example on the distance from each of the vertices, each one embodying a pure base product.

The computer system may perform some of the calculations necessary to determine the fractions of each of the base products that lead to a mixture of the desired color.

The computer system may be a smartphone, a camera phone, a tablet, or a personal computer. As an alternative, it is incorporated into the housing of the dispenser.

The computer system may have a camera. The latter can be used notably for capturing an image of the user and/or of the mixture.

The computer system may be designed to display an image of a face, in order to make it easier to identify the areas to which the mixture is to be applied.

Coupling of the Dispensing System to a Spray Means

The dispensing system may have or be connected to a means of spraying the mixture, preferably an airbrush.

The dispenser may have three cartridges containing makeup products of different colors.

The airbrush may have a stylus defining the pickup chamber, the stylus being fixed to the dispenser or to an outlet interface fixed to the dispenser, or forming an integral part of this outlet interface.

The dispensing system may have a circuit controlling operation of the dispenser, allowing the proportion of base products delivered to the pickup chamber to be varied while the airbrush is in operation. The proportions may be modified depending on the movement of the airbrush relative to the surface onto which the mixture is sprayed. This movement may be mechanized, if appropriate.

This control circuit may have or be constituted by a computer system as defined above.

The housing of the dispenser may act as a hand grip when the assembly is being handled for delivering the mixture.

The dispenser may have a camera and/or one or more sensors such as accelerometers so as to automatically locate the area to which the mixture is applied, and so as to be able to automatically regulate the color depending on the position, if appropriate.

A further subject of the invention is a method for applying makeup using an assembly as defined above, in which a mixture is sprayed onto the skin using the spray means, notably the airbrush.

The composition of the mixture can be modified as the airbrush is moved relative to the skin. A graduated effect can be achieved.

This aspect of the invention is based on the observation that the dispenser can be used to supply the spray system, notably the airbrush, while at the same time allowing the dispensing system to be responsive enough to allow a change in the color of the mixture dispensed while the face is being made up, notably as the area to be made up changes.

It may be advantageous for the dispensing of products to be performed iteratively, notably with dispensing times that are not phase-shifted between the various products.

This may make it easier to vary the composition of the mixture dispensed over time.

The mixture may be created directly in the airbrush, with practically no troublesome dead volume, thus allowing the mixture sprayed to be changed in real time.

The depression created in the pickup chamber is strong enough to entrain the base products without in any way impeding the metering.

The depression which prevails in the pickup chamber is for example between 10 mbar and 200 mbar, better still between 50 and 150 mbar, even better still between 75 and 125 mbar.

The viscosity of the base products as measured at 1 atm and 25° C. with a CONTRAVES TV rotary viscometer fitted with an MS-r3 or MS-r4 measuring bar at a frequency of 60 Hz after 10 minutes of rotation of the measuring bar is, for example, between 0.05 Pa·s and 50 Pa·s.

The cross section of the passages along which the base products arrive in the chamber is, for example, between 1 and 3 mm², better still between 2 and 3 mm².

The product is preferably supplied continuously.

It is also possible to apply immiscible or reactive base products, such as an aqueous gel and an oily gel, simultaneously, and these will be deposited directly onto the skin in a pixelated manner, producing a kind of gel/gel in situ, reactive silicones, or colorants that react with one another. The ratios of base products can be adjusted depending on the particular result desired. For example, in the case of aqueous gels and oily gels, the ratio corresponding to the volume of the first base product to the volume of the second base product could be varied between 10/1 and 1/10, better still between 5/1 and 1/5.

In one particular embodiment of the invention, the system chooses a viscosity less than or equal to $10^{-2}$ Pa·s for spray applications and a high viscosity for applications by hand or with a tool.

Location or Auto-Location System

The dispensing system according to the invention may have a location or auto-location system.

A location system is the name given to a means via which the person inputs the area that she is to treat. This can be performed notably using systems that leave at least one hand free. Thus, an interface of a computer system such as a touch screen, a joystick, or voice recognition system can be used.

An auto-location system is the name given to a means for inputting the area that is to be treated without intervention on the part of the person. This can be achieved using one or more accelerometers which deduce, from the movements, the directions targeted by the person or by a camera and an image recognition system.

Examples of dispensing systems have been described above with reference to the drawing. The description of these figures also applies to this aspect of the invention, and this description will not be repeated here.

Example 1 (Second Aspect of the Invention)

| Several base products are created (the proportions are by mass) | | | | | | |
|---|---|---|---|---|---|---|
| Base product | Iron oxide/ titanium oxide | Carpobopol 980 Polymer (Lubrizol) | 10% Aqueous ammonia with phosphoric acid qs pH 9.9 | Jaguar HP 60 (Solvay Novecare) | Glycerol | water |
| A1 | | 2% | | | 6% | qs 100% |
| B1 | | 2.44% | 0.2% | | 6% | qs 100% |
| C1 | 5% | | | 0.2% | 6% | qs 100% |

The pH values and viscosities are:
A1: pH=2.84 Viscosity=0.65 Pa·s
B1: pH=9.90 Viscosity=0.044 Pa·s
C1: pH=6.80 Viscosity=0.04 Pa·s The viscosity of the products is measured at 1 atm and 25° C. with a CONTRAVES TV rotary viscometer fitted with an MS-r3 or MS-r4 measuring bar at a frequency of 60 Hz after 10 minutes of rotation of the measuring bar.

The dispensing system was tested with:
A1 → Compartment 1
B1 → Compartment 2
C1 → Compartment 3

Test 1
A first mixture was created for the following volumetric proportions A: 50%, B: 0%, C: 50%

The system is used to deliver 200 mg of product. The mixture is thus spread very easily (since it is very fluid, viscosity=0.45 Pa·s).

Test 2
A second mixture was created for A: 30%, B: 20%, C: 40%

The system is used to deliver 200 mg of product. The mixture is thus spread easily in a thick layer over the areas to be covered (since it is thick, viscosity=1.9 Pa·s).

Test 3
A third mixture was created for A: 40%, B: 40%, C: 20%

The system is used to deliver 200 mg of product. The mixture covers little but is fairly viscous (viscosity=4.7 Pa·s.). It is ideal for areas such as the forehead. It does not run on application and maintains a natural appearance.

Example 2 (Second Aspect of the Invention)

The following formula Z is prepared:

| Carbopol 980 Polymer (Lubrizol) | 2% |
|---|---|
| 10% Aqueous ammonia in water | 2.44% |
| Water qs | 100% |

| Base product | Iron oxide | Titanium oxide | Carpobopol 980 Polymer (Lubrizol) | 10% Aqueous ammonia in water | Jaguar HP 60 | Glycerol | water |
|---|---|---|---|---|---|---|---|
| A1 | | 5% | 2% | 2.44% | | 6% | qs 100% |
| B1 | | 5% | 0.2% | 0.395% | | 6% | qs 100% |
| C1 | 5% | | | | 0.2% | 6% | qs 100% |

The pH values and viscosities are:
A1: pH=9.44 Viscosity=7.8 Pa·s
B1: pH=9.02 Viscosity=0.047 Pa·s
C1: pH=6.80 Viscosity=0.04 Pa·s The viscosity of the products is measured at 1 atm and 25° C. with a CONTRAVES TV rotary viscometer fitted with an MS-r3 or MS-r4 measuring bar at a frequency of 60 Hz after 10 minutes of rotation of the measuring bar.

The system was tested with:
A1→Compartment 1
B1→Compartment 2
C1→Compartment 3

Test 1

A first mixture was created for A: 50%, B: 0%, C: 50%

The result is beige and thick (viscosity=4.701 Pa·s), ideal for extensive coverage of marked areas of skin.

Test 2

A second mixture was created for A: 20%, B: 30%, C: 50%

The result is also beige but much more fluid (viscosity=1.9 Pa·s) than in test 1. The mixture is thus spread easily in a thick layer over the areas to be covered (since it is thick).

Test 3

A third mixture was created for A: 40%, B: 40%, C: 20%

The result is lighter and of intermediate viscosity (viscosity=3.75 Pa·s), ideal for treating the under-eye area.

C) System for Obtaining Films Having Properties Suitable for the Various Locations on the Face The precision of the color obtained is a very important factor for obtaining a quality result. However, it is also necessary, in order to obtain the most attractive results, that the product provide the best possible film quality.

Film quality is understood to be the quality of deposition following application to the skin and then drying.

Good quality of the film is not a simple concept. This is because some film qualities are suited to particular areas of the face and other qualities are suited to other areas of the face.

It is desirable for the properties of the film to be able to be adapted to the different parts of the face in order to be able to make up or care for the entire face with one and the same system. It is known that the treatment of the lips requires a degree of suppleness and it is therefore necessary for the film to be somewhat oily. It is known that the treatment of the area around the eye requires a film that is drier and has more of a tightening effect. It is known that the treatment of the base requires a film that is not cohesive in that it does not form a single film after application. Other areas, which are less mobile, may benefit from films that are resistant without causing discomfort (for example, the forehead).

Usually, the solution consists in using a series of products created for such and such a part of the face. This approach, which is very widespread, presents the problem of the number of references to be provided in order to cover all the needs in terms of color.

Given the desire to be able to vary the concentrations of colored ingredients (in order that the user can have the most suitable color(s) for each area), it is difficult to provide a single film quality. One possibility is to provide users with several systems for varying colors that are mounted with products that provide one type of film quality for some and other film qualities for others.

However, this approach is not realistic since it requires the user to have several mixing systems.

Another possibility is to provide users with a single system for varying colors that is mounted with products that provide one type of film quality for some and other film qualities for others. In this case, depending on the area to be treated, the user will mount products or other products. However, this approach is not realistic since it requires the user to continuously change the cartridges of product within their system.

Another possibility is to provide users with a single system for varying colors that is mounted with an entire set of cartridges of base products that provide a variety of film qualities. In this case, depending on the area to be treated, the system will use such and such a product without the user needing to change the cartridges of product in the compartments of the system. However, this approach is not realistic since it requires the system to have a very large number of compartments, requiring complex and expensive technology.

We have thus sought to propose a simple system for regulating the concentration of colored ingredients and of film quality.

This system is especially advantageous for rapidly treating (without having to change systems or cartridges) all of the areas of the face, varying the color thereof, and ensuring suitable film qualities.

It also allows the user to test their colors and film qualities until the best performance in terms of visual effect and comfort has been achieved.

Thus, one subject of the invention, according to a third aspect, is a system for dispensing a product, comprising a dispenser that receives at least two cartridges containing a first base product and a second base product, respectively, the dispenser allowing the delivery of at least these two base products in adjustable proportions in order to form a film, at least one property of which varies depending on the adjustment.

According to this third aspect, the invention may have one or more of the following preferred features:
the property of the film that varies is its flexibility, the property of the film that varies is its oily nature,
the property of the film that varies is its tightening nature,
the two base products are chosen to react with one another to form a film,
the first base product comprises a reactive silicone and the second base product comprises a catalyst that brings about the crosslinking of the reactive silicone,
the reactive silicone comprises a mixture of telechelic polyorganosiloxane bearing a vinyl function at the two chain ends and polyhydrogenosiloxane,
the catalyst is platinum based,
the first base product comprises a film-forming polymer and the second base product comprises an oily compound that is liquid at room temperature,
the film-forming polymer has a glass transition temperature Tg greater than or equal to 30° C., better still greater than or equal to 60° C.,
the film-forming polymer is chosen from vinyl, notably acrylic, polymers or copolymers,
the film-forming polymer being lipsoluble,
the first and second base products contain different respective film-forming polymers,
the film-forming polymer of the first base product having a glass transition temperature Tg1 and the polymer of the second base product having a glass transition temperature Tg2 different than Tg1, wherein preferably Tg1>60° C. and Tg2<10° C.,
the first base product comprises a polymer or copolymer chosen from methacrylic polymers and copolymers, polyamides, alkyl celluloses, polymers and copolymers of vinylpyrrolidone, and silicone resins, the second base product comprises a polymer or copolymer chosen from acrylic polymers and copolymers, vinyl polymers and copolymers and polycondensates such as polyesters and polyurethanes, the first base product comprises an oily compound with a melting point $Tf1 > 20°$ C. and the second base product comprises an oily compound with a melting point $Tf2 < 20°$ C.

This third aspect of the invention also relates to a method for applying a cosmetic, makeup and/or care, product to human keratin materials, comprising the setting of the dispenser depending on the area to be treated, and the dispensing of the product by base products being picked up from the cartridges in the proportions corresponding to the setting of the dispenser.

According to its third aspect, the invention is thus based on:

a dispensing system at least two compartments these compartments comprise compounds that form a film by contact and are chosen such that, by combining them, a range of film qualities is obtained.

According to this third aspect, the invention makes it possible to treat one or more areas of the face and to obtain mixtures that are very precise in terms of color faithfulness and comfort and suitable durability for obtaining particularly effective effects. Hereinbelow, the term "area" is used to denote a defined part of the face, fairly small in surface area, covering between 1 cm$^2$ and 100 cm$^2$, better still ranging from 2 cm$^2$ to 50 cm$^2$.

Hereinbelow, the concept of "makeup" is extended beyond the provision of color or of concealing capacity. This concept applies here for all treatments in which a film is deposited on the skin, said film being colored, concealing, or not. For example, the concept comprises the application of a protective film (with screening agents) or a treating film (with biological active agents) or a tightening film.

Film quality is understood as meaning the mechanical properties of the film. Although the mechanical properties form a continuum, the films can be split up into a number of classes of mechanical properties:

1) Oily film
2) Flexible film
3) Rigid film
4) Tightening film

The system according to the invention can vary the film produced. Thus, depending on the adjustments chosen, the mechanical properties of the film are not the same. In a preferred embodiment of the invention, the system can, depending on adjustments, produce films of one category or another. (or over the three categories)

The quality of the film is tackled by applying a film with a thickness of 400 μm to a flexible support (sheet of parchment paper), and then allowing it to dry for one day. In the end, the following tests are carried out to qualify the film:

Thus, several scenarios are distinguished:

1) Oily film: When the support is folded with a radius of curvature of 1 cm, the film remains attached to its support. When the film is rubbed with an absorbent paper (for example kitchen towel) for a few seconds, all or some of the film is found on the absorbent paper.

2) Flexible film: When the support is folded with a radius of curvature of 1 cm, the film remains attached to its support. When the film is rubbed with an absorbent paper (for example kitchen towel) for a few seconds, no transfer of the film to the absorbent paper is noted.

3) Rigid film: When the support is folded with a radius of curvature of 1 cm, the film at least partially detaches from its support.

4) Tightening films are particular cases that bring about an effect of contraction of the support during drying.

The dispensing system is preferably as defined for the two first aspects of the invention that are described above.

Dispensing System

Thus, the dispensing system may consist, according to the third aspect of the invention, as for the first and second aspects of the invention, of a single device operating autonomously, preferably able to be manipulated in one hand, or of a device that operates in interaction with other components or devices. It may for example entail various outlet interfaces which are mounted on the dispenser depending on the type of makeup to be created, as will be specified below. It may also entail a computer system which exchanges information with the dispenser in order to operate the latter, this computer system comprising, for example, a portable terminal such as a smartphone, a camera phone, a tablet, a laptop computer or a dedicated terminal.

Preferably, the dispenser is designed to pressurize one or more compartments containing the base product(s), via volumetric metering devices, preferably a motor causing a piston to move in the corresponding compartment.

The dispenser may be formed of a housing and of at least two or three compartments, and preferably an identical number of motors. For example, the rotation of the motors drives endless screws which push the pistons of each compartment. The advancing movement of the pistons is, for example, controlled by the number of command pulses sent to the motors and/or by the length of time for which the latter are operating. The motors may be powered in sequence or preferably simultaneously.

For example, the motors are powered during an elementary operating cycle for a short duration one after the other or at the same time as one another, so as to dispense corresponding microdoses.

The elementary cycles are repeated, possibly with a pause between them, giving the base products time to flow out of the compartments.

The compartments may be defined by cartridges, which are removed when they become empty. As an alternative, the compartments are permanently present and refilled once they become empty.

Each cartridge may be closed by a stopper that can be removed to allow the cartridge to be cleaned.

Preferably, the housing of the dispenser is of elongate shape along a longitudinal axis, making it easier to handle, and the cartridges are disposed about this axis, inside the housing.

Preferably, the cartridges are inserted from the rear and the mixture is delivered from the front. The cartridges may be inserted individually or, as an alternative, the cartridges constitute a one-piece assembly as they are inserted.

The cartridges may each have a volumetric metering mechanism comprising a piston moved by a drive mechanism of the dispenser in a direction accompanied by a reduction in the internal volume containing the base product and the expulsion of some product. It may be advantageous for the cartridges to have at least a region of their wall that is transparent so that the color of the product contained therein can be seen.

The drive mechanism may have a motorization system formed of motors coupled to gearboxes, of elongate shape parallel to the longitudinal axis of the dispenser, and positioned between the cartridges. Positioning the motors and cartridges in this way makes the dispenser particularly compact.

The base product can leave the corresponding cartridge in a sealed manner, then flow along a passage provided for this purpose in the housing of the dispenser, before leaving the latter.

The cartridges advantageously end in an end piece produced in such a way that, once the cartridge has been inserted into the housing of the dispenser, the end of the end piece terminates flush with the housing. As an alternative, the end piece is long enough to protrude beyond the housing and thus connect various outlet interfaces that can be attached to the housing of the dispenser.

By virtue of the drive mechanism having motors for causing the pistons to advance, it is possible to precisely deliver mixtures in very small quantities. Thus, the drive mechanism can deliver the base products with a minimum flow rate less than or equal to 50 µL/s, better still less than or equal to 20 µL/s, even better still less than or equal to 10 µL/s. Preferably, the drive mechanism delivers flow rates of between 20 and 100 µL/s, better still between 40 µL/s and 60 µL/s. It is thus possible to easily create a mixture of around 10 mg. Such a dispensing system is therefore ideal for achieving small touches of makeup, for covering an area of 1 cm$^2$, better still an area of 0.5 cm$^2$, for example.

It is also possible to create larger quantities of mixture such as the quantities needed to make up a cheek or a face. These quantities remain relatively low, however, for example a quantity of between 100 and 500 mg, better still between 150 and 250 mg.

Thus, one subject of the invention, according to one aspect thereof, is a dispensing system comprising a dispenser having a housing, and at least one cartridge received in the housing of the dispenser, this cartridge having a body and a piston capable of moving in the body, the housing comprising a motorized drive mechanism for moving the piston of the cartridge.

Preferably, the cartridge has a dispensing end piece through which the product exits, and this dispensing end piece is driven in rotation by the drive mechanism for moving the piston. The end piece may have at least one rotation-proofing relief, better still two diametrically opposed rotation-proofing studs.

The end piece may bear a seal, notably an O-ring seal. Thus, when changing the cartridge, the seal is also changed, making it possible to get around the problem of seal wear.

The dispenser may have an electronic board for controlling the motorized drive mechanism, this electronic board having the end piece(s) passing through it. This may make it possible to produce a board extending across substantially the entire cross section of the dispenser so that all the electronic components of the dispenser can be grouped together on a single board, thus improving compactness and reliability. The board may extend substantially perpendicularly to the longitudinal axis of the housing. The board may bear a switch for controlling operation of the dispenser.

The dispensing system may be designed to operate in at least two dispensing modes.

In a first mode, referred to as "continuous", the mixture is dispensed as long as pressure is applied to the control switch.

In a second mode, referred to as "dose", a predefined quantity of the mixture is dispensed for each press of the switch.

The end piece(s) may terminate at one end of the housing. This may make it possible to reduce the dead volume, as will be explained in detail below.

The end piece(s) may have at their end a shutoff system for preventing the products from drying out in the duct, for example a self-healing membrane.

The cartridge may have a hollow screw onto which the piston is screwed, the piston being able to move axially along the screw as the latter turns; the piston is prevented from turning in the body of the cartridge. For example, the friction of the piston against the body of the cartridge may be enough to prevent it from turning when the screw turns.

Preferably, rotation is rendered impossible with a cartridge body of non-circular cross section and a piston that is not deformable.

The torque of the motors may be determined electronically depending on the current drawn, and may be used for example to detect that the piston has reached the end of its travel. Information regarding the torque may be transmitted remotely to a computer system that has a man-machine interface, in order that correct operation of the dispenser can be monitored.

In order to adjust the shade, the dispensing system according to the invention has to allow the user to vary the volume delivered from each compartment.

Preferably, the dispenser is operated by a computer system built into the dispenser or external thereto, the dispenser then being able to exchange information with the computer system using a wireless or wired protocol.

The dispenser may thus be operated so as to allow the shade to be adjusted by controlled simultaneous or sequential dispensing of several base products of different colors.

The dispensing of the base products may be continuous; in such a case, the volumes of each of the base products are dispensed in a single shot, simultaneously or in succession.

In the case of simultaneous dispensing, it is beneficial to be able to adjust the respective flow rates of the various base products in order for the dispensed mixture to correspond to the desired mixture at all times. Such a dispensing mode may be suitable in particular when dispensing the mixture by spraying, using an airbrush. To adjust the flow rates it is possible, for example, to alter the speed at which the pistons move, for example in the case where the pistons are driven by an endless screw, by varying the rotational speed of the motors that drive the screw. The products may also be dispensed in a pulsed manner with a dispensing time and a pause in each cycle. By altering the duty cycle it is possible to alter the flow rate.

All the products may be delivered simultaneously during the dispensing time or, as an alternative, the cycles of the various products are phase-shifted from one another so that one product is dispensed while the other products are paused.

In one particular embodiment of the invention, the mixture is delivered into a cavity of a container which may close hermetically or not, for example in the form of a cup, into which an applicator, particularly a stylus or a brush may be slipped. Such a dispensing system is especially suited to liners, glosses and other formulations applied without direct contact with the hands. This container may be removable.

For example, it is used as a lip-color dispenser and has a dispensing system, for example using a screw. When it is not removable, the container may be produced with the body of the dispenser. When it is removable, it may constitute one output interface among others that can be mounted on the dispenser.

The compartments, and in particular the cartridges, may contain all or part of the drive mechanism and, for example, the motorizing system or, better still, part of the motorizing system, the purpose of this being to reduce the number of moving parts in the body of the dispenser outside the cartridges. For example, the cartridges contain the rotor of the motor. Once the cartridges have been installed in the body of the dispenser, the rotors are made to interact with the stators.

The dispensing system is advantageously arranged in such a way as to allow the running of preprogrammed sequences in which the mixture delivered by the system is modified continuously or discontinuously. A "graduated" mode makes it possible for example to progress gradually from a mixture A to a mixture B. In the case where the application is by spraying, notably using an airbrush, this makes it possible for graduations to be achieved simply. An "alternate" mode makes it possible for example to switch quickly from a mixture A to a mixture B several times in succession. In the case of application by spraying, a multilayer application can thus be achieved, with different formulations for two superposed adjacent coats. Another mode makes it possible for example to offer several preprogrammed successive mixtures, the computer system each time indicating to the user how these should be used, for example by display on a screen.

In the case of manual application, the mixtures are dispensed for example into a cup. The person applies the makeup to the recommended place with a corresponding mixture taken from the cup, then, if necessary, cleans out the cup and commands delivery of a new mixture; the operation is repeated as many times as necessary until the person is fully made up.

The mixtures dispensed can be homogenized in various ways depending on the type of use. In the case of manual application, it can be done directly on the application area at the time of application or in the cup before the mixture is picked up; in the case of an airbrush application, the pipe of the airbrush is used as a mixing chamber; if the mixture is dispensed into a container for later use, homogenization can be performed by hand or by passing the dispensed products through a mixing chamber situated between the dispenser and the container or incorporated directly into the container, as described in detail below.

The product may be delivered by the dispensing system and used extemporaneously. As an alternative, the product delivered by the dispensing system is packaged and used later, for example on several occasions, with, for example, at least one day's interval between two uses.

Example of Implementing the Adjustment of the Film Quality

Compartment 1 contains a composition C1.
Compartment 2 contains a composition C2.
The contact between C1 and C2, at different ratios, brings about different film qualities.

Implementation a:

Two ingredients that are able to react with one another (in two separate compartments) can be used and the relative proportions can be adjusted.

Typically, in C1, there is a product containing a reactive silicone and, in C2, there is a product containing the catalyst thereof. Depending on the adjustments, the properties of the film will be different.

The "reactive silicone" may typically be a mixture of telechelic polyorganosiloxane bearing a vinyl function at the two chain ends (available notably in the Andisil VS™ range from AB Specialty Silicones), and polyhydrogenosiloxane (available notably in the Andisil XL™ range from AB Specialty Silicones).

The "catalyst" may typically be a platinum-based catalyst such as the reference PT-50175F available from Umicore.

Implementation b:

It is also possible to use a film-forming polymer A and an oily compound that is liquid at room temperature B. By placing A in a product intended for compartment 1 and B in a product intended for compartment 2, it is possible, by adjusting the mixtures, to vary the final film quality.

A "film-forming polymer" is understood to be a polymer that is capable of forming, by itself or in the presence of an auxiliary film-forming agent, a macroscopically continuous film that adheres to keratin materials, and preferably a cohesive film, and better still a film of which the cohesion and mechanical properties are such that said film may be isolable and manipulable in isolation, for example when said film is prepared by pouring onto a non-stick surface, for instance a Teflon-coated or silicone-coated surface.

It is chosen preferably from polymers having a glass transition temperature (Tg) greater than 30° C., preferably greater than 60 C.

Among the film-forming polymers that may be used in the composition of the present invention, mention may be made of synthetic polymers, of free-radical type or of polycondensate type, polymers of natural origin, and mixtures thereof.

A "free-radical film-forming polymer" is understood to be a polymer obtained by polymerization of unsaturated and especially ethylenically unsaturated monomers, each monomer being capable of homopolymerizing (unlike polycondensates).

The film-forming polymers of free-radical type may notably be vinyl polymers or copolymers, notably acrylic polymers.

The vinyl film-forming polymers may result from the polymerization of ethylenically unsaturated monomers containing at least one acid group and/or esters of these acid monomers and/or amides of these acid monomers.

Monomers bearing an acid group which may be used are α,β-ethylenic unsaturated carboxylic acids such as acrylic acid, methacrylic acid, crotonic acid, maleic acid or itaconic acid. (Meth)acrylic acid and crotonic acid are preferably used, and more preferably (meth)acrylic acid.

The esters of acidic monomers are advantageously chosen from (meth)acrylic acid esters (also known as (meth)acrylates), notably alkyl (meth)acrylates, in particular C1-C30 and preferably C1-C20 alkyl (meth)acrylates, aryl (meth)acrylates, in particular C6-C10 aryl (meth)acrylates, and hydroxyalkyl (meth)acrylates, in particular C2-C6 hydroxyalkyl (meth)acrylates. Mention may be made, among alkyl (meth)acrylates, of methyl methacrylate, ethyl methacrylate, butyl methacrylate, isobutyl methacrylate, 2-ethylhexyl methacrylate, lauryl methacrylate or cyclohexyl methacrylate.

Mention may be made, among hydroxyalkyl (meth)acrylates, of hydroxyethyl acrylate, 2-hydroxypropyl acrylate, hydroxyethyl methacrylate or 2-hydroxypropyl methacrylate.

Mention may be made, among aryl (meth)acrylates, of benzyl acrylate and phenyl acrylate.

The (meth)acrylic acid esters which are particularly preferred are the alkyl (meth)acrylates.

Examples of amides of acid monomers that may be mentioned are (meth)acrylamides, and notably N-alkyl (meth)acrylamides, in particular C2-C12 alkyl(meth)acrylamides. Mention may be made, among the N-alkyl(meth)acrylamides, of N-ethylacrylamide, N-(t-butyl)acrylamide, N-(t-octyl)acrylamide and N-undecylacrylamide.

The vinyl film-forming polymers may also result from the homopolymerization or copolymerization of monomers chosen from vinyl esters and styrene monomers. In particular, these monomers may be polymerized with acid monomers and/or esters thereof and/or amides thereof, such as those mentioned above.

Examples of vinyl esters that may be mentioned are vinyl acetate, vinyl neodecanoate, vinyl pivalate, vinyl benzoate and vinyl t-butylbenzoate.

Styrene monomers that may be mentioned are styrene and alpha-methylstyrene.

Among the film-forming polycondensates that may be mentioned are polyurethanes, polyesters, polyester-amides, polyamides, epoxyester resins and polyureas. The polyurethanes may be chosen from anionic, cationic, nonionic and amphoteric polyurethanes, polyurethane-acrylics, polyurethane-polyvinyl-pyrrolidones, polyester-polyurethanes, polyether-polyurethanes, polyureas and polyurea-polyurethanes, and mixtures thereof.

The polyesters may be obtained, in a known manner, by polycondensation of dicarboxylic acids with polyols, especially diols.

The dicarboxylic acid may be aliphatic, alicyclic or aromatic. Examples of such acids that may be mentioned include: oxalic acid, malonic acid, dimethylmalonic acid, succinic acid, glutaric acid, adipic acid, pimelic acid, 2,2-dimethylglutaric acid, azelaic acid, suberic acid, sebacic acid, fumaric acid, maleic acid, itaconic acid, phthalic acid, dodecanedioic acid, 1,3-cyclohexanedicarboxylic acid, 1,4-cyclohexanedicarboxylic acid, isophthalic acid, terephthalic acid, 2,5-norbornanedicarboxylic acid, diglycolic acid, thiodipropionic acid, 2,5-naphthalenedicarboxylic acid, 2,6-naphthalenedicarboxylic acid. These dicarboxylic acid monomers may be used alone or as a combination of at least two dicarboxylic acid monomers. Among these monomers, the ones preferentially chosen are phthalic acid, isophthalic acid and terephthalic acid.

The diol may be chosen from aliphatic, alicyclic and aromatic diols. The diol used is preferably chosen from: ethylene glycol, diethylene glycol, triethylene glycol, 1,3-propanediol, cyclohexanedimethanol and 4-butanediol. Other polyols that may be used are glycerol, pentaerythritol, sorbitol and trimethylolpropane.

The polyesteramides may be obtained in a manner analogous to that of the polyesters, by polycondensation of diacids with diamines or amino alcohols. Diamines that may be used are ethylenediamine, hexamethylenediamine and meta- or para-phenylenediamine. An amino alcohol that may be used is monoethanolamine.

The polyester may also comprise at least one monomer bearing at least one group —SO3M, with M representing a hydrogen atom, an ammonium ion NH4+ or a metal ion such as, for example, an Na+, Li+, K+, Mg2+, Ca2+, Cu2+, Fe2+ or Fe3+ ion. A difunctional aromatic monomer comprising such a group —SO3M may notably be used.

The aromatic nucleus of the difunctional aromatic monomer also bearing a group —SO3M as described above may be chosen, for example, from benzene, naphthalene, anthracene, biphenyl, oxybiphenyl, sulfonylbiphenyl and methylenebiphenyl nuclei. As examples of difunctional aromatic monomers also bearing a group —SO3M, mention may be made of: sulfoisophthalic acid, sulfoterephthalic acid, sulfophthalic acid and 4-sulfonaphthalene-2,7-dicarboxylic acid.

According to one example of a composition according to the invention, the film-forming polymer may be a polymer dissolved in a liquid fatty phase comprising organic solvents or oils (the film-forming polymer is thus said to be a liposoluble polymer). The liquid fatty phase preferably comprises a volatile oil, optionally mixed with a nonvolatile oil.

Examples of liposoluble polymers that may be mentioned are copolymers of a vinyl ester (the vinyl group being directly linked to the oxygen atom of the ester group and the vinyl ester containing a saturated, linear or branched hydrocarbon-based radical of 1 to 19 carbon atoms, linked to the carbonyl of the ester group) and of at least one other monomer which may be a vinyl ester (other than the vinyl ester already present), an α-olefin (containing from 8 to 28 carbon atoms), an alkyl vinyl ether (in which the alkyl group comprises from 2 to 18 carbon atoms) or an allyl or methallyl ester (containing a saturated, linear or branched hydrocarbon-based radical of 1 to 19 carbon atoms, linked to the carbonyl of the ester group).

These copolymers may be crosslinked with the aid of crosslinking agents, which may be either of the vinyl type or of the allylic or methallylic type, such as tetraallyloxyethane, divinylbenzene, divinyl octanedioate, divinyl dodecanedioate and divinyl octadecanedioate.

Examples of these copolymers that may be mentioned include the following copolymers: vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethylpropionate/vinyl stearate, allyl dimethylpropionate/vinyl stearate, vinyl propionate/vinyl stearate, crosslinked with 0.2% divinylbenzene, vinyl dimethylpropionate/vinyl laurate, crosslinked with 0.2% divinylbenzene, vinyl acetate/octadecyl vinyl ether, crosslinked with 0.2% tetraallyloxyethane, vinyl acetate/allyl stearate, crosslinked with 0.2% divinylbenzene, vinyl acetate/1-octadecene crosslinked with 0.2% divinylbenzene, and allyl propionate/allyl stearate, crosslinked with 0.2% divinylbenzene.

Examples of liposoluble film-forming polymers that may be mentioned include copolymers of a vinyl ester and of at least one other monomer that may be a vinyl ester, especially vinyl neodecanoate, vinyl benzoate and vinyl t-butylbenzoate, an α-olefin, an alkyl vinyl ether or an allylic or methallylic ester.

Liposoluble film-forming polymers that may also be mentioned include liposoluble copolymers, and in particular those resulting from the copolymerization of vinyl esters containing from 9 to 22 carbon atoms or of alkyl acrylates or methacrylates, the alkyl radicals containing from 10 to 20 carbon atoms.

Such liposoluble copolymers may be chosen from copolymers of polyvinyl stearate, polyvinyl stearate crosslinked with divinylbenzene, with diallyl ether or with diallyl phthalate, polystearyl (meth)acrylate copolymers, polyvinyl laurate and polylauryl (meth)acrylate, these poly(meth)acrylates possibly being crosslinked with ethylene glycol dimethacrylate or tetraethylene glycol dimethacrylate.

The liposoluble copolymers defined above are known and are described notably in the application FR-A-2232303; they may have a weight-average molecular weight ranging from 2000 to 500 000 and preferably from 4000 to 200 000.

As liposoluble film-forming polymers that may be used in the invention, mention may also be made of polyalkylenes and notably copolymers of C2-C20 alkenes, such as polybutene, alkylcelluloses with a linear or branched, saturated or unsaturated C1-C8 alkyl radical, for instance ethylcellulose and propylcellulose, copolymers of vinylpyrrolidone (VP) and in particular copolymers of vinylpyrrolidone and of C2 to C40 and better still C3 to C20 alkene. As examples of VP copolymers that may be used in the invention, mention may be made of the copolymers of VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene or VP/acrylic acid/lauryl methacrylate.

Mention may also be made of silicone resins, which are generally soluble or swellable in silicone oils. The nomenclature of silicone resins is known under the name "MDTQ", the resin being described as a function of the various siloxane monomer units that it comprises, each of the letters "MDTQ" characterizing a type of unit. As examples, mention may be made of polymethylsilsesquioxane resins, polypropylsilsesquioxane resins, and trimethyl siloxysilicate resins (TMS).

An "oily compound liquid at room temperature" is understood to be an oil that remains on the skin at room temperature and atmospheric pressure for at least several hours, and that notably has a vapor pressure of less than 0.13 Pa (0.01 mmHg).

These nonvolatile oils may be hydrocarbon-based oils, notably of animal or plant origin, silicone oils, or mixtures thereof. A "hydrocarbon-based oil" is understood to be an oil mainly containing hydrogen and carbon atoms and possibly oxygen, nitrogen, sulfur and/or phosphorus atoms.

Nonvolatile hydrocarbon-based oils that may especially be mentioned include:
- hydrocarbon-based oils of animal origin,
- hydrocarbon-based oils of plant origin such as triglycerides constituted by fatty acid esters of glycerol, the fatty acids of which may have chain lengths varying from C4 to C24, these chains possibly being linear or branched, and saturated or unsaturated; these oils are in particular heptanoic or octanoic acid triglycerides, or alternatively wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passion-flower oil and musk rose oil; shea butter; or else caprylic/capric acid triglycerides,
- synthetic ethers containing from 10 to 40 carbon atoms,
- linear or branched hydrocarbons of mineral or synthetic origin, such as petroleum jelly, polydecenes, hydrogenated polyisobutene, squalane and liquid paraffins, and mixtures thereof,
- synthetic esters such as oils of formula R1COOR2 in which R1 represents a linear or branched fatty acid residue containing from 1 to 40 carbon atoms and R2 represents a notably branched hydrocarbon-based chain containing from 1 to 40 carbon atoms, on the condition that R1+R2≥10, for instance purcellin oil (cetostearyl octanoate), isopropyl myristate, isopropyl palmitate, C12 to C15 alkyl benzoates, hexyl laurate, diisopropyl adipate, isononyl isononanoate, isodecyl neopentanoate, 2-ethylhexyl palmitate, isostearyl isostearate, 2-hexyldecyl laurate, 2-octyldecyl palmitate, 2-octyldodecyl myristate, alkyl or polyalkyl heptanoates, octanoates, decanoates or ricinoleates such as propylene glycol dioctanoate; hydroxylated esters such as isostearyl lactate, diisostearyl malate and 2-octyldodecyl lactate; polyol esters and pentaerythritol esters,
- fatty alcohols that are liquid at room temperature, with a branched and/or unsaturated carbon-based chain containing from 12 to 26 carbon atoms, for instance octyldodecanol, isostearyl alcohol, oleyl alcohol, 2-hexyldecanol, 2-butyloctanol and 2-undecylpentadecanol,
- higher fatty acids such as oleic acid, linoleic acid or linolenic acid, and mixtures thereof, The nonvolatile silicone oils that may be used in the composition according to the invention may be nonvolatile polydimethylsiloxanes (PDMSs), polydimethylsiloxanes comprising alkyl or alkoxy groups, that are pendent and/or at the end of a silicone chain, the groups each containing from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes, and mixtures thereof.

Implementation c:

It is also possible to use a film-forming polymer A and a film-forming polymer B. By placing A in a product intended for compartment 1 and B in a product intended for compartment 2, it is possible, by adjusting the mixtures, to vary the final film quality.

Use is typically made of a film-forming polymer A of high Tg (typically >60° C.) and a film-forming polymer B of low Tg (typically <10° C.), from those described above.

The film-forming polymer A of high Tg is preferably chosen from methacrylic polymers or copolymers, polyamides, alkylcelluloses such as ethylcellulose and propylcellulose, polymers and copolymers of vinylpyrrolidone, and silicone resins.

The film-forming polymer B of low Tg is preferably chosen from acrylic polymers or copolymers, vinyl copolymers, and polycondensates such as polyesters and polyurethanes.

Implementation d:

It is also possible to use an oily compound with a melting point>room temperature (wax) A and an oily compound that is liquid at room temperature B. By placing A in a product intended for compartment 1 and B in a product intended for compartment 2, it is possible, by adjusting the mixtures, to vary the final film quality.

An "oily compound with a melting point>room temperature" is understood to be a fatty substance that is solid at room temperature.

Pasty fatty substances can be defined with the aid of at least one of the following physicochemical properties:
- a viscosity of 0.1 to 40 Pa·s (1 to 400 poises), measured at 40° C. with a CONTRAVES TV rotary viscometer fitted with an MS-r3 or MS-r4 measuring bar at a frequency of 60 Hz,
- a melting point of 25-70° C., preferably 25-55° C.

As waxes that may be used according to the invention, mention may be made of:
- waxes of animal origin, such as beeswax, spermaceti, lanolin wax and lanolin derivatives, plant waxes such as carnauba wax, candelilla wax, ouricury wax, Japan wax, cocoa butter, cork fiber wax or sugarcane wax,
- mineral waxes, for example paraffin wax, petroleum jelly wax, lignite wax, microcrystalline waxes or ozokerites,
- synthetic waxes, including polyethylene waxes and the waxes obtained by Fisher-Tropsch synthesis, silicone waxes, in particular substituted linear polysiloxanes; examples that may be mentioned include polyether silicone waxes, alkyl or alkoxy dimethicones containing from 16 to 45 carbon atoms, alkyl methicones, hydrogenated oils that are solid at 25° C., such as hydrogenated castor oil, hydrogenated jojoba oil, hydrogenated palm oil, hydrogenated tallow or hydrogenated coconut oil, and fatty esters that are solid at 25° C., for instance C20-C40 alkyl stearate, and/or mixtures thereof.

Preferably, use will be made of polyethylene waxes, microcrystalline waxes, carnauba waxes, hydrogenated jojoba oil, candelilla waxes, beeswaxes, and/or mixtures thereof.

Optimization

It is very advantageous to have as few compartments as possible.

Thus, if the system is desired to be able to adjust the color (this being the main aim), it will be necessary to provide two compartments in addition to the two intended for controlling the film quality. Thus, it will be necessary to provide:

compartments 1 and 2 containing the ingredients for varying the quality of the film, and other compartments (3 or 4 for example), for placing the ingredients M for varying the color therein.

It is also possible to place the active agents M in compartments 1 or 2 or 1 and 2.

In this way, the total number of compartments is reduced to 3, or even 2, rather than 4.

For example, the active agents M are put in the products that are placed in compartments 1 and 2. In compartment 1, M is set at a high concentration, and in compartment 2, M is set at a low concentration.

The active agents that produce the film and regulate the properties thereof are thus placed in compartments 1 and 2. A wax in emulsion is put in the product in compartment 1 and an oil is put in the product in compartment 2.

If the system is used with a majority setting in 1, a product with a concentration of wax and active agent M is obtained.

The majority setting in 1 can then be used on eye contour areas where extensive coverage and a dry film are desired.

The majority setting in 2 can be used as a "foundation product" on the entire surface of the face, notably when the user has dry skin. The low level of pigment ensures a natural appearance and the oily nature of the film does not have a bothersome effect.

It is possible to place an active agent M1 in a product intended for compartment 1 and an active agent M2 in a product intended for compartment 2. For example, M1 is a yellow pigment and M2 is a red pigment.

The active agents that produce the film and regulate the properties thereof are thus placed in compartments 1 and 2. For example, a reactive silicone in emulsion is put in the product in compartment 1 and a catalyst is put in the product in compartment 2.

If the system with the majority setting in 1 is used, a product with a high reactive silicone/catalyst ratio and a high concentration of yellow pigment is obtained.

The majority setting in 1 can then be used on the face where the yellow color is suitable and the oily film provides a high level of mobility and thus comfort.

The majority setting in 2 can be used on the lips, where the red color is suitable and greater resistance of the film, due to greater crosslinking, will give better durability.

It is possible to place the active agents M in a compartment 3. For example, a yellow pigment is placed therein.

The active agents that produce the film and regulate the properties thereof are placed in compartments 1 and 2. For example, a wax in emulsion is put in the product in compartment 1 and an oil is put in the product in compartment 2.

If the system with a 70/20/10 setting is used, a film that covers little but is suitable for areas subjected to rubbing, for example the neck, will be obtained.

If the system with a 20/70/10 setting is used, a result that covers little and is very comfortable, suitable for the large surfaces of the face, will be obtained.

If the system with a 30/10/60 setting is used, a result that covers highly, suitable for example for very marked areas, will be obtained.

If the system with a 10/30/60 setting is used, a result that covers highly and is very comfortable, suitable for example for making up the eyelashes, will be obtained.

The invention according to this third aspect is not limited to active agents that provide coloring effects. It is possible to use care active agents such as anti-aging, antioxidant, anti-wrinkle, antiperspirant, mark-preventing, photoprotective and moisturizing active agents.

It is also possible to mix active agents that provide coloring effects and care effects.

Use for Making Up One or More Precise Areas of the Skin

The dispensing system allows makeup to be applied, day after day, with only the areas that need to be hidden being treated. To this end, small doses of makeup are delivered, and are applied specifically and sequentially to the corresponding areas. Each small dose is created using the mixture suited to the area.

In one preferred embodiment of the invention, the dispensing system waits for information regarding which area is to be treated and then delivers the corresponding mixture. It may use a preprogrammed look-up table for that purpose, this table being the result for example of a learning process as defined below.

In one particularly advantageous embodiment, the programming takes into account the resistance and comfort to be achieved in order to obtain optimum results. As an alternative, the dispensing system informs the person, when delivering a mixture, of the area to which the person is to apply the mixture. Thus, the dispensing system may follow an application program in which it delivers, in a given order, the various mixtures that are to be applied.

In one particular embodiment of the invention, the dispensing system is informed as to the quantities to be delivered. For that, it memorizes the relationship between the color, the area of the face and the quantity needed, thereby making it possible to reduce costs and wastage of product, and to cover the skin only lightly, thus avoiding occlusion effects. In so doing, it is possible to use products that have a high covering capability and provide too much cover to be applied to the whole of the face. Thus, it is possible to obtain makeup of natural or even undetectable appearance.

The dispensing system may also make it possible, by facilitating the dispensing of small quantities and rapid use thereof, to reduce the time for which the products are kept, thus making it possible to reduce the risks of the products changing and/or to reduce the amounts of preservative to be used.

The dispensing system is suited to treating the areas that are to be concealed, without having to conceal the entire face.

When the user is looking for the color to apply to an area of the face, it is advantageous to memorize the color best suited to each area, and the dispensing system is thus advantageously designed to memorize this color and the corresponding area. Thus, by using the memorized information, on each use, the same mixture can be delivered for each area or, if several areas are being treated, the same series of mixtures can be delivered for the same series of areas.

The dispensing system may also be designed to allow an area to be treated by varying the colors application after application. Thus, the person may make up her lips using different colors that she chooses on a day-by-day basis to suit her tastes. This approach is also suitable for the eyelids or eyelashes, and for face makeup because the person may fancy a change of foundation color. For example, on weekdays, the person applies a pale colored foundation, with a more tanned foundation color at the weekends, or may have eye makeup in one color one day and another color another day.

The dispensing system may be designed to allow the user to change color to suit her tastes according to the day, the time, what she is wearing, and the weather. Thus, a system to assist with decision making is advantageously provided to guide the user in her choices of color.

An assistance system may also be provided for balancing the colors on the same face and contribute toward a successful overall makeup look.

It may be desirable for several people in the same group, for example a family, to be able to use the dispensing system, thus reducing costs and minimizing the space taken up. This solution is particularly suited to travel or hotels, campsites, airplanes, campervans, boutiques, schools, etc. For that, provision may be made for the dispensing system to be able to be informed as to which person is using it, so as to access pre-stored personal data.

Continuous Use for Graduated Makeup

In this application, the dispensing system changes the formulation of the mixture while it is delivering the product. In addition, the outlet for the base products or for the mixture is moved relative to a container or a support defining an application surface. In one particular embodiment of the invention, the dispensing system is designed to calculate the way in which the mixture evolves as a function of the color C1 of one area to be treated and of the color C2 of another area to be treated. For example, with the knowledge that the chin requires a color C1 and that the cheek requires a color C2, the dispensing system may vary the formulation of the mixture while it is delivering it in order to graduate the color between these two colors. This makes it possible for example to better conceal imperfections of the face while ensuring that the end result is realistic, or allows color to be graduated for beautifying purposes. The dispensing system may also be designed such that the user can command a variation in color of the mixture dispensed without the start and/or end colors having been set beforehand. To do that, the dispensing system may possess a location or auto-location system and deduce from a look-up table the colors C1 and C2 that it has to create and therefore the changes in the mixture that it has to make.

The dispensing system may have an outlet head, in particular in the case of an airbrush, which is mobile and steered. This option then makes it possible to achieve graduated effects without moving the rest of the dispensing system. For example, the dispensing system is located near to the cheek, then a control system is triggered that will automatically steer the variation in formulation of the mixture and the movement of the outlet head so as, for example, to make the center of the cheek redder than the periphery thereof, with a graduation between the two.

The dispensing system may even be used to create tailor-made products that are kept for several applications.

It is also possible to produce solid or semi-solid products.

Manufacture of "Bespoke" Compacts or Other Solid or Semi-Solid Products

The dispensing system may be designed to allow a mixture to be chosen and delivered to a container such as a cup. The mixture preferably comprises compounds which are such that the mixture can set solid.

More preferably, use is made of compounds that make the setting especially rapid. These compounds are either deposited in the container before or after it is filled with the other ingredients, or are provided in the compartments of the dispenser with the other constituents of the base products, or are contained in the dispenser in a compartment especially designed to contain them.

Specific compositions which may harden quickly by chemical, biochemical or physicochemical reaction after discharge may thus be dispensed.

These compositions are especially designed for the creation of compacts, namely they:
set solid,
yield a material that can crumble if rubbed, and are preferably colored.

Preferably, these compositions are very rich in solid particles, with for example more than 10% by mass of solid particles relative to the total mass of the composition, better still more than 20% by mass of solid particles relative to the total mass of the composition, even better still more than 30% by mass of solid particles relative to the total mass of the composition, preferably between 10 and 40% by mass of solid particles relative to the total mass of the composition.

These compositions may contain absorbent particles or reactive compounds, such as those that react in contact with the air, for example cyanoacrylate or alpha-silanes or those which react to light, notably UV.

The container into which the mixture is dispensed may contain a compound A and the dispensed compositions may contain a compound B, A and B being chosen to react with one another and solidify the mixture.

In one particular embodiment of the invention, the dispensing system incorporates a heating means, for example with an electrical resistor, to create lipsticks or other waxy products. In that case, the base products are heated before being delivered.

The dispensing system may also comprise a means for supplying heat and/or light energy, after the mixture has been dispensed into a container, for example an electrical resistor or an LED, notably UV. This energy may accelerate the setting-solid of the dispensed mixture.

Preferably, the mixture is homogenized before it sets solid.

Creation of Color Palettes

The dispensing system may have a support, having several regions, and may be designed to automatically generate several mixtures deposited in said regions, for example a series of colors suited to various parts of the face.

The support may define several cavities to receive the mixtures or may bear several containers, for example in the form of cups, potentially cups that are separable from the support.

In one particular case, the support adopts the shape of a face with regions for receiving the mixtures for targeted application areas.

The support may be able to move, notably to rotate, with respect to the body of the dispenser and, for example, may be driven in its movement by the dispenser so that various spaces or containers can be filled in succession.

Cup-Type Dispenser

There is a benefit to having a dispensing system capable of delivering a mixture that the user can easily pick up. Moreover, in cases in which the base products delivered by the dispensing system are not already blended, there is a need to allow the user to perform the mixing easily.

The dispensing system preferably has a cup and a dispenser for filling the cup with at least one product, the cup being secured to the dispenser at least while it is being filled.

The cup is sometimes also known as a "crucible" and that term should be understood in its broadest sense.

A "cup secured to the dispenser" should be understood as meaning that the cup is held, notably immobilized, at least temporarily, on the dispenser, being for example fixed to the latter by screws, magnetic attraction, clip-fastening, bayonet locking, clamping, or produced with a part of the dispenser body by material molding. When it is secured to the dispenser, the cup allows the latter to be manipulated in one hand, the cup remaining in place on the dispenser while the latter is being moved around.

The dispenser may be offered to the user with the cup already in place.

As an alternative, the cup is installed by the user the first time the dispensing system is used.

The cup is preferably less deep than it is wide, making access to it easier and allowing the product, notably the mixture, to be picked up with an applicator or a finger.

Preferably, the cup is separable from the dispenser and constitutes one outlet interface that can be chosen from a collection of outlet interfaces that can be mounted on the dispenser, at the choice of the user and according to the making up to be performed, as described in detail below.

Preferably, the dispensing system comprises several filling orifices for filling with different base products, opening into the cup. Thus, the mixing of these products may take place in the cup.

The cup preferably has a bottom that is concave toward the outside, making it easier for the user to clean it between two uses.

In addition, this may make the product easier for the user to pick up and the base products easier to mix.

Preferably, the dispenser allows at least two base products to be delivered into the cup, in adjustable proportions, and better still at least three products.

In one exemplary embodiment, the dispensing system has at least two cups that can be selectively fed by the dispenser. This may allow the user to fill these two cups quickly with mixtures with different characteristics. This may facilitate the testing of colored substances and/or allow the preparation of several different color mixtures intended for making up respective areas of the face. The cups may be associated with identifiers that remind the user of the area of the face for which a mixture contained in a given cup is intended.

The cups may be able to move relative to the dispenser, being for example borne by a mobile support such as a turret that is rotatable with respect to the dispenser or by a slide capable of translational movement with respect to the dispenser.

The dispensing system may comprise a lid for closing the cup. This closure lid is preferably transparent so that the user can see the color of the mixture contained inside.

When the cup is separable from the dispenser it may if necessary be introduced into a housing that allows it to be transported more easily, this housing being able, if necessary, to contain a mirror and/or an applicator. The lid of the housing may in this case act as a lid for the cup.

The volume of the cup may be between 2 and 1000 mm$^3$, better still between 100 and 1000 mm$^3$, even better still between 250 and 750 mm$^3$.

The base product(s) delivered into the cup are preferably foundations, but as an alternative may be makeup products for the lips or eyelids.

The cup preferably has a shape that exhibits symmetry of revolution. As an alternative, it has a polygonal or some other contour. Its largest inside diameter, or that of the inscribed circle in the case of a noncircular contour, is preferably between 2 and 100 mm, preferentially between 5 and 40 mm. Its depth is preferably between 1 and 10 mm, better still between 3 and 8 mm. Preferably, the size and shape of the cup either allow direct application of the mixture to the skin or allow the mixture to be picked up on a finger or using an applicator. The cup may be made of an elastically deformable material, making it possible for example to turn the concavity of the bottom of the cup inside out and empty it more easily or use it to apply the product.

The cup may have no blender; in that case, the base products may arrive in the cup from the dispenser in the unmixed state, via distinct respective dispensing orifices. As an alternative, the dispenser incorporates a blender and the base products arrive in the cup already blended.

The cup may also incorporate a static blender as described in detail below, which is fed via distinct filling orifices of the dispenser and which preferably delivers the mixture into a cavity of the cup situated above the blender.

A further subject of the invention is a method for preparing a makeup product, comprising the step of filling a cup of a dispensing system as defined above with at least one base product from the dispenser.

Several products may be delivered into the bottom of the cup, then blended using a finger or an applicator, or a static blender incorporated into the cup.

The cup is preferably filled from beneath. Dispensing systems using a sonotrode have been proposed in the past.

The cup according to the invention is not intended to vibrate in order to dispense the product(s) conveyed by the feed passage(s) supplying it. It differs from a sonotrode. Preferably, the cup is made of plastic.

Blender Incorporated into the Outlet Interface

There is a benefit in having a dispensing system capable of delivering a mixture that can easily be used, notably picked up by the user, without the need for an additional mixing action on the part of the user.

The dispensing system may have a dispenser having outlet passages for base products and an outlet interface that is separable from the dispenser, this interface having a static blender that preferably delivers the mixture into a cavity where it can be picked up.

The static blender may be situated under the abovementioned cavity. The dispensing system is then particularly suited to the creation of compacts, using cups with an in-built static blender as outlet interfaces. In that case, the cavity of the cup is filled with product from beneath. After passing into the static blender, the blended base products cover the blender.

It is possible to use several outlet interfaces and to fill them with different respective mixtures, without the need to purge the blender, thereby reducing losses of product. The outlet interface may be a single-use interface, if necessary.

Preferably, the static blender has a central chamber communicating with base product intake ducts. This central chamber may communicate with a peripheral chamber having a series of partitions which act as deflectors for the mixture and create shearing thereof.

The peripheral chamber may have a perforated annular partition defining perforations through which the mixture passes as it circulates in the peripheral chamber. The central and peripheral chambers may be closed at the top by a wall which defines the end wall of the cavity receiving the mixture.

The end wall of the peripheral chamber may be of helical shape about the axis of the cup and of a height that decreases in the direction toward the outlet. The latter may open ahead of a connecting ramp connecting the end wall of the peripheral chamber and the top wall of the blender, this connecting ramp preferably being a portion of a helix extending the helix formed by the end wall of the peripheral chamber.

Preferably, the peripheral chamber comprises the abovementioned annular partition and radial partitions that force the mixture to circulate alternately between upper and lower regions of the peripheral chamber and between radially inner and outer regions, the mixture circulating for example from an upper and radially outer region to a lower and radially outer region by passing through the abovementioned annular partition.

The blender may have an outer body in which a component forming the core of the blender is housed, the outer body radially closing the peripheral chamber on the outside and comprising an upright that separates the central and peripheral chambers.

The outer body of the blender and the core of the blender may each be produced as a single piece by injection molding.

Reduced Dead Volume

There is benefit to be had in reducing the losses of product when changing the formulation of the mixture and in allowing the color of the mixture to be varied as quickly as possible during application, particularly when the dispenser is coupled to an airbrush.

The base product can leave the corresponding cartridge through an outlet passage of the cartridge, this outlet passage opening out at the outside of the dispenser or near the external surface thereof.

The outlet passage may notably open into an area in which the mixture is picked up or close to this area, notably less than 5 mm away, better still less than 3 mm away, better still less than 1 mm away, or even better still flush therewith.

The cross section of the outlet passage is, for example, between 1 and 3 $mm^2$.

Thus, each base product coming from a cartridge can leave the dispenser without mixing with a base product from another cartridge and the dead volume that cannot be picked up and is likely to increase the inertia of the system is minimized. The product is more quickly available without having to circulate through special passages in the housing of the dispenser, thereby avoiding a painstaking purging step in the event of a cartridge change.

The outside of the dispenser may be the product pickup area, notably when the dispenser is produced with a cup that is not designed to be removed, into which the mixture is dispensed, or a dispensing area intended for the mounting of a removable outlet interface, which defines the pickup area. This outlet interface may have a cup as defined above. This mounting area corresponds for example to the outside of the housing of the dispenser in the absence of an outlet interface.

The mounting area may be substantially planar and perpendicular to the longitudinal axis of the dispenser housing.

The dispenser may have three cartridges of base products.

The dispenser may have housings for receiving the cartridges, which are preferably received removably in the dispenser. The latter may comprise passages for ducts for the cartridges defining the outlet passages.

The length of these ducts is preferably such that the ducts are set back slightly from the end or lie flush with the cavity used for picking up the product or, as an alternative, are set back slightly from or lie flush with the end face of the housing of the dispenser that defines the mounting area.

These ducts of the cartridges may be end pieces used for causing the pistons to move within the cartridges, as described in detail above.

Multiple outlet interfaces There is a need to be able, using the same dispensing system, to achieve different makeup looks easily and be able, if so desired, to make up areas as different as the skin, the lips, the eyelashes or eyebrows.

The dispensing system may comprise an assembly having a dispenser of at least one cosmetic product, in particular makeup, and at least two outlet interfaces, each of which can be mounted removably on the dispenser, these outlet interfaces being able to receive the product(s) delivered by the dispenser, preferably being chosen from the following:
an outlet interface having a container, notably a cup, allowing the product to be picked up using a finger or using an applicator,
an outlet interface allowing the product to be delivered to a spray system, notably an airbrush,
an outlet interface having several regions for receiving the product, which can move relative to the dispenser,
an outlet interface that allows the product to be delivered to a dispensing end piece.

Preferably, the assembly comprises at least three of said outlet interfaces, or better still the four outlet interfaces.

The dispenser may comprise at least two different base products and allow these to be delivered in variable proportions and, preferably, the dispenser comprises three different base products and allows these to be delivered in variable proportions.

Each outlet interface may have a base allowing it to be fixed to the dispenser. This fixing may be done using screws for example, but preferably the base is designed to allow an outlet interface to be removed and replaced without the need for tools. It is, for example, a quarter-turn fixing or a fixing using an external locking ring.

The outlet interface and/or the housing of the dispenser may comprise seals allowing sealed communication between the housing of the dispenser and the outlet interface. If appropriate, the dispenser is designed to recognize the outlet interface mounted above, for example by virtue of the outlet interface having identifiers in the form of specific reliefs which are detected by the dispenser, or in the form of an electronic chip that the dispenser recognizes. That may allow the operation of the dispenser to be adapted to the outlet interface mounted above. The dispenser may communicate information about the outlet interface it is bearing to a computer system, and the computer system may, on the basis of this information, display a specific screen and/or run a specific program for controlling the operating parameters of the dispenser so as, for example, to adapt the dose dispensed and/or the flow rate to the type of outlet interface.

The user may be initially offered several outlet interfaces with a common dispenser within one and the same package, for example a case or a cardboard box.

A further subject of the invention is a makeup method involving the step of selecting an outlet interface, mounting it on the dispenser, and delivering the product(s) contained in the dispenser to the interface.

Mapping and Learning

The term "mapping" should be understood here as meaning a process of indexing a color with an area, with recording.

The mapping may relate to applications to areas smaller than 1 cm$^2$. However, the naked eye then has difficulty in discerning whether the result obtained is adequate, and it is preferable to substitute an instrumented evaluation with magnification for evaluation by the naked eye. Small quantities of colored substance may be applied with a finger, using conventional tools such as brushes, or using specialist applicators.

The map may be generated during a learning period in which the user carries out tests with mixtures on different areas of the face; once created, the map can then be used for everyday makeup. This learning period may take account of the resistance and the comfort. In the process, the user tests several rheologies and inputs the best adjustment obtained.

Specific graphic interfaces can be used during the learning period and during the period of use of the map.

In particular, the dispensing system may be used with a graphic interface in which the operator sees the face, which is for example a schematic, figurative or accurate representation such as a photograph or a 3D simulation. In that case, the operator can point at part of the face on the screen to show and/or deliver the appropriate color.

The graphic interface may also show the other areas of the face where use of that same color is appropriate.

To create the map, the operator applies a color, then makes an assessment.

The areas of the face can be treated one after the other; for example, the exercise is carried out on part of the cheek, then on the nose, etc.

Another option is to create a given mixture and apply this same mixture to several areas. The operator then needs to look for the area of the face to which the color is suited. The mixture is then indexed in the computer system which attributes it to the area(s) of the face for which it is suitable.

A learning process for a dispensing system according to the invention, comprising a dispenser for dispensing a mixture of variable color, and a computer system for selecting a color and for storing data, comprises the steps of
  a) selecting at least one color with the aid of an interface of the computer system,
  b) delivering, with the aid of the dispenser, at least one mixture of the selected color,
  c) evaluating the mixture(s) dispensed following the application thereof to at least one area of the face,
  d) memorizing the characteristics of at least one mixture, notably a mixture that the user wishes to be able to recall, and of at least one area on which it has been tested.

This memorizing can be carried out notably with a view to subsequent dispensing of this mixture for making up said area.

Preferably, the computer system is designed to allow the user to indicate whether or not the result of the test is satisfactory, or even to inform same of the comparison with a test carried out earlier.

It is also possible to create a given mixture and to look for the area of the face for which it is suitable. The mixture is then recorded, being attributed to the area(s) of the face for which it is suitable, in a look-up table that will be used subsequently in order to deduce which mixture to use on the basis of an area of the skin.

The same procedure can be adopted with other mixtures in order to create a map of the entire face and thus have a complete look-up table for the face.

It is also possible to create a given mixture, apply it to a given area, and then vary the mixture until the most suitable mixture is obtained. The mixture is then recorded, being attributed to the area(s) of the face for which it is suitable, in a look-up table that will be used subsequently in order to deduce which mixture to use on the basis of an area of the skin.

Preferably, the computer system evaluates and memorizes the quantities used area by area. Such a method, which uses "test patches" makes it possible to identify the product(s) required by the person wishing to apply makeup. Thus, the dispensing system can be used at sales outlets to advise people wishing to apply makeup or at home in order to define correctly which products to order.

The interface of the computer system preferably has a touch screen displaying the color of the mixture when it is selected.

The interface may display a face and allow the computer system to be informed by selecting the area on the face displayed.

The computer system is preferably designed to allow an area, mixture reconstruction parameters, and the date of the test and/or any other identifier of the mixture to be associated with one another.

The computer system is preferably also designed to allow at least one of the following data: the name of the area, the period of the year, the name of an event, a user identifier and the age of the user, to additionally be associated with said area, with the mixture reconstruction parameters, and with the date or identifier of the mixture.

Steps a) to c) may be repeated at least once before the characteristics of the mixture are memorized in step d).

The computer system may be designed to search a database for the reference of a commercial product on the basis of the characteristics of the mixture identified as being suitable for at least one given area, and to relay this information to the user.

The selection in step a) may be carried out using an expert system, which may or may not be external to the computer system.

The expert system may analyze an image of the user in order to propose a mixture color at least on the basis of the image analyzed.

Step a) may be preceded by the computer system proposing to the user a color and an area to be tested with a mixture of this color.

The computer system may be designed to allow the user to inform same of his or her assessment of the result of the test in step c) and to generate a proposal to modify the mixture to be selected upon return to step a).

The computer system may be designed to propose at least one color of mixture in step a) depending on an application area of which it has been informed by the user.

The computer system may be designed to propose at least one application area in step a), on the basis of a color of which it has been informed by the user.

The dispenser may deliver, in step b), at least two mixtures of different colors, preferably separate, so that they can be applied simultaneously to the test area.

This may allow time to be saved and make it easier to compare the results.

A further subject of the invention is a method of making up using a dispensing system according to this aspect of the invention, in which:
- a) the user sends the computer system a request regarding a need for makeup,
- b) in return, the computer system generates a proposed color for making up an associated zone, on the basis of the learning performed beforehand, and
- c) the computer system operates the dispenser to produce the mixture of the proposed color, notably if this is validated by the user.

Such a method may use a map previously established with the user.

A further subject of the invention is a computer program product containing code instructions which, when run in a computer system, allow the computer system to be made to:
- allow the user to select at least one color and/or one application area, notably using an interface such as a touch screen,
- operate a dispenser in such a way as to deliver a mixture of the color selected by the user,
- allow the user to trigger the memorizing of the color of the mixture and of an associated application area, notably with a view to subsequently dispensing the same mixture, notably on the same area.

The computer program product may comprise code instructions which, when run in a computer system, allow the computer system to be made to:
- receive a request from the user regarding a need for makeup, notably using an interface such as a touch screen,
- propose, on the basis at least of data generated by the learning process as defined above, at least one color and/or one application area,
- operate a dispenser to produce the mixture of the proposed color, notably if this is validated by the user.

Remote Assistance

It is desirable to be able to assist the user in applying makeup, notably in choosing the correct colorings, by virtue of a method of applying makeup involving the steps of:
- allowing a video link to be established, for example over the Internet, between a camera on a first site and a second site,
- allowing the second site to directly or indirectly operate a dispenser present at the first site, this dispenser making it possible to vary the color of a mixture dispensed,
- allowing a person present at the first site to apply the mixture dispensed and to send a corresponding image to the second site, so as to receive in return information relating to the makeup result.

The second site may notably have a viewing screen which allows an adviser sitting at this screen to see the makeup result with the product dispensed by the dispenser and advise the person who has applied the makeup. This adviser may in return influence the dispenser to alter the color of the mixture and adapt it to best suit the face of the person present at the first site. Thus, this person controls the mixture delivered by the dispenser. The first person may make herself up under the gaze of the second. The second person sees the result of the test on their screen and can thus correct the mixture that this second person will control remotely until the ideal makeup is obtained.

If appropriate, the video acquisition can be calibrated using a test pattern or with the mixture dispensed by the dispenser onto a reference surface. That then allows a more faithful display of the makeup applied at the first site.

Preferably, the video link between the two sites is a two-way link.

The first site may receive a tutorial from the second site, if appropriate.

Identifiers of the base products may be communicated to the second site; this may make it possible to precisely determine the color of each of the base products.

The method may involve memorizing the dispenser setting parameters once a given mixture is considered to be satisfactory. Preferably, this memory storage may be commanded from the second site. The memory storage may be in the computer system present at the first site and/or on an external server.

One alternative may be to have one person working to help several apply makeup. This embodiment makes it possible to develop makeup artists and their work, either within an institute or over the Internet. It also allows people with limited capabilities, such as people with poor eyesight, or people who have difficulty discerning colors, or the elderly, or those lacking in self-confidence to apply makeup.

Operation Via Touch-Sensitive Interface

There is a need to make it easier to control the dispensing system and notably the choice of the color of the mixture dispensed.

In another of its aspects, independently of or in combination with the other aspects thereof, and notably with the foregoing, one subject of the invention is thus a dispensing system comprising a dispenser and a computer system for operating the dispenser, this computer system comprising a touch screen on which the color of the mixture may be displayed and a selection means that can be moved over the screen in order to vary the color of the mixture dispensed.

Preferably, the screen displays end-point colors between which the color of the mixture can be selected by moving the selection means between these end-point colors.

The screen may display a scale of colors between at least two colors, or an area, notably of triangular outline, within which the selection means can be moved. This area may locally show the color of the mixture depending for example on the distance from each of the vertices, each one embodying a pure base product.

The computer system may perform some of the calculations necessary to determine the fractions of each of the base products that lead to a mixture of the desired color.

The computer system may be a smartphone, a camera phone, a tablet, or a personal computer. As an alternative, it is incorporated into the housing of the dispenser.

The computer system may have a camera. The latter can be used notably for capturing an image of the user and/or of the mixture.

The computer system may be designed to display an image of a face, in order to make it easier to identify the areas to which the mixture is to be applied.

Coupling of the Dispensing System to a Spray Means

The dispensing system may have or be connected to a means of spraying the mixture, preferably an airbrush.

A subject of the invention is also an assembly comprising:
- a spray means, preferably an airbrush having a pickup chamber subjected to a stream of entrainment air,
- a dispenser having at least two compartments containing different base products, the products being delivered to the spray means preferably via distinct distribution orifices.

The dispenser may have three cartridges containing makeup products of different colors.

The airbrush may have a stylus defining the pickup chamber, the stylus being fixed to the dispenser or to an outlet interface fixed to the dispenser, or forming an integral part of this outlet interface.

The dispensing system may have a circuit controlling operation of the dispenser, allowing the proportion of base products delivered to the pickup chamber to be varied while the airbrush is in operation. The proportions may be modified depending on the movement of the airbrush relative to the surface onto which the mixture is sprayed. This movement may be mechanized, if appropriate.

This control circuit may have or be constituted by a computer system as defined above.

The housing of the dispenser may act as a hand grip when the assembly is being handled for delivering the mixture.

The dispenser may have a camera and/or one or more sensors such as accelerometers so as to automatically locate the area to which the mixture is applied, and so as to be able to automatically regulate the color depending on the position, if appropriate.

A further subject of the invention is a method for applying makeup using an assembly as defined above, in which a mixture is sprayed onto the skin using the spray means, notably the airbrush.

The composition of the mixture can be modified as the airbrush is moved relative to the skin. A graduated effect can be achieved.

This aspect of the invention is based on the observation that the dispenser can be used to supply the spray system, notably the airbrush, while at the same time allowing the dispensing system to be responsive enough to allow a change in the color of the mixture dispensed while the face is being made up, notably as the area to be made up changes.

It may be advantageous for the dispensing of products to be performed iteratively, notably with dispensing times that are not phase-shifted between the various products.

This may make it easier to vary the composition of the mixture dispensed over time.

The mixture may be created directly in the airbrush, with practically no troublesome dead volume, thus allowing the mixture sprayed to be changed in real time.

The depression created in the pickup chamber is strong enough to entrain the base products without in any way impeding the metering.

The depression which prevails in the pickup chamber is for example between 10 mbar and 200 mbar, better still between 50 and 150 mbar, even better still between 75 and 125 mbar.

The viscosity of the base products as measured at 1 atm and 25° C. with a CONTRAVES TV rotary viscometer fitted with an MS-r3 or MS-r4 measuring bar at a frequency of 60 Hz after 10 minutes of rotation of the measuring bar is, for example, between 0.05 Pa·s and 50 Pa·s.

The cross section of the passages along which the base products arrive in the chamber is, for example, between 1 and 3 mm², better still between 2 and 3 mm².

The product is preferably supplied continuously.

It is also possible to apply immiscible or reactive base products, such as an aqueous gel and an oily gel, simultaneously, and these will be deposited directly onto the skin in a pixelated manner, producing a kind of gel/gel in situ, reactive silicones, or colorants that react with one another. The ratios of base products can be adjusted depending on the particular result desired. For example, in the case of aqueous gels and oily gels, the ratio corresponding to the volume of the first base product to the volume of the second base product could be varied between 10/1 and 1/10, better still between 5/1 and 1/5.

Location or Auto-Location System

The dispensing system according to the invention may have a location or auto-location system.

A location system is the name given to a means via which the person inputs the area that she is to treat. This can be performed notably using systems that leave at least one hand free. Thus, an interface of a computer system such as a touch screen, a joystick, or voice recognition system can be used.

An auto-location system is the name given to a means for inputting the area that is to be treated without intervention on the part of the person. This can be achieved using one or more accelerometers which deduce, from the movements, the directions targeted by the person or by a camera and an image recognition system.

An example of a dispensing system that can be used to implement the invention according to this third aspect has already been described with reference to the figures.

Therefore, the description of the figures will not be repeated here.

Example 1 (Third Aspect of the Invention)

Several base products are created (the proportions are by mass)

| | |
|---|---|
| A1: | |
| Ultrahold strong from BASF | 10% |
| (acrylate copolymer of Tg = 80° C.) | |
| Carbopol Ultrez 10 (Lubrizol) * | 1% |
| Monoethanolamine qs | pH 9 |
| Water qs | 100% |
| B1: | |
| AQ 1350 (Eastman chemicals) | 10% |
| (polyester bearing a sulfonic function, Tg = 0° C.) | |
| Carbopol Ultrez 10 (Lubrizol) * | 1% |
| Monoethanolamine qs | pH 9 |
| Water qs | 100% |
| C1: | |
| Pigments (iron oxide, titanium dioxide 20/80) | 20% |
| (polyester bearing a sulfonic function, Tg = 0° C.) | |
| Carbopol (Lubrizol) * | 1% |
| Monoethanolamine qs | pH 9 |
| Water qs | 100% |

* Crosslinked carboxyvinyl homopolymer synthesized in the ethyl acetate/cyclohexane mixture Test Mixtures are created:

The system is used to deliver doses of 50 to 200 mg of product. The mixtures are then spread little by little, dose by dose.

Proportions of 50/10/40 for making up the cheekbones in order to give a colored and shiny effect (500 mg)

20/40/40 for the eyelids in order to confer color and a slight shine thereon. The flexibility of the film is enough not to cause discomfort in this sensitive and supple part of the body (100 mg total)

20/20/60 for concealing local imperfections such as dark marks. (200 mg total)

Example 2 (Third Aspect of the Invention)

Several formulations are created

| | |
|---|---|
| A1: | |
| Ultrahold strong from BASF * (Tg = 80° C.) | 10% |
| Jaguar HP 60 (Rhodia) | 1% |
| Monoethanolamine qs | pH 9 |
| Water qs | 100% |
| B1: | |
| AQ 1350 (Eastman chemicals) (polyester bearing a sulfonic function, Tg = 0° C.) | 10% |
| Jaguar HP 60 (Rhodia) | 1% |
| Monoethanolamine qs | pH 9 |
| Water qs | 100% |
| C1: | |
| Mexoryl SX (UVA screening agent) | 20% |
| Jaguar HP 60 (Rhodia) | 1% |
| Monoethanolamine qs | pH 9 |
| Water qs | 100% |

* Acrylic acid/ethyl acrylate/N-tert-butylacrylamide terpolymer

The system is tested with:
A1 → Compartment 1
B1 → Compartment 2
C1 → Compartment 3
Test
Mixtures are created:
The system is used to deliver doses of 50 to 200 mg of product. The mixtures are then spread little by little, dose by dose.

Proportions of 50/10/40 for protecting moles (500 mg)

20/40/40 for protecting the entire face. The flexibility of the film is enough not to cause discomfort in this sensitive and supple part of the body (100 mg total)

20/20/60 for treating and protecting the area around the eyes, avoiding the risks of the appearance of marks.

D) Dispensing System for Creating Mixtures with Compositions Having a High Solvent Content This fourth aspect of the invention relates more particularly to dispensing methods and systems, notably for dispensing a makeup, care, fragrancing and hygiene product.

Many people wish to make themselves up in order to enhance their appearance, particularly their face. They also wish to be able to protect their skin in order to maintain an attractive appearance or to treat the skin in order to correct defects.

There are two types of reason why these people may wish to do this:

Local treatments (typically over several square centimeters). This may be to conceal marks, wrinkles or pores, protect moles from UV light, treat wrinkles or pores, or apply odorous compounds.

Treatments over large surfaces (100 cm2 or more), notably to change the look of the face by changing color or realizing protection against UV radiation.

In these different cases, the operation involves applying a product containing one or more ingredients and covering the skin or an area of skin therewith.

Thus, compositions containing insoluble ingredients (pigments for makeup, powders for anti-grease effects) are applied. These ingredients may be conveyed in water, for example.

Ingredients that are soluble in the medium are also applied. In this case, there are two scenarios:

When the ingredients are soluble in water, water can be used as solvent.

When the ingredients are soluble in organic solvents but insoluble or insufficiently soluble in water, formulation is frequently carried out in a formulation containing water, combining these ingredients with peptizers, surfactants or compatibilizing molecules. The compositions are water- or water+oil-based. This approach has the limitation of leaving surfactants/peptizers on the skin, causing certain defects such as a sticky touch.

Another approach is to dissolve them in an organic solvent.

Approach I: Dissolution of the Ingredients in a Heavy Organic Solvent.

They can be dissolved in a heavy organic solvent (having a high boiling point (>100° C.)), such as oil. This approach is often unsatisfactory since, even though numerous tests have been carried out to find relatively unobtrusive organic solvents (in the sense that they are not noticed once they have been applied), the limitation of this approach is that it is not very comfortable, both during application (hands become greasy) and afterward (impression of feeling a greasy layer on the skin). Moreover, the layers produced fairly quickly lose their effect (if only by wear or evaporation). There are two situations:

a) If these compositions are applied globally, the discomfort and elimination are significant problems. In order to reduce discomfort, the best thing is to apply limited quantities of composition. This increases the risks of elimination, causing a need to reapply the composition.

b) If these compositions are applied locally, it is especially the problem of wear that is problematic. This is because, if an uncontrolled movement removes the film in certain areas, the effect is lost. (loss of concealing/protective power etc. in the case of makeup/photoprotective compositions etc.).

Thus, in both situations, there is a need to apply the compositions successively, and in small quantities, during the day. In particular for the local treatment, since the necessary doses can vary from dose to dose, there is a need to be able to regulate the quantity and/or the quality of the ingredient(s). This need also exists for global treatments, since, from application to application, it is necessary to be able to regulate the quantity and/or the quality of the ingredient(s). For example, if makeup has been applied in the morning, and the makeup needs to be reapplied at lunchtime, it will be necessary for the concentration of concealing ingredients to be adapted to the situation (more or less depending on the elimination).

Approach II: Dissolution of the Ingredients in a Light Organic Solvent.

It is also possible to use a lighter solvent (ethanol for example). These solvents leave few if any traces, which is an advantage. The speed of drying of the organic solvent is a drawback, notably for global treatments. For local treatments, the speed of drying is not so bothersome, since the composition is applied a little at a time. For global treatments, the speed of drying requires that the product be applied a little at a time.

In both cases, it is advantageous to be able to vary the quality and/or quantity of the ingredients.

a) For global treatments, since the speed of drying makes spreading impossible, it is necessary to be able to vary the quantities of ingredients. This is because, when a makeup composition (which thus comprises concealing ingredients) is applied, it is found that certain areas are more covered than others. This irregularity, which is detrimental to the appearance, needs to be corrected by the application of further touches, the ingredient concentration of which will need to be adapted to the situation. Little concealing ingredient if the irregularity is small. High concentration of concealing ingredient if the irregularity is large.

b) For local treatments, it is necessary to be able to regulate the quantity and/or quality of ingredient since it is desired i) to adapt these parameters to the situation of each area of the face, ii) to be able to apply small touches little by little. For example, in order to conceal a mark, a first touch will be applied that contains a high concentration of concealing ingredient. Next, by eye or with a device, the quantity to be added will be estimated. Thus, it will certainly be necessary to make a second application at the same location, by putting on a layer of composition with fewer concealing ingredients. And so on until a perfect result is obtained in that the mark is no longer visible.

Thus, in the case in which the ingredients are conveyed in a composition based on a light organic solvent, there is also a need to be able to regulate the quantity and/or the quality of the ingredient(s) and to apply a little at a time.

Particular case of fragrancing or refreshing compositions.

Here too, the user wishes to be able to apply the compositions to their face. Either in small localized touches (perfumes), or more globally (refreshing compositions). In the first case, the fragrancing ingredients are generally insoluble or not very soluble in water. It is thus necessary to dissolve them in an organic base which may be a heavy or light solvent. In the second case, the composition may also contain fragrancing ingredients. Thus, the compositions are generally fragrancing ingredients in ethanol (colognes). There is a need to vary the quantities of fragrancing ingredients in order to alter the effect obtained.

In summary, there are several needs to make available in small quantities oily or light-solvent-based compositions where the quality and/or the quantity of ingredients (soluble or particulate or soluble+particulate) in these compositions can be controlled.

It will be understood that, in all of these situations, it is necessary for the system to be able to deliver small touches of composition (with the correct setting) in small amounts of time. Typically a few seconds or less. It will also be understood that the system has to be easy to use during the day and thus preferably portable. It will also be understood that the system has to be easy to control, with as few human actions as possible. Thus, the system has to be able to be programmed, in particular programmed for the personal needs of the user.

Thus, consideration is given to systems formed of:
1) a dispensing system
2) several compartments in which cartridges containing the compositions are placed
3) the compositions do not contain the same quantities and/or quality of ingredients
4) a control system The production of such a system is associated with precision problems. Without sufficient precision, the quantities delivered and thus the mixtures are sometimes far from the quantities desired. Several tests have been carried out with different cartridges and tests have been run to vary the quantities and/or qualities of ingredients. It is apparent that the adjustments are made poorly and the quantities and/or qualities of ingredients obtained are far from the targets.

Thus, one subject of the invention, according to a fourth of its aspects, is a system for dispensing a cosmetic product, comprising a dispenser that receives at least two cartridges that each have a reservoir containing a base product, a first base product comprising at least one organic solvent, the cartridge that contains it having a body made of at least one of the thermoplastic materials chosen from the list comprising simple polyolefins, polyvinylchloride (PVC), polyamides and semi-aromatic polyamides, polyphenylene sulfide (PPS), polybismaleimide, polyurethanes, polyesters, polyepoxides, polyether-block-amide, polyacetal, polyetherketone, polyetherimides (PEI), polyimides, polyamide-imide (PAI), FEP (perfluorinated ethylene propylene), PFA (polyfluoroalkoxy), ECTFE (ethylene chloro trifluoro ethylene), and ETFE (ethylene tetrafluoroethylene), and mixtures thereof, and preferably simple polyolefins, polyvinylchloride (PVC), polyamides and semi-aromatic polyamides, polyphenylene sulfide (PPS), polybismaleimide, and mixtures thereof.

According to this fourth aspect of the invention, the latter may also have one or more of the following features:
the cartridge comprises the first base product and, besides the body of the cartridge, comprises other components exposed to the first base product, at least one of these components and preferably all of these components being chosen from the above list.
the total content of organic solvent(s) in the first base product is greater than or equal to the total water content of the first base product,
the total content of organic solvent(s) in the first base product is greater than or equal to 50% relative to all of the solvents, the cartridges are identical, except for their content and a possible identifier,
at least one of the compositions comprises a perfume,
the cartridges are received in a removable manner in the dispenser, each product leaves the cartridge through an outlet passage of the cartridge, the outlet passage being defined by a dispensing end piece of the cartridge, said end piece being driven in rotation relative to a body of the cartridge by a drive mechanism of the dispenser in order to dispense the base product contained in the cartridge.

The invention according to this fourth aspect is thus based on the use of a dispensing system having cartridges, base products, and control, the cartridges being formed from particular materials. As a result, precision is good.

The invention according to this aspect thus makes it possible to provide a solution to this question of the delivery of small quantities of oily or light-solvent-based compositions where the quality and/or the quantity of ingredients (soluble or particulate or soluble+particulate) can be controlled. As a result, it is possible to apply makeup globally or to small areas, it is possible to treat defects (wrinkles, pores, marks), apply protective elements globally or in precise areas, and to perfume oneself. It is also possible to find the most suitable adjustments of formulation. Specifically, the system makes it possible to deliver small quantities and as a result, after application, it is possible to identify whether the adjustment is suitable or to find a new one. It is thus a means of finding ideal adjustments.

Besides the advantage of providing a solution to these problems, it is also possible to benefit from the system for applying an oil or a mixture of oils (thus when the oils form the ingredient) in particular with essential oils.

Generally, the invention according to this fourth aspect is used in all scenarios in which the vehicle is rich in organic solvent, heavy and/or light, greater than 50% relative to all of the solvents, and in particular greater than 80% relative to the water of the solvents. For example, a fragrancing composition comprising 20% odorous ingredient+70% ethanol+ 10% water is considered to have 87.5% organic solvent (70/80).

The invention according to these aspects can treat cases in which the composition contains, in addition to the organic solvent(s), ingredients that are soluble in the solvent. It also applies to compositions that contain particulate ingredients in addition to the organic solvent(s). (pigments, powders, screening agents).

It is possible to be in a hybrid situation in which several cartridges are used in one and the same system, some of these cartridges having compositions rich in organic solvents and others not. Thus, it is possible to employ the system:

1) All the cartridges are according to the invention (with selected materials), whether or not they are rich in organic solvent.
2) Cartridges according to the invention (with selected materials) for the compositions rich in organic solvent and cartridges outside the invention for compositions which are not rich in organic solvent.

Situation 1) is preferred because it is simpler in terms of the industrial logistics of manufacturing and recycling.

The invention allows one or more areas to be treated. Hereinbelow, the term "area" is used to denote a defined part of the face, fairly small in surface area, covering between 1 cm2 and 100 cm2, better still ranging from 2 cm2 to 50 cm2.

Dispensing System

The dispensing system according to this aspect of the invention may consist of a single device operating autonomously, preferably able to be manipulated in one hand, or of a device that operates in interaction with other components or devices. It may for example entail various outlet interfaces which are mounted on the dispenser depending on the type of effects to be created, as will be specified below. It may also entail a computer system which exchanges information with the dispenser in order to operate the latter, this computer system comprising, for example, a portable terminal such as a smartphone, a camera phone, a tablet, a laptop computer or a dedicated terminal.

Preferably, the dispenser is designed to pressurize one or more compartments containing the base product(s), via volumetric metering devices, preferably a motor causing a piston to move in the corresponding compartment.

The dispenser may be formed of a housing and of at least two or three compartments, and preferably an identical number of motors. For example, the rotation of the motors drives endless screws which push the pistons of each compartment. The advancing movement of the pistons is, for example, controlled by the number of command pulses sent to the motors and/or by the length of time for which the latter are operating. The motors may be powered in sequence or preferably simultaneously.

For example, the motors are powered during an elementary operating cycle for a short duration one after the other or at the same time as one another, so as to dispense corresponding microdoses.

The elementary cycles are repeated, possibly with a pause between them, giving the base products time to flow out of the compartments.

The compartments may be defined by cartridges, which are removed when they become empty. As an alternative, the compartments are permanently present and refilled once they become empty.

Each cartridge may be closed by a stopper that can be removed to allow the cartridge to be cleaned.

Preferably, the housing of the dispenser is of elongate shape along a longitudinal axis, making it easier to handle, and the cartridges are disposed about this axis, inside the housing.

Preferably, the cartridges are inserted from the rear and the mixture is delivered from the front. The cartridges may be inserted individually or, as an alternative, the cartridges constitute a one-piece assembly as they are inserted.

The cartridges may each have a volumetric metering mechanism comprising a piston moved by a drive mechanism of the dispenser in a direction accompanied by a reduction in the internal volume containing the base product and the expulsion of some product. It may be advantageous for the cartridges to have at least a region of their wall that is transparent so that the color of the product contained therein can be seen.

The drive mechanism may have a motorization system formed of motors coupled to gearboxes, of elongate shape parallel to the longitudinal axis of the dispenser, and positioned between the cartridges. Positioning the motors and cartridges in this way makes the dispenser particularly compact.

The base product can leave the corresponding cartridge in a sealed manner, then flow along a passage provided for this purpose in the housing of the dispenser, before leaving the latter.

The cartridges advantageously end in an end piece produced in such a way that, once the cartridge has been inserted into the housing of the dispenser, the end of the end piece terminates flush with the housing. As an alternative, the end piece is long enough to protrude beyond the housing and thus connect various outlet interfaces that can be attached to the housing of the dispenser.

By virtue of the drive mechanism having motors for causing the pistons to advance, it is possible to precisely deliver mixtures in very small quantities. Thus, the drive mechanism can deliver the base products with a minimum flow rate less than or equal to 50 µL/s, better still less than or equal to 20 µL/s, even better still less than or equal to 10 µL/s. Preferably, the drive mechanism delivers flow rates of between 20 and 100 L/s, better still between 40 µL/s and 60 µL/s. It is thus possible to easily create a mixture of around 10 mg. Such a dispensing system is therefore ideal for achieving small touches of makeup, for covering an area of 1 $cm^2$, better still an area of 0.5 $cm^2$, for example.

It is also possible to create larger quantities of mixture such as the quantities needed to make up a cheek or a face. These quantities remain relatively low, however, for example a quantity of between 100 and 500 mg, better still between 150 and 250 mg.

Thus, one subject of the invention, according to one aspect thereof, is a dispensing system comprising a dispenser having a housing, and at least one cartridge received in the housing of the dispenser, this cartridge having a body and a piston capable of moving in the body, the housing comprising a motorized drive mechanism for moving the piston of the cartridge.

Preferably, the cartridge has a dispensing end piece through which the product exits, and this dispensing end piece is driven in rotation by the drive mechanism for moving the piston. The end piece may have at least one rotation-proofing relief, better still two diametrically opposed rotation-proofing studs.

The end piece may bear a seal, notably an O-ring seal. Thus, when changing the cartridge, the seal is also changed, making it possible to get around the problem of seal wear.

The dispenser may have an electronic board for controlling the motorized drive mechanism, this electronic board having the end piece(s) passing through it. This may make it possible to produce a board extending across substantially the entire cross section of the dispenser so that all the electronic components of the dispenser can be grouped together on a single board, thus improving compactness and reliability. The board may extend substantially perpendicularly to the longitudinal axis of the housing. The board may bear a switch for controlling operation of the dispenser.

The dispensing system may be designed to operate in at least two dispensing modes.

In a first mode, referred to as "continuous", the mixture is dispensed as long as pressure is applied to the control switch.

In a second mode, referred to as "dose", a predefined quantity of the mixture is dispensed for each press of the switch.

The end piece(s) may terminate at one end of the housing. This may make it possible to reduce the dead volume, as will be explained in detail below.

The end piece(s) may have at their end a shutoff system for preventing the products from drying out in the duct, for example a self-healing membrane.

The cartridge may have a hollow screw onto which the piston is screwed, the piston being able to move axially along the screw as the latter turns; the piston is prevented from turning in the body of the cartridge. For example, the friction of the piston against the body of the cartridge may be enough to prevent it from turning when the screw turns.

Preferably, rotation is rendered impossible with a cartridge body of non-circular cross section and a piston that is not deformable.

The torque of the motors may be determined electronically depending on the current drawn, and may be used for example to detect that the piston has reached the end of its travel. Information regarding the torque may be transmitted remotely to a computer system that has a man-machine interface, in order that correct operation of the dispenser can be monitored.

In order to adjust the effect, the dispensing system according to the invention has to allow the user to vary the volume delivered from each compartment.

Preferably, the dispenser is operated by a computer system built into the dispenser or external thereto, the dispenser then being able to exchange information with the computer system using a wireless or wired protocol.

The dispenser may thus be operated so as to allow the effect to be adjusted by controlled simultaneous or sequential dispensing of several different base products.

The dispensing of the base products may be continuous; in such a case, the volumes of each of the base products are dispensed in a single shot, simultaneously or in succession.

In the case of simultaneous dispensing, it is beneficial to be able to adjust the respective flow rates of the various base products in order for the dispensed mixture to correspond to the desired mixture at all times. Such a dispensing mode may be suitable in particular when dispensing the mixture by spraying, using an airbrush. To adjust the flow rates it is possible, for example, to alter the speed at which the pistons move, for example in the case where the pistons are driven by an endless screw, by varying the rotational speed of the motors that drive the screw. The products may also be dispensed in a pulsed manner with a dispensing time and a pause in each cycle. By altering the duty cycle it is possible to alter the flow rate.

All the products may be delivered simultaneously during the dispensing time or, as an alternative, the cycles of the various products are phase-shifted from one another so that one product is dispensed while the other products are paused.

In one particular embodiment of the invention, the mixture is delivered into a cavity of a container which may close hermetically or not, for example in the form of a cup, into which an applicator, particularly a stylus or a brush may be slipped. Such a dispensing system is especially suited to liners, glosses and other formulations applied without direct contact with the hands. This container may be removable.

For example, it is used as a lip-color dispenser and has a dispensing system, for example using a screw. When it is not removable, the container may be produced with the body of the dispenser. When it is removable, it may constitute one output interface among others that can be mounted on the dispenser.

The compartments, and in particular the cartridges, may contain all or part of the drive mechanism and, for example, the motorizing system or, better still, part of the motorizing system, the purpose of this being to reduce the number of moving parts in the body of the dispenser outside the cartridges. For example, the cartridges contain the rotor of the motor. Once the cartridges have been installed in the body of the dispenser, the rotors are made to interact with the stators.

The dispensing system is advantageously arranged in such a way as to allow the running of preprogrammed sequences in which the mixture delivered by the system is modified continuously or discontinuously. A "graduated" mode makes it possible for example to progress gradually from a mixture A to a mixture B. In the case where the application is by spraying, notably using an airbrush, this makes it possible for graduations to be achieved simply. An "alternate" mode makes it possible for example to switch quickly from a mixture A to a mixture B several times in succession. In the case of application by spraying, a multilayer application can thus be achieved, with different formulations for two superposed adjacent coats. Another mode makes it possible for example to offer several preprogrammed successive mixtures, the computer system each time indicating to the user how these should be used, for example by display on a screen.

In the case of manual application, the mixtures are dispensed for example into a cup. The person applies the makeup to the recommended place with a corresponding mixture taken from the cup, then, if necessary, cleans out the cup and commands delivery of a new mixture; the operation is repeated as many times as necessary until the person has treated their face fully.

The mixtures dispensed can be homogenized in various ways depending on the type of use. In the case of manual application, it can be done directly on the application area at the time of application or in the cup before the mixture is picked up; in the case of an airbrush application, the pipe of the airbrush is used as a mixing chamber; if the mixture is dispensed into a container for later use, homogenization can be performed by hand or by passing the dispensed products through a mixing chamber situated between the dispenser and the container or incorporated directly into the container, as described in detail below.

The product may be delivered by the dispensing system and used extemporaneously. As an alternative, the product delivered by the dispensing system is packaged and used later, for example on several occasions, with, for example, at least one day's interval between two uses.

Details about the Organic Solvents

Organic solvents are understood to be liquid carbon-based compounds or liquid silicone compounds or liquid salts (known as ionic liquids).

For example: Ethanol or other alcohols, acetone, alkyl acetates, alkylene carbonate, pentane, hexane, octane, decane, isododecane, hexadecane and other alkanes, dimethicones, dialkylimidazolium acetate, dialkylimidazolium hexafluorophosphate, etc.

In one particular case, the solvent is gaseous at standard temperature, and liquid if it is held under pressure. In this case, the solvents may be isopentane, butane or certain fluorinated compounds, the boiling point of which is close to room temperature (0-20° C.).

The solvents may be mixtures of the ingredients mentioned above.

The cartridges introduced into the system may contain a base product containing solvents or mixtures of different solvents.

Cartridges and Materials

According to this fourth aspect of the invention, the cartridges have a body and moving parts intended to push the product that the body contains.

The parts of the cartridge which are not involved in the precision of metering, such as the parts that conduct the composition to the outlet orifice, and any exterior coverings, are not covered by the definitions of the invention according to this fourth aspect in terms of the choice of materials.

In order to obtain good precision of delivery (and thus in the creation of mixtures), the materials are preferably chosen from those listed below: For the body of the cartridge and the moving parts, the plastics selected are preferably:

Simple polyolefins
Polyvinylchloride (PVC)
Polyamide and semi-aromatic polyamide
Polyphenylene sulfide (PPS)
Polybismaleimide
Less preferably:
Polyurethanes
Polyester
Polyepoxides
Polyether-block-amide
Polyacetal
Polyester
Polyetherketone
Polyetherimides (PEI)
Polyimides
Polyamide-imide (PAI)
Certain fluorinated polymers: FEP (perfluorinated ethylene propylene), PFA (polyfluoroalkoxy), ECTFE (ethylene chloro trifluoro ethylene), ETFE (ethylene tetrafluoroethylene)
The following are excluded:
Polystyrene and ABS
Polymethyl methacrylate (PMMA)
Phenoplasts,
Aminoplasts,
Polycarbonate
Polyphenyl oxide (PPO)
Polysulfones
PET
Polyolefins These are polyethylenes of different densities that are produced with different comonomers (other alkenes, in particular alpha-olefins (butene, hexene, octene or propylene) and/or vinyl acetate, vinyl alcohol, acrylic esters). Their production is conventional for a person skilled in the art, employing polymerization conditions that result in high contents in the form of crystals. They are:

a) Very low density linear polyethylene (VLDPE). (density in the region of 0.855 to 0.91 g/cm3).
b) High-pressure low density polyethylene (LDPE) (low density polyethylene) (density in the region of 0.915 to 0.935 g/cm3).
c) Linear low density polyethylene (LLDPE) (density in the region of 0.91 to 0.93 g/cm3).
d) High and medium density polyethylenes (HDPE and MDPE) (density in the region of 0.930 to 0.945 g/cm3 for the former and 0.945 to 0.970 g/cm3 for the latter).
e) UHMW (ultra high molecular weight) polyethylenes (density in the region of 0.94 g/cm3).

Preference is given to c, d and e for the invention, these giving the greatest precision.

The polyolefins are also polypropylenes. Only the "isotactic" versions are suitable (level of isotacticity at least 90%). They can be produced with or without comonomer (ethylene). The copolymerized versions (PPCO) are known as block copolymers or random copolymers and employ around 1% to 30% ethylene.

It is also possible to use non-crystalline or low-crystallinity polyolefins. In this case, a monomer of the vinyl chloride type is used. The polymer obtained (PVC) is of low crystallinity (in general <10%) but high density (1.4 g/cm$^3$). The "plasticizer-free" form is preferably used.

PE and PP are obtainable from numerous suppliers such as Basell, Exxon Mobil, Arkema, Dow, etc.

PVCs are obtainable from numerous suppliers such as Shin Etsu, Solvay, Arkema, etc.

Polyamides

The following are usable:

The polyamides PAn (—CO—NH—R)n
a) PA6 (n=6)
b) PA 12 (n=12)

The polyamides PAnm (—CONHR1-NHCOR2) where R1=(CH2)n and R2=(CH2)m
c) PA66 (n and m=6)
d) PA610 (n=6 and m=10)
e) PA612 (n=6 and m=10)

Preference is given to b), d) and e).

Examples of PA6: Grilon from EMS, Minlon from Dupont
Examples of PA66: Grilon T from EMS, Zytel from Dupont
Examples of PA610: Ultramid S from BASF
Examples of PA612: Vestamid D from Degussa
Polyphenylene sulfides (-Ph-S-)n
Examples of PPS: Ryton from Chevron Phillips, Primet from Solvay
Polybismaleimide
Example of PBMI: Kinel from Neopreg Implementation Process Several implementation processes are possible to produce the parts according to the fourth aspect of the invention:

a) Injection in a mold
b) Machining

For practical reasons, a) is preferred.

Use for Treating One or More Precise Areas of the Skin

The dispensing system allows makeup to be applied, or the skin to be treated in order to care for it, protect it or perfume it, day after day, with only the precise areas being treated. To this end, small doses of product are delivered, and are applied specifically and sequentially to the corresponding areas. Each small dose is created using the mixture suited to the area.

In one preferred embodiment of the invention, the dispensing system waits for information regarding which area is to be treated and then delivers the corresponding mixture. It may use a preprogrammed look-up table for that purpose, this table being the result for example of a learning process as defined below. As an alternative, the dispensing system informs the person, when delivering a mixture, of the area to which the person is to apply the mixture. Thus, the dispensing system may follow an application program in which it delivers, in a given order, the various mixtures that are to be applied.

In one particular embodiment of the invention, the dispensing system is informed as to the quantities to be delivered. For that, it memorizes the relationship between the color or the effect, the area of the face and the quantity needed, thereby making it possible to reduce costs and wastage of product, and to cover the skin only lightly, thus avoiding occlusion effects. In so doing, it is possible to use products that have a high covering capability and provide too much cover to be applied to the whole of the face. Thus, it is possible to obtain makeup results or other treatments of natural or even undetectable appearance.

The dispensing system may also make it possible, by facilitating the dispensing of small quantities and rapid use thereof, to reduce the time for which the products are kept, thus making it possible to reduce the risks of the products changing and/or reduce the amounts of preservative to be used.

In the case of concealing products, the dispensing system is suited to treating the areas that are to be concealed, without having to conceal the entire face.

When the user is looking for the product to apply to an area of the face, it is advantageous to memorize the mixture (ratio between the products in the compartments) best suited to each area, and the dispensing system is thus advantageously designed to memorize the effect, the ratios and the corresponding area. Thus, by using the memorized information, on each use, the same mixture can be delivered for each area or, if several areas are being treated, the same series of mixtures can be delivered for the same series of areas.

The dispensing system may also be designed to allow an area to be treated by varying the effects application after application. Thus, the person may make up her skin using different colors or perfume her skin with different notes that she chooses on a day-by-day basis to suit her tastes. For example, on weekdays, the person applies a pale colored foundation, with a more tanned foundation color at the weekends, or may have eye makeup in one color one day and another color another day. For example, on weekdays, the person applies a given perfume, and at the weekend a different one.

The system is also designed to deliver touches depending on the result of the application of different touches. Thus, if it is apparent to the user that, following the application of several touches, there is something missing for perfecting the result, the system can deliver, on demand, a mixture for realizing a touch which will complete the result.

For example, in the case of the color, if the user applies ethanol-based foundations, given the speed of evaporation, it is possible for certain areas of the face to be colored less than others. The user could then ask the system for a mixture that is less concentrated in colorant in order to complete the color in the areas lacking same.

Idem for perfumes. If the person applies a touch of perfume at one location and then another touch of (different) perfume to another area, the person may desire completing the olfactory impression by applying to the same areas or to a different area another touch of (different) mixture.

The system is thus provided to propose variations and an interface for translating simple orders into the production of a mixture.

The dispensing system may be designed to allow the user to change the ingredients to suit her tastes according to the day, the time, what she is wearing, and the weather. Thus, a system to assist with decision making is advantageously provided to guide the user in her choices of effects.

An assistance system may also be provided for balancing the effects on the same face and contribute toward a successful overall treatment.

It may be desirable for several people in the same group, for example a family, to be able to use the dispensing system, thus reducing costs and minimizing the space taken up. This solution is particularly suited to travel or hotels, campsites, airplanes, campervans, boutiques, schools, etc. For that, provision may be made for the dispensing system to be able to be informed as to which person is using it, so as to access pre-stored personal data.

Continuous Use for Graduated Treatment

In this application, the dispensing system changes the formulation of the mixture while it is delivering the product.

This functionality is all the more important given that the speed of drying is rapid and limits the possibilities of spreading.

In addition, the outlet for the base products or for the mixture is moved relative to a container or a support defining an application surface. In one particular embodiment of the invention, the dispensing system is designed to calculate the way in which the mixture evolves as a function of the color or the effect C1 of one area to be treated and of the color or the effect C2 of another area to be treated. For example, with the knowledge that the chin requires a color C1 and that the cheek requires a color C2, the dispensing system may vary the formulation of the mixture while it is delivering it in order to graduate the color between these two colors. This makes it possible for example to better conceal imperfections of the face while ensuring that the end result is realistic, or allows color to be graduated for beautifying purposes. The dispensing system may also be designed such that the user can command a variation in effect of the mixture dispensed without the start and/or end effects having been set beforehand. To do that, the dispensing system may possess a location or auto-location system and deduce from a look-up table the effects C1 and C2 that it has to create and therefore the changes in the mixture that it has to make.

The fourth aspect of the invention is applicable to the color and to photoprotection. The same concept is applicable to fragrancing products, in the case of which the user may wish to have perfume graduations. For example, he may create a perfume graduation along the neck in order to share a richness of odor with an approaching person.

The invention is applicable to protective compositions. The person could create graduations of protective indices, thereby creating, after being exposed to the sun, a tanning result that is itself graduated.

The dispensing system may have an outlet head, in particular in the case of an airbrush, which is mobile and steered. This option then makes it possible to achieve graduated effects without moving the rest of the dispensing system. For example, the dispensing system is located near to the cheek, then a control system is triggered that will automatically steer the variation in formulation of the mixture and the movement of the outlet head so as, for example, to make the center of the cheek redder than the periphery thereof, with a graduation between the two.

The dispensing system may even be used to create tailor-made products that are kept for several applications.

It is also possible to produce solid or semi-solid products. In this case, the system is used with formulations that are rich in solid ingredients and a relatively small quantity (less than 70% and preferably less than 50%) of a light or heavy organic solvent.

Manufacture of "Bespoke" Compacts or Other Solid or Semi-Solid Products

The dispensing system may be designed to allow a mixture to be chosen and delivered to a container such as a cup. The mixture preferably comprises compounds which are such that the mixture can set solid.

More preferably, use is made of compounds that make the setting especially rapid. These compounds are either deposited in the container before or after it is filled with the other ingredients, or are provided in the compartments of the dispenser with the other constituents of the base products, or are contained in the dispenser in a compartment especially designed to contain them.

Specific compositions which may harden quickly by chemical, biochemical or physicochemical reaction after discharge may thus be dispensed.

These compositions are especially designed for the creation of compacts, namely they:

set solid, yield a material that can crumble if rubbed.

Preferably, these compositions are very rich in solid particles, with for example more than 10% by mass of solid particles relative to the total mass of the composition, better still more than 20% by mass of solid particles relative to the total mass of the composition, even better still more than 30% by mass of solid particles relative to the total mass of the composition, preferably between 10 and 40% by mass of solid particles relative to the total mass of the composition.

Preferably, one or more of the compositions introduced into the system contain oil. (at least 20% by mass).

These compositions may contain absorbent particles or reactive compounds, such as those that react in contact with the air, for example cyanoacrylate or alpha-silanes or those which react to light, notably UV.

The container into which the mixture is dispensed may contain a compound A and the dispensed compositions may contain a compound B, A and B being chosen to react with one another and solidify the mixture.

In one particular embodiment of the invention, the dispensing system incorporates a heating means, for example with an electrical resistor, to create lipsticks or other waxy products. In that case, the base products are heated before being delivered.

The dispensing system may also comprise a means for supplying heat and/or light energy, after the mixture has been dispensed into a container, for example an electrical resistor or an LED, notably UV. This energy may accelerate the setting-solid of the dispensed mixture.

Preferably, the mixture is homogenized before it sets solid.

Creation of Color Palettes

The dispensing system may have a support, having several regions, and may be designed to automatically generate several mixtures deposited in said regions, for example a series of colors suited to various parts of the face.

The support may define several cavities to receive the mixtures or may bear several containers, for example in the form of cups, potentially cups that are separable from the support.

In one particular case, the support adopts the shape of a face with regions for receiving the mixtures for targeted application areas.

The support may be able to move, notably to rotate, with respect to the body of the dispenser and, for example, may be driven in its movement by the dispenser so that various spaces or containers can be filled in succession.

Creation of Other Palettes

The invention may be implemented to make odor palettes or care palettes (with care active agents) or protective palettes (with a UV screening agent).

Cup-Type Dispenser

There is a benefit to having a dispensing system capable of delivering a mixture that the user can easily pick up. Moreover, in cases in which the base products delivered by the dispensing system are not already blended, there is a need to allow the user to perform the mixing easily.

In one of its aspects, independently of or in combination with the other aspects thereof, and notably with the foregoing, one subject of the invention is a system for dispensing at least one makeup or care or protective or fragrancing product, having a cup and a dispenser for filling the cup with at least one product, the cup being secured to the dispenser at least while it is being filled.

The cup is sometimes also known as a "crucible" and that term should be understood in its broadest sense.

A "cup secured to the dispenser" should be understood as meaning that the cup is held, notably immobilized, at least temporarily, on the dispenser, being for example fixed to the latter by screws, magnetic attraction, clip-fastening, bayonet locking, clamping, or produced with a part of the dispenser body by material molding. When it is secured to the dispenser, the cup allows the latter to be manipulated in one hand, the cup remaining in place on the dispenser while the latter is being moved around.

The dispenser may be offered to the user with the cup already in place.

As an alternative, the cup is installed by the user the first time the dispensing system is used.

The cup is preferably less deep than it is wide, making access to it easier and allowing the product, notably the mixture, to be picked up with an applicator or a finger.

Preferably, the cup is separable from the dispenser and constitutes one outlet interface that can be chosen from a collection of outlet interfaces that can be mounted on the dispenser, at the choice of the user and according to the effect to be created, as described in detail below.

Preferably, the dispensing system comprises several filling orifices for filling with different base products, opening into the cup. Thus, the mixing of these products may take place in the cup.

The cup preferably has a bottom that is concave toward the outside, making it easier for the user to clean it between two uses.

In addition, this may make the product easier for the user to pick up and the base products easier to mix.

Preferably, the dispenser allows at least two base products to be delivered into the cup, in adjustable proportions, and better still at least three products.

In one exemplary embodiment, the dispensing system has at least two cups that can be selectively fed by the dispenser. This may allow the user to fill these two cups quickly with mixtures with different characteristics. This may facilitate the testing of substances and/or allow the preparation of several different mixtures intended for treating respective areas of the face. The cups may be associated with identifiers that remind the user of the area of the face for which a mixture contained in a given cup is intended.

The cups may be able to move relative to the dispenser, being for example borne by a mobile support such as a turret that is rotatable with respect to the dispenser or by a slide capable of translational movement with respect to the dispenser.

The dispensing system may comprise a lid for closing the cup. This closure lid is preferably transparent so that the user can see the color of the mixture contained inside.

When the cup is separable from the dispenser it may if necessary be introduced into a housing that allows it to be transported more easily, this housing being able, if necessary, to contain a mirror and/or an applicator. The lid of the housing may in this case act as a lid for the cup.

The volume of the cup may be between 2 and 1000 mm$^3$, better still between 100 and 1000 mm$^3$, even better still between 250 and 750 mm$^3$.

The base product(s) delivered into the cup are preferably foundations, but as an alternative may be makeup products for the lips or eyelids.

The cup preferably has a shape that exhibits symmetry of revolution. As an alternative, it has a polygonal or some other contour. Its largest inside diameter, or that of the inscribed circle in the case of a noncircular contour, is preferably between 2 and 100 mm, preferentially between 5 and 40 mm. Its depth is preferably between 1 and 10 mm, better still between 3 and 8 mm. Preferably, the size and shape of the cup either allow direct application of the mixture to the skin or allow the mixture to be picked up on a finger or an applicator. The cup may be made of an elastically deformable material, making it possible for example to turn the concavity of the bottom of the cup inside out and empty it more easily or use it to apply the product.

The cup may have no blender; in that case, the base products may arrive in the cup from the dispenser in the unmixed state, via distinct respective dispensing orifices. As an alternative, the dispenser incorporates a blender and the base products arrive in the cup already blended.

The cup may also incorporate a static blender as described in detail below, which is fed via distinct filling orifices of the dispenser and which preferably delivers the mixture into a cavity of the cup situated above the blender.

A further subject of the invention is a method for preparing a makeup, perfuming, care or protective product, comprising the step of filling a cup of a dispensing system as defined above with at least one base product from the dispenser.

Several products may be delivered into the bottom of the cup, then blended using a finger or an applicator, or a static blender incorporated into the cup.

The cup is preferably filled from beneath. Dispensing systems using a sonotrode have been proposed in the past.

The cup according to the invention is not intended to vibrate in order to dispense the product(s) conveyed by the feed passage(s) supplying it. It differs from a sonotrode.

Preferably, the cup is made of plastic.

Blender Incorporated into the Outlet Interface

There is a benefit in having a dispensing system capable of delivering a mixture that can easily be used, notably picked up by the user, without the need for an additional mixing action on the part of the user.

In one of its aspects, independently of or in combination with the other aspects thereof, and notably with the foregoing, one subject of the invention is a dispensing system having a dispenser having outlet passages for base products and an outlet interface that is separable from the dispenser, this interface having a static blender that preferably delivers the mixture into a cavity where it can be picked up.

The static blender may be situated under the abovementioned cavity. The dispensing system is then particularly suited to the creation of compacts, using cups with an in-built static blender as outlet interfaces. In that case, the cavity of the cup is filled with product from beneath. After passing into the static blender, the blended base products cover the blender.

According to this aspect of the invention, it is possible to use several outlet interfaces and to fill them with different respective mixtures, without the need to purge the blender, thereby reducing losses of product. The outlet interface may be a single-use interface, if necessary.

Preferably, the static blender has a central chamber communicating with base product intake ducts. This central chamber may communicate with a peripheral chamber having a series of partitions which act as deflectors for the mixture and create shearing thereof.

The peripheral chamber may have a perforated annular partition defining perforations through which the mixture passes as it circulates in the peripheral chamber. The central and peripheral chambers may be closed at the top by a wall which defines the end wall of the cavity receiving the mixture.

The end wall of the peripheral chamber may be of helical shape about the axis of the cup and of a height that decreases in the direction toward the outlet. The latter may open ahead of a connecting ramp connecting the end wall of the peripheral chamber and the top wall of the blender, this connecting ramp preferably being a portion of a helix extending the helix formed by the end wall of the peripheral chamber.

Preferably, the peripheral chamber comprises the abovementioned annular partition and radial partitions that force the mixture to circulate alternately between upper and lower regions of the peripheral chamber and between radially inner and outer regions, the mixture circulating for example from an upper and radially outer region to a lower and radially outer region by passing through the abovementioned annular partition.

The blender may have an outer body in which a component forming the core of the blender is housed, the outer body radially closing the peripheral chamber on the outside and comprising an upright that separates the central and peripheral chambers.

The outer body of the blender and the core of the blender may each be produced as a single piece by injection molding.

Reduced Dead Volume

There is benefit to be had in reducing the losses of product when changing the formulation of the mixture and in allowing the color of the mixture to be varied as quickly as possible during application, particularly when the dispenser is coupled to an airbrush.

In one of its aspects, independently of or in combination with the other aspects thereof, and notably with the foregoing, one subject of the invention is a system for dispensing a makeup or care or protective or fragrancing product, having a dispenser that receives at least two cartridges that each have a reservoir containing a base product, the latter leaving the cartridge through an outlet passage of the cartridge, this outlet passage opening to outside of the dispenser or near the external surface thereof.

The outlet passage may notably open into an area in which the mixture is picked up or close to this area, notably less than 5 mm away, better still less than 3 mm away, better still less than 1 mm away, or even better still flush therewith.

The cross section of the outlet passage is, for example, between 1 and 3 mm$^2$.

Thus, each base product coming from a cartridge can leave the dispenser without mixing with a base product from another cartridge and the dead volume that cannot be picked up and is likely to increase the inertia of the system is minimized. The product is more quickly available without having to circulate through special passages in the housing of the dispenser, thereby avoiding a painstaking purging step in the event of a cartridge change.

The outside of the dispenser may be the product pickup area, notably when the dispenser is produced with a cup that is not designed to be removed, into which the mixture is dispensed, or a dispensing area intended for the mounting of a removable outlet interface, which defines the pickup area. This outlet interface may have a cup as defined above. This mounting area corresponds for example to the outside of the housing of the dispenser in the absence of an outlet interface. The mounting area may be substantially planar and perpendicular to the longitudinal axis of the dispenser housing.

The dispenser may have three cartridges of base products.

The dispenser may have housings for receiving the cartridges, which are preferably received removably in the dispenser. The latter may comprise passages for ducts for the cartridges defining the outlet passages.

The length of these ducts is preferably such that the ducts are set back slightly from the end or lie flush with the cavity used for picking up the product or, as an alternative, are set back slightly from or lie flush with the end face of the housing of the dispenser that defines the mounting area.

These ducts of the cartridges may be end pieces used for causing the pistons to move within the cartridges, as described in detail above.

Multiple Outlet Interfaces

There is a need to be able, using the same dispensing system, to achieve different makeup looks or care effects or protective effects or fragrancing effects easily and be able, if so desired, to treat areas as different as the skin, the lips, the eyelashes or eyebrows, the neck, and the hair.

A subject of the invention is also a dispensing system comprising an assembly having a dispenser of at least one cosmetic product, in particular a makeup, care, protective or fragrancing product, and at least two outlet interfaces, each of which can be mounted removably on the dispenser, these outlet interfaces being able to receive the product(s) delivered by the dispenser, preferably being chosen from the following:
- an outlet interface having a container, notably a cup, allowing the product to be picked up using a finger or using an applicator,
- an outlet interface allowing the product to be delivered to a spray system, notably an airbrush,
- an outlet interface having several regions for receiving the product, which can move relative to the dispenser,
- an outlet interface that allows the product to be delivered to a dispensing end piece.

Preferably, the assembly comprises at least three of said outlet interfaces, or better still the four outlet interfaces.

The dispenser may comprise at least two different base products and allow these to be delivered in variable proportions and, preferably, the dispenser comprises three different base products and allows these to be delivered in variable proportions.

Each outlet interface may have a base allowing it to be fixed to the dispenser. This fixing may be done using screws for example, but preferably the base is designed to allow an outlet interface to be removed and replaced without the need for tools. It is, for example, a quarter-turn fixing or a fixing using an external locking ring.

The outlet interface and/or the housing of the dispenser may comprise seals allowing sealed communication between the housing of the dispenser and the outlet interface. If appropriate, the dispenser is designed to recognize the outlet interface mounted above, for example by virtue of the outlet interface having identifiers in the form of specific reliefs which are detected by the dispenser, or in the form of an electronic chip that the dispenser recognizes. That may allow the operation of the dispenser to be adapted to the outlet interface mounted above. The dispenser may communicate information about the outlet interface it is bearing to a computer system, and the computer system may, on the basis of this information, display a specific screen and/or run a specific program for controlling the operating parameters of the dispenser so as, for example, to adapt the dose dispensed and/or the flow rate to the type of outlet interface.

The user may be initially offered several outlet interfaces with a common dispenser within one and the same package, for example a case or a cardboard box.

A further subject of the invention is a makeup or care or protective or fragrancing method involving the step of selecting an outlet interface, mounting it on the dispenser, and delivering the product(s) contained in the dispenser to the interface.

Mapping and Learning

The term "mapping" should be understood here as meaning a process of indexing a color, odor, protection, care with an area, with recording.

The mapping may relate to applications to areas smaller than 1 cm$^2$. However, the naked eye then has difficulty in discerning whether the result obtained is adequate, and it is preferable to substitute an instrumented evaluation with magnification for evaluation by the naked eye. Small quantities of substance may be applied with a finger, using conventional tools such as brushes, or using specialist applicators.

The map may be generated during a learning period in which the user carries out tests with mixtures on different areas of the face; once created, the map can then be used for everyday makeup or care or protection or fragrancing.

Specific graphic interfaces can be used during the learning period and during the period of use of the map.

In particular, the dispensing system may be used with a graphic interface in which the operator sees the face, which is for example a schematic, figurative or accurate representation such as a photograph or a 3D simulation. In that case, the operator can point at part of the face on the screen to show and/or deliver the appropriate color and/or care and/or protection and/or odor.

The graphic interface may also show the other areas of the face where use of that same color or care or protection or odor is appropriate.

To create the map, the operator applies a color or care or protection or odor, then makes an assessment.

The areas of the face can be treated one after the other; for example, the exercise is carried out on part of the cheek, then on the nose, etc.

Another option is to create a given mixture and apply this same mixture to several areas. The operator then needs to look for the area of the face to which the color or care or protection or odor is suited. The mixture is then indexed in the computer system which attributes it to the area(s) of the face for which it is suitable.

A subject of the invention is also a learning process for a dispensing system, comprising a dispenser for dispensing a variable mixture, and a computer system for selecting an effect and for storing data, comprising the steps of
- a) selecting at least one effect with the aid of an interface of the computer system,
- b) delivering, with the aid of the dispenser, at least one mixture in order to approach the selected effect,
- c) evaluating the mixture(s) dispensed following the application thereof to at least one area of the face, (visual, comfort, odor, touch)
- d) memorizing the characteristics of at least one mixture, notably a mixture that the user wishes to be able to recall, and of at least one area on which it has been tested.

This memorizing can be carried out notably with a view to subsequent dispensing of this mixture for treating said area.

Preferably, the computer system is designed to allow the user to indicate whether or not the result of the test is satisfactory, or even to inform same of the comparison with a test carried out earlier.

It is also possible to create a given mixture and to look for the area of the face for which it is suitable. The mixture is then recorded, being attributed to the area(s) of the face for which it is suitable, in a look-up table that will be used subsequently in order to deduce which mixture to use on the basis of an area of the skin.

The same procedure can be adopted with other mixtures in order to create a map of the entire face and thus have a complete look-up table for the face.

It is also possible to create a given mixture, apply it to a given area, and then vary the mixture until the most suitable mixture is obtained. The mixture is then recorded, being attributed to the area(s) of the face for which it is suitable, in a look-up table that will be used subsequently in order to deduce which mixture to use on the basis of an area of the skin.

Preferably, the computer system evaluates and memorizes the quantities used area by area. Such a method, which uses "test patches" makes it possible to identify the product(s) required by the person wishing to apply makeup or care for their skin or protect their skin or perfume themselves. Thus, the dispensing system can be used at sales outlets to advise people wishing to apply makeup or care for their skin or protect their skin or perfume themselves or at home in order to define correctly which products to order.

The interface of the computer system preferably has a touch screen displaying the color of the mixture when it is selected.

The interface may display a face and allow the computer system to be informed by selecting the area on the face displayed.

The computer system is preferably designed to allow an area, mixture reconstruction parameters, and the date of the test and/or any other identifier of the mixture to be associated with one another.

The computer system is preferably also designed to allow at least one of the following data: the name of the area, the period of the year, the name of an event, a user identifier and the age of the user, to additionally be associated with said area, with the mixture reconstruction parameters, and with the date or identifier of the mixture.

Steps a) to c) may be repeated at least once before the characteristics of the mixture are memorized in step d).

The computer system may be designed to search a database for the reference of a commercial product on the basis of the characteristics of the mixture identified as being suitable for at least one given area, and to relay this information to the user.

The selection in step a) may be carried out using an expert system, which may or may not be external to the computer system.

The expert system may analyze an image of the user in order to propose a mixture at least on the basis of the image analyzed.

Step a) may be preceded by the computer system proposing to the user a color or other effect and an area to be tested with a mixture of this color or this effect.

The computer system may be designed to allow the user to inform same of his or her assessment of the result of the test in step c) and to generate a proposal to modify the mixture to be selected upon return to step a).

The computer system may be designed to propose at least one effect of mixture in step a) depending on an application area of which it has been informed by the user.

The computer system may be designed to propose at least one application area in step a), on the basis of an effect of which it has been informed by the user.

The dispenser may deliver, in step b), at least two different mixtures, preferably separate, so that they can be applied simultaneously to the test area.

This may allow time to be saved and make it easier to compare the results.

A further subject of the invention is a makeup or fragrancing or care or protection method using a dispensing system according to this aspect of the invention, in which:
- a) the user sends the computer system a request regarding a need,
- b) in return, the computer system generates a proposal for treating an associated zone, on the basis of the learning performed beforehand, and
- c) the computer system operates the dispenser to produce the proposed mixture, notably if this is validated by the user.

Such a method may use a map previously established with the user.

A further subject of the invention is a computer program product containing code instructions which, when run in a computer system, allow the computer system to be made to:
- allow the user to select at least one effect and/or one application area, notably using an interface such as a touch screen,
- operate a dispenser in such a way as to deliver a mixture selected by the user,
- allow the user to trigger the memorizing of the mixture and of an associated application area, notably with a view to subsequently dispensing the same mixture, notably on the same area.

The computer program product may comprise code instructions which, when run in a computer system, allow the computer system to be made to:
- receive a request from the user regarding a need, notably using an interface such as a touch screen,
- propose, on the basis at least of data generated by the learning process as defined above, at least and/or one application area,
- operate a dispenser to produce the proposed mixture, notably if this is validated by the user.

Remote Assistance

It is desirable to be able to assist the user in applying makeup or caring for or protecting their skin or perfuming themselves, notably in choosing the correct colorings, olfactory notes or care or protection effects.

In one of its aspects, independently of or in combination with the other aspects thereof, and notably with the foregoing, one subject of the invention is thus a makeup or care or protection or fragrancing method involving the steps of:
- allowing a video link to be established, for example over the Internet, between a camera on a first site and a second site,
- allowing the second site to directly or indirectly operate a dispenser present at the first site, this dispenser making it possible to vary the color, protective or care effect or odor of a mixture dispensed,
- allowing a person present at the first site to apply the mixture dispensed and to send a corresponding image or comments to the second site, so as to receive in return information relating to the application result.

The same concept is applicable to the care or protection of the skin.

The second site may notably have a viewing screen which allows an adviser sitting at this screen to see or hear or read the comments about the makeup or care or protection or fragrancing result with the product dispensed by the dispenser and advise the person who has applied the makeup. This adviser may in return influence the dispenser to alter the color or care or protection or odor of the mixture and adapt it to best suit the face of the person present at the first site. Thus, this person controls the mixture delivered by the dispenser. The first person may make herself up, or care for or protect her skin or perfume herself under the gaze of the second. The second person sees the result of the test on their screen and can thus correct the mixture that this second person will control remotely until the ideal effect is obtained.

If appropriate, the video acquisition can be calibrated using a test pattern or with the mixture dispensed by the dispenser onto a reference surface. That then allows a more faithful display of the makeup or care or protection applied at the first site.

Preferably, the video link between the two sites is a two-way link.

The first site may receive a tutorial from the second site, if appropriate.

Identifiers of the base products may be communicated to the second site; this may make it possible to precisely determine the color of each of the base products.

The method may involve memorizing the dispenser setting parameters once a given mixture is considered to be satisfactory. Preferably, this memory storage may be commanded from the second site. The memory storage may be in the computer system present at the first site and/or on an external server.

One alternative may be to have one person working to help several apply makeup, care for or protect their skin or perfume themselves. This embodiment makes it possible to develop makeup artists or "beauty coaches" or "perfume coaches" and their work, either within an institute or over the Internet. It also allows people with limited capabilities, such as people with poor eyesight, or people who have difficulty discerning colors, or the elderly, or those lacking in self-confidence to apply makeup or protect or care for or perfume themselves.

Operation Via Touch-Sensitive Interface

There is a need to make it easier to control the dispensing system and notably the choice of the effects of the mixture dispensed.

A further subject of the invention is a dispensing system having a dispenser and a computer system for operating the dispenser, this computer system having a touch screen on which the color of the mixture or the expected effect can be displayed, and a selection means movable on the screen, in order to vary the color or the protective or care effect or the odor of the dispensed mixture.

Preferably, the screen displays end-point effects between which the effect of the mixture can be selected by moving the selection means between these end points.

The screen may display a scale of effects in the form of a line or area (triangular contour).

The computer system may perform some of the calculations necessary to determine the fractions of each of the base products that lead to a mixture of the desired effect.

The computer system may be a smartphone, a camera phone, a tablet, or a personal computer. As an alternative, it is incorporated into the housing of the dispenser.

The computer system may have a camera. The latter can be used notably for capturing an image of the user and/or of the mixture.

The computer system may be designed to display an image of a face, in order to make it easier to identify the areas to which the mixture is to be applied.

Coupling of the Dispensing System to a Spray Means

The dispensing system may have or be connected to a means of spraying the mixture, preferably an airbrush.

According to another of its aspects, the invention seeks to improve still further the dispensing systems having a spray system, preferably an airbrush, and one subject of the invention is an assembly comprising:
- a spray means, preferably an airbrush having a pickup chamber subjected to a stream of entrainment air,
- a dispenser having at least two compartments containing different base products, the products being delivered to the spray means preferably via distinct distribution orifices.

The dispenser may have three cartridges containing makeup products of different colors, or fragrancing, care and protection products.

The airbrush may have a stylus defining the pickup chamber, the stylus being fixed to the dispenser or to an outlet interface fixed to the dispenser, or forming an integral part of this outlet interface.

The dispensing system may have a circuit controlling operation of the dispenser, allowing the proportion of base products delivered to the pickup chamber to be varied while the airbrush is in operation. The proportions may be modified depending on the movement of the airbrush relative to the surface onto which the mixture is sprayed. This movement may be mechanized, if appropriate.

This control circuit may have or be constituted by a computer system as defined above.

The housing of the dispenser may act as a hand grip when the assembly is being handled for delivering the mixture.

The dispenser may have a camera and/or one or more sensors such as accelerometers so as to automatically locate the area to which the mixture is applied, and so as to be able to automatically regulate the color or the protective or care effect or perfume depending on the position, if appropriate.

A further subject of the invention is a makeup or care or protection of fragrancing method using an assembly as defined above, in which a mixture is sprayed onto the skin using the spray means, notably the airbrush.

The composition of the mixture can be modified as the airbrush is moved relative to the skin. A graduated effect can be achieved.

This aspect of the invention is based on the observation that the dispenser can be used to supply the spray system, notably the airbrush, while at the same time allowing the dispensing system to be responsive enough to allow a change in the color of the mixture dispensed while the face is being treated, notably as the area to be treated changes.

It may be advantageous for the dispensing of products to be performed iteratively, notably with dispensing times that are not phase-shifted between the various products.

This may make it easier to vary the composition of the mixture dispensed over time.

The mixture may be created directly in the airbrush, with practically no troublesome dead volume, thus allowing the mixture sprayed to be changed in real time.

The depression created in the pickup chamber is strong enough to entrain the base products without in any way impeding the metering.

The depression which prevails in the pickup chamber is for example between 10 mbar and 200 mbar, better still between 50 and 150 mbar, even better still between 75 and 125 mbar.

The viscosity of the base products as measured at 1 atm and 25° C. with a CONTRAVES TV rotary viscometer fitted with an MS-r3 or MS-r4 measuring bar at a frequency of 60 Hz after 10 minutes of rotation of the measuring bar is, for example, between 0.001 Pa·s and 50 Pa·s.

The cross section of the passages along which the base products arrive in the chamber is, for example, between 1 and 3 $mm^2$, better still between 2 and 3 $mm^2$.

The product is preferably supplied continuously.

It is also possible to apply immiscible or reactive base products, such as an aqueous gel and an oily gel, simultaneously, and these will be deposited directly onto the skin in a pixelated manner, producing a kind of gel/gel in situ, reactive silicones, or colorants that react with one another. The ratios of base products can be adjusted depending on the particular result desired. For example, in the case of aqueous gels and oily gels, the ratio corresponding to the volume of the first base product to the volume of the second base product could be varied between 10/1 and 1/10, better still between 5/1 and 1/5.

Location or Auto-Location System

The dispensing system according to the invention may have a location or auto-location system.

A location system is the name given to a means via which the person inputs the area that she is to treat. This can be performed notably using systems that leave at least one hand free. Thus, an interface of a computer system such as a touch screen, a joystick, or voice recognition system can be used.

An auto-location system is the name given to a means for inputting the area that is to be treated without intervention on the part of the person. This can be achieved using one or more accelerometers which deduce, from the movements, the directions targeted by the person or by a camera and an image recognition system.

The dispensing system may be of the kind illustrated in the above-described figures, respecting the choice of materials according to the fourth aspect of the invention, notably for all the parts that move relative to one another.

Therefore, the figures will not all be described again, it being understood that the dispensing system is not limited to one makeup product and is intended to dispense care products, antisun products or perfumes.

Thus, as regards the description of the user interface, the buttons present on the screen may make it possible for example to input the name of the makeup or care or protection or perfume or of the user, to display the selected area, to choose the color or care or protection or odor, and to inform the computer system as to whether or not the result of the test carried out is acceptable, or even, as illustrated, to provide information regarding the assessment of the result relative to a test carried out previously, namely, for example, better or "not as good". The screen may also display a button allowing the choice of a color, protection, care or odor and an area to be memorized after a test has been performed on the area in question.

The choice of color or protection or care or odor is made for example with a scale similar to the one described with reference to FIG. 36.

The computer system is designed to memorize the data in the form of a look-up table for example, so as to associate an area of the face with the parameters that allow the mixture dispensed during the test to be reproduced. These parameters include, for example, the relative contents of each of the base products of the dispenser in the mixture, the quantity Q dispensed, and additional data such as, for example, the name of the area, the date the mixture was dispensed and/or any other mixture identifier, identifiers of the base products, the period of the year, notably the season, the age of the user, his or her sex, his or her given or family name, the name of an event associated with the makeup, protection, care or fragrancing, for example a birthday, amongst other data, and the quantity of product suitable for the area. The ancillary data may allow the user to reproduce more easily an effect considered suitable for a time of year or recalling a life event, or to give a rejuvenating effect.

These data may be memorized in the computer system 100, for example in the abovementioned device and/or on a remote server with which the device is in communication, or alternatively in an electronic memory incorporated into the dispenser 11.

Thus, according to the invention, the user may make the dispenser deliver a first substance, and apply it to a first area of the face, then judge whether or not it is suitable. If the result is satisfactory, the user may record it, indexing it to the area; if the result is unsatisfactory, the user may command a new substance in order to repeat the above operations.

The computer system can be used in this context in various ways.

For example, as illustrated in FIG. 40, in a step 1010, the user selects a color or care or protection or odor to test, using for example the scale 1011 displayed on the screen, by moving the adjusting button 1012.

Next, the choice is transmitted to the dispenser 11, in step 1015.

For example, the device transmits the quantities of each of the base products to be dispensed and the electronic circuit 81 takes charge of operating the motors accordingly.

In step 1016, the user presses the control button 12 of the dispenser 11, this causing, for example, a dose of the mixture, in the color or care effect, protective effect or odor selected by the user, to be dispensed.

The mixture is, for example, dispensed into the cup 115 then picked up and applied by the user to the cheeks or any other area instructed on the interface, in step 1020.

In variants, the product is applied using an airbrush or by any other means as described above.

The user then, in step 1022, informs the computer system of the result using the buttons 1021.

If the user indicates that the result is satisfactory, the system suggests for example that he/she validate the parameters of the test using a button so as to memorize these parameters in step 1031.

If the user does not consider the result to be satisfactory and makes this known using the button 1032, the result can nevertheless be automatically saved in step 1034.

Thus, each area can be indexed not only with the suitable color(s) or care(s) or protection(s) or odor(s), but also with the color(s) or care(s) or protection(s) or odor(s) that is/are not at all suited to this area.

The user can then perform a further test on the same area by returning to step 1010.

If the user is satisfied with the result, he or she may also wish to carry out a further test, for example on a different area of the face.

If appropriate, if the user is not satisfied, the interface may suggest that the user indicate whether the result is considered better than or not as good as the previous test, using corresponding buttons 1040 and 1041.

In that case, the computer system may be designed to determine whether, in light of the information input by the user, a proposal can be automatically made as to what color or care or protection or odor to test next.

If appropriate, a questionnaire may be displayed to assist the computer system in proposing a color or care or protection or odor in light of the tests carried out and the way in which the user or a professional assisting the user has assessed these tests.

For example, if the color is considered "unsuitable", the system may receive from the user additional information, for example "too light", which will assist the system in proposing a new color better suited to the user's expectations.

It may be advantageous for the computer system to be able to receive information comparing the result against the previous tests, for example "it's better" or "it's not as good" and, from there, for the system to be capable of deducing what new color or care or protection or odor to propose.

Another option is for the computer system to be able to receive comparison information regarding a comparison against a target, for example "it's almost ideal" and, from there, for the system to be capable of automatically adjusting its color or care or protection or odor modifications.

In this particular instance, if it receives the information that the desired result has almost been achieved, the system can adopt small levels of color or care or protection or odor change and revise the scale of adjustment accordingly.

If the dispensing system itself proposes the mixtures to be tested, these may be based on preprogrammed test scenarios and the system may alter how the scenario is followed through according to the successes or failures of the assessment. Thus, for example if, from the third application of product, it receives information that the color or care or protection or odor is almost ideal for the user, the dispensing system may exit the program and thereafter allow itself to be guided by instructions from the operator.

In general, the user may be assisted by an expert system in the choice of colors or cares or protections or odors to test. This expert system is, for example, a program run on the device with which the dispenser communicates or on the dispenser itself, and which is based on the answers to a questionnaire and/or on measurements, for example of the color of the skin, taken by a specific sensor or by a camera. The user can thus get assistance from an instrumented evaluation, for example a color, image or odor sensor. The expert system can even be implemented on a remote server with which the device or the dispenser exchanges information. The operator may even send an image of his or her face to a specialist, who can preprogram the starting color or care or protection or odor choice. In another exemplary embodiment, the user presents the computer system with a photo of his or her face, and the computer system is designed to analyze this and create a program defining the areas to be tested and the first products to be delivered, both in terms of color, care, protection and odor and in terms of quantity. For example, the computer system may be designed to automatically select the colors, cares, protection or odor to propose to the user by capturing a photograph in step 1070, as illustrated in FIG. 42. For example, the device which communicates with the dispenser 11 is equipped with a camera, and the user takes a photograph of his or her face. The image is then analyzed in step 1071, and colors color or care or protection or odor are proposed for each area of the face in step 1072, for example in accordance with predefined color combination rules.

The dispensing system may be oriented by the user to decide on the color or care or protection or odor and also on the quantity of product to be delivered. For example, the user may indicate "nose" or "blemish" and the dispensing system is designed to adapt the dose dispensed according to a memorized map of doses to be dispensed depending on the areas to be treated.

The computer system may guide the user in the choice of colors or care or protection or odor of the mixture to be tested, so as to limit the number of tests needed until the user obtains a result that pleases him or her.

It is thus possible, as illustrated in FIG. 41, that after a mixture dispensed by the dispenser has been applied to a given area of the face in step 1060, the computer system will ask the user whether or not the result is satisfactory and will, of its own accord, if the result is considered to be unsatisfactory, make a change 1061 to the dispenser parameters in order to modify the mixture dispensed.

The user then only has to perform a new test with the modified mixture.

When a mixture is indicated as being satisfactory, the computer system can memorize the corresponding parameters so as to allow the mixture to be recreated at a later date.

The system can then begin the above steps afresh for a new application area.

During the successive tests, the operator does not need to treat the entire face. He or she may for example choose between 3 and 8, for example 5, small areas. The dispensing system is then advantageously designed to interpolate and/or extrapolate the data regarding the colors or cares or protections or odors considered to be suitable, so as to calculate the colors that ought to be considered suitable for areas for which the exercise has not been conducted.

At the end of the learning stage, the system may generate a display of the suitable colors or cares or protections or odors on the various areas, tested or calculated.

The dispensing system may be designed to indicate whether certain colors or cares or protections or odors appear to be incorrect, doing so on the strength of a comparison against standard maps it has in memory. Thus, it may propose that the user repeat all or some of the mapping exercise.

Once the computer system has completed its learning, i.e. once the colors or cares or protections or odors of mixtures have been identified as being agreeable to the user for making-up certain areas, the user wishing to apply makeup or to care for or protect or perfume themselves only has to call up the area that is to be treated, in step 1080 of FIG. 43, and the system will be able to automatically propose a suitable mixture color or care or protection or odor to the user in step 1081.

In the variant illustrated in FIG. 44, the user selects a color or care or protection or odor in step 1090 and the computer system proposes, in step 1091, an area in which to apply a mixture of this color or care or protection or odor, on the basis of information previously collected on the basis of the tests performed.

The area proposed is, for example, the area in which an identical or very similar color or care or protection or odor has already been applied and the result considered acceptable by the user.

FIG. 46 illustrates an example of an implementation of the invention in which, having carried out tests on various zones in step 2010, the user informs the system of the mixture(s) he or she considers to afford the best result, this allowing the system to know the corresponding parameters in step 2012. Next, in step 2014, the system may propose to the user references of commercial products that have the same properties or very similar properties.

In one variant, the system sends the parameters to a remote manufacturing center so that a composition that has the same formulation or the same properties as that of the mixture that the user has tested and found to be satisfactory can be produced.

FIG. 45 illustrates the possibility of using the dispenser to dispense several doses 2020a to 2020d of different mixtures, next to one another on a support 2021, so as to allow these to be applied to adjacent distinct regions of the same area.

The user can, in a single hit, apply a series of colors or cares or protections or odors in order rapidly to home in on the appropriate color or care or protection or odor. The substances present on the support 2021 may have been chosen by the operator him- or herself or proposed by the dispensing system.

The support 2021 is, for example, able to move with respect to the housing of the dispenser and is moved sequentially to deposit the corresponding mixtures in the various zones 2020a to 2020d, being for example similar to the supports described with reference to FIG. 29 or 29A. The user can thus easily compare the results between the various regions and inform the system of which mixture produces the best effect.

FIG. 47 illustrates a system that assists the user in treating his or her face, notably in choosing the correct color or care or protection or odor.

This system makes it possible to establish a video link, for example over the Internet, between a camera 2060 at a first site 2061 and a second site 2062.

The camera 2060 is, for example, built into a tablet or a smartphone that constitutes the computer system 100.

The second site 2062 is allowed to operate the dispenser 11 present at the first site 2061 either directly or indirectly.

Thus, the person present at the first site can apply the mixture dispensed and send to the second site 2062 a corresponding image, and in return receive information relating to the result.

The second site 2062 may have a display screen 2064 that allows an adviser sitting at this screen to see the result or understand, via the comments, the result with the mixture dispensed by the dispenser and advise the person. This adviser may in return influence the dispenser 11 to alter the color, care, protection or odor of the mixture and adapt it to best suit the face of the person present at the first site. The protocol for the exchange of data between the two sites thus allows command instructions to be sent to the dispenser 11, either directly or via the computer system 100 present at the first site. Thus, the person present at the second site controls the mixture delivered by the dispenser 11. The first person may make herself up, or care for or protect or perfume herself under the gaze of the second. The second person sees the result of the test on their screen and can thus correct the mixture that this second person will control remotely until the ideal treatment is obtained.

Preferably, the video link between the two sites is a two-way link, such that the user present at the first site can see an image of the adviser on the screen of the computer system. This adviser can send the user present at the first site a tutorial if need be.

The memorizing of the setting parameters of the dispenser 11, once a given mixture has been considered satisfactory, may be commanded from the second site.

The interface may be used to define makeup or care or protection or odor programs in which the order of the areas to be treated or the order of the products to propose is defined.

Examples

A dispenser 11 of the kind illustrated in FIG. 3 and described above in connection with the three first aspects of the invention is created.

In order to illustrate the fourth aspect of the invention, several materials were investigated for the body part and the moving parts.

MDPE (Dow)
HDPE (Dow)
Polyacetal (POM)
PET

Apart from the polyacetal, created by machining, the others are created by injection.

Example 1 (Fourth Aspect of the Invention)

A set of three base products are created (the proportions are by mass)

| F1: | |
|---|---|
| Anethole | 6% (aniseed odor) |
| Water | 5% |
| Absolute ethanol qs | 100 |
| F2: | |
| Phenylethyl ethanol | 6% (rose odor) |
| Water | 5% |
| Absolute ethanol qs | 100: |
| F3: | |
| Jaguar HP 60 | 2% |
| Water qs | 100% |

Test 1

The three base products were placed in three cartridges with:

F1 in a cartridge made of HDPE
F2 in a cartridge made of HDPE
F3 in a cartridge made of PET The three cartridges were placed in the three compartments C1, C2 and C3.

Next, at t=0, a first mixture M0 with the following volumetric proportions was created: C1 30%, C2 30%, C3 40%.

Next, at t=1j, a second mixture M1 with the same ratios was created.

Next, at t=30j, a third mixture M30 with the same ratios was created.

Finally, a mixture M with the same compositions and the same ratios was created by hand (balance of precision).

Next, the mixtures were presented to experts.

The mixtures created M0, M1 and M30 were satisfactory since they were similar in olfactory terms to the mixture M (a mixture of rose and aniseed).

The result obtained with POM was still acceptable at t=1j. The result obtained with PS was unacceptable since virtually no perfume (compared with M) could be smelled.

Test 2

The compositions F1 and F3 were reversed by changing cartridge.

Thus, the three formulations were placed in three cartridges with:

F1 in a cartridge made of PET
F2 in a cartridge made of HDPE
F3 in a cartridge made of HDPE The three cartridges were placed in the three compartments C1, C2 and C3.

Next, as before, a first mixture M0 was created at t=0: C1 30%, C2 30%, C3 40%.

Next, at t=1j, a second mixture M1 with the same ratios was created.

Next, at t=30j, a third mixture M30 with the same ratios was created.

Finally, a mixture M with the same compositions and the same ratios was created by hand (balance of precision).

Next, the mixtures were presented to experts.

The mixture created M0 was satisfactory since it was similar in olfactory terms to the mixture M (a mixture of rose and aniseed). The others (M1 and M30) were not satisfactory since they were different in olfactory terms (the results did not contain the aniseed aspect).

Test 3

F1 was introduced into a cartridge made of POM.

Thus, the three formulations were placed in three cartridges with:

F1 in a cartridge made of POM
F2 in a cartridge made of HDPE
F3 in a cartridge made of PET The three cartridges were placed in the three compartments C1, C2 and C3.

Next, as before, a first mixture M0 was created at t=0: C1 30%, C2 30%, C3 40%.

Next, at t=1j, a second mixture M1 with the same ratios was created.

Next, at t=30j, a third mixture M30 with the same ratios was created.

Finally, a mixture M with the same compositions and the same ratios was created by hand (balance of precision).

Next, the mixtures were presented to experts.

The mixtures created M0 and M1 were satisfactory since they were similar in olfactory terms to the mixture M (a mixture of rose and aniseed). The last (M30) was not satisfactory since it was different in olfactory terms (the results did not contain the aniseed aspect).

Example 2 (Fourth Aspect of the Invention)

The configuration in example 1, test 1 was recreated.

Perfume experts were asked to choose their ideal mixture.

For that, each attempted several mixtures, varying the contents of C1, C2 and C3, in order to change the odor and the strength of the perfume. Each time, they produced 100 mg of composition, which they tested by olfactory assessment as per their taste.

They selected three mixtures which they stored in the system.

Each day, they could use these three mixtures as desired at the particular time. For that, they chose the quantities to be delivered. The system was sufficiently precise to be able to release particularly small doses while respecting the odor of the mixture created. (to 20 mg)

Example 3 (Fourth Aspect of the Invention)

A set of three compositions was created:

| | | |
|---|---|---|
| F1: | | |
| Curcumin | 0.5% | (orange color) |
| Sunflower plant oil qs | 100 | |
| F2: | | |
| Solvent red 27 | 0.5% | (brick red color) |
| Sunflower plant oil qs | 100: | |
| F3: | | |
| Sunflower plant oil | | |

Test 1

The three formulations were placed in three cartridges with:

F1 in a cartridge made of MDPE
F2 in a cartridge made of MDPE
F3 in a cartridge made of MDPE The three cartridges were placed in the three compartments C1, C2 and C3.

At t=0, an expert used a first mixture M0: C1 20%, C2 0%, C3 80%.

Next, he applied this mixture, by touches of 100 mg, to the face of a person with dark skin.

This was followed by completion by delivering a second mixture P0: C1 20%, C2 20%, C3 60% to be applied to the cheeks.

This was followed by completion by delivering a third mixture Q0: C1 20%, C2 60%, C3 20% to be applied to the eyelids.

Once having left the expert with the system and the instructions, the person reproduced at her home the same applications once a month. A matching result was obtained.

Test 2

This consisted in carrying out the same operation using other cartridges:

F1 in a cartridge made of MDPE
F2 in a cartridge made of PET
F3 in a cartridge made of MDPE The test was the same as in example 3, test 1.

After 1 month, the result matched, but after 2 months, the result did not match (orange color in the three areas).

Example 4 (Fourth Aspect of the Invention)

The configuration in example 2, test 1 was recreated.

A person was asked to find the color that suited her best for making up her lips.

For that, she attempted several mixtures, varying the contents of C1, C2 and C3, in order to change the color and the strength of the color. Each time, 100 mg of composition were created, and were tested by color assessment on the back of the hand.

They selected a mixture which they stored in the system. They were able to use their mixture each day.

Example 5 (Fourth Aspect of the Invention)

A set of three compositions was created:

| | |
|---|---|
| F1: | |
| Curcumin | 2% (orange color) |
| Isopropyl myristate qs | 100% |
| F2: | |
| Ethanol | 100% |
| F3: | |
| Isopropyl myristate | 100% |

The three formulations were placed in three cartridges with:
F1 in a cartridge made of HDPE
F2 in a cartridge made of HDPE
F3 in a cartridge made of HDPE
The three cartridges were placed in the three compartments C1, C2 and C3.

At t=0, an expert used a first mixture M0: C1 10%, C2 0%, C3 90%.

Next, it was applied to the face of a person.

The next day, the expert asked the person about the comfort she had felt.

She raised the content of C2 by 10 points at the expense of C3 and so on until the mixture that produced the best comfort from area to area was found.

Next, she varied the content of C1 until the best color intensity was found.

She finished by finding the most suitable mixture for each area.

The person was able to start with the system and apply her mixtures area by area.

E) System for Adjusting the Level of Coverage of a Foundation without Affecting the Level of Mattness/Shine In the case of marked skin, most of the time, the areas of skin that are marked make up only a small proportion of the surface of the face. In order to treat these areas of skin, it is usual to use either a product that covers highly (but entails concealing effect defects) or a product that covers little (but has the drawback of leaving the marks visible). It is possible to use several products with different covering effects, but these generally have different levels of shine/mattness, making the makeup highly visible. (and can make the marked areas stand out).

A solution is required for giving access to an entire range of covering levels, which can be applied to one and the same face without the differences being detectable.

There are very few solutions for solving these problems.

A first approach is to buy numerous products and try them all out. This approach is costly and often gives rise to waste insofar as only a small number of the colored substances tried are generally kept.

A second approach is to test out various products in store. That is not always suitable, because it is very difficult to get a feeling for the results in just a few moments and at a location missing the usual landmarks. In particular, in order to fully assess the makeup effect in store, it would be necessary to be able to have the same lighting as will be found in future conditions of use, and this is something that is rarely possible. In general, it is only by testing out makeup over the course of a day that one can determine whether or not it is suitable. In addition, while certain stores have advisers and allow testing, this is not the case for a large number of other sales outlets and Internet sales.

Another approach has been tested but not developed. This consists in creating one's products by hand by mixing several colored products. This may prove relatively difficult to do because it is not very easy to reproduce the same mixture exactly a number of times over, and it is awkward to quickly create the mixtures one needs at the moment of applying the makeup.

Of the tests that have been able to be attempted for automating the manufacture of a customized cosmetic composition, many are those in which the proposed solutions allow mixtures to be created in quantities of around 100 g or sometimes less, but not in the very small proportions generally needed by a person applying makeup, namely in the region of one gram or much less.

In order to illustrate this problem, consider the case of somebody wishing to hide two imperfections in the region of one cm2 on her face. For the first area, she needs to find the corresponding mixture, then deliver a very small quantity, for example around 10 mg, thereof. For the second, she needs to change the setting of the dispenser, then, once again, deliver a very small quantity.

Therefore, for a great many people, choosing the colored substances that will yield the best results remains a difficult matter.

There is therefore a need to make searching for a makeup product that meets the expectations of a consumer and that allows this consumer to create mixtures under reliable conditions and in various quantities easier.

There is also a need to apply several products with different concealing capacities to the same face. In particular, people can have areas of the face that are marked to a greater or lesser extent and thus require different concealing strengths. It is therefore advantageous to be able to have a means for producing concealing formulations with different concealing strengths.

The production of concealing products by mixing presents a significant problem. Since they are based on particulate ingredients (pigments, nacres), mixtures are thus obtained which, depending on the level of concealing chosen (and thus the quantity of particulate ingredients) confer different mattness/shine aspects on the skin.

There is therefore a need to improve the dispensing systems for delivering products of variable color while retaining the same level of mattness/shine, in order notably to make these easier to use and improve the quality of the makeup.

According to its fifth aspect, the invention is based upon a dispensing system that allows mixtures to be generated from base products. These base products may be of different colors, such that the color of the mixture can be varied. The base products may even make it possible to vary the coverage of the mixture, such that the color resulting from applying the mixture to human keratin materials varies, being fairly close to that of said materials. The base products may also vary the color and the coverage. Thus, the idea of color is to be understood in a broad sense and encompasses mixtures of which the color varies after application as a result of variations in their level of coverage and in the color of the underlying skin.

According to a fifth of its aspects, the subject of the present invention is a system for dispensing a product, comprising a dispenser that receives at least two cartridges that each have a reservoir containing first and second base products, respectively, the first base product comprising a pigment, the second base product comprising a filler distinct from the pigment of the first base product, the dispenser making it possible to deliver at least these two base products in adjustable proportions.

The invention according to this fifth aspect may also have one or more of the following features:
- the particle size D50 by volume of the filler is between 100 nm and 1 mm, better still between 1 micron and 100 microns, even better still between 2 microns and 50 microns,
- the particle size D50 by volume of the pigment is between 100 nm and 25 microns, better still between 200 nm and 10 microns,
- the pigment may be chosen from mineral pigments, and preferably hydrophobic modified mineral pigments, notably those of iron oxide or titanium oxide,
- the pigment may have a coating comprising at least one lipophilic or hydrophobic compound,
- the filler may be chosen from talc, mica, silica, kaolin, poly-β-alanine powder and polyethylene powder, tetrafluoroethylene polymer powders, nylon powders, polymethyl methacrylate powders, lauroyllysine, starch, boron nitride, hollow polymer microspheres such as those of polyvinylidene chloride/acrylonitrile, acrylic acid copolymer microspheres, silicone resin microbeads, polyorganosiloxane elastomer particles, precipitated calcium carbonate, magnesium carbonate, magnesium hydrogen carbonate, hydroxyapatite, barium sulfate, aluminum oxides, polyurethane powders, composite fillers, hollow silica microspheres, and glass or ceramic microcapsules, the particles that are in the form of hollow sphere portions, and mixtures thereof, preferably being talc or mica,
- the filler may have a coating comprising at least one lipophilic or hydrophobic compound,
- the first base product and the second base product may comprise an inverse emulsion,
- the mass content of pigment in the first base product may be greater than or equal to 5% and preferably greater than 10%
- the mass content of filler in the second base product may be greater than or equal to 0.5%, preferably greater than 1%
- the system may comprise a third cartridge with a third base product,
- the cartridges may be received in a removable manner in the dispenser, each product may leave the cartridge through an outlet passage of the cartridge, the outlet passage being defined by a dispensing end piece of the cartridge, said end piece being driven in rotation relative to a body of the cartridge by a drive mechanism of the dispenser in order to dispense the base product contained in the cartridge.

According to this fifth aspect of the invention, a subject thereof is also a method for applying a cosmetic, makeup and/or care, product to human keratin materials, comprising the setting of the dispenser depending on the area to be treated, and the dispensing of the product by base products being picked up from the cartridges in the proportions corresponding to the setting of the dispenser.

Therefore, according to this fifth aspect, the invention is based on a dispensing system, compartments containing at least two different base products which contain (the two) particulate ingredients chosen to create a concealing effect. These formulations preferably contain an inverse emulsion that has a pigment concentration for the one part and a filler concentration for the other. Thus, by creating mixtures, the shine and mattness do not change. It is thus possible to vary the level of coverage while retaining the same appearance. The system may be programmed to deliver, for each location on the face, the best covering mixture (neither too much nor too little). The overall appearance will not make it possible to tell that the face has been treated with different levels of coverage. The system may also be used to vary the level of coverage as desired and depending on the time, for example more covering for an evening, lighter for the daytime.

Dispensing System

The dispensing system may consist of a single device operating autonomously, preferably able to be manipulated in one hand, or of a device that operates in interaction with other components or devices. It may for example entail various outlet interfaces which are mounted on the dispenser depending on the type of makeup to be created, as will be specified below. It may also entail a computer system which exchanges information with the dispenser in order to operate the latter, this computer system comprising, for example, a portable terminal such as a smartphone, a camera phone, a tablet, a laptop computer or a dedicated terminal.

Preferably, the dispenser is designed to pressurize one or more compartments containing the base product(s), via volumetric metering devices, preferably a motor causing a piston to move in the corresponding compartment.

The dispenser may be formed of a housing and of at least two or three compartments, and preferably an identical number of motors. For example, the rotation of the motors drives endless screws which push the pistons of each compartment. The advancing movement of the pistons is, for example, controlled by the number of command pulses sent to the motors and/or by the length of time for which the latter are operating. The motors may be powered in sequence or preferably simultaneously.

For example, the motors are powered during an elementary operating cycle for a short duration one after the other or at the same time as one another, so as to dispense corresponding microdoses.

The elementary cycles are repeated, possibly with a pause between them, giving the base products time to flow out of the compartments.

The compartments may be defined by cartridges, which are removed when they become empty. As an alternative, the compartments are permanently present and refilled once they become empty.

Each cartridge may be closed by a stopper that can be removed to allow the cartridge to be cleaned.

Preferably, the housing of the dispenser is of elongate shape along a longitudinal axis, making it easier to handle, and the cartridges are disposed about this axis, inside the housing.

Preferably, the cartridges are inserted from the rear and the mixture is delivered from the front. The cartridges may be inserted individually or, as an alternative, the cartridges constitute a one-piece assembly as they are inserted.

The cartridges may each have a volumetric metering mechanism comprising a piston moved by a drive mechanism of the dispenser in a direction accompanied by a reduction in the internal volume containing the base product and the expulsion of some product. It may be advantageous for the cartridges to have at least a region of their wall that is transparent so that the color of the product contained therein can be seen.

The drive mechanism may have a motorization system formed of motors coupled to gearboxes, of elongate shape parallel to the longitudinal axis of the dispenser, and positioned between the cartridges. Positioning the motors and cartridges in this way makes the dispenser particularly compact.

The base product can leave the corresponding cartridge in a sealed manner, then flow along a passage provided for this purpose in the housing of the dispenser, before leaving the latter.

The cartridges advantageously end in an end piece produced in such a way that, once the cartridge has been inserted into the housing of the dispenser, the end of the end piece terminates flush with the housing. As an alternative, the end piece is long enough to protrude beyond the housing and thus connect various outlet interfaces that can be attached to the housing of the dispenser.

By virtue of the drive mechanism having motors for causing the pistons to advance, it is possible to precisely deliver mixtures in very small quantities. Thus, the drive mechanism can deliver the base products with a minimum flow rate less than or equal to 50 µL/s, better still less than or equal to 20 µL/s, even better still less than or equal to 10 µL/s. Preferably, the drive mechanism delivers flow rates of between 20 and 100 µL/s, better still between 40 µL/s and 60 µL/s. It is thus possible to easily create a mixture of around 10 mg. Such a dispensing system is therefore ideal for achieving small touches of makeup, for covering an area of 1 cm$^2$, better still an area of 0.5 cm$^2$, for example.

It is also possible to create larger quantities of mixture such as the quantities needed to make up a cheek or a face. These quantities remain relatively low, however, for example a quantity of between 100 and 500 mg, better still between 150 and 250 mg.

Thus, one subject of the invention, according to one aspect thereof, is a dispensing system comprising a dispenser having a housing, and at least one cartridge received in the housing of the dispenser, this cartridge having a body and a piston capable of moving in the body, the housing comprising a motorized drive mechanism for moving the piston of the cartridge.

Preferably, the cartridge has a dispensing end piece through which the product exits, and this dispensing end piece is driven in rotation by the drive mechanism for moving the piston. The end piece may have at least one rotation-proofing relief, better still two diametrically opposed rotation-proofing studs.

The end piece may bear a seal, notably an O-ring seal. Thus, when changing the cartridge, the seal is also changed, making it possible to get around the problem of seal wear.

The dispenser may have an electronic board for controlling the motorized drive mechanism, this electronic board having the end piece(s) passing through it. This may make it possible to produce a board extending across substantially the entire cross section of the dispenser so that all the electronic components of the dispenser can be grouped together on a single board, thus improving compactness and reliability. The board may extend substantially perpendicularly to the longitudinal axis of the housing. The board may bear a switch for controlling operation of the dispenser.

The dispensing system may be designed to operate in at least two dispensing modes.

In a first mode, referred to as "continuous", the mixture is dispensed as long as pressure is applied to the control switch.

In a second mode, referred to as "dose", a predefined quantity of the mixture is dispensed for each press of the switch.

The end piece(s) may terminate at one end of the housing. This may make it possible to reduce the dead volume, as will be explained in detail below.

The end piece(s) may have at their end a shutoff system for preventing the products from drying out in the duct, for example a self-healing membrane.

The cartridge may have a hollow screw onto which the piston is screwed, the piston being able to move axially along the screw as the latter turns; the piston is prevented from turning in the body of the cartridge. For example, the friction of the piston against the body of the cartridge may be enough to prevent it from turning when the screw turns.

Preferably, rotation is rendered impossible with a cartridge body of non-circular cross section and a piston that is not deformable.

The torque of the motors may be determined electronically depending on the current drawn, and may be used for example to detect that the piston has reached the end of its travel. Information regarding the torque may be transmitted remotely to a computer system that has a man-machine interface, in order that correct operation of the dispenser can be monitored.

In order to adjust the shade, the dispensing system according to the invention has to allow the user to vary the volume delivered from each compartment.

Preferably, the dispenser is operated by a computer system built into the dispenser or external thereto, the dispenser then being able to exchange information with the computer system using a wireless or wired protocol.

The dispenser may thus be operated so as to allow the shade to be adjusted by controlled simultaneous or sequential dispensing of several base products of different colors.

The dispensing of the base products may be continuous; in such a case, the volumes of each of the base products are dispensed in a single shot, simultaneously or in succession.

In the case of simultaneous dispensing, it is beneficial to be able to adjust the respective flow rates of the various base products in order for the dispensed mixture to correspond to the desired mixture at all times. Such a dispensing mode may be suitable in particular when dispensing the mixture by spraying, using an airbrush. To adjust the flow rates it is possible, for example, to alter the speed at which the pistons move, for example in the case where the pistons are driven by an endless screw, by varying the rotational speed of the motors that drive the screw. The products may also be dispensed in a pulsed manner with a dispensing time and a pause in each cycle. By altering the duty cycle it is possible to alter the flow rate.

All the products may be delivered simultaneously during the dispensing time or, as an alternative, the cycles of the various products are phase-shifted from one another so that one product is dispensed while the other products are paused.

In one particular embodiment of the invention, the mixture is delivered into a cavity of a container which may close hermetically or not, for example in the form of a cup, into which an applicator, particularly a stylus or a brush may be slipped. Such a dispensing system is especially suited to liners, glosses and other formulations applied without direct contact with the hands. This container may be removable.

For example, it is used as a lip-color dispenser and has a dispensing system, for example using a screw. When it is not removable, the container may be produced with the body of the dispenser. When it is removable, it may constitute one output interface among others that can be mounted on the dispenser.

The compartments, and in particular the cartridges, may contain all or part of the drive mechanism and, for example, the motorizing system or, better still, part of the motorizing system, the purpose of this being to reduce the number of moving parts in the body of the dispenser outside the cartridges. For example, the cartridges contain the rotor of the motor. Once the cartridges have been installed in the body of the dispenser, the rotors are made to interact with the stators.

The dispensing system is advantageously arranged in such a way as to allow the running of preprogrammed sequences in which the mixture delivered by the system is modified continuously or discontinuously. A "graduated" mode makes it possible for example to progress gradually from a mixture A to a mixture B. In the case where the application is by spraying, notably using an airbrush, this makes it possible for graduations to be achieved simply. An "alternate" mode makes it possible for example to switch quickly from a mixture A to a mixture B several times in succession. In the case of application by spraying, a multilayer application can thus be achieved, with different formulations for two superposed adjacent coats. Another mode makes it possible for example to offer several preprogrammed successive mixtures, the computer system each time indicating to the user how these should be used, for example by display on a screen.

In the case of manual application, the mixtures are dispensed for example into a cup. The person applies the makeup to the recommended place with a corresponding mixture taken from the cup, then, if necessary, cleans out the cup and commands delivery of a new mixture; the operation is repeated as many times as necessary until the person is fully made up.

The mixtures dispensed can be homogenized in various ways depending on the type of use. In the case of manual application, it can be done directly on the application area at the time of application or in the cup before the mixture is picked up; in the case of an airbrush application, the pipe of the airbrush is used as a mixing chamber; if the mixture is dispensed into a container for later use, homogenization can be performed by hand or by passing the dispensed products through a mixing chamber situated between the dispenser and the container or incorporated directly into the container, as described in detail below.

The product may be delivered by the dispensing system and used extemporaneously. As an alternative, the product delivered by the dispensing system is packaged and used later, for example on several occasions, with, for example, at least one day's interval between two uses.

Particulate Ingredients

The particulate ingredients are typically particles with a size of between 100 nm and 1 mm, better still between 200 nm and 100 microns, even better still between 200 nm and 50 microns.

Within the meaning of the invention, the "size" of a particle is understood to be the D50 volume average size, which corresponds to the particle size defined such that 50% by volume of the particles have a size less than D50.

The volume average size may be assessed by light diffraction using a Malvern MasterSizer laser particle size analyzer, said particles to be evaluated being dispersed in a liquid medium, for instance octyldodecyl neopentanoate.

The particulate ingredients are pigments and fillers:

Pigments

The term "pigments" is understood to mean white or colored, mineral or organic particles, which are insoluble in an aqueous medium, and which are intended to color and/or opacify the resulting composition and/or film. These pigments may be white or colored, and mineral and/or organic.

According to one embodiment, the size of the pigment particles according to the invention is between 100 nm and 25 µm, preferably between 200 nm and 10 µm.

The pigments used according to the invention are chosen preferably from mineral pigments, and preferably from hydrophobic modified mineral pigments.

The hydrophobic modified mineral pigments are more particularly hydrophobic modified pigments of iron oxide and/or titanium dioxide.

The composition according to the invention comprises advantageously at least one pigment coated with at least one lipophilic or hydrophobic compound.

The coating may also comprise at least one additional non-lipophilic compound.

Within the meaning of the invention, the "coating" of a pigment according to the invention generally denotes the total or partial surface treatment of the pigment with a surface agent, absorbed, adsorbed or grafted onto said pigment.

The surface-treated pigments may be prepared according to surface treatment techniques of chemical, electronic, mechanochemical or mechanical nature that are well known to a person skilled in the art. Commercial products may also be used.

The surface agent may be absorbed, adsorbed or grafted onto the pigments by evaporation of solvent, chemical reaction and creation of a covalent bond.

According to one variant, the surface treatment is constituted of a coating of the pigments.

The coating may be realized, for example, by adsorption of a liquid surface agent onto the surface of the solid particles by simple mixing with stirring of the particles and of said surface agent, optionally with heating, prior to the incorporation of the particles into the other ingredients of the makeup or care composition.

The coating may be realized, for example, by chemical reaction of a surface agent with the surface of the solid pigment particles and creation of a covalent bond between the surface agent and the particles. This method is notably described in the U.S. Pat. No. 4,578,266.

The chemical surface treatment may consist in diluting the surface agent in a volatile solvent, dispersing the pigments in this mixture and then slowly evaporating off the volatile solvent, so that the surface agent is deposited at the surface of the pigments.

According to a particular embodiment of the invention, the pigments may be coated according to the invention with at least one compound chosen from silicone surface agents; fluoro surface agents; fluorosilicone surface agents; metal soaps; N-acylamino acids or salts thereof; lecithin and derivatives thereof, isopropyl triisostearyl titanate; isostearyl sebacate; natural plant or animal waxes; polar synthetic waxes; fatty esters; phospholipids; and mixtures thereof.

According to one particular embodiment, the pigments may be coated with at least one compound chosen from N-acylamino acids or salts thereof, isopropyl triisostearyl titanate; silicone surface agents; natural plant or animal waxes; hydrogenated lecithin, fatty esters; and mixtures thereof.

According to a more particularly preferred embodiment, the pigments may be coated with an N-acylamino acid and/or a salt thereof, in particular with a glutamic acid derivative and/or a salt thereof, especially a stearoyl glutamate, for instance aluminum stearoyl glutamate.

According to one more particularly preferred embodiment, use will be made of hydrophobic coated pigments chosen from titanium dioxides and iron oxides coated with aluminum stearoyl glutamate, sold, for example, under the reference NAI® by Miyoshi Kasei.

Fillers

These fillers are colorless or white solid particles of any form, which are in a form that is insoluble and dispersed in the medium of the composition.

As illustrations of these fillers, mention may be made of talc, mica, silica, kaolin, poly-β-alanine powder and polyethylene powder, tetrafluoroethylene polymer powders (Teflon®), nylon powders, polymethyl methacrylate powders, lauroyllysine, starch, boron nitride, hollow polymer microspheres such as those of polyvinylidene chloride/acrylonitrile, for instance Expancel® (Nobel Industrie), acrylic acid copolymer microspheres, silicone resin microbeads (for example Tospearls® from Toshiba), polyorganosiloxane elastomer particles, precipitated calcium carbonate, magnesium carbonate, magnesium hydrogen carbonate, hydroxyapatite, barium sulfate, aluminum oxides, polyurethane powders, composite fillers, hollow silica microspheres, and glass or ceramic microcapsules. Use may also be made of particles that are in the form of hollow sphere portions, as described in the patent applications JP-2003 128 788 and JP-2000 191 789.

The fillers may have a coating comprising at least one lipophilic or hydrophobic compound.

The coating may be realized, for example, by adsorption of a liquid surface agent onto the surface of the solid particles by simple mixing with stirring of the particles and of said surface agent, optionally with heating, prior to the incorporation of the particles into the other ingredients of the makeup or care composition.

The coating may be realized, for example, by chemical reaction of a surface agent with the surface of the solid filler particles and creation of a covalent bond between the surface agent and the particles.

The chemical surface treatment may consist in diluting the surface agent in a volatile solvent, dispersing the pigments in this mixture and then slowly evaporating off the volatile solvent, so that the surface agent is deposited at the surface of the fillers.

According to one particular embodiment of the invention, the fillers may be coated according to the invention with at least one compound chosen from silicone surface agents; fluoro surface agents; fluorosilicone surface agents; metal soaps; N-acylamino acids or salts thereof; lecithin and derivatives thereof, isopropyl triisostearyl titanate; isostearyl sebacate; natural plant or animal waxes; polar synthetic waxes; fatty esters; phospholipids; and mixtures thereof.

According to one particular embodiment, the fillers may be coated with at least one compound chosen from N-acylamino acids or salts thereof, isopropyl triisostearyl titanate; silicone surface agents; natural plant or animal waxes; hydrogenated lecithin, fatty esters; and mixtures thereof.

According to a more particularly preferred embodiment, the fillers may be coated with an N-acylamino acid and/or a salt thereof, in particular with a glutamic acid derivative and/or a salt thereof, especially a stearoyl glutamate, for instance aluminum stearoyl glutamate.

According to one more particularly preferred embodiment, use will be made of hydrophobic coated fillers chosen from talc and mica coated with aluminum stearoyl glutamate, sold, for example, under the reference NAI® by Miyoshi Kasei.

Inverse Emulsions/Anhydrous Compositions

According to the invention, when a composition is said to be in the form of an inverse emulsion, it will be understood that it can also alternately be in another form depending on the composition in question.

A base product may be in the form of an emulsion, for example an O/W, W/O, O/W/O or W/O/W emulsion, and preferably a W/O inverse emulsion, or in the form of an anhydrous composition, comprising notably carbon-based compounds and/or silicone compounds, such as hydrocarbon-based oils and/or silicone oils.

The emulsions according to the invention are preferably water-in-oil (W/O) emulsions, also known as inverse emulsions, namely constituted of an oily continuous phase in which the aqueous phase is dispersed in the form of droplets so as to observe a mixture that is macroscopically homogeneous to the naked eye.

Use for Making Up One or More Precise Areas of the Skin

The dispensing system allows makeup to be applied, day after day, with only the areas that need to be hidden being treated. To this end, small doses of makeup are delivered, and are applied specifically and sequentially to the corresponding areas. Each small dose is created using the mixture suited to the area.

In one preferred embodiment of the invention, the dispensing system waits for information regarding which area is to be treated and then delivers the corresponding mixture. It may use a preprogrammed look-up table for that purpose, this table being the result for example of a learning process as defined below. As an alternative, the dispensing system informs the person, when delivering a mixture, of the area to which the person is to apply the mixture. Thus, the dispensing system may follow an application program in which it delivers, in a given order, the various mixtures that are to be applied.

In one particular embodiment of the invention, the dispensing system is informed as to the quantities to be delivered. For that, it memorizes the relationship between the color, the area of the face and the quantity needed, thereby making it possible to reduce costs and wastage of product, and to cover the skin only lightly, thus avoiding occlusion effects. In so doing, it is possible to use products that have a high covering capability and provide too much cover to be applied to the whole of the face. Thus, it is possible to obtain makeup of natural or even undetectable appearance.

The system thus makes it possible to carry out localized applications, specifically making it possible to obtain the same level of mattness/shine.

The dispensing system may also make it possible, by facilitating the dispensing of small quantities and rapid use thereof, to reduce the time for which the products are kept, thus making it possible to reduce the risks of the products changing and/or to reduce the amounts of preservative to be used.

The dispensing system is suited to treating the areas that are to be concealed, without having to conceal the entire face.

It may also be used to conceal one or more marks, with a single level of mattness/shine.

In an especially advantageous variant, the system may be used to apply to the base of the face a formulation that is less concealing and then one or two applications to precise areas of the face of formulations that are more concealing. It is also possible to start with applications to the precise areas of the face of concealing formulations and then to apply to the base of the face an application of a formulation that is less concealing.

In the second case, time is taken, before applying the second layer, to wait for the film produced by the application to the precise areas to become sufficiently cohesive so that the second layer does not remove the first layer.

Alternatively, the second layer is applied without rubbing (spray for example, or sponge).

When the user is looking for the color to apply to an area of the face, it is advantageous to memorize the color best suited to each area, and the dispensing system is thus advantageously designed to memorize this color and the corresponding area. Thus, by using the memorized information, on each use, the same mixture can be delivered for each area or, if several areas are being treated, the same series of mixtures can be delivered for the same series of areas.

The dispensing system may also be designed to allow an area to be treated by varying the colors application after application. Thus, the person may make up her lips using different colors that she chooses on a day-by-day basis to suit her tastes. This approach is also suitable for the eyelids or eyelashes, and for face makeup because the person may fancy a change of foundation color. For example, on weekdays, the person applies a pale colored foundation, with a more tanned foundation color at the weekends, or may have eye makeup in one color one day and another color another day. Idem for variations in coverage.

The dispensing system may be designed to allow the user to change color to suit her tastes according to the day, the time, what she is wearing, and the weather. Thus, a system to assist with decision making is advantageously provided to guide the user in her choices of color (broadly speaking).

An assistance system may also be provided for balancing the colors on the same face and to contribute toward a successful overall makeup look.

It may be desirable for several people in the same group, for example a family, to be able to use the dispensing system, thus reducing costs and minimizing the space taken up. This solution is particularly suited to travel or hotels, campsites, airplanes, campervans, boutiques, schools, etc. For that, provision may be made for the dispensing system to be able to be informed as to which person is using it, so as to access pre-stored personal data.

Continuous Use for Graduated Makeup

In this application, the dispensing system changes the formulation of the mixture while it is delivering the product. In addition, the outlet for the base products or for the mixture is moved relative to a container or a support defining an application surface. In one particular embodiment of the invention, the dispensing system is designed to calculate the way in which the mixture evolves as a function of the color C1 of one area to be treated and of the color C2 of another area to be treated. For example, with the knowledge that the chin requires a color C1 and that the cheek requires a color C2, the dispensing system may vary the formulation of the mixture while it is delivering it in order to graduate the color between these two colors. This makes it possible for example to better conceal imperfections of the face while ensuring that the end result is realistic, or allows color to be graduated for beautifying purposes. The dispensing system may also be designed such that the user can command a variation in color of the mixture dispensed without the start and/or end colors having been set beforehand. To do that, the dispensing system may possess a location or auto-location system and deduce from a look-up table the colors C1 and C2 that it has to create and therefore the changes in the mixture that it has to make.

These different effects could be created with a constant mattness/shine effect.

The dispensing system may have an outlet head, in particular in the case of an airbrush, which is mobile and steered. This option then makes it possible to achieve graduated effects without moving the rest of the dispensing system. For example, the dispensing system is located near to the cheek, then a control system is triggered that will automatically steer the variation in formulation of the mixture and the movement of the outlet head so as, for example, to make the center of the cheek redder than the periphery thereof, with a graduation between the two.

The dispensing system may even be used to create tailor-made products that are kept for several applications.

It is also possible to produce solid or semi-solid products.

Manufacture of "Bespoke" Compacts or Other Solid or Semi-Solid Products

The dispensing system may be designed to allow a mixture to be chosen and delivered to a container such as a cup. The mixture preferably comprises compounds which are such that the mixture can set solid.

More preferably, use is made of compounds that make the setting especially rapid. These compounds are either deposited in the container before or after it is filled with the other ingredients, or are provided in the compartments of the dispenser with the other constituents of the base products, or are contained in the dispenser in a compartment especially designed to contain them.

Specific compositions which may harden quickly by chemical, biochemical or physicochemical reaction after discharge may thus be dispensed.

These compositions are especially designed for the creation of compacts, namely they:
  set solid,
  yield a material that can crumble if rubbed, and are preferably colored.

Preferably, these compositions are very rich in solid particles, with for example more than 10% by mass of solid particles relative to the total mass of the composition, better still more than 20% by mass of solid particles relative to the total mass of the composition, even better still more than 30% by mass of solid particles relative to the total mass of the composition, preferably between 10 and 40% by mass of solid particles relative to the total mass of the composition. These compositions may contain absorbent particles or reactive compounds, such as those that react in contact with the air, for example cyanoacrylate or alpha-silanes or those which react to light, notably UV.

The container into which the mixture is dispensed may contain a compound A and the dispensed compositions may contain a compound B, A and B being chosen to react with one another and solidify the mixture.

In one particular embodiment of the invention, the dispensing system incorporates a heating means, for example with an electrical resistor, to create lipsticks or other waxy products. In that case, the base products are heated before being delivered.

The dispensing system may also comprise a means for supplying heat and/or light energy, after the mixture has been dispensed into a container, for example an electrical resistor or an LED, notably UV. This energy may accelerate the setting-solid of the dispensed mixture.

Preferably, the mixture is homogenized before it sets solid.

The products, with different coverage, will have equivalent mattness/shine effects.

Creation of Color Palettes

The dispensing system may have a support, having several regions, and may be designed to automatically generate several mixtures deposited in said regions, for example a series of colors suited to various parts of the face.

The support may define several cavities to receive the mixtures or may bear several containers, for example in the form of cups, potentially cups that are separable from the support.

In one particular case, the support adopts the shape of a face with regions for receiving the mixtures for targeted application areas.

The support may be able to move, notably to rotate, with respect to the body of the dispenser and, for example, may be driven in its movement by the dispenser so that various spaces or containers can be filled in succession.

The products in the palette may have different coverage while having equivalent mattness/shine effects.

Cup-Type Dispenser

There is a benefit to having a dispensing system capable of delivering a mixture that the user can easily pick up. Moreover, in cases in which the base products delivered by the dispensing system are not already blended, there is a need to allow the user to perform the mixing easily.

A further subject of the invention is a system for dispensing at least one makeup product, having a cup and a dispenser for filling the cup with at least one product, the cup being secured to the dispenser at least while it is being filled.

The cup is sometimes also known as a "crucible" and that term should be understood in its broadest sense.

A "cup secured to the dispenser" should be understood as meaning that the cup is held, notably immobilized, at least temporarily, on the dispenser, being for example fixed to the latter by screws, magnetic attraction, clip-fastening, bayonet locking, clamping, or produced with a part of the dispenser body by material molding. When it is secured to the dispenser, the cup allows the latter to be manipulated in one hand, the cup remaining in place on the dispenser while the latter is being moved around.

The dispenser may be offered to the user with the cup already in place.

As an alternative, the cup is installed by the user the first time the dispensing system is used.

The cup is preferably less deep than it is wide, making access to it easier and allowing the product, notably the mixture, to be picked up with an applicator or a finger.

Preferably, the cup is separable from the dispenser and constitutes one outlet interface that can be chosen from a collection of outlet interfaces that can be mounted on the dispenser, at the choice of the user and according to the making up to be performed, as described in detail below.

Preferably, the dispensing system comprises several filling orifices for filling with different base products, opening into the cup. Thus, the mixing of these products may take place in the cup.

The cup preferably has a bottom that is concave toward the outside, making it easier for the user to clean it between two uses.

In addition, this may make the product easier for the user to pick up and the base products easier to mix.

Preferably, the dispenser allows at least two base products to be delivered into the cup, in adjustable proportions, and better still at least three products.

In one exemplary embodiment, the dispensing system has at least two cups that can be selectively fed by the dispenser. This may allow the user to fill these two cups quickly with mixtures with different characteristics. This may facilitate the testing of colored substances and/or allow the preparation of several different color mixtures intended for making up respective areas of the face. The cups may be associated with identifiers that remind the user of the area of the face for which a mixture contained in a given cup is intended.

The cups may be able to move relative to the dispenser, being for example borne by a mobile support such as a turret that is rotatable with respect to the dispenser or by a slide capable of translational movement with respect to the dispenser.

The dispensing system may comprise a lid for closing the cup. This closure lid is preferably transparent so that the user can see the color of the mixture contained inside.

When the cup is separable from the dispenser it may if necessary be introduced into a housing that allows it to be transported more easily, this housing being able, if necessary, to contain a mirror and/or an applicator. The lid of the housing may in this case act as a lid for the cup.

The volume of the cup may be between 2 and 1000 mm$^3$, better still between 100 and 1000 mm$^3$, even better still between 250 and 750 mm$^3$.

The base product(s) delivered into the cup are preferably foundations, but as an alternative may be makeup products for the lips or eyelids.

The cup preferably has a shape that exhibits symmetry of revolution. As an alternative, it has a polygonal or some other contour. Its largest inside diameter, or that of the inscribed circle in the case of a noncircular contour, is preferably between 2 and 100 mm, preferentially between 5 and 40 mm. Its depth is preferably between 1 and 10 mm, better still between 3 and 8 mm. Preferably, the size and shape of the cup either allow direct application of the mixture to the skin or allow the mixture to be picked up on a finger or using an applicator. The cup may be made of an elastically deformable material, making it possible for example to turn the concavity of the bottom of the cup inside out and empty it more easily or use it to apply the product.

The cup may have no blender; in that case, the base products may arrive in the cup from the dispenser in the unmixed state, via distinct respective dispensing orifices. As an alternative, the dispenser incorporates a blender and the base products arrive in the cup already blended.

The cup may also incorporate a static blender as described in detail below, which is fed via distinct filling orifices of the dispenser and which preferably delivers the mixture into a cavity of the cup situated above the blender.

A further subject of the invention is a method for preparing a makeup product, comprising the step of filling a cup of a dispensing system as defined above with at least one base product from the dispenser.

The products, with different coverage, will have equivalent mattness/shine effects.

Several products may be delivered into the bottom of the cup, then blended using a finger or an applicator, or a static blender incorporated into the cup.

The cup is preferably filled from beneath. Dispensing systems using a sonotrode have been proposed in the past.

The cup according to the invention is not intended to vibrate in order to dispense the product(s) conveyed by the feed passage(s) supplying it. It differs from a sonotrode.

Preferably, the cup is made of plastic.

Blender Incorporated into the Outlet Interface

There is a benefit in having a dispensing system capable of delivering a mixture that can easily be used, notably picked up by the user, without the need for an additional mixing action on the part of the user.

In one of its aspects, independently of or in combination with the other aspects thereof, and notably with the foregoing, one subject of the invention is a dispensing system having a dispenser having outlet passages for base products and an outlet interface that is separable from the dispenser, this interface having a static blender that preferably delivers the mixture into a cavity where it can be picked up.

The static blender may be situated under the abovementioned cavity. The dispensing system is then particularly suited to the creation of compacts, using cups with an in-built static blender as outlet interfaces. In that case, the cavity of the cup is filled with product from beneath. After passing into the static blender, the blended base products cover the blender.

According to this aspect of the invention, it is possible to use several outlet interfaces and to fill them with different respective mixtures, without the need to purge the blender, thereby reducing losses of product. The outlet interface may be a single-use interface, if necessary.

Preferably, the static blender has a central chamber communicating with base product intake ducts. This central chamber may communicate with a peripheral chamber having a series of partitions which act as deflectors for the mixture and create shearing thereof.

The peripheral chamber may have a perforated annular partition defining perforations through which the mixture passes as it circulates in the peripheral chamber. The central and peripheral chambers may be closed at the top by a wall which defines the end wall of the cavity receiving the mixture.

The end wall of the peripheral chamber may be of helical shape about the axis of the cup and of a height that decreases in the direction toward the outlet. The latter may open ahead of a connecting ramp connecting the end wall of the peripheral chamber and the top wall of the blender, this connecting ramp preferably being a portion of a helix extending the helix formed by the end wall of the peripheral chamber.

Preferably, the peripheral chamber comprises the abovementioned annular partition and radial partitions that force the mixture to circulate alternately between upper and lower regions of the peripheral chamber and between radially inner and outer regions, the mixture circulating for example from an upper and radially outer region to a lower and radially outer region by passing through the abovementioned annular partition.

The blender may have an outer body in which a component forming the core of the blender is housed, the outer body radially closing the peripheral chamber on the outside and comprising an upright that separates the central and peripheral chambers.

The outer body of the blender and the core of the blender may each be produced as a single piece by injection molding.

Reduced Dead Volume

There is benefit to be had in reducing the losses of product when changing the formulation of the mixture and in allowing the color of the mixture to be varied as quickly as possible during application, particularly when the dispenser is coupled to an airbrush.

In one of its aspects, independently of or in combination with the other aspects thereof, and notably with the foregoing, one subject of the invention is a system for dispensing a makeup product, having a dispenser that receives at least two cartridges that each have a reservoir containing a base product, the latter leaving the cartridge through an outlet passage of the cartridge, this outlet passage opening to outside of the dispenser or near the external surface thereof.

The outlet passage may notably open into an area in which the mixture is picked up or close to this area, notably less than 5 mm away, better still less than 3 mm away, better still less than 1 mm away, or even better still flush therewith.

The cross section of the outlet passage is, for example, between 1 and 3 mm$^2$.

Thus, each base product coming from a cartridge can leave the dispenser without mixing with a base product from another cartridge and the dead volume that cannot be picked up and is likely to increase the inertia of the system is minimized. The product is more quickly available without having to circulate through special passages in the housing of the dispenser, thereby avoiding a painstaking purging step in the event of a cartridge change.

The outside of the dispenser may be the product pickup area, notably when the dispenser is produced with a cup that is not designed to be removed, into which the mixture is dispensed, or a dispensing area intended for the mounting of a removable outlet interface, which defines the pickup area. This outlet interface may have a cup as defined above. This mounting area corresponds for example to the outside of the housing of the dispenser in the absence of an outlet interface. The mounting area may be substantially planar and perpendicular to the longitudinal axis of the dispenser housing.

The dispenser may have three cartridges of base products.

The dispenser may have housings for receiving the cartridges, which are preferably received removably in the dispenser. The latter may comprise passages for ducts for the cartridges defining the outlet passages.

The length of these ducts is preferably such that the ducts are set back slightly from the end or lie flush with the cavity used for picking up the product or, as an alternative, are set back slightly from or lie flush with the end face of the housing of the dispenser that defines the mounting area.

These ducts of the cartridges may be end pieces used for causing the pistons to move within the cartridges, as described in detail above.

Multiple Outlet Interfaces

There is a need to be able, using the same dispensing system, to achieve different makeup looks easily and be able, if so desired, to make up areas as different as the skin, the lips, the eyelashes or eyebrows.

In one of its aspects, independently of or in combination with the other aspects thereof, and notably with the foregoing, one subject of the invention is a dispensing system comprising an assembly comprising a dispenser of at least one cosmetic, notably makeup, product and at least two outlet interfaces, each of which can be mounted removably on the dispenser, these outlet interfaces which are able to receive the product or products delivered by the dispenser preferably being chosen from among the following:

- an outlet interface having a container, notably a cup, allowing the product to be picked up using a finger or using an applicator,
- an outlet interface allowing the product to be delivered to a spray system, notably an airbrush,
- an outlet interface having several regions for receiving the product, which can move relative to the dispenser,
- an outlet interface that allows the product to be delivered to a dispensing end piece.

Preferably, the assembly comprises at least three of said outlet interfaces, or better still the four outlet interfaces.

The dispenser may comprise at least two different base products and allow these to be delivered in variable proportions and, preferably, the dispenser comprises three different base products and allows these to be delivered in variable proportions.

Each outlet interface may have a base allowing it to be fixed to the dispenser. This fixing may be done using screws for example, but preferably the base is designed to allow an outlet interface to be removed and replaced without the need for tools. It is, for example, a quarter-turn fixing or a fixing using an external locking ring.

The outlet interface and/or the housing of the dispenser may comprise seals allowing sealed communication between the housing of the dispenser and the outlet interface. If appropriate, the dispenser is designed to recognize the outlet interface mounted above, for example by virtue of the outlet interface having identifiers in the form of specific reliefs which are detected by the dispenser, or in the form of an electronic chip that the dispenser recognizes. That may allow the operation of the dispenser to be adapted to the outlet interface mounted above. The dispenser may communicate information about the outlet interface it is bearing to a computer system, and the computer system may, on the basis of this information, display a specific screen and/or run a specific program for controlling the operating parameters of the dispenser so as, for example, to adapt the dose dispensed and/or the flow rate to the type of outlet interface.

The user may be initially offered several outlet interfaces with a common dispenser within one and the same package, for example a case or a cardboard box.

A further subject of the invention is a makeup method involving the step of selecting an outlet interface, mounting it on the dispenser, and delivering the product(s) contained in the dispenser to the interface.

Mapping and Learning

The term "mapping" should be understood here as meaning a process of indexing a color with an area, with recording.

It may be the case that a person requires several levels of coverage with a single mattness/shine for all areas.

It may also be the case that she requires several levels of coverage with one level of mattness/shine on one part of the face and another level of mattness/shine for another area. For example, she has several marks on the forehead and several marks on the cheeks. Thus, she may want to create several levels of coverage for the forehead with one level of mattness/shine for this surface. She may want to create several levels of coverage for the cheeks with one level of mattness/shine for this surface.

The mapping may relate to applications to areas smaller than 1 cm². However, the naked eye then has difficulty in discerning whether the result obtained is adequate, and it is preferable to substitute an instrumented evaluation with magnification for evaluation by the naked eye. Small quantities of colored substance may be applied with a finger, using conventional tools such as brushes, or using specialist applicators.

The map may be generated during a learning period in which the user carries out tests with mixtures on different areas of the face; once created, the map can then be used for everyday makeup.

Specific graphic interfaces can be used during the learning period and during the period of use of the map.

In particular, the dispensing system may be used with a graphic interface in which the operator sees the face, which is for example a schematic, figurative or accurate representation such as a photograph or a 3D simulation. In that case, the operator can point at part of the face on the screen to show and/or deliver the appropriate color.

The graphic interface may also show the other areas of the face where use of that same color is appropriate.

To create the map, the operator applies a color, then makes an assessment.

The areas of the face can be treated one after the other; for example, the exercise is carried out on part of the cheek, then on the nose, etc.

Another option is to create a given mixture and apply this same mixture to several areas. The operator then needs to look for the area of the face to which the color is suited. The mixture is then indexed in the computer system which attributes it to the area(s) of the face for which it is suitable.

A subject of the invention is also a learning process for a dispensing system, comprising a dispenser for dispensing a mixture of variable color, and a computer system for selecting a color and for storing data, comprising the steps of:

a) selecting at least one color with the aid of an interface of the computer system, b) delivering, with the aid of the dispenser, at least one mixture of the selected color, c) evaluating the mixture(s) dispensed following the application thereof to at least one area of the face, d) memorizing the characteristics of at least one mixture, notably a mixture that the user wishes to be able to recall, and of at least one area on which it has been tested.

This memorizing can be carried out notably with a view to subsequent dispensing of this mixture for making up said area.

Preferably, the computer system is designed to allow the user to indicate whether or not the result of the test is satisfactory, or even to inform same of the comparison with a test carried out earlier.

It is also possible to create a given mixture and to look for the area of the face for which it is suitable. The mixture is then recorded, being attributed to the area(s) of the face for which it is suitable, in a look-up table that will be used subsequently in order to deduce which mixture to use on the basis of an area of the skin.

The same procedure can be adopted with other mixtures in order to create a map of the entire face and thus have a complete look-up table for the face.

It is also possible to create a given mixture, apply it to a given area, and then vary the mixture until the most suitable mixture is obtained. The mixture is then recorded, being attributed to the area(s) of the face for which it is suitable, in a look-up table that will be used subsequently in order to deduce which mixture to use on the basis of an area of the skin.

Preferably, the computer system evaluates and memorizes the quantities used area by area. Such a method, which uses "test patches" makes it possible to identify the product(s) required by the person wishing to apply makeup. Thus, the dispensing system can be used at sales outlets to advise people wishing to apply makeup or at home in order to define correctly which products to order.

The interface of the computer system preferably has a touch screen displaying the color of the mixture when it is selected.

The interface may display a face and allow the computer system to be informed by selecting the area on the face displayed.

The computer system is preferably designed to allow an area, mixture reconstruction parameters, and the date of the test and/or any other identifier of the mixture to be associated with one another.

The computer system is preferably also designed to allow at least one of the following data: the name of the area, the period of the year, the name of an event, a user identifier and the age of the user, to additionally be associated with said area, with the mixture reconstruction parameters, and with the date or identifier of the mixture.

Steps a) to c) may be repeated at least once before the characteristics of the mixture are memorized in step d).

The computer system may be designed to search a database for a reference of a commercial product on the basis of the characteristics of the mixture identified as being suitable for at least one given area, and to relay this information to the user.

The selection in step a) may be carried out using an expert system, which may or may not be external to the computer system.

The expert system may analyze an image of the user in order to propose a mixture color at least on the basis of the image analyzed.

Step a) may be preceded by the computer system proposing to the user a color and an area to be tested with a mixture of this color.

The computer system may be designed to allow the user to inform same of his or her assessment of the result of the test in step c) and to generate a proposal to modify the mixture to be selected upon return to step a).

The computer system may be designed to propose at least one color of mixture in step a) depending on an application area of which it has been informed by the user.

The computer system may be designed to propose at least one application area in step a), on the basis of a color of which it has been informed by the user.

The dispenser may deliver, in step b), at least two mixtures of different colors, preferably separate, so that they can be applied simultaneously to the test area.

This may allow time to be saved and make it easier to compare the results.

A further subject of the invention is a method of making up using a dispensing system according to this aspect of the invention, in which:
a) the user sends the computer system a request regarding a need for makeup,
b) in return, the computer system generates a proposed color for making up an associated zone, on the basis of the learning performed beforehand, and
c) the computer system operates the dispenser to produce the mixture of the proposed color, notably if this is validated by the user.

Such a method may use a map previously established with the user.

A further subject of the invention is a computer program product containing code instructions which, when run in a computer system, allow the computer system to be made to:
allow the user to select at least one color and/or one application area, notably using an interface such as a touch screen,
operate a dispenser in such a way as to deliver a mixture of the color selected by the user,
allow the user to trigger the memorizing of the color of the mixture and of an associated application area, notably with a view to subsequently dispensing the same mixture, notably on the same area.

The computer program product may comprise code instructions which, when run in a computer system, allow the computer system to be made to:
receive a request from the user regarding a need for makeup, notably using an interface such as a touch screen,
propose, on the basis at least of data generated by the learning process as defined above, at least one color and/or one application area,
operate a dispenser to produce the mixture of the proposed color, notably if this is validated by the user.

The person may incorporate into the map the level of mattness/shine that she desires for each area of the face, area by area or set of areas by set of areas. The system will then interpret the mixtures it needs to create to ensure the colors and coverage desired and the wanted mattness/shine.

The map may subsequently be modified. Thus, it is possible to create the map in terms of the colors/coverage in the first instance, and then refine the map by subsequently defining the levels of mattness/shine.

Remote Assistance

It is desirable to be able to assist the user in applying makeup, notably in choosing the correct colorings.

In one of its aspects, independently of or in combination with the other aspects thereof, and notably with the foregoing, one subject of the invention is thus a method of applying makeup involving the steps of:
allowing a video link to be established, for example over the Internet, between a camera on a first site and a second site,
allowing the second site to directly or indirectly operate a dispenser present at the first site, this dispenser making it possible to vary the color of a mixture dispensed,
allowing a person present at the first site to apply the mixture dispensed and to send a corresponding image to the second site, so as to receive in return information relating to the makeup result.

The second site may notably have a viewing screen which allows an adviser sitting at this screen to see the makeup result with the product dispensed by the dispenser and advise the person who has applied the makeup. This adviser may in return influence the dispenser to alter the color of the mixture and adapt it to best suit the face of the person present at the first site. Thus, this person controls the mixture delivered by the dispenser. The first person may make herself up under the gaze of the second. The second person sees the result of the test on their screen and can thus correct the mixture that this second person will control remotely until the ideal makeup is obtained.

If appropriate, the video acquisition can be calibrated using a test pattern or with the mixture dispensed by the dispenser onto a reference surface. That then allows a more faithful display of the makeup applied at the first site.

Preferably, the video link between the two sites is a two-way link.

The first site may receive a tutorial from the second site, if appropriate.

Identifiers of the base products may be communicated to the second site; this may make it possible to precisely determine the color of each of the base products.

The method may involve memorizing the dispenser setting parameters once a given mixture is considered to be satisfactory. Preferably, this memory storage may be commanded from the second site. The memory storage may be in the computer system present at the first site and/or on an external server.

One alternative may be to have one person working to help several apply makeup. This embodiment makes it possible to develop makeup artists and their work, either within an institute or over the Internet. It also allows people with limited capabilities, such as people with poor eyesight, or people who have difficulty discerning colors, or the elderly, or those lacking in self-confidence to apply makeup.

Operation Via Touch-Sensitive Interface

There is a need to make it easier to control the dispensing system and notably the choice of the color of the mixture dispensed.

A further subject of the invention is a dispensing system having a dispenser and a computer system for operating the dispenser, this computer system having a touch screen on which the color of the mixture can be displayed, and a selection means movable on the screen, in order to vary the color of the dispensed mixture.

Preferably, the screen displays end-point colors between which the color of the mixture can be selected by moving the selection means between these end-point colors.

The screen may display a scale of colors between at least two colors, or an area, notably of triangular outline, within which the selection means can be moved. This area may locally show the color of the mixture depending for example on the distance from each of the vertices, each one embodying a pure base product.

The computer system may perform some of the calculations necessary to determine the fractions of each of the base products that lead to a mixture of the desired color.

The computer system may be a smartphone, a camera phone, a tablet, or a personal computer. As an alternative, it is incorporated into the housing of the dispenser.

The computer system may have a camera. The latter can be used notably for capturing an image of the user and/or of the mixture.

The computer system may be designed to display an image of a face, in order to make it easier to identify the areas to which the mixture is to be applied.

Coupling of the Dispensing System to a Spray Means

The dispensing system may have or be connected to a means of spraying the mixture, preferably an airbrush.

Another of the aspects of the invention is to improve still further the dispensing systems that comprise a spray system, preferably an airbrush, and according to one of its aspects, independently of or in combination with the other aspects, and notably the foregoing, one subject of the invention is an assembly comprising:

- a spray means, preferably an airbrush having a pickup chamber subjected to a stream of entrainment air,
- a dispenser having at least two compartments containing different base products, the products being delivered to the spray means preferably via distinct distribution orifices.

The dispenser may have three cartridges containing makeup products of different colors.

The airbrush may have a stylus defining the pickup chamber, the stylus being fixed to the dispenser or to an outlet interface fixed to the dispenser, or forming an integral part of this outlet interface.

The dispensing system may have a circuit controlling operation of the dispenser, allowing the proportion of base products delivered to the pickup chamber to be varied while the airbrush is in operation. The proportions may be modified depending on the movement of the airbrush relative to the surface onto which the mixture is sprayed. This movement may be mechanized, if appropriate.

This control circuit may have or be constituted by a computer system as defined above.

The housing of the dispenser may act as a hand grip when the assembly is being handled for delivering the mixture.

The dispenser may have a camera and/or one or more sensors such as accelerometers so as to automatically locate the area to which the mixture is applied, and so as to be able to automatically regulate the color depending on the position, if appropriate.

A further subject of the invention is a method for applying makeup using an assembly as defined above, in which a mixture is sprayed onto the skin using the spray means, notably the airbrush.

The composition of the mixture can be modified as the airbrush is moved relative to the skin. A graduated effect can be achieved.

This aspect of the invention is based on the observation that the dispenser can be used to supply the spray system, notably the airbrush, while at the same time allowing the dispensing system to be responsive enough to allow a change in the color of the mixture dispensed while the face is being made up, notably as the area to be made up changes.

It may be advantageous for the dispensing of products to be performed iteratively, notably with dispensing times that are not phase-shifted between the various products.

This may make it easier to vary the composition of the mixture dispensed over time.

The mixture may be created directly in the airbrush, with practically no troublesome dead volume, thus allowing the mixture sprayed to be changed in real time.

The depression created in the pickup chamber is strong enough to entrain the base products without in any way impeding the metering.

The depression which prevails in the pickup chamber is for example between 10 mbar and 200 mbar, better still between 50 and 150 mbar, even better still between 75 and 125 mbar.

The viscosity of the base products as measured at 1 atm and 25° C. with a CONTRAVES TV rotary viscometer fitted with an MS-r3 or MS-r4 measuring bar at a frequency of 60 Hz after 10 minutes of rotation of the measuring bar is, for example, between 0.05 Pa·s and 50 Pa·s.

The cross section of the passages along which the base products arrive in the chamber is, for example, between 1 and 3 $mm^2$, better still between 2 and 3 $mm^2$.

The product is preferably supplied continuously.

It is also possible to apply immiscible or reactive base products, such as an aqueous gel and an oily gel, simultaneously, and these will be deposited directly onto the skin in a pixelated manner, producing a kind of gel/gel in situ, reactive silicones, or colorants that react with one another. The ratios of base products can be adjusted depending on the particular result desired. For example, in the case of aqueous gels and oily gels, the ratio corresponding to the volume of the first base product to the volume of the second base product could be varied between 10/1 and 1/10, better still between 5/1 and 1/5.

Location or Auto-Location System

The dispensing system according to the invention may have a location or auto-location system.

A location system is the name given to a means via which the person inputs the area that she is to treat. This can be performed notably using systems that leave at least one hand free. Thus, an interface of a computer system such as a touch screen, a joystick, or voice recognition system can be used.

An auto-location system is the name given to a means for inputting the area that is to be treated without intervention on the part of the person. This can be achieved using one or more accelerometers which deduce, from the movements, the directions targeted by the person or by a camera and an image recognition system.

The invention may be implemented according to this fifth aspect with the aid of the examples illustrated in the figures, which are described above and the description of which will not be repeated here.

Example (Fifth Aspect of the Invention)

Several base products having particulate ingredients are created.

Base products F1 and F2 are rich in pigment (and are different colors). Base product F3 is rich in filler

| | F1 mass % | F2 mass % | F3 mass % |
|---|---|---|---|
| Dimethicone copolyol sold under the reference KF 6017 by the company Shin-Etsu | 2 | 2 | 2 |
| Etsu Bis PEG/PPG-14/14 dimethicone + Cyclopentasiloxane sold under the reference Abil EM 97 by the company Goldschmidt | 1 | 1 | 1 |
| Cyclopentasiloxane | 17.65 | 17.65 | 17.65 |
| Phenyl trimethicone sold under the reference DC556 by the company Dow Corning | 2 | 2 | 2 |
| Ethyl hexyl methoxycinnamate | 3 | 3 | 3 |
| Squalane | 1 | 1 | 1 |
| Cyclopentasiloxane | 7 | 7 | 7 |
| Yellow iron oxide coated with aluminum stearoyl glutamate NAI-C33-9001-10 from the company Miyoshi Kasei | 2 | 1.1 | 1.33 |
| Red iron oxide coated with aluminum stearoyl glutamate NAI-C33-8001-10 from the company Miyoshi Kasei | 0.2 | 0.6 | 0.13 |
| Black iron oxide coated with aluminum stearoyl glutamate NAI-C33-7001-10 from the company Miyoshi Kasei | 0.15 | 0.15 | 0.1 |
| Titanium dioxide (anatase) coated with aluminum stearoyl glutamate NAI-TAO-77891 from the company Miyoshi Kasei | 9.65 | 10.15 | 6.44 |
| Talc coated with aluminum stearoyl glutamate NAI-TA-13R from the company Miyoshi Kasei | 0 | 0 | 1.5 |
| Talc sold under the reference Micro Ace P3 by the company Nippion Talc | 0.5 | 0.5 | 0.5 |
| Nylon 12 powder sold under the reference SP 500 by the company Toray Industries | 0.5 | 0.5 | 0.5 |
| Demineralized water | 36.15 | 36.15 | 38.65 |
| 1,3-Butylene glycol | 3 | 3 | 3 |
| Magnesium sulfate | 0.7 | 0.7 | 0.7 |
| Hydrogenated maltose solution | 0.5 | 0.5 | 0.5 |
| Denatured 96° ethyl alcohol | 13 | 13 | 13 |
| TOTAL | 100 | 100 | 100 |

Procedure

The constituents of phase A are weighed out in the main beaker and are stirred with a Moritz blender (1000 rpm) while maintaining at room temperature. Phase B is prepared separately by milling three times in a three-roll mill the mixture of pigments and of cyclopentasiloxane. This phase B is then added, with continued stirring, along with the fillers (phase C).

The aqueous phase D is also prepared separately, by weighing out in a beaker the butylene glycol, the magnesium sulfate, the hydrogenated maltose solution, and water at room temperature. The aqueous phase D is stirred using a magnetic bar until homogenized. C D E The emulsion is made at room temperature: the aqueous phase D is poured into the fatty phase while gradually increasing the stirring speed (Moritz blender) up to 4000 rpm. Stirring is continued for 7 minutes. Finally, phase E (ethyl alcohol) is added for the last 3 minutes of 5 the emulsification.

Test

The dispensing system is used to create several mixtures (the proportions within the mixture are volumetric):

M1: A 50%, B 20%, C 30%
M2: A 50%, B 0%, C 50%
M3: A 50%, B 40%, C 10%

Mixtures M1, M2, M3 are applied to different areas of the face. Different coverages and different colors (more or less pink) but with equivalent levels of mattness are obtained.

F) Dispensing System for Customizing the Level of Photoprotection of a Foundation without Modifying its Level of Mattness and Shine Women need to be able to make themselves up and protect themselves from the sun. Since the UV level can vary from one day to another and thus also the need for photoprotection, it is necessary to be able to provide access to an entire range of photoprotection levels, while at the same time providing access to a range of color and coverage.

In the case of marked skin, most of the time, the areas of skin that are marked make up only a small proportion of the surface of the face. They require especially high protection since these areas are known to be able to change under solar irradiation and in particular create more marks.

Other areas, such as scars, also require a high level of protection.

By contrast, the base of the skin requires less protection, it being understood that people tan it for esthetic reasons. It is therefore necessary to be able to provide makeup products that contain little or no screening agent.

A solution is required for giving access to an entire range of photoprotection levels, which can be applied to one and the same face without the differences being detectable.

There are very few solutions for solving these problems.

A first approach is to buy numerous makeup products with screening agents and try them all out. This approach is costly and often gives rise to waste insofar as only a small number of the products tested are generally kept.

A second approach is to test out various products in store. That is not always suitable, because it is very difficult to get a feeling for the results in just a few moments and at a location missing the usual landmarks. In particular, in order to fully assess the makeup effect in store, it would be necessary to be able to have the same lighting as will be found in future conditions of use, and this is something that is rarely possible. In general, it is only by testing out makeup over the course of a day that one can determine whether or not it is suitable. In addition, while certain stores have advisers and allow testing, this is not the case for a large number of other sales outlets and Internet sales.

Another approach has been tested but not developed. This consists in creating one's products by hand by mixing several colored products. This may prove relatively difficult to do because it is not very easy to reproduce the same mixture exactly a number of times over, and it is awkward to quickly create the mixtures one needs at the moment of applying the makeup.

Dispensers for dispensing a cosmetic composition of variable color are also known.

Of the tests that have been able to be attempted for automating the manufacture of a customized cosmetic composition, many are those in which the proposed solutions allow mixtures to be created in quantities of around 100 g or sometimes less, but not in the very small proportions generally needed by a person applying makeup, namely in the region of one gram or much less.

In order to illustrate this problem, consider the case of somebody wishing to hide two imperfections in the region of one cm2 on her face. For the first area, she needs to find the corresponding mixture, then deliver a very small quantity, for example around 10 mg, thereof. For the second, she needs to change the setting of the dispenser, then, once again, deliver a very small quantity.

Therefore, for a great many people, choosing the colored substances that will yield the best results remains a difficult matter.

There is therefore a need to make searching for a screening makeup product that meets the expectations of a consumer and that allows this consumer to create mixtures under reliable conditions and in various quantities easier.

Therefore, according to certain aspects, the invention seeks to make it easier to make up the face with photoprotection, and notably to find the products best suited to the various areas thereof.

There is also a need to improve the dispensing systems for delivering products of variable color, in order notably to make these easier to use and improve the quality of the makeup.

There is also a need to apply several products with different photoprotective capacities to the same face. In particular, people can have areas of the face that are marked to a greater or lesser extent and thus require different photoprotection strengths. It is therefore advantageous to be able to have a means for producing photoprotective formulations with different photoprotection strengths.

The production of concealing and photoprotective products by mixing presents a significant problem. Since they are based on oily ingredients (organic screening agents), mixtures are thus obtained which, depending on the level of photoprotection chosen (and thus the quantity of oily ingredients) confer different mattness/shine aspects on the skin.

There is therefore a need to improve the dispensing systems for delivering products of variable photoprotection while retaining the same level of mattness/shine, in order notably to make these easier to use and improve the quality of the makeup and photoprotection.

Thus, one subject of the invention, according to a sixth of its aspects, is a system for dispensing a product, comprising a dispenser that receives at least two cartridges containing first and second base products, respectively, the first base product comprising, notably in the form of an inverse emulsion, an organic sunscreen and an oil, the second base product comprising an oil, the dispenser making it possible to deliver at least these two base products in adjustable proportions, the concentration of sunscreen in the first base product being greater than that of the second base product, and the concentration of oil in the second base product being greater than that of the first base product.

According to this sixth aspect, the invention may have one or more of the following features:
the mass content of the organic sunscreen in the first base product is greater than or equal to 2% of the mass of the first base product, better still greater than or equal to 4% of the mass of the first base product, for example between 4% and 30%,
the mass content of oil(s) in the second base product is greater than or equal to 10% of the mass of the second base product, preferably greater than 15% of the mass of the second base product, preferably greater than or equal to 20%, for example between 20% and 60%, the second base product not containing any organic sunscreen,
the second base product comprises an organic sunscreen,
at least one of the first and second base products contains a coloring agent,
the coloring agent is chosen from pigments, notably iron oxides,
each of the first and second base products comprises a coloring agent,
at least one of the first and second base products contains a colorless filler,
each of the first and second base products comprises a colorless filler,
the dispensing system comprises a third cartridge with a third base product,
the cartridges are received in a removable manner in the dispenser,
each product leaves the cartridge through an outlet passage of the cartridge, the outlet passage being defined by a dispensing end piece of the cartridge, said end piece being driven in rotation relative to a body of the cartridge by a drive mechanism of the dispenser in order to dispense the base product contained in the cartridge.

A further subject of the invention according to this sixth aspect is a process for adjusting a system as described above, comprising the adjustment of the dispenser depending on the area to be treated with the product and/or the intensity of the UV radiation.

According to this sixth aspect, the invention is based on a dispensing system that allows mixtures to be generated from base products. These base products may be of different colors, such that the color of the mixture can be varied. The base products make it possible to vary the level of photoprotection of the mixture. The base products may also vary the color and the coverage. Thus, the idea of color is to be understood in a broad sense and encompasses mixtures of which the color varies after application as a result of variations in their level of coverage and in the color of the underlying skin.

According to its sixth aspect, the invention is based on a dispensing system, compartments containing at least two different formulations which contain organic screening ingredients chosen to create a screening effect. These formulations preferably contain an inverse emulsion that has an organic screening agent concentration for the one part and an oil concentration for the other. Thus, by creating mixtures, the shine and mattness do not change. It is thus possible to vary the level of screening while retaining the same appearance.

The dispensing system may be programmed to deliver, for each location on the face, the best screening mixture (neither too much nor too little). The overall appearance will not make it possible to tell that the face has been treated with different levels of screening. The system can also be used to vary the level of screening as desired and depending on the time. (for example, more screening at lunchtime, less for the afternoon).

Dispensing System

The dispensing system may consist of a single device operating autonomously, preferably able to be manipulated in one hand, or of a device that operates in interaction with other components or devices. It may for example entail various outlet interfaces which are mounted on the dispenser depending on the type of makeup to be created, as will be specified below. It may also entail a computer system which exchanges information with the dispenser in order to operate the latter, this computer system comprising, for example, a portable terminal such as a smartphone, a camera phone, a tablet, a laptop computer or a dedicated terminal.

Preferably, the dispenser is designed to pressurize one or more compartments containing the base product(s), via volumetric metering devices, preferably a motor causing a piston to move in the corresponding compartment.

The dispenser may be formed of a housing and of at least two or three compartments, and preferably an identical number of motors. For example, the rotation of the motors drives endless screws which push the pistons of each compartment. The advancing movement of the pistons is, for example, controlled by the number of command pulses sent to the motors and/or by the length of time for which the latter are operating. The motors may be powered in sequence or preferably simultaneously.

For example, the motors are powered during an elementary operating cycle for a short duration one after the other or at the same time as one another, so as to dispense corresponding microdoses.

The elementary cycles are repeated, possibly with a pause between them, giving the base products time to flow out of the compartments.

The compartments may be defined by cartridges, which are removed when they become empty. As an alternative, the compartments are permanently present and refilled once they become empty.

Each cartridge may be closed by a stopper that can be removed to allow the cartridge to be cleaned.

Preferably, the housing of the dispenser is of elongate shape along a longitudinal axis, making it easier to handle, and the cartridges are disposed about this axis, inside the housing.

Preferably, the cartridges are inserted from the rear and the mixture is delivered from the front. The cartridges may be inserted individually or, as an alternative, the cartridges constitute a one-piece assembly as they are inserted.

The cartridges may each have a volumetric metering mechanism comprising a piston moved by a drive mechanism of the dispenser in a direction accompanied by a reduction in the internal volume containing the base product and the expulsion of some product. It may be advantageous for the cartridges to have at least a region of their wall that is transparent so that the color of the product contained therein can be seen.

The drive mechanism may have a motorization system formed of motors coupled to gearboxes, of elongate shape parallel to the longitudinal axis of the dispenser, and positioned between the cartridges. Positioning the motors and cartridges in this way makes the dispenser particularly compact.

The base product can leave the corresponding cartridge in a sealed manner, then flow along a passage provided for this purpose in the housing of the dispenser, before leaving the latter.

The cartridges advantageously end in an end piece produced in such a way that, once the cartridge has been inserted into the housing of the dispenser, the end of the end piece terminates flush with the housing. As an alternative, the end piece is long enough to protrude beyond the housing and thus connect various outlet interfaces that can be attached to the housing of the dispenser.

By virtue of the drive mechanism having motors for causing the pistons to advance, it is possible to precisely deliver mixtures in very small quantities. Thus, the drive mechanism can deliver the base products with a minimum flow rate less than or equal to 50 L/s, better still less than or equal to 20 µL/s, even better still less than or equal to 10 µL/s. Preferably, the drive mechanism delivers flow rates of between 20 and 100 µL/s, better still between 40 µL/s and 60 µL/s. It is thus possible to easily create a mixture of around 10 mg. Such a dispensing system is therefore ideal for achieving small touches of makeup, for covering an area of 1 cm$^2$, better still an area of 0.5 cm$^2$, for example. It is also possible to create larger quantities of mixture such as the quantities needed to make up a cheek or a face. These quantities remain relatively low, however, for example a quantity of between 100 and 500 mg, better still between 150 and 250 mg.

Thus, one subject of the invention, according to one aspect thereof, is a dispensing system comprising a dispenser having a housing, and at least one cartridge received in the housing of the dispenser, this cartridge having a body and a piston capable of moving in the body, the housing comprising a motorized drive mechanism for moving the piston of the cartridge.

Preferably, the cartridge has a dispensing end piece through which the product exits, and this dispensing end piece is driven in rotation by the drive mechanism for moving the piston. The end piece may have at least one rotation-proofing relief, better still two diametrically opposed rotation-proofing studs.

The end piece may bear a seal, notably an O-ring seal. Thus, when changing the cartridge, the seal is also changed, making it possible to get around the problem of seal wear.

The dispenser may have an electronic board for controlling the motorized drive mechanism, this electronic board having the end piece(s) passing through it. This may make it possible to produce a board extending across substantially the entire cross section of the dispenser so that all the electronic components of the dispenser can be grouped together on a single board, thus improving compactness and reliability. The board may extend substantially perpendicularly to the longitudinal axis of the housing. The board may bear a switch for controlling operation of the dispenser.

The dispensing system may be designed to operate in at least two dispensing modes.

In a first mode, referred to as "continuous", the mixture is dispensed as long as pressure is applied to the control switch.

In a second mode, referred to as "dose", a predefined quantity of the mixture is dispensed for each press of the switch.

The end piece(s) may terminate at one end of the housing. This may make it possible to reduce the dead volume, as will be explained in detail below.

The end piece(s) may have at their end a shutoff system for preventing the products from drying out in the duct, for example a self-healing membrane.

The cartridge may have a hollow screw onto which the piston is screwed, the piston being able to move axially along the screw as the latter turns; the piston is prevented from turning in the body of the cartridge. For example, the friction of the piston against the body of the cartridge may be enough to prevent it from turning when the screw turns.

Preferably, rotation is rendered impossible with a cartridge body of non-circular cross section and a piston that is not deformable.

The torque of the motors may be determined electronically depending on the current drawn, and may be used for example to detect that the piston has reached the end of its travel. Information regarding the torque may be transmitted remotely to a computer system that has a man-machine interface, in order that correct operation of the dispenser can be monitored.

In order to adjust the shade, the dispensing system according to the invention has to allow the user to vary the volume delivered from each compartment.

Preferably, the dispenser is operated by a computer system built into the dispenser or external thereto, the dispenser then being able to exchange information with the computer system using a wireless or wired protocol.

The dispenser may thus be operated so as to allow the shade to be adjusted by controlled simultaneous or sequential dispensing of several base products of different colors.

The dispensing of the base products may be continuous; in such a case, the volumes of each of the base products are dispensed in a single shot, simultaneously or in succession.

In the case of simultaneous dispensing, it is beneficial to be able to adjust the respective flow rates of the various base products in order for the dispensed mixture to correspond to the desired mixture at all times. Such a dispensing mode may be suitable in particular when dispensing the mixture by spraying, using an airbrush. To adjust the flow rates it is possible, for example, to alter the speed at which the pistons move, for example in the case where the pistons are driven by an endless screw, by varying the rotational speed of the motors that drive the screw. The products may also be dispensed in a pulsed manner with a dispensing time and a pause in each cycle. By altering the duty cycle it is possible to alter the flow rate.

All the products may be delivered simultaneously during the dispensing time or, as an alternative, the cycles of the various products are phase-shifted from one another so that one product is dispensed while the other products are paused.

In one particular embodiment of the invention, the mixture is delivered into a cavity of a container which may close hermetically or not, for example in the form of a cup, into which an applicator, particularly a stylus or a brush may be slipped. Such a dispensing system is especially suited to liners, glosses and other formulations applied without direct contact with the hands. This container may be removable.

For example, it is used as a lip-color dispenser and has a dispensing system, for example using a screw. When it is not removable, the container may be produced with the body of the dispenser. When it is removable, it may constitute one output interface among others that can be mounted on the dispenser.

The compartments, and in particular the cartridges, may contain all or part of the drive mechanism and, for example, the motorizing system or, better still, part of the motorizing system, the purpose of this being to reduce the number of moving parts in the body of the dispenser outside the cartridges. For example, the cartridges contain the rotor of the motor. Once the cartridges have been installed in the body of the dispenser, the rotors are made to interact with the stators.

The dispensing system is advantageously arranged in such a way as to allow the running of preprogrammed sequences in which the mixture delivered by the system is modified continuously or discontinuously. A "graduated" mode makes it possible for example to progress gradually from a mixture A to a mixture B. In the case where the application is by spraying, notably using an airbrush, this makes it possible for graduations to be achieved simply. An "alternate" mode makes it possible for example to switch quickly from a mixture A to a mixture B several times in succession. In the case of application by spraying, a multilayer application can thus be achieved, with different formulations for two superposed adjacent coats. Another mode makes it possible for example to offer several preprogrammed successive mixtures, the computer system each time indicating to the user how these should be used, for example by display on a screen.

In the case of manual application, the mixtures are dispensed for example into a cup. The person applies the makeup to the recommended place with a corresponding mixture taken from the cup, then, if necessary, cleans out the cup and commands delivery of a new mixture; the operation is repeated as many times as necessary until the person is fully made up.

The mixtures dispensed can be homogenized in various ways depending on the type of use. In the case of manual application, it can be done directly on the application area at the time of application or in the cup before the mixture is picked up; in the case of an airbrush application, the pipe of the airbrush is used as a mixing chamber; if the mixture is dispensed into a container for later use, homogenization can be performed by hand or by passing the dispensed products through a mixing chamber situated between the dispenser and the container or incorporated directly into the container, as described in detail below.

The product may be delivered by the dispensing system and used extemporaneously. As an alternative, the product delivered by the dispensing system is packaged and used later, for example on several occasions, with, for example, at least one day's interval between two uses.

Screening Ingredients

The screening ingredients are chosen from liquid lipophilic organic UV screening agents. The term "liquid lipophilic organic UV screening agent" is understood to mean any organic chemical molecule that is capable of absorbing at least UV radiation in the wavelength range between 280 and 400 nm, said molecule being in liquid form at ambient temperature (20-25° C.) and at atmospheric pressure (760 mmHg) and capable of being miscible in an oily phase.

The liquid organic UV screening agents that are usable according to the invention may be chosen from
liquid lipophilic β,β-diphenylacrylate compounds
liquid lipophilic salicylate compounds
liquid lipophilic cinnamate compounds
and mixtures thereof.

i) β,β-Diphenylacrylate Compounds

Among the liquid lipophilic organic UVB screening agents that are usable according to the invention, mention may be made of the liquid lipophilic alkyl β,β-diphenylacrylate or α-cyano-β,β-diphenylacrylate compounds of formula (I) below:

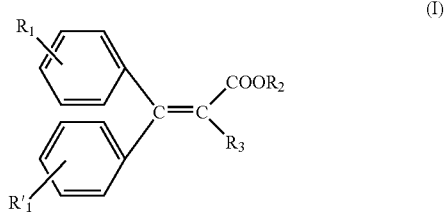

in which $R_1$ to $R_3$ can have the following meanings:
$R_1$ and $R'_1$, which may be identical or different, represent a hydrogen atom, a straight-chain or branched-chain $C_1$-$C_8$ alkoxy radical or a straight-chain or branched-chain $C_1$-$C_4$ alkyl radical;
$R_1$ and $R'_1$ being in the para meta position;
$R_2$ represents a straight-chain or branched-chain $C_1$-$C_{12}$ alkyl radical;
$R_3$ represents a hydrogen atom or the CN radical.

Among the straight-chain or branched-chain $C_1$-$C_8$ alkoxy radicals, mention may be made, for example, of methoxy, ethoxy, n-propoxy, isopropoxy, n-butoxy, isobutoxy, tert-butoxy, n-amyloxy, isoamyloxy, neopentyloxy, n-hexyloxy, n-heptyloxy, n-octyloxy and 2-ethylhexyloxy radicals.

Among the straight-chain or branched-chain $C_1$-$C_4$ alkyl radicals, mention may more particularly be made of methyl, ethyl, n-propyl, isopropyl, n-butyl, isobutyl and tert-butyl radicals. For the $C_1$-$C_{12}$ alkyl radicals, mention may be made, by way of example, in addition to those mentioned above, of n-amyl, isoamyl, neopentyl, n-hexyl, n-heptyl, n-octyl, 2-ethylhexyl, decyl and lauryl radicals.

Among the compounds of general formula (I), the following compounds are more particularly preferred:
2-ethylhexyl α-cyano-β,β-diphenylacrylate or Octocrylene, sold notably under the trade name Uvinul N539® by BASF;
ethyl α-cyano-β,β-diphenylacrylate such as Etocrylene, sold notably under the trade name Uvinul N35® by BASF;
2-ethylhexyl β,β-diphenylacrylate;
ethyl β,β-di(4'-methoxyphenyl)acrylate.

Among the compounds of general formula (I), the compound 2-ethylhexyl 2-cyano-3,3-diphenylacrylate or Octocrylene is even more particularly preferred.

ii) Salicylate Compounds

Among the liquid lipophilic salicylate compounds that are usable according to the invention, mention may be made of:
Homosalate, sold under the name Eusolex HMS® by Rona/EM Industries,
Ethylhexyl salicylate, sold under the name Neo Heliopan OS® by Symrise.

iii) Cinnamate Compounds

Among the liquid lipophilic cinnamate compounds that are usable according to the invention, mention may be made of:
Ethylhexyl Methoxycinnamate, sold notably under the trade name Parsol MCX® by DSM Nutritional Products,
Isopropyl Methoxycinnamate,
Isoamyl Methoxycinnamate, sold under the trade name Neo Heliopan E 1000 by Symrise.

Among the liquid lipophilic screening agents according to the invention, use will more particularly be made of the compound Ethylhexyl Methoxycinnamate.

Among the nonvolatile fluoro and/or silicone oils, mention may be made of:
optionally partially hydrocarbon-based and/or silicone fluoro oils, for instance fluorosilicone oils, fluoropolyethers and fluorosilicones as described in EP-A-847 752;
silicone oils such as nonvolatile polydimethylsiloxanes (PDMSs); phenylated silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethyl-siloxysilicates.

According to one particular mode of the invention, the oily phase comprises at least one silicone oil as defined above and at least one liquid lipophilic organic UV-screening agent as defined above.

According to one particular mode of the invention, the oily phase comprises at least Ethylhexyl Methoxycinnamate.

Oils

The term "oils" is understood to mean an oil that remains on the skin at room temperature and atmospheric pressure for at least several hours, and that notably has a vapor pressure of less than 0.13 Pa (0.01 mmHg).

These nonvolatile oils may be hydrocarbon-based oils, notably of animal or plant origin, silicone oils, or mixtures thereof. A "hydrocarbon-based oil" is understood to be an oil mainly containing hydrogen and carbon atoms and possibly oxygen, nitrogen, sulfur and/or phosphorus atoms.

Nonvolatile hydrocarbon-based oils that may especially be mentioned include:
hydrocarbon-based oils of animal origin,
hydrocarbon-based oils of plant origin such as triglycerides constituted by fatty acid esters of glycerol, the fatty acids of which may have chain lengths varying from C4 to C24, these chains possibly being linear or branched, and saturated or unsaturated; these oils are in particular heptanoic or octanoic acid triglycerides, or alternatively wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passion-flower oil and musk rose oil; shea butter; or else caprylic/capric acid triglycerides,
synthetic ethers containing from 10 to 40 carbon atoms,
linear or branched hydrocarbons of mineral or synthetic origin, such as petroleum jelly, polydecenes, hydrogenated polyisobutene, squalane and liquid paraffins, and mixtures thereof,
synthetic esters such as oils of formula R1COOR2 in which R1 represents a linear or branched fatty acid residue containing from 1 to 40 carbon atoms and R2 represents a notably branched hydrocarbon-based chain containing from 1 to 40 carbon atoms, on the condition that R1+R2≥10, for instance purcellin oil (cetostearyl octanoate), isopropyl myristate, isopropyl palmitate, C12 to C15 alkyl benzoates, hexyl laurate, diisopropyl adipate, isononyl isononanoate, isodecyl neopentanoate, 2-ethylhexyl palmitate, isostearyl isostearate, 2-hexyldecyl laurate, 2-octyldecyl palmitate, 2-octyldodecyl myristate, alkyl or polyalkyl heptanoates, octanoates, decanoates or ricinoleates such as propylene glycol dioctanoate; hydroxylated esters such as isostearyl lactate, diisostearyl malate and 2-octyldodecyl lactate; polyol esters and pentaerythritol esters,
fatty alcohols that are liquid at room temperature, with a branched and/or unsaturated carbon-based chain containing from 12 to 26 carbon atoms, for instance octyldodecanol, isostearyl alcohol, oleyl alcohol, 2-hexyldecanol, 2-butyloctanol and 2-undecylpentadecanol,
higher fatty acids such as oleic acid, linoleic acid or linolenic acid, and mixtures thereof.

The nonvolatile silicone oils that may be used in the composition according to the invention may be nonvolatile polydimethylsiloxanes (PDMSs), polydimethylsiloxanes comprising alkyl or alkoxy groups, that are pendent and/or at the end of a silicone chain, the groups each containing from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes, and mixtures thereof.

Preferably, the oily phase comprises at least one silicone oil, even more preferably chosen from:
volatile cyclic silicone oils having a viscosity at room temperature of less than 8 cSt and containing notably from 4 to 7 silicon atoms, these silicones optionally comprising alkyl or alkoxy groups containing from 1 to 10 carbon atoms, in particular chosen from hexamethylcyclotrisiloxane, octamethylcyclotetrasiloxane, decamethylcyclopentasiloxane and dodecamethylcyclohexasiloxane (cyclohexasiloxane), and mixtures thereof;

volatile or nonvolatile polydimethylsiloxanes (PDMSs) (INCI name: Dimethicone);

phenylated silicones;

polydimethylsiloxanes comprising aliphatic groups, in particular alkyl groups, or alkoxy groups, which are pendent and/or at the end of the silicone chain; these groups each comprising from 6 to 24 carbon atoms, and more particularly caprylyl methicone, such as the commercial product Dow Corning FZ-3196® from the company Dow Corning;

mixtures thereof.

Inverse Emulsions/Anhydrous Compositions

According to the invention, when a composition is said to be in the form of an inverse emulsion, it will be understood that it can also alternately be in another form depending on the composition in question.

A base product may be in the form of an emulsion, for example an O/W, W/O, O/W/O or W/O/W emulsion, and preferably a W/O inverse emulsion, or in the form of an anhydrous composition, comprising notably carbon-based compounds and/or silicone compounds, such as hydrocarbon-based oils and/or silicone oils.

The emulsions according to the sixth aspect of the invention are preferably water-in-oil (W/O) emulsions, also known as inverse emulsions, namely constituted of an oily continuous phase in which the aqueous phase is dispersed in the form of droplets so as to observe a mixture that is macroscopically homogeneous to the naked eye.

Use for Making Up One or More Precise Areas of the Skin

The dispensing system allows makeup to be applied, day after day, with only the areas that need to be hidden being treated. To this end, small doses of makeup with a greater or lesser screening action are delivered, and are applied specifically and sequentially to the corresponding areas. Each small dose is created using the mixture suited to the area.

In one preferred embodiment of the invention, the dispensing system waits for information regarding which area is to be treated and then delivers the corresponding mixture. It may use a preprogrammed look-up table for that purpose, this table being the result for example of a learning process as defined below. As an alternative, the dispensing system informs the person, when delivering a mixture, of the area to which the person is to apply the mixture. Thus, the dispensing system may follow an application program in which it delivers, in a given order, the various mixtures that are to be applied.

In one particular embodiment of the invention, the dispensing system is informed as to the quantities to be delivered. For that, it memorizes the relationship between the necessary screening, the area of the face and the quantity needed, thereby making it possible to reduce costs and wastage of product, and to cover the skin only lightly, thus avoiding occlusion effects. In so doing, it is possible to use products that have a high screening action and provide too much screening to be applied to the whole of the face. Thus, it is possible to obtain makeup results of natural or even undetectable appearance, but with an especially effective level of screening.

The system thus makes it possible to carry out localized applications of a variety of screening capacities, specifically making it possible to obtain the same level of mattness/shine.

The dispensing system may also make it possible, by facilitating the dispensing of small quantities and rapid use thereof, to reduce the time for which the products are kept, thus making it possible to reduce the risks of the products changing and/or to reduce the amounts of preservative to be used.

The dispensing system is suited to treating the areas that are to be protected, without having to screen out UV for the entire face.

It may also be used to conceal and/or protect one or more marks, with a single level of mattness/shine.

In an especially advantageous variant, the system may be used to apply to the base of the face a formulation with little screening action and then one or two applications to precise areas of the face of formulations that have more of a screening action. It is also possible to start with applications to the precise areas of the face of screening formulations and then to apply to the base of the face an application of a formulation with little screening action.

In the second case, time is taken, before applying the second layer, to wait for the film produced by the application to the precise areas to become sufficiently cohesive so that the second layer does not remove the first layer.

Alternatively, the second layer is applied without rubbing (spray for example, or sponge).

When the user is looking for the screening action to apply to an area of the face, it is advantageous to memorize the screening action best suited to each area, and the dispensing system is thus advantageously designed to memorize this screening action and the corresponding area. Thus, by using the memorized information, on each use, the same mixture can be delivered for each area or, if several areas are being treated, the same series of mixtures can be delivered for the same series of areas.

The dispensing system may also be designed to allow an area to be treated by varying the screening action application after application. For example, on weekdays, the person applies a pale colored foundation with a low screening action, and at the weekend a foundation with a more tanned color and a high screening action.

The dispensing system may be designed to allow the user to change color and/or screening action to suit her tastes according to the day, the time, what she is wearing, and the weather. Thus, a system to assist with decision making is advantageously provided to guide the user in her choices of color and screening action.

An assistance system may also be provided for balancing the colors on the same face and to contribute toward a successful overall makeup look.

It may be desirable for several people in the same group, for example a family, to be able to use the dispensing system, thus reducing costs and minimizing the space taken up. This solution is particularly suited to travel or hotels, campsites, airplanes, campervans, boutiques, schools, etc. For that, provision may be made for the dispensing system to be able to be informed as to which person is using it, so as to access pre-stored personal data.

Continuous Use for Graduated Screening

In this application, the dispensing system changes the formulation of the mixture while it is delivering the product. In addition, the outlet for the base products or for the mixture is moved relative to a container or a support defining an application surface. In one particular embodiment of the invention, the dispensing system is designed to calculate the way in which the mixture evolves as a function of the screening F1 of one area to be treated and of the screening F2 of another area to be treated.

These different effects could be created with a constant mattness/shine effect.

The dispensing system may have an outlet head, in particular in the case of an airbrush, which is mobile and steered. This option then makes it possible to achieve graduated effects without moving the rest of the dispensing system. For example, the dispensing system is located near to the cheek, then a control system is triggered that will automatically steer the variation in formulation of the mixture and the movement of the outlet head so as, for example, to make the center of the cheek redder than the periphery thereof, with a graduation between the two.

The dispensing system may even be used to create tailor-made products that are kept for several applications.

It is also possible to produce solid or semi-solid products.

Manufacture of "Bespoke" Compacts or Other Solid or Semi-Solid Products

The dispensing system may be designed to allow a mixture to be chosen and delivered to a container such as a cup. The mixture preferably comprises compounds which are such that the mixture can set solid.

More preferably, use is made of compounds that make the setting especially rapid. These compounds are either deposited in the container before or after it is filled with the other ingredients, or provided in the compartments of the dispenser with the other constituents of the base products, or are contained in the dispenser in a compartment especially designed to contain them.

Specific compositions which may harden quickly by chemical, biochemical or physicochemical reaction after discharge may thus be dispensed.

These compositions are especially designed for the creation of compacts, namely they:

set solid, yield a material that can crumble if rubbed, and are preferably colored.

Preferably, these compositions are very rich in solid particles, with for example more than 10% by mass of solid particles relative to the total weight of the composition, better still more than 20% by mass of solid particles relative to the total mass of the composition, even better still more than 30% by mass of solid particles relative to the total mass of the composition, preferably between 10 and 40% by mass of solid particles relative to the total mass of the composition.

These compositions may contain absorbent particles or reactive compounds, such as those that react in contact with the air, for example cyanoacrylate or alpha-silanes or those which react to light, notably UV.

The container into which the mixture is dispensed may contain a compound A and the dispensed compositions may contain a compound B, A and B being chosen to react with one another and solidify the mixture.

Preferably, the mixture is homogenized before it sets solid.

The products, with different screening actions, will have equivalent mattness/shine effects.

Creation of Screening Palettes

The dispensing system may have a support, having several regions, and may be designed to automatically generate several mixtures deposited in said regions, for example a series of colors suited to various parts of the face.

The support may define several cavities to receive the mixtures or may bear several containers, for example in the form of cups, potentially cups that are separable from the support.

In one particular case, the support adopts the shape of a face with regions for receiving the mixtures for targeted application areas.

The support may be able to move, notably to rotate, with respect to the body of the dispenser and, for example, may be driven in its movement by the dispenser so that various spaces or containers can be filled in succession.

The products in the palette may have different coverage while having equivalent mattness/shine effects.

Cup-Type Dispenser

There is a benefit to having a dispensing system capable of delivering a mixture that the user can easily pick up. Moreover, in cases in which the base products delivered by the dispensing system are not already blended, there is a need to allow the user to perform the mixing easily.

A further subject of the invention is a system for dispensing at least one makeup product, having a cup and a dispenser for filling the cup with at least one product, the cup being secured to the dispenser at least while it is being filled.

The cup is sometimes also known as a "crucible" and that term should be understood in its broadest sense.

A "cup secured to the dispenser" should be understood as meaning that the cup is held, notably immobilized, at least temporarily, on the dispenser, being for example fixed to the latter by screws, magnetic attraction, clip-fastening, bayonet locking, clamping, or produced with a part of the dispenser body by material molding. When it is secured to the dispenser, the cup allows the latter to be manipulated in one hand, the cup remaining in place on the dispenser while the latter is being moved around.

The dispenser may be offered to the user with the cup already in place.

As an alternative, the cup is installed by the user the first time the dispensing system is used.

The cup is preferably less deep than it is wide, making access to it easier and allowing the product, notably the mixture, to be picked up with an applicator or a finger.

Preferably, the cup is separable from the dispenser and constitutes one outlet interface that can be chosen from a collection of outlet interfaces that can be mounted on the dispenser, at the choice of the user and according to the making up to be performed, as described in detail below.

Preferably, the dispensing system comprises several filling orifices for filling with different base products, opening into the cup. Thus, the mixing of these products may take place in the cup.

The cup preferably has a bottom that is concave toward the outside, making it easier for the user to clean it between two uses.

In addition, this may make the product easier for the user to pick up and the base products easier to mix.

Preferably, the dispenser allows at least two base products to be delivered into the cup, in adjustable proportions, and better still at least three products.

In one exemplary embodiment, the dispensing system has at least two cups that can be selectively fed by the dispenser. This may allow the user to fill these two cups quickly with mixtures with different characteristics. The cups may be associated with identifiers that remind the user of the area of the face for which a mixture contained in a given cup is intended.

The cups may be able to move relative to the dispenser, being for example borne by a mobile support such as a turret that is rotatable with respect to the dispenser or by a slide capable of translational movement with respect to the dispenser.

The dispensing system may comprise a lid for closing the cup. This closure lid is preferably transparent so that the user can see the color of the mixture contained inside.

When the cup is separable from the dispenser it may if necessary be introduced into a housing that allows it to be transported more easily, this housing being able, if necessary, to contain a mirror and/or an applicator. The lid of the housing may in this case act as a lid for the cup.

The volume of the cup may be between 2 and 1000 mm$^3$, better still between 100 and 1000 mm$^3$, even better still between 250 and 750 mm$^3$.

The base product(s) delivered into the cup are preferably foundations, but as an alternative may be makeup products for the lips or eyelids.

The cup preferably has a shape that exhibits symmetry of revolution. As an alternative, it has a polygonal or some other contour. Its largest inside diameter, or that of the inscribed circle in the case of a noncircular contour, is preferably between 2 and 100 mm, preferentially between 5 and 40 mm. Its depth is preferably between 1 and 10 mm, better still between 3 and 8 mm. Its depth is preferably between 1 and 10 mm. Preferably, the size and shape of the cup either allow direct application of the mixture to the skin or allow the mixture to be picked up on a finger or an applicator. The cup may be made of an elastically deformable material, making it possible for example to turn the concavity of the bottom of the cup inside out and empty it more easily or use it to apply the product.

The cup may have no blender; in that case, the base products may arrive in the cup from the dispenser in the unmixed state, via distinct respective dispensing orifices. As an alternative, the dispenser incorporates a blender and the base products arrive in the cup already blended.

The cup may also incorporate a static blender as described in detail below, which is fed via distinct filling orifices of the dispenser and which preferably delivers the mixture into a cavity of the cup situated above the blender.

A further subject of the invention is a method for preparing a screening makeup product, comprising the step of filling a cup of a dispensing system as defined above with at least one base product from the dispenser.

The products, with different coverage, will have equivalent mattness/shine effects.

Several products may be delivered into the bottom of the cup, then blended using a finger or an applicator, or a static blender incorporated into the cup.

The cup is preferably filled from beneath. Dispensing systems using a sonotrode have been proposed in the past.

The cup according to the invention is not intended to vibrate in order to dispense the product(s) conveyed by the feed passage(s) supplying it. It differs from a sonotrode.

Preferably, the cup is made of plastic.

Blender Incorporated into the Outlet Interface

There is a benefit in having a dispensing system capable of delivering a mixture that can easily be used, notably picked up by the user, without the need for an additional mixing action on the part of the user.

In one of its aspects, independently of or in combination with the other aspects thereof, and notably with the foregoing, one subject of the invention is a dispensing system having a dispenser having outlet passages for base products and an outlet interface that is separable from the dispenser, this interface having a static blender that preferably delivers the mixture into a cavity where it can be picked up.

The static blender may be situated under the abovementioned cavity. The dispensing system is then particularly suited to the creation of compacts, using cups with an in-built static blender as outlet interfaces. In that case, the cavity of the cup is filled with product from beneath. After passing into the static blender, the blended base products cover the blender.

According to this aspect of the invention, it is possible to use several outlet interfaces and to fill them with different respective mixtures, without the need to purge the blender, thereby reducing losses of product. The outlet interface may be a single-use interface, if necessary.

Preferably, the static blender has a central chamber communicating with base product intake ducts. This central chamber may communicate with a peripheral chamber having a series of partitions which act as deflectors for the mixture and create shearing thereof.

The peripheral chamber may have a perforated annular partition defining perforations through which the mixture passes as it circulates in the peripheral chamber. The central and peripheral chambers may be closed at the top by a wall which defines the end wall of the cavity receiving the mixture.

The end wall of the peripheral chamber may be of helical shape about the axis of the cup and of a height that decreases in the direction toward the outlet. The latter may open ahead of a connecting ramp connecting the end wall of the peripheral chamber and the top wall of the blender, this connecting ramp preferably being a portion of a helix extending the helix formed by the end wall of the peripheral chamber.

Preferably, the peripheral chamber comprises the abovementioned annular partition and radial partitions that force the mixture to circulate alternately between upper and lower regions of the peripheral chamber and between radially inner and outer regions, the mixture circulating for example from an upper and radially outer region to a lower and radially outer region by passing through the abovementioned annular partition.

The blender may have an outer body in which a component forming the core of the blender is housed, the outer body radially closing the peripheral chamber on the outside and comprising an upright that separates the central and peripheral chambers.

The outer body of the blender and the core of the blender may each be produced as a single piece by injection molding.

Reduced Dead Volume

There is benefit to be had in reducing the losses of product when changing the formulation of the mixture and in allowing the color of the mixture to be varied as quickly as possible during application, particularly when the dispenser is coupled to an airbrush.

In one of its aspects, independently of or in combination with the other aspects thereof, and notably with the foregoing, one subject of the invention is a system for dispensing a makeup product, having a dispenser that receives at least two cartridges that each have a reservoir containing a base product, the latter leaving the cartridge through an outlet passage of the cartridge, this outlet passage opening to outside of the dispenser or near the external surface thereof.

The outlet passage may notably open into an area in which the mixture is picked up or close to this area, notably less than 5 mm away, better still less than 3 mm away, better still less than 1 mm away, or even better still flush therewith.

The cross section of the outlet passage is, for example, between 1 and 3 mm$^2$.

Thus, each base product coming from a cartridge can leave the dispenser without mixing with a base product from another cartridge and the dead volume that cannot be picked up and is likely to increase the inertia of the system is minimized. The product is more quickly available without having to circulate through special passages in the housing of the dispenser, thereby avoiding a painstaking purging step in the event of a cartridge change.

The outside of the dispenser may be the product pickup area, notably when the dispenser is produced with a cup that is not designed to be removed, into which the mixture is dispensed, or a dispensing area intended for the mounting of a removable outlet interface, which defines the pickup area. This outlet interface may have a cup as defined above. This mounting area corresponds for example to the outside of the housing of the dispenser in the absence of an outlet interface. The mounting area may be substantially planar and perpendicular to the longitudinal axis of the dispenser housing.

The dispenser may have three cartridges of base products.

The dispenser may have housings for receiving the cartridges, which are preferably received removably in the dispenser. The latter may comprise passages for ducts for the cartridges defining the outlet passages.

The length of these ducts is preferably such that the ducts are set back slightly from the end or lie flush with the cavity used for picking up the product or, as an alternative, are set back slightly from or lie flush with the end face of the housing of the dispenser that defines the mounting area.

These ducts of the cartridges may be end pieces used for causing the pistons to move within the cartridges, as described in detail above.

Multiple Outlet Interfaces

There is a need to be able, using the same dispensing system, to achieve different makeup looks easily and be able, if so desired, to make up and/or protect areas as different as the skin, the lips, the neck, etc.

In one of its aspects, independently of or in combination with the other aspects thereof, and notably with the foregoing, one subject of the invention is a dispensing system comprising an assembly comprising a dispenser of at least one cosmetic, notably makeup and/or photoprotective, product and at least two outlet interfaces, each of which can be mounted removably on the dispenser, these outlet interfaces which are able to receive the product or products delivered by the dispenser preferably being chosen from among the following:
- an outlet interface having a container, notably a cup, allowing the product to be picked up using a finger or using an applicator,
- an outlet interface allowing the product to be delivered to a spray system, notably an airbrush,
- an outlet interface having several regions for receiving the product, which can move relative to the dispenser,
- an outlet interface that allows the product to be delivered to a dispensing end piece.

Preferably, the assembly comprises at least three of said outlet interfaces, or better still the four outlet interfaces.

The dispenser may comprise at least two different base products and allow these to be delivered in variable proportions and, preferably, the dispenser comprises three different base products and allows these to be delivered in variable proportions.

Each outlet interface may have a base allowing it to be fixed to the dispenser. This fixing may be done using screws for example, but preferably the base is designed to allow an outlet interface to be removed and replaced without the need for tools. It is, for example, a quarter-turn fixing or a fixing using an external locking ring.

The outlet interface and/or the housing of the dispenser may comprise seals allowing sealed communication between the housing of the dispenser and the outlet interface. If appropriate, the dispenser is designed to recognize the outlet interface mounted above, for example by virtue of the outlet interface having identifiers in the form of specific reliefs which are detected by the dispenser, or in the form of an electronic chip that the dispenser recognizes. That may allow the operation of the dispenser to be adapted to the outlet interface mounted above. The dispenser may communicate information about the outlet interface it is bearing to a computer system, and the computer system may, on the basis of this information, display a specific screen and/or run a specific program for controlling the operating parameters of the dispenser so as, for example, to adapt the dose dispensed and/or the flow rate to the type of outlet interface.

The user may be initially offered several outlet interfaces with a common dispenser within one and the same package, for example a case or a cardboard box.

A further subject of the invention is a makeup method involving the step of selecting an outlet interface, mounting it on the dispenser, and delivering the product(s) contained in the dispenser to the interface.

Mapping and Learning

The term "mapping" should be understood here as meaning a process of indexing a color with an area, with recording.

It may be the case that a person requires several levels of screening with a single mattness/shine for all areas.

It may also be the case that she requires several levels of screening with one level of mattness/shine on one part of the face and another level of mattness/shine for another area. For example, she has several marks on the forehead and several marks on the cheeks. Thus, she may want to create several levels of screening for the forehead with one level of mattness/shine for this surface. She may want to create several levels of screening for the cheeks with one level of mattness/shine for this surface.

The mapping may relate to applications to areas smaller than 1 $cm^2$. However, the naked eye then has difficulty in discerning whether the result obtained is adequate, and it is preferable to substitute an instrumented evaluation with magnification for evaluation by the naked eye. Small quantities of colored substance may be applied with a finger, using conventional tools such as brushes, or using specialist applicators.

The map may be generated during a learning period in which the user carries out tests with mixtures on different areas of the face; once created, the map can then be used for everyday makeup.

Specific graphic interfaces can be used during the learning period and during the period of use of the map.

In particular, the dispensing system may be used with a graphic interface in which the operator sees the face, which is for example a schematic, figurative or accurate representation such as a photograph or a 3D simulation. In that case, the operator can point at part of the face on the screen to show and/or deliver the appropriate color.

The graphic interface may also show the other areas of the face where use of that same color is appropriate.

To create the map, the operator applies a color, then makes an assessment.

The areas of the face can be treated one after the other; for example, the exercise is carried out on part of the cheek, then on the nose, etc.

Another option is to create a given mixture and apply this same mixture to several areas. The operator then needs to look for the area of the face to which the color is suited. The mixture is then indexed in the computer system which attributes it to the area(s) of the face for which it is suitable.

In one of its aspects, independently of or in combination with the other aspects thereof, and notably with the foregoing, one subject of the invention is a learning process for a dispensing system comprising a dispenser for dispensing a mixture of variable color, and a computer system for selecting a color and for storing data, comprising the steps of.
- a) selecting at least one color with the aid of an interface of the computer system,
- b) delivering, with the aid of the dispenser, at least one mixture of the selected color,
- c) evaluating the mixture(s) dispensed following the application thereof to at least one area of the face,
- d) memorizing the characteristics of at least one mixture, notably a mixture that the user wishes to be able to recall, and of at least one area on which it has been tested.

This memorizing can be carried out notably with a view to subsequent dispensing of this mixture for making up said area.

Preferably, the computer system is designed to allow the user to indicate whether or not the result of the test is satisfactory, or even to inform same of the comparison with a test carried out earlier.

It is also possible to create a given mixture and to look for the area of the face for which it is suitable. The mixture is then recorded, being attributed to the area(s) of the face for which it is suitable, in a look-up table that will be used subsequently in order to deduce which mixture to use on the basis of an area of the skin.

The same procedure can be adopted with other mixtures in order to create a map of the entire face and thus have a complete look-up table for the face.

It is also possible to create a given mixture, apply it to a given area, and then vary the mixture until the most suitable mixture is obtained. The mixture is then recorded, being attributed to the area(s) of the face for which it is suitable, in a look-up table that will be used subsequently in order to deduce which mixture to use on the basis of an area of the skin.

Preferably, the computer system evaluates and memorizes the quantities used area by area. Such a method, which uses "test patches" makes it possible to identify the product(s) required by the person wishing to apply makeup. Thus, the dispensing system can be used at sales outlets to advise people wishing to apply makeup or at home in order to define correctly which products to order.

The interface of the computer system preferably has a touch screen displaying the color of the mixture when it is selected.

The interface may display a face and allow the computer system to be informed by selecting the area on the face displayed.

The computer system is preferably designed to allow an area, mixture reconstruction parameters, and the date of the test and/or any other identifier of the mixture to be associated with one another.

The computer system is preferably also designed to allow at least one of the following data: the name of the area, the period of the year, the name of an event, a user identifier and the age of the user, to additionally be associated with said area, with the mixture reconstruction parameters, and with the date or identifier of the mixture.

Steps a) to c) may be repeated at least once before the characteristics of the mixture are memorized in step d).

The computer system may be designed to search a database for the reference of a commercial product on the basis of the characteristics of the mixture identified as being suitable for at least one given area, and to relay this information to the user.

The selection in step a) may be carried out using an expert system, which may or may not be external to the computer system.

The expert system may analyze an image of the user in order to propose a mixture color at least on the basis of the image analyzed.

Step a) may be preceded by the computer system proposing to the user a color and an area to be tested with a mixture of this color.

The computer system may be designed to allow the user to inform same of his or her assessment of the result of the test in step c) and to generate a proposal to modify the mixture to be selected upon return to step a).

The computer system may be designed to propose at least one color of mixture in step a) depending on an application area of which it has been informed by the user.

The computer system may be designed to propose at least one application area in step a), on the basis of a color of which it has been informed by the user.

The dispenser may deliver, in step b), at least two mixtures of different colors, preferably separate, so that they can be applied simultaneously to the test area.

This may allow time to be saved and make it easier to compare the results.

A further subject of the invention is a method of making up using a dispensing system according to this aspect of the invention, in which:
- a) the user sends the computer system a request regarding a need for makeup,
- b) in return, the computer system generates a proposed color for making up an associated zone, on the basis of the learning performed beforehand, and
- c) the computer system operates the dispenser to produce the mixture of the proposed color, notably if this is validated by the user.

Such a method may use a map previously established with the user.

A further subject of the invention is a computer program product containing code instructions which, when run in a computer system, allow the computer system to be made to:
- allow the user to select at least one color and/or one application area, notably using an interface such as a touch screen,
- operate a dispenser in such a way as to deliver a mixture of the color selected by the user,
- allow the user to trigger the memorizing of the color of the mixture and of an associated application area, notably with a view to subsequently dispensing the same mixture, notably on the same area.

The computer program product may comprise code instructions which, when run in a computer system, allow the computer system to be made to:
- receive a request from the user regarding a need for makeup, notably using an interface such as a touch screen,
- propose, on the basis at least of data generated by the learning process as defined above, at least one color and/or one application area,
- operate a dispenser to produce the mixture of the proposed color, notably if this is validated by the user.

The person may incorporate into the map the level of mattness/shine that she desires for each area of the face, area by area or set of areas by set of areas. The system will then interpret the mixtures it needs to create to ensure the colors and coverage desired and the wanted mattness/shine.

The map may subsequently be modified. Thus, it is possible to create the map in terms of the colors/coverage/screening in the first instance, and then refine the map by subsequently defining the levels of mattness/shine.

Remote Assistance

It is desirable to be able to assist the user in applying makeup and/or protecting themselves, notably in choosing the correct colorings.

In one of its aspects, independently of or in combination with the other aspects thereof, and notably with the foregoing, one subject of the invention is thus a method of applying screening makeup involving the steps of:
- allowing a video link to be established, for example over the Internet, between a camera on a first site and a second site,
- allowing the second site to directly or indirectly operate a dispenser present at the first site, this dispenser making it possible to vary the color of a mixture dispensed,
- allowing a person present at the first site to apply the mixture dispensed and to send a corresponding image to the second site, so as to receive in return information relating to the makeup result.

The second site may notably have a viewing screen which allows an adviser sitting at this screen to see the makeup result with the product dispensed by the dispenser and advise the person who has applied the makeup and/or protected themselves. This adviser may in return influence the dispenser to alter the color of the mixture and adapt it to best suit the face of the person present at the first site. Thus, this person controls the mixture delivered by the dispenser. The first person may make herself up under the gaze of the second. The second person sees the result of the test on their screen and can thus correct the mixture that this second person will control remotely until the ideal makeup is obtained. They can provide advice as to the level of screening.

If appropriate, the video acquisition can be calibrated using a test pattern or with the mixture dispensed by the dispenser onto a reference surface. That then allows a more faithful display of the makeup applied at the first site.

Preferably, the video link between the two sites is a two-way link.

The first site may receive a tutorial from the second site, if appropriate.

Identifiers of the base products may be communicated to the second site; this may make it possible to precisely determine the color of each of the base products.

The method may involve memorizing the dispenser setting parameters once a given mixture is considered to be satisfactory. Preferably, this memory storage may be commanded from the second site. The memory storage may be in the computer system present at the first site and/or on an external server.

One alternative may be to have one person working to help several apply makeup. This embodiment makes it possible to develop makeup artists and their work, either within an institute or over the Internet. It also allows people with limited capabilities, such as people with poor eyesight, or people who have difficulty discerning colors, or the elderly, or those lacking in self-confidence to apply makeup.

Operation Via Touch-Sensitive Interface

There is a need to make it easier to control the dispensing system and notably the choice of the color of the mixture dispensed.

A further subject of the invention is a dispensing system having a dispenser and a computer system for operating the dispenser, this computer system having a touch screen on which the color of the mixture can be displayed, and a selection means movable on the screen, in order to vary the color of the dispensed mixture.

Preferably, the screen displays end-point colors between which the color of the mixture can be selected by moving the selection means between these end-point colors.

The screen may display a scale of colors between at least two colors, or an area, notably of triangular outline, within which the selection means can be moved. This area may locally show the color of the mixture depending for example on the distance from each of the vertices, each one embodying a pure base product.

The computer system may perform some of the calculations necessary to determine the fractions of each of the base products that lead to a mixture of the desired color.

The computer system may be a smartphone, a camera phone, a tablet, or a personal computer. As an alternative, it is incorporated into the housing of the dispenser.

The computer system may have a camera. The latter can be used notably for capturing an image of the user and/or of the mixture.

The computer system may be designed to display an image of a face, in order to make it easier to identify the areas to which the mixture is to be applied.

Coupling of the Dispensing System to a Spray Means

The dispensing system may have or be connected to a means of spraying the mixture, preferably an airbrush.

A subject of the invention is also an assembly comprising:
- a spray means, preferably an airbrush having a pickup chamber subjected to a stream of entrainment air,
- a dispenser having at least two compartments containing different base products, the products being delivered to the spray means preferably via distinct distribution orifices.

The dispenser may have three cartridges containing makeup products of different colors.

The airbrush may have a stylus defining the pickup chamber, the stylus being fixed to the dispenser or to an outlet interface fixed to the dispenser, or forming an integral part of this outlet interface.

The dispensing system may have a circuit controlling operation of the dispenser, allowing the proportion of base products delivered to the pickup chamber to be varied while the airbrush is in operation. The proportions may be modified depending on the movement of the airbrush relative to the surface onto which the mixture is sprayed. This movement may be mechanized, if appropriate.

This control circuit may have or be constituted by a computer system as defined above.

The housing of the dispenser may act as a hand grip when the assembly is being handled for delivering the mixture.

The dispenser may have a camera and/or one or more sensors such as accelerometers so as to automatically locate the area to which the mixture is applied, and so as to be able to automatically regulate the color depending on the position, if appropriate.

A further subject of the invention is a method for applying makeup using an assembly as defined above, in which a mixture is sprayed onto the skin using the spray means, notably the airbrush.

The composition of the mixture can be modified as the airbrush is moved relative to the skin. A graduated effect can be achieved.

This aspect of the invention is based on the observation that the dispenser can be used to supply the spray system, notably the airbrush, while at the same time allowing the dispensing system to be responsive enough to allow a change in the color of the mixture dispensed while the face is being made up, notably as the area to be made up changes.

It may be advantageous for the dispensing of products to be performed iteratively, notably with dispensing times that are not phase-shifted between the various products.

This may make it easier to vary the composition of the mixture dispensed over time.

The mixture may be created directly in the airbrush, with practically no troublesome dead volume, thus allowing the mixture sprayed to be changed in real time.

The depression created in the pickup chamber is strong enough to entrain the base products without in any way impeding the metering.

The depression which prevails in the pickup chamber is for example between 10 mbar and 200 mbar, better still between 50 and 150 mbar, even better still between 75 and 125 mbar.

The viscosity of the base products as measured at 1 atm and 25° C. with a CONTRAVES TV rotary viscometer fitted with an MS-r3 or MS-r4 measuring bar at a frequency of 60 Hz after 10 minutes of rotation of the measuring bar is, for example, between 0.05 Pa·s and 50 Pa·s.

The cross section of the passages along which the base products arrive in the chamber is, for example, between 1 and 3 mm², better still between 2 and 3 mm².

The product is preferably supplied continuously.

It is also possible to apply immiscible or reactive base products, such as an aqueous gel and an oily gel, simultaneously, and these will be deposited directly onto the skin in a pixelated manner, producing a kind of gel/gel in situ, reactive silicones, or colorants that react with one another. The ratios of base products can be adjusted depending on the particular result desired. For example, in the case of aqueous gels and oily gels, the ratio corresponding to the volume of the first base product to the volume of the second base product could be varied between 10/1 and 1/10, better still between 5/1 and 1/5.

Location or Auto-Location System

The dispensing system according to the invention may have a location or auto-location system.

A location system is the name given to a means via which the person inputs the area that she is to treat. This can be performed notably using systems that leave at least one hand free. Thus, an interface of a computer system such as a touch screen, a joystick, or voice recognition system can be used.

An auto-location system is the name given to a means for inputting the area that is to be treated without intervention on the part of the person. This can be achieved using one or more accelerometers which deduce, from the movements, the directions targeted by the person or by a camera and an image recognition system.

The invention according to this sixth aspect can be implemented with a dispensing system as described above with reference to the figures, which will not be described again.

Example (Sixth Aspect of the Invention)

Several base products having screening and oily ingredients are created.

The formulation F1 is rich in UV screening agent. The formulation F2 is rich in oil.

| | F1 mass % | F2 mass % |
|---|---|---|
| Dimethicone copolyol sold under the reference KF 6017 by the company Shin-Etsu | 2 | 2 |
| Etsu Bis PEG/PPG-14/14 dimethicone + Cyclopentasiloxane sold under the reference Abil EM 97 by the company Goldschmidt | 1 | 1 |
| Cyclopentasiloxane | 17.65 | 17.65 |
| Phenyl trimethicone sold under the reference DC556 by the company Dow Corning | 0 | 5 |
| Ethyl hexyl methoxycinnamate | 5 | 0 |
| Squalane | 1 | 1 |
| Cyclopentasiloxane | 7 | 7 |
| Yellow iron oxide coated with aluminum stearoyl glutamate NAI-C33-9001-10 from the company Miyoshi Kasei | 1.45 | 1.45 |
| Red iron oxide coated with aluminum stearoyl glutamate NAI-C33-8001-10 from the company Miyoshi Kasei | 0.4 | 0.4 |
| Black iron oxide coated with aluminum stearoyl glutamate NAI-C33-7001-10 from the company Miyoshi Kasei | 0.15 | 0.15 |
| Titanium dioxide (anatase) coated with aluminum stearoyl glutamate NAI-TAO-77891 from the company Miyoshi Kasei | 10 | 10 |
| Talc sold under the reference Micro Ace P3 by the company Nippion Talc | 0.5 | 0.5 |
| Nylon 12 powder sold under the reference SP 500 by the company Toray Industries | 0.5 | 0.5 |
| Demineralized water | 36.15 | 36.15 |
| 1,3-Butylene glycol | 3 | 3 |
| Magnesium sulfate | 0.7 | 0.7 |
| Hydrogenated maltose solution | 0.5 | 0.5 |
| Denatured 96° ethyl alcohol | 13 | 13 |
| TOTAL | 100 | 100 |

Procedure

The constituents of phase A are weighed out in the main beaker and are stirred with a Moritz blender (1000 rpm) while maintaining at room temperature. Phase B is prepared separately by milling three times in a three-roll mill the mixture of pigments and of cyclopentasiloxane. This phase B is then added, with continued stirring, along with the fillers (phase C).

The aqueous phase D is also prepared separately, by weighing out in a beaker the butylene glycol, the magnesium sulfate, the hydrogenated maltose solution, and water at room temperature. The aqueous phase D is stirred using a magnetic bar until homogenized. C D E The emulsion is made at room temperature: the aqueous phase D is poured into the fatty phase while gradually increasing the stirring speed (Moritz blender) up to 4000 rpm. Stirring is continued for 7 minutes. Finally, phase E (ethyl alcohol) is added for the last 3 minutes of 5 the emulsification.

Test

The dispensing system was tested with:

F1 in compartment A

F2 in compartment B

The system was used to create several mixtures (volumetric proportions):

M1: A 30%, B 70%

M2: A 70%, B 30%

M1 and M2 were applied to different areas of the face. Different filtering actions but with equivalent levels of mattness were obtained.

G) Dispensing System for Customizing Foundations and their Matting Power Depending on the Areas of the Face In the case of overall makeup or the making up of marked skin, there is a desire to have the most attractive appearance as possible. However, in order to perfect the esthetics of the face, it is not enough to apply the best color at the right location. Thus, it is apparent that the ideal level of mattness/shine may be different depending on the area in question. Some people prefer areas such as the cheeks to be shiny. By contrast, they prefer other areas such as the forehead to be matt.

There are very few solutions for solving this problem.

A first approach is to buy numerous products and try them all out. This approach is costly and often gives rise to waste insofar as only a small number of the colored substances tried are generally kept.

A second approach is to test out various products in store. That is not always suitable, because it is very difficult to get a feeling for the results in just a few moments and at a location missing the usual landmarks. In particular, in order to fully assess the makeup effect in store, it would be necessary to be able to have the same lighting as will be found in future conditions of use, and this is something that is rarely possible. In general, it is only by testing out makeup over the course of a day that one can determine whether or not it is suitable. In addition, while certain stores have advisers and allow testing, this is not the case for a large number of other sales outlets and Internet sales.

Another approach has been tested but not developed. This is to create one's products by hand by mixing several colored products. This may prove relatively difficult to do because it is not very easy to reproduce the same mixture exactly a number of times over, and it is awkward to quickly create the mixtures one needs at the moment of applying the makeup.

Dispensers for dispensing a cosmetic composition of variable color are also known.

Of the tests that have been able to be attempted for automating the manufacture of a customized cosmetic composition, many are those in which the proposed solutions allow mixtures to be created in quantities of around 100 g or sometimes less, but not in the very small proportions generally needed by a person applying makeup, namely in the region of one gram or much less.

In order to illustrate this problem, consider the case of somebody wishing to make up their face with a graduation of mattness/shine that goes from matt to shiny from the nose (matt) to the cheeks (shiny) and then to the edge of the face (matt). To create this effect, it is necessary for the person to be able to apply several touches of product, of the same color but with different and controllable levels of mattness/shine. Two products are not enough since they result in demarcations between the areas. Thus, there is a need to rapidly and reliably have small quantities of product with variable mattness/shine. The touches may be for example in the region of 10-50 mg per touch and serve to cover only areas of a few cm². The same exercise is even more difficult if, to avoid a kind of uniformity, the person may wish to vary the color (color and coverage) while varying the level of mattness/shine.

Therefore, according to certain aspects, the invention seeks to make it easier to make up the face and notably to find the most suitable products in terms of mattness/shine for the different areas thereof and to rapidly obtain a result with levels of mattness/shine suited to the different areas.

The invention also seeks to obtain a given color with different levels of mattness/shine.

According to its seventh aspect, the invention is based upon a dispensing system that allows mixtures to be generated from base products. These base products may be of different colors (or colorless), such that the mattness/shine of the mixture can be varied. The base products may even make it possible to vary the coverage and/or color of the mixture, such that the color resulting from applying the mixture to human keratin materials varies, being fairly close to that of said materials. Thus, according to this seventh aspect, the invention makes it possible to fix a color and/or shine and vary the mattness/shine or vary them all. The idea of color is to be understood in a broad sense and encompasses mixtures of which the color varies after application as a result of variations in their level of coverage and in the color of the underlying skin.

Thus, according to a seventh of its aspects, the subject of the invention is a system for dispensing a product, comprising a dispenser that receives at least two cartridges that each have a reservoir containing first and second base products, respectively, the first base product comprising at least one of an oil, an interference pigment or a pigment with a metallic tint, the second base product comprising a matting filler, the dispenser making it possible to deliver at least these two base products in adjustable proportions.

According to this seventh aspect, the invention may have one or more of the following preferred features:
the first base product contains an oil,
the first base product contains an interference pigment,
the first base product contains a pigment with a metallic tint,
the particle size D50 by volume of the pigment and of the filler is between 100 nm and 1 mm, better still between 200 nm and 100 microns, even better still between 200 nm and 50 microns,
the filler is chosen from talc, mica, silica, kaolin, poly-β-alanine powder and polyethylene powder, tetrafluoroethylene polymer powders, nylon powders, polymethyl methacrylate powders, lauroyllysine, starch, boron nitride, hollow polymer microspheres such as those of polyvinylidene chloride/acrylonitrile, acrylic acid copolymer microspheres, silicone resin microbeads, polyorganosiloxane elastomer particles, precipitated calcium carbonate, magnesium carbonate, magnesium hydrogen carbonate, hydroxyapatite, barium sulfate, aluminum oxides, polyurethane powders, composite fillers, hollow silica microspheres, and glass or ceramic microcapsules, the particles that are in the form of hollow sphere portions, and mixtures thereof, and is preferably chosen from talc, mica, silica, nylon powders, polymethyl methacrylate powders, and mixtures thereof, and is even more preferably talc,
the filler may have a coating comprising at least one lipophilic or hydrophobic compound,
the first base product and the second base product comprise an inverse emulsion,
the mass content of filler in the second base product is greater than or equal to 0.5% of the mass of the first base product, preferably greater than 1% of the mass of the first base product, even more preferably between 1% and 5% of the mass of the first base product,
the dispensing system comprises a third cartridge with a third base product,
the cartridges are received in a removable manner in the dispenser,
each base product leaves the cartridge through an outlet passage of the cartridge, the outlet passage being defined by a dispensing end piece of the cartridge, said end piece being driven in rotation relative to a body of the cartridge by a drive mechanism of the dispenser in order to dispense the base product contained in the cartridge.

According to its seventh aspect, a subject of the invention is also a method for applying a cosmetic, makeup and/or care, product to human keratin materials, comprising the setting of the dispenser depending on the area to be treated, and the dispensing of the product by base products being picked up from the cartridges in the proportions corresponding to the setting of the dispenser.

Thus, according to its seventh aspect, the invention is based on a dispensing system having compartments containing at least two different formulations which preferably contain inverse emulsions that have a concentration of oils, nacres, or particles with a metallic tint, for the one part, and a concentration of (matting) fillers for the other.

It is thus possible to vary the level of mattness/shine while retaining the same color appearance.

The system may be programmed to deliver, for each location on the face, the best matting or shiny mixture (neither too much nor too little). The overall appearance will not make it possible to tell that the face has been treated, since it comes close to the appearance of a natural face.

Dispensing System

The dispensing system may consist of a single device operating autonomously, preferably able to be manipulated in one hand, or of a device that operates in interaction with other components or devices. It may for example entail various outlet interfaces which are mounted on the dispenser depending on the type of makeup to be created, as will be specified below. It may also entail a computer system which exchanges information with the dispenser in order to operate the latter, this computer system comprising, for example, a portable terminal such as a smartphone, a camera phone, a tablet, a laptop computer or a dedicated terminal.

Preferably, the dispenser is designed to pressurize one or more compartments containing the base product(s), via volumetric metering devices, preferably a motor causing a piston to move in the corresponding compartment.

The dispenser may be formed of a housing and of at least two or three compartments, and preferably an identical number of motors. For example, the rotation of the motors drives endless screws which push the pistons of each compartment. The advancing movement of the pistons is, for example, controlled by the number of command pulses sent to the motors and/or by the length of time for which the latter are operating. The motors may be powered in sequence or preferably simultaneously.

For example, the motors are powered during an elementary operating cycle for a short duration one after the other or at the same time as one another, so as to dispense corresponding microdoses.

The elementary cycles are repeated, possibly with a pause between them, giving the base products time to flow out of the compartments.

The compartments may be defined by cartridges, which are removed when they become empty. As an alternative, the compartments are permanently present and refilled once they become empty.

Each cartridge may be closed by a stopper that can be removed to allow the cartridge to be cleaned.

Preferably, the housing of the dispenser is of elongate shape along a longitudinal axis, making it easier to handle, and the cartridges are disposed about this axis, inside the housing.

Preferably, the cartridges are inserted from the rear and the mixture is delivered from the front. The cartridges may be inserted individually or, as an alternative, the cartridges constitute a one-piece assembly as they are inserted.

The cartridges may each have a volumetric metering mechanism comprising a piston moved by a drive mechanism of the dispenser in a direction accompanied by a reduction in the internal volume containing the base product and the expulsion of some product. It may be advantageous for the cartridges to have at least a region of their wall that is transparent so that the color of the product contained therein can be seen.

The drive mechanism may have a motorization system formed of motors coupled to gearboxes, of elongate shape parallel to the longitudinal axis of the dispenser, and positioned between the cartridges. Positioning the motors and cartridges in this way makes the dispenser particularly compact.

The base product can leave the corresponding cartridge in a sealed manner, then flow along a passage provided for this purpose in the housing of the dispenser, before leaving the latter.

The cartridges advantageously end in an end piece produced in such a way that, once the cartridge has been inserted into the housing of the dispenser, the end of the end piece terminates flush with the housing. As an alternative, the end piece is long enough to protrude beyond the housing and thus connect various outlet interfaces that can be attached to the housing of the dispenser.

By virtue of the drive mechanism having motors for causing the pistons to advance, it is possible to precisely deliver mixtures in very small quantities. Thus, the drive mechanism can deliver the base products with a minimum flow rate less than or equal to 50 L/s, better still less than or equal to 20 µL/s, even better still less than or equal to 10 µL/s. Preferably, the drive mechanism delivers flow rates of between 20 and 100 µL/s, better still between 40 µL/s and 60 µL/s. It is thus possible to easily create a mixture of around 10 mg. Such a dispensing system is therefore ideal for achieving small touches of makeup, for covering an area of 1 cm$^2$, better still an area of 0.5 cm$^2$, for example.

It is also possible to create larger quantities of mixture such as the quantities needed to make up a cheek or a face. These quantities remain relatively low, however, for example a quantity of between 100 and 500 mg, better still between 150 and 250 mg.

The dispenser preferably has a housing, and at least one cartridge received in the housing of the dispenser, this cartridge having a body and a piston that is able to move in the body, the housing having a motorized drive mechanism for moving the piston of the cartridge.

Preferably, the cartridge has a dispensing end piece through which the product exits, and this dispensing end piece is driven in rotation by the drive mechanism for moving the piston. The end piece may have at least one rotation-proofing relief, better still two diametrically opposed rotation-proofing studs.

The end piece may bear a seal, notably an O-ring seal. Thus, when changing the cartridge, the seal is also changed, making it possible to get around the problem of seal wear.

The dispenser may have an electronic board for controlling the motorized drive mechanism, this electronic board having the end piece(s) passing through it. This may make it possible to produce a board extending across substantially the entire cross section of the dispenser so that all the electronic components of the dispenser can be grouped together on a single board, thus improving compactness and reliability. The board may extend substantially perpendicularly to the longitudinal axis of the housing. The board may bear a switch for controlling operation of the dispenser.

The dispensing system may be designed to operate in at least two dispensing modes.

In a first mode, referred to as "continuous", the mixture is dispensed as long as pressure is applied to the control switch.

In a second mode, referred to as "dose", a predefined quantity of the mixture is dispensed for each press of the switch.

The end piece(s) may terminate at one end of the housing. This may make it possible to reduce the dead volume, as will be explained in detail below.

The end piece(s) may have at their end a shutoff system for preventing the products from drying out in the duct, for example a self-healing membrane.

The cartridge may have a hollow screw onto which the piston is screwed, the piston being able to move axially along the screw as the latter turns; the piston is prevented from turning in the body of the cartridge. For example, the friction of the piston against the body of the cartridge may be enough to prevent it from turning when the screw turns.

Preferably, rotation is rendered impossible with a cartridge body of non-circular cross section and a piston that is not deformable.

The torque of the motors may be determined electronically depending on the current drawn, and may be used for example to detect that the piston has reached the end of its travel. Information regarding the torque may be transmitted remotely to a computer system that has a man-machine interface, in order that correct operation of the dispenser can be monitored.

In order to adjust the shade, the dispensing system according to the invention has to allow the user to vary the volume delivered from each compartment.

Preferably, the dispenser is operated by a computer system built into the dispenser or external thereto, the dispenser then being able to exchange information with the computer system using a wireless or wired protocol.

The dispenser may thus be operated so as to allow the shade to be adjusted by controlled simultaneous or sequential dispensing of several base products of different colors.

The dispensing of the base products may be continuous; in such a case, the volumes of each of the base products are dispensed in a single shot, simultaneously or in succession.

In the case of simultaneous dispensing, it is beneficial to be able to adjust the respective flow rates of the various base products in order for the dispensed mixture to correspond to the desired mixture at all times. Such a dispensing mode may be suitable in particular when dispensing the mixture by spraying, using an airbrush. To adjust the flow rates it is possible, for example, to alter the speed at which the pistons move, for example in the case where the pistons are driven by an endless screw, by varying the rotational speed of the motors that drive the screw. The products may also be dispensed in a pulsed manner with a dispensing time and a pause in each cycle. By altering the duty cycle it is possible to alter the flow rate.

All the products may be delivered simultaneously during the dispensing time or, as an alternative, the cycles of the various products are phase-shifted from one another so that one product is dispensed while the other products are paused.

In one particular embodiment of the invention, the mixture is delivered into a cavity of a container which may close hermetically or not, for example in the form of a cup, into which an applicator, particularly a stylus or a brush may be slipped.

When it is not removable, the container may be produced with the body of the dispenser. When it is removable, it may constitute one output interface among others that can be mounted on the dispenser.

The compartments, and in particular the cartridges, may contain all or part of the drive mechanism and, for example, the motorizing system or, better still, part of the motorizing system, the purpose of this being to reduce the number of moving parts in the body of the dispenser outside the cartridges. For example, the cartridges contain the rotor of the motor. Once the cartridges have been installed in the body of the dispenser, the rotors are made to interact with the stators.

The dispensing system is advantageously arranged in such a way as to allow the running of preprogrammed sequences in which the mixture delivered by the system is modified continuously or discontinuously. A "graduated" mode makes it possible for example to progress gradually from a mixture A to a mixture B. In the case where the application is by spraying, notably using an airbrush, this makes it possible for graduations to be achieved simply. An "alternate" mode makes it possible for example to switch quickly from a mixture A to a mixture B several times in succession. In the case of application by spraying, a multilayer application can thus be achieved, with different formulations for two superposed adjacent coats. Another mode makes it possible for example to offer several preprogrammed successive mixtures, the computer system each time indicating to the user how these should be used, for example by display on a screen.

In the case of manual application, the mixtures are dispensed for example into a cup. The person applies the makeup to the recommended place with a corresponding mixture taken from the cup, then, if necessary, cleans out the cup and commands delivery of a new mixture; the operation is repeated as many times as necessary until the person is fully made up.

The mixtures dispensed can be homogenized in various ways depending on the type of use. In the case of manual application, it can be done directly on the application area at the time of application or in the cup before the mixture is picked up; in the case of an airbrush application, the pipe of the airbrush is used as a mixing chamber; if the mixture is dispensed into a container for later use, homogenization can be performed by hand or by passing the dispensed products through a mixing chamber situated between the dispenser and the container or incorporated directly into the container, as described in detail below.

The product may be delivered by the dispensing system and used extemporaneously. As an alternative, the product delivered by the dispensing system is packaged and used later, for example on several occasions, with, for example, at least one day's interval between two uses.

According to its seventh aspect, the invention is based on a dispensing system, compartments containing at least two different formulations which may contain inverse emulsions that have a concentration of oils, nacres, or particles with a metallic tint, for the one part, and a concentration of (matting) fillers for the other.

Oils

The term "oils" is understood to mean an oil that remains on the skin at room temperature and atmospheric pressure for at least several hours, and that notably has a vapor pressure of less than 0.13 Pa (0.01 mmHg).

These nonvolatile oils may be hydrocarbon-based oils, notably of animal or plant origin, silicone oils, or mixtures thereof. A "hydrocarbon-based oil" is understood to be an oil mainly containing hydrogen and carbon atoms and possibly oxygen, nitrogen, sulfur and/or phosphorus atoms.

Nonvolatile hydrocarbon-based oils that may especially be mentioned include:

hydrocarbon-based oils of animal origin, hydrocarbon-based oils of plant origin such as triglycerides constituted by fatty acid esters of glycerol, the fatty acids of which may have chain lengths varying from C4 to C24, these chains possibly being linear or branched, and saturated or unsaturated; these oils are in particular heptanoic or octanoic acid triglycerides, or alternatively wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passion-flower oil and musk rose oil; shea butter; or else caprylic/capric acid triglycerides, synthetic ethers containing from 10 to 40 carbon atoms, linear or branched hydrocarbons of mineral or synthetic origin, such as petroleum jelly, polydecenes, hydrogenated polyisobutene, squalane and liquid paraffins, and mixtures thereof, synthetic esters such as oils of formula R1COOR2 in which R1 represents a linear or branched fatty acid residue containing from 1 to 40 carbon atoms and R2 represents a notably branched hydrocarbon-based chain containing from 1 to 40 carbon atoms, on the condition that R1+R2≥10, for instance purcellin oil (cetostearyl octanoate), isopropyl myristate, isopropyl palmitate, C12 to C15 alkyl benzoates, hexyl laurate, diisopropyl adipate, isononyl isononanoate, isodecyl neopentanoate, 2-ethylhexyl palmitate, isostearyl isostearate, 2-hexyldecyl laurate, 2-octyldecyl palmitate, 2-octyldodecyl myristate, alkyl or polyalkyl heptanoates, octanoates, decanoates or ricinoleates such as propylene glycol dioctanoate; hydroxylated esters such as isostearyl lactate, diisostearyl malate and 2-octyldodecyl lactate; polyol esters and pentaerythritol esters, fatty alcohols that are liquid at room temperature, with a branched and/or unsaturated carbon-based chain containing from 12 to 26 carbon atoms, for instance octyldodecanol, isostearyl alcohol, oleyl alcohol, 2-hexyldecanol, 2-butyloctanol and 2-undecylpentadecanol, higher fatty acids such as oleic acid, linoleic acid or linolenic acid, and mixtures thereof.

The nonvolatile silicone oils that may be used in the composition according to the invention may be nonvolatile polydimethylsiloxanes (PDMSs), polydimethylsiloxanes comprising alkyl or alkoxy groups, that are pendent and/or at the end of a silicone chain, the groups each containing from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes, and mixtures thereof.

Preferably, the oily phase comprises at least one silicone oil, even more preferably chosen from:

volatile cyclic silicone oils having a viscosity at room temperature of less than 8 cSt and containing notably from 4 to 7 silicon atoms, these silicones optionally comprising alkyl or alkoxy groups containing from 1 to 10 carbon atoms, in particular chosen from hexamethylcyclotrisiloxane, octamethylcyclotetrasiloxane, decamethylcyclopentasiloxane and dodecamethylcyclohexasiloxane (cyclohexasiloxane), and mixtures thereof;

volatile or nonvolatile polydimethylsiloxanes (PDMSs) (INCI name: Dimethicone);

phenylated silicones;

polydimethylsiloxanes comprising aliphatic groups, in particular alkyl groups, or alkoxy groups, which are pendent and/or at the end of the silicone chain; these groups each comprising from 6 to 24 carbon atoms, and more particularly caprylyl methicone, such as the commercial product Dow Corning FZ-3196® from the company Dow Corning;

mixtures thereof.

Interference Pigment (Nacres)

An "interference pigment", also known as "nacres", should be understood as meaning iridescent or non-iridescent colored particles of any shape, especially produced by certain molluscs in their shell or alternatively synthesized, which have a color effect via optical interference.

The nacres may be chosen from nacreous pigments such as titanium mica coated with an iron oxide, titanium mica coated with bismuth oxychloride, titanium mica coated with chromium oxide, titanium mica coated with an organic dye and also nacreous pigments based on bismuth oxychloride. They may also be mica particles, at the surface of which are superposed at least two successive layers of metal oxides and/or of organic dyestuffs.

Examples of nacres that may also be mentioned include natural mica covered with titanium oxide, with iron oxide, with natural pigment or with bismuth oxychloride.

The nacres may more particularly have a yellow, pink, red, bronze, orange, brown, gold and/or coppery color or tint.

Advantageously, the nacres according to the invention are micas covered with titanium dioxide or with iron oxide, and also bismuth oxychloride.

Particles with a Metallic Tint

Within the meaning of the present invention, the term "particles with a metallic glint" is understood to mean any compound of which the nature, size, structure and surface finish allow it to reflect the incident light, notably in a non-iridescent manner.

The particles with a metallic tint that are usable in the invention are in particular chosen from:

particles of at least one metal and/or of at least one metal derivative;

particles comprising a monomaterial or multimaterial organic or inorganic substrate, at least partially coated with at least one layer with a metallic tint comprising at least one metal and/or at least one metal derivative; and mixtures of said particles.

Among the metals that may be present in said particles, mention may for example be made of Ag, Au, Cu, Al, Ni, Sn, Mg, Cr, Mo, Ti, Zr, Pt, Va, Rb, W, Zn, Ge, Te and Se, and mixtures or alloys thereof. Ag, Au, Cu, Al, Zn, Ni, Mo and Cr, and mixtures or alloys thereof (for example bronzes and brasses) are preferred metals.

The term "metal derivatives" denotes compounds derived from metals, especially oxides, fluorides, chlorides and sulfides.

Fillers

These fillers are colorless or white solid particles of any form, which are in a form that is insoluble and dispersed in the medium of the composition.

As illustrations of these fillers, mention may be made of talc, mica, silica, kaolin, poly-β-alanine powder and polyethylene powder, tetrafluoroethylene polymer powders (Teflon®), nylon powders, polymethyl methacrylate powders, lauroyllysine, starch, boron nitride, hollow polymer microspheres such as those of polyvinylidene chloride/acrylonitrile, for instance Expancel® (Nobel Industrie), acrylic acid copolymer microspheres, silicone resin microbeads (for example Tospearls® from Toshiba), polyorganosiloxane elastomer particles, precipitated calcium carbonate, magnesium carbonate, magnesium hydrogen carbonate, hydroxyapatite, barium sulfate, aluminum oxides, polyurethane powders, composite fillers, hollow silica microspheres, and glass or ceramic microcapsules. Use may also be made of particles that are in the form of hollow sphere portions, as described in the patent applications JP-2003 128 788 and JP-2000 191 789.

The fillers may have a coating comprising at least one lipophilic or hydrophobic compound.

Inverse Emulsions/Anhydrous Compositions

According to the invention, when a composition is said to be in the form of an inverse emulsion, it will be understood that it can also alternately be in another form depending on the composition in question.

A base product may be in the form of an emulsion, for example an O/W, W/O, O/W/O or W/O/W emulsion, and preferably a W/O inverse emulsion, or in the form of an anhydrous composition, comprising notably carbon-based compounds and/or silicone compounds, such as hydrocarbon-based oils and/or silicone oils.

The emulsions according to the seventh aspect of the invention are preferably water-in-oil (W/O) emulsions, also known as inverse emulsions, namely constituted of an oily continuous phase in which the aqueous phase is dispersed in the form of droplets so as to observe a mixture that is macroscopically homogeneous to the naked eye.

Use for Making Up One or More Precise Areas of the Skin

The dispensing system allows makeup to be applied, day after day, with only the areas that need to be hidden being treated. To this end, small doses of makeup are delivered, and are applied specifically and sequentially to the corresponding areas. Each small dose is created using the mixture suited to the area.

In one preferred embodiment of the invention, the dispensing system waits for information regarding which area is to be treated and then delivers the corresponding mixture. It may use a preprogrammed look-up table for that purpose, this table being the result for example of a learning process as defined below. As an alternative, the dispensing system informs the person, when delivering a mixture, of the area to which the person is to apply the mixture. Thus, the dispensing system may follow an application program in which it delivers, in a given order, the various mixtures that are to be applied.

In one particular embodiment of the invention, the dispensing system is informed as to the quantities to be delivered. For that, it memorizes the relationship between the mattness/shine, the area of the face and the quantity needed, thereby making it possible to reduce costs and wastage of product, and to cover the skin only lightly, thus avoiding occlusion effects. In so doing, it is possible to use products that have a high matting action and provide too much matting or are very shiny or too shiny to be applied to the whole of the face. Thus, it is possible to obtain makeup of natural or even undetectable appearance.

The dispensing system may also make it possible, by facilitating the dispensing of small quantities and rapid use thereof, to reduce the time for which the products are kept, thus making it possible to reduce the risks of the products changing and/or to reduce the amounts of preservative to be used.

The dispensing system is suited to treating the areas that are to be concealed, without having to conceal the entire face.

In an especially advantageous variant, the system may be used to apply to the base of the face a matt formulation and then one or two applications to precise areas of the face of more shiny formulations. It is also possible to start with applications to the precise areas of the face of shiny formulations and then to apply to the base of the face an application of a more matt formulation.

In the second case, time is taken, before applying the second layer, to wait for the film produced by the application to the precise areas to become sufficiently cohesive so that the second layer does not remove the first layer.

Alternatively, the second layer is applied without rubbing (spray for example, or sponge).

When the user is looking for the mattness/shine to apply to an area of the face, it is advantageous to memorize the mattness/shine best suited to each area, and the dispensing system is thus advantageously designed to memorize this mattness/shine and the corresponding area. Thus, by using the memorized information, on each use, the same mixture can be delivered for each area or, if several areas are being treated, the same series of mixtures can be delivered for the same series of areas.

The dispensing system may also be designed to allow an area to be treated by varying the mattness/shine application after application. Thus, the person may make up her lips using different colors that she chooses on a day-by-day basis to suit her tastes. This approach is also suitable for the eyelids, and for face makeup because the person may fancy a change of foundation color. For example, on weekdays, the person applies a colored foundation that is more matt, and at the weekend a foundation that is more shiny.

The dispensing system may be designed to allow the user to change mattness/shine in addition to color/coverage parameters to suit her tastes according to the day, the time, what she is wearing, and the weather. Thus, a system to assist with decision making is advantageously provided to guide the user in her choices of mattness/shine and/or color (broadly speaking).

An assistance system may also be provided for balancing the mattness/shine on the same face and contribute toward a successful overall makeup look.

It may be desirable for several people in the same group, for example a family, to be able to use the dispensing system, thus reducing costs and minimizing the space taken up. This solution is particularly suited to travel or hotels, campsites, airplanes, campervans, boutiques, schools, etc. For that, provision may be made for the dispensing system to be able to be informed as to which person is using it, so as to access pre-stored personal data.

Continuous Use for Makeup with Graduated Mattness/Shine

In this application, the dispensing system changes the formulation of the mixture while it is delivering the product. In addition, the outlet for the base products or for the mixture is moved relative to a container or a support defining an application surface. In one particular embodiment of the invention, the dispensing system is designed to calculate the way in which the mixture evolves as a function of the mattness/shine C1 of one area to be treated and of the mattness/shine C2 of another area to be treated. For example, with the knowledge that the chin requires a mattness/shine C1 and that the cheek requires a mattness/shine C2, the dispensing system may vary the formulation of the mixture while it is delivering it in order to graduate the mattness/shine between these two points. This makes it possible for example to better conceal imperfections of the face while ensuring that the end result is realistic, or allows mattness/shine to be graduated for beautifying purposes. The dispensing system may also be designed such that the user can command a variation in mattness/shine of the mixture dispensed without the start and/or end mattness/shine having been set beforehand. To do that, the dispensing system may possess a location or auto-location system and deduce from a look-up table the mattness/shine C1 and C2 that it has to create and therefore the changes in the mixture that it has to make.

The dispensing system may have an outlet head, in particular in the case of an airbrush, which is mobile and steered. This option then makes it possible to achieve graduated effects without moving the rest of the dispensing system. For example, the dispensing system is located near to the cheek, then a control system is triggered that will automatically steer the variation in formulation of the mixture and the movement of the outlet head so as, for example, to make the center of the cheek redder than the periphery thereof, with a graduation between the two.

The dispensing system may even be used to create tailor-made products that are kept for several applications.

It is also possible to produce solid or semi-solid products.

Manufacture of "Bespoke" Compacts or Other Solid or Semi-Solid Products

The dispensing system may be designed to allow a mixture to be chosen and delivered to a container such as a cup. The mixture preferably comprises compounds which are such that the mixture can set solid.

More preferably, use is made of compounds that make the setting especially rapid. These compounds are either deposited in the container before or after it is filled with the other ingredients, or are provided in the compartments of the dispenser with the other constituents of the base products, or are contained in the dispenser in a compartment especially designed to contain them.

Specific compositions which may harden quickly by chemical, biochemical or physicochemical reaction after discharge may thus be dispensed.

These compositions are especially designed for the creation of compacts, namely they:
  set solid,
  yield a material that can crumble if rubbed, and are preferably colored.

Preferably, these compositions are very rich in solid particles, with for example more than 10% by mass of solid particles relative to the total weight of the composition, better still more than 20% by mass of solid particles relative to the total mass of the composition, even better still more than 30% by mass of solid particles relative to the total mass of the composition, preferably between 10 and 40% by mass of solid particles relative to the total mass of the composition.

These compositions may contain absorbent particles or reactive compounds, such as those that react in contact with the air, for example cyanoacrylate or alpha-silanes or those which react to light, notably UV.

The container into which the mixture is dispensed may contain a compound A and the dispensed compositions may contain a compound B, A and B being chosen to react with one another and solidify the mixture.

In one particular embodiment of the invention, the dispensing system incorporates a heating means, for example with an electrical resistor, to create lipsticks or other waxy products. In that case, the base products are heated before being delivered.

The dispensing system may also comprise a means for supplying heat and/or light energy, after the mixture has been dispensed into a container, for example an electrical resistor or an LED, notably UV. This energy may accelerate the setting-solid of the dispensed mixture.

Preferably, the mixture is homogenized before it sets solid.

Creation of Mattness/Shine Palettes

The dispensing system may have a support, having several regions, and may be designed to automatically generate several mixtures deposited in said regions, for example a series of mattness/shine suited to various parts of the face.

The support may define several cavities to receive the mixtures or may bear several containers, for example in the form of cups, potentially cups that are separable from the support.

In one particular case, the support adopts the shape of a face with regions for receiving the mixtures for targeted application areas.

The support may be able to move, notably to rotate, with respect to the body of the dispenser and, for example, may be driven in its movement by the dispenser so that various spaces or containers can be filled in succession.

The products in the palette may have different colors while having different mattness/shine effects.

Cup-Type Dispenser

There is a benefit to having a dispensing system capable of delivering a mixture that the user can easily pick up. Moreover, in cases in which the base products delivered by the dispensing system are not already blended, there is a need to allow the user to perform the mixing easily.

A further subject of the invention is a system for dispensing at least one makeup product, having a cup and a dispenser for filling the cup with at least one product, the cup being secured to the dispenser at least while it is being filled.

The cup is sometimes also known as a "crucible" and that term should be understood in its broadest sense.

A "cup secured to the dispenser" should be understood as meaning that the cup is held, notably immobilized, at least temporarily, on the dispenser, being for example fixed to the latter by screws, magnetic attraction, clip-fastening, bayonet locking, clamping, or produced with a part of the dispenser body by material molding. When it is secured to the dispenser, the cup allows the latter to be manipulated in one hand, the cup remaining in place on the dispenser while the latter is being moved around.

The dispenser may be offered to the user with the cup already in place.

As an alternative, the cup is installed by the user the first time the dispensing system is used.

The cup is preferably less deep than it is wide, making access to it easier and allowing the product, notably the mixture, to be picked up with an applicator or a finger.

Preferably, the cup is separable from the dispenser and constitutes one outlet interface that can be chosen from a collection of outlet interfaces that can be mounted on the dispenser, at the choice of the user and according to the making up to be performed, as described in detail below.

Preferably, the dispensing system comprises several filling orifices for filling with different base products, opening into the cup. Thus, the mixing of these products may take place in the cup.

The cup preferably has a bottom that is concave toward the outside, making it easier for the user to clean it between two uses.

In addition, this may make the product easier for the user to pick up and the base products easier to mix.

Preferably, the dispenser allows at least two base products to be delivered into the cup, in adjustable proportions, and better still at least three products.

In one exemplary embodiment, the dispensing system has at least two cups that can be selectively fed by the dispenser. This may allow the user to fill these two cups quickly with mixtures with different characteristics. This may facilitate the testing of colored substances and/or allow the preparation of several mixtures of different colors and mattness/shine intended for making up respective areas of the face. The cups may be associated with identifiers that remind the user of the area of the face for which a mixture contained in a given cup is intended.

The cups may be able to move relative to the dispenser, being for example borne by a mobile support such as a turret that is rotatable with respect to the dispenser or by a slide capable of translational movement with respect to the dispenser.

The dispensing system may comprise a lid for closing the cup. This closure lid is preferably transparent so that the user can see the appearance of the mixture contained inside.

When the cup is separable from the dispenser it may if necessary be introduced into a housing that allows it to be transported more easily, this housing being able, if necessary, to contain a mirror and/or an applicator. The lid of the housing may in this case act as a lid for the cup.

The volume of the cup may be between 2 and 1000 mm$^3$, better still between 100 and 1000 mm$^3$, even better still between 250 and 750 mm$^3$.

The base product(s) delivered into the cup are preferably foundations, but as an alternative may be makeup products for the lips or eyelids.

The cup preferably has a shape that exhibits symmetry of revolution. As an alternative, it has a polygonal or some other contour. Its largest inside diameter, or that of the inscribed circle in the case of a noncircular contour, is preferably between 2 and 100 mm, preferentially between 5 and 40 mm. Its depth is preferably between 1 and 10 mm, better still between 3 and 8 mm. Its depth is preferably between 1 and 10 mm. Preferably, the size and shape of the cup either allow direct application of the mixture to the skin or allow the mixture to be picked up on a finger or using an applicator. The cup may be made of an elastically deformable material, making it possible for example to turn the concavity of the bottom of the cup inside out and empty it more easily or use it to apply the product.

The cup may have no blender; in that case, the base products may arrive in the cup from the dispenser in the unmixed state, via distinct respective dispensing orifices. As an alternative, the dispenser incorporates a blender and the base products arrive in the cup already blended.

The cup may also incorporate a static blender as described in detail below, which is fed via distinct filling orifices of the dispenser and which preferably delivers the mixture into a cavity of the cup situated above the blender.

A further subject of the invention is a method for preparing a makeup product, comprising the step of filling a cup of a dispensing system as defined above with at least one base product from the dispenser.

The products will have different mattness/shine effects.

Several products may be delivered into the bottom of the cup, then blended using a finger or an applicator, or a static blender incorporated into the cup.

The cup is preferably filled from beneath. Dispensing systems using a sonotrode have been proposed in the past.

The cup according to the invention is not intended to vibrate in order to dispense the product(s) conveyed by the feed passage(s) supplying it. It differs from a sonotrode.

Preferably, the cup is made of plastic.

Blender Incorporated into the Outlet Interface

There is a benefit in having a dispensing system capable of delivering a mixture that can easily be used, notably picked up by the user, without the need for an additional mixing action on the part of the user.

A further subject of the invention is a dispensing system having a dispenser having outlet passages for base products and an outlet interface that is separable from the dispenser, this interface having a static blender that preferably delivers the mixture into a cavity where it can be picked up.

The static blender may be situated under the abovementioned cavity. The dispensing system is then particularly suited to the creation of compacts, using cups with an in-built static blender as outlet interfaces. In that case, the cavity of the cup is filled with product from beneath. After passing into the static blender, the blended base products cover the blender.

It is possible to use several outlet interfaces and to fill them with different respective mixtures, without the need to purge the blender, thereby reducing losses of product. The outlet interface may be a single-use interface, if necessary.

Preferably, the static blender has a central chamber communicating with base product intake ducts. This central chamber may communicate with a peripheral chamber having a series of partitions which act as deflectors for the mixture and create shearing thereof.

The peripheral chamber may have a perforated annular partition defining perforations through which the mixture passes as it circulates in the peripheral chamber. The central and peripheral chambers may be closed at the top by a wall which defines the end wall of the cavity receiving the mixture.

The end wall of the peripheral chamber may be of helical shape about the axis of the cup and of a height that decreases in the direction toward the outlet. The latter may open ahead of a connecting ramp connecting the end wall of the peripheral chamber and the top wall of the blender, this connecting ramp preferably being a portion of a helix extending the helix formed by the end wall of the peripheral chamber.

Preferably, the peripheral chamber comprises the abovementioned annular partition and radial partitions that force the mixture to circulate alternately between upper and lower regions of the peripheral chamber and between radially inner and outer regions, the mixture circulating for example from an upper and radially outer region to a lower and radially outer region by passing through the abovementioned annular partition.

The blender may have an outer body in which a component forming the core of the blender is housed, the outer body radially closing the peripheral chamber on the outside and comprising an upright that separates the central and peripheral chambers.

The outer body of the blender and the core of the blender may each be produced as a single piece by injection molding.

Reduced Dead Volume

There is benefit to be had in reducing the losses of product when changing the formulation of the mixture and in allowing the product of the mixture to be varied as quickly as possible during application, particularly when the dispenser is coupled to an airbrush.

The base product can leave the cartridge through an outlet passage of the cartridge, this outlet passage opening out at the outside of the dispenser or near the external surface thereof The outlet passage may notably open into an area in which the mixture is picked up or close to this area, notably less than 5 mm away, better still less than 3 mm away, better still less than 1 mm away, or even better still flush therewith.

The cross section of the outlet passage is, for example, between 1 and 3 mm$^2$.

Thus, each base product coming from a cartridge can leave the dispenser without mixing with a base product from another cartridge and the dead volume that cannot be picked up and is likely to increase the inertia of the system is minimized. The product is more quickly available without having to circulate through special passages in the housing of the dispenser, thereby avoiding a painstaking purging step in the event of a cartridge change.

The outside of the dispenser may be the product pickup area, notably when the dispenser is produced with a cup that is not designed to be removed, into which the mixture is dispensed, or a dispensing area intended for the mounting of a removable outlet interface, which defines the pickup area. This outlet interface may have a cup as defined above. This mounting area corresponds for example to the outside of the housing of the dispenser in the absence of an outlet interface. The mounting area may be substantially planar and perpendicular to the longitudinal axis of the dispenser housing.

The dispenser may have three cartridges of base products.

The dispenser may have housings for receiving the cartridges, which are preferably received removably in the dispenser. The latter may comprise passages for ducts for the cartridges defining the outlet passages.

The length of these ducts is preferably such that the ducts are set back slightly from the end or lie flush with the cavity used for picking up the product or, as an alternative, are set back slightly from or lie flush with the end face of the housing of the dispenser that defines the mounting area.

These ducts of the cartridges may be end pieces used for causing the pistons to move within the cartridges, as described in detail above.

Multiple Outlet Interfaces

There is a need to be able, using the same dispensing system, to achieve different makeup looks easily and be able, if so desired, to make up areas as different as the skin, the lips, the eyelashes or eyebrows.

The dispensing system may comprise an assembly having a dispenser of at least one cosmetic product, in particular makeup, and at least two outlet interfaces, each of which can be mounted removably on the dispenser, these outlet interfaces being able to receive the product(s) delivered by the dispenser, preferably being chosen from the following:
  an outlet interface having a container, notably a cup, allowing the product to be picked up using a finger or using an applicator,
  an outlet interface allowing the product to be delivered to a spray system, notably an airbrush,
  an outlet interface having several regions for receiving the product, which can move relative to the dispenser,
  an outlet interface that allows the product to be delivered to a dispensing end piece.

Preferably, the assembly comprises at least three of said outlet interfaces, or better still the four outlet interfaces.

The dispenser may comprise at least two different base products and allow these to be delivered in variable proportions and, preferably, the dispenser comprises three different base products and allows these to be delivered in variable proportions.

Each outlet interface may have a base allowing it to be fixed to the dispenser. This fixing may be done using screws for example, but preferably the base is designed to allow an outlet interface to be removed and replaced without the need for tools. It is, for example, a quarter-turn fixing or a fixing using an external locking ring.

The outlet interface and/or the housing of the dispenser may comprise seals allowing sealed communication between the housing of the dispenser and the outlet interface. If appropriate, the dispenser is designed to recognize the outlet interface mounted above, for example by virtue of the outlet interface having identifiers in the form of specific reliefs which are detected by the dispenser, or in the form of an electronic chip that the dispenser recognizes. That may allow the operation of the dispenser to be adapted to the outlet interface mounted above. The dispenser may communicate information about the outlet interface it is bearing to a computer system, and the computer system may, on the basis of this information, display a specific screen and/or run a specific program for controlling the operating parameters of the dispenser so as, for example, to adapt the dose dispensed and/or the flow rate to the type of outlet interface.

The user may be initially offered several outlet interfaces with a common dispenser within one and the same package, for example a case or a cardboard box.

A further subject of the invention is a makeup method involving the step of selecting an outlet interface, mounting it on the dispenser, and delivering the product(s) contained in the dispenser to the interface.

Mapping and Learning

The term "mapping" should be understood here as meaning a process of indexing a mattness/shine with an area, with recording.

It may be the case that a person requires several levels of mattness/shine with a single color and/or coverage for all areas.

The mapping may relate to applications to areas smaller than 1 cm$^2$. However, the naked eye then has difficulty in discerning whether the result obtained is adequate, and it is preferable to substitute an instrumented evaluation with magnification for evaluation by the naked eye. Small quantities of colored substance may be applied with a finger, using conventional tools such as brushes, or using specialist applicators.

The map may be generated during a learning period in which the user carries out tests with mixtures on different areas of the face; once created, the map can then be used for everyday makeup.

Specific graphic interfaces can be used during the learning period and during the period of use of the map.

In particular, the dispensing system may be used with a graphic interface in which the operator sees the face, which is for example a schematic, figurative or accurate representation such as a photograph or a 3D simulation. In that case, the operator can point at part of the face on the screen to show and/or deliver the appropriate mattness/shine.

The graphic interface may also show the other areas of the face where use of that same mattness/shine is appropriate.

To create the map, the operator applies a color (of given mattness/shine), then makes an assessment.

The areas of the face can be treated one after the other; for example, the exercise is carried out on part of the cheek, then on the nose, etc.

Another option is to create a mixture of given mattness/shine and apply this same mixture to several areas. The operator then needs to look for the area of the face to which the mattness/shine is suited. The mixture is then indexed in the computer system which attributes it to the area(s) of the face for which it is suitable.

In one of its aspects, independently of or in combination with the other aspects thereof, and notably with the foregoing, one subject of the invention is a learning process for a dispensing system comprising a dispenser for dispensing a mixture of variable mattness/shine, and a computer system for selecting a mattness/shine and for storing data, comprising the steps of:
 a) selecting at least one mattness/shine with the aid of an interface of the computer system,
 b) delivering, with the aid of the dispenser, at least one mixture of the selected mattness/shine,
 c) evaluating the mixture(s) dispensed following the application thereof to at least one area of the face,
 d) memorizing the characteristics of at least one mixture, notably a mixture that the user wishes to be able to recall, and of at least one area on which it has been tested.

This memorizing can be carried out notably with a view to subsequent dispensing of this mixture for making up said area.

Preferably, the computer system is designed to allow the user to indicate whether or not the result of the test is satisfactory, or even to inform same of the comparison with a test carried out earlier.

It is also possible to create a mixture of given mattness/shine and to look for the area of the face for which it is suitable. The mixture is then recorded, being attributed to the area(s) of the face for which it is suitable, in a look-up table that will be used subsequently in order to deduce which mixture to use on the basis of an area of the skin.

The same procedure can be adopted with other mixtures in order to create a map of the entire face and thus have a complete look-up table for the face.

It is also possible to create a given mixture, apply it to a given area, and then vary the mixture until the most suitable mixture is obtained. The mixture is then recorded, being attributed to the area(s) of the face for which it is suitable, in a look-up table that will be used subsequently in order to deduce which mixture to use on the basis of an area of the skin.

Preferably, the computer system evaluates and memorizes the quantities used area by area. Such a method, which uses "test patches" makes it possible to identify the product(s) required by the person wishing to apply makeup. Thus, the dispensing system can be used at sales outlets to advise people wishing to apply makeup or at home in order to define correctly which products to order.

The interface of the computer system preferably has a touch screen displaying the mattness/shine of the mixture when it is selected.

The interface may display a face and allow the computer system to be informed by selecting the area on the face displayed.

The computer system is preferably designed to allow an area, mixture reconstruction parameters, and the date of the test and/or any other identifier of the mixture to be associated with one another.

The computer system is preferably also designed to allow at least one of the following data: the name of the area, the period of the year, the name of an event, a user identifier and the age of the user, to additionally be associated with said area, with the mixture reconstruction parameters, and with the date or identifier of the mixture.

Steps a) to c) may be repeated at least once before the characteristics of the mixture are memorized in step d).

The computer system may be designed to search a database for the reference of a commercial product on the basis of the characteristics of the mixture identified as being suitable for at least one given area, and to relay this information to the user.

The selection in step a) may be carried out using an expert system, which may or may not be external to the computer system.

The expert system may analyze an image of the user in order to propose a mixture mattness/shine at least on the basis of the image analyzed.

Step a) may be preceded by the computer system proposing to the user a mattness/shine and an area to be tested with a mixture of this mattness/shine.

The computer system may be designed to allow the user to inform same of his or her assessment of the result of the test in step c) and to generate a proposal to modify the mixture to be selected upon return to step a).

The computer system may be designed to propose at least one mattness/shine of mixture in step a) depending on an application area of which it has been informed by the user.

The computer system may be designed to propose at least one application area in step a), on the basis of a mattness/shine of which it has been informed by the user.

The dispenser may deliver, in step b), at least two mixtures of different mattness/shine, preferably separate, so that they can be applied simultaneously to the test area.

This may allow time to be saved and make it easier to compare the results.

A further subject of the invention is a method of making up using a dispensing system according to this aspect of the invention, in which:
 a) the user sends the computer system a request regarding a need for makeup,
 b) in return, the computer system generates a proposed mattness/shine for making up an associated zone, on the basis of the learning performed beforehand, and
 c) the computer system operates the dispenser to produce the mixture of the proposed mattness/shine, notably if this is validated by the user.

Such a method may use a map previously established with the user.

A further subject of the invention is a computer program product containing code instructions which, when run in a computer system, allow the computer system to be made to:
 allow the user to select at least one mattness/shine and/or one application area, notably using an interface such as a touch screen,
 operate a dispenser in such a way as to deliver a mixture of the mattness/shine selected by the user,
 allow the user to trigger the memorizing of the mattness/shine of the mixture and of an associated application area, notably with a view to subsequently dispensing the same mixture, notably on the same area.

The computer program product may comprise code instructions which, when run in a computer system, allow the computer system to be made to:

receive a request from the user regarding a need for makeup, notably using an interface such as a touch screen, propose, on the basis at least of data generated by the learning process as defined above, at least one mattness/shine and/or one application area, operate a dispenser to produce the mixture of the proposed mattness/shine, notably if this is validated by the user.

The person may incorporate into the map the level of mattness/shine that she desires for each area of the face, area by area or set of areas by set of areas. The system will then interpret the mixtures it needs to create to ensure the colors and coverage desired and the wanted mattness/shine.

The map may subsequently be modified. Thus, it is possible to create the map in terms of the mattness/shine in the first instance, and then refine the map by subsequently defining the levels of color and coverage.

Remote Assistance

It is desirable to be able to assist the user in applying makeup, notably in choosing the correct mattness/shine.

In one of its aspects, independently of or in combination with the other aspects thereof, and notably with the foregoing, one subject of the invention is thus a method of applying makeup involving the steps of.

allowing a video link to be established, for example over the Internet, between a camera on a first site and a second site, allowing the second site to directly or indirectly operate a dispenser present at the first site, this dispenser making it possible to vary the mattness/shine of a mixture dispensed, allowing a person present at the first site to apply the mixture dispensed and to send a corresponding image to the second site, so as to receive in return information relating to the makeup result.

The second site may notably have a viewing screen which allows an adviser sitting at this screen to see the makeup result with the product dispensed by the dispenser and advise the person who has applied the makeup. This adviser may in return influence the dispenser to alter the mattness/shine of the mixture and adapt it to best suit the face of the person present at the first site. Thus, this person controls the mixture delivered by the dispenser. The first person may make herself up under the gaze of the second. The second person sees the result of the test on their screen and can thus correct the mixture that this second person will control remotely until the ideal makeup is obtained.

If appropriate, the video acquisition can be calibrated using a test pattern or with the mixture dispensed by the dispenser onto a reference surface. That then allows a more faithful display of the makeup applied at the first site.

Preferably, the video link between the two sites is a two-way link.

The first site may receive a tutorial from the second site, if appropriate.

Identifiers of the base products may be communicated to the second site; this may make it possible to precisely determine the color of each of the base products.

The method may involve memorizing the dispenser setting parameters once a given mixture is considered to be satisfactory. Preferably, this memory storage may be commanded from the second site. The memory storage may be in the computer system present at the first site and/or on an external server.

One alternative may be to have one person working to help several apply makeup. This embodiment makes it possible to develop makeup artists and their work, either within an institute or over the Internet. It also allows people with limited capabilities, such as people with poor eyesight, or people who have difficulty discerning colors, or the elderly, or those lacking in self-confidence to apply makeup.

Operation Via Touch-Sensitive Interface

There is a need to make it easier to control the dispensing system and notably the choice of the mattness/shine of the mixture dispensed.

In another of its aspects, independently of or in combination with the other aspects thereof, and notably with the foregoing, one subject of the invention is thus a dispensing system comprising a dispenser and a computer system for operating the dispenser, this computer system comprising a touch screen on which the mattness/shine of the mixture may be displayed and a selection means that can be moved over the screen in order to vary the mattness/shine of the mixture dispensed.

Preferably, the screen displays mattness/shine end points between which the mattness/shine of the mixture can be selected by moving the selection means between these mattness/shine end points.

The screen may display a scale of mattness/shine between at least two mattnesses/shines, or an area, notably of triangular outline, within which the selection means can be moved. This area may locally show the mattness/shine of the mixture depending for example on the distance from each of the vertices, each one embodying a pure base product.

The computer system may perform some of the calculations necessary to determine the fractions of each of the base products that lead to a mixture of the desired mattness/shine.

The computer system may be a smartphone, a camera phone, a tablet, or a personal computer. As an alternative, it is incorporated into the housing of the dispenser.

The computer system may have a camera. The latter can be used notably for capturing an image of the user and/or of the mixture.

The computer system may be designed to display an image of a face, in order to make it easier to identify the areas to which the mixture is to be applied.

Coupling of the Dispensing System to a Spray Means

The dispensing system may have or be connected to a means of spraying the mixture, preferably an airbrush.

Another of the aspects of the invention is to improve still further the dispensing systems that comprise a spray system, preferably an airbrush, and according to one of its aspects, independently of or in combination with the other aspects, and notably the foregoing, one subject of the invention is an assembly comprising:

a spray means, preferably an airbrush having a pickup chamber subjected to a stream of entrainment air, a dispenser having at least two compartments containing different base products, the products being delivered to the spray means preferably via distinct distribution orifices.

The dispenser may have three cartridges containing makeup products of different mattness/shine.

The airbrush may have a stylus defining the pickup chamber, the stylus being fixed to the dispenser or to an outlet interface fixed to the dispenser, or forming an integral part of this outlet interface.

The dispensing system may have a circuit controlling operation of the dispenser, allowing the proportion of base products delivered to the pickup chamber to be varied while the airbrush is in operation. The proportions may be modified depending on the movement of the airbrush relative to the surface onto which the mixture is sprayed. This movement may be mechanized, if appropriate.

This control circuit may have or be constituted by a computer system as defined above.

The housing of the dispenser may act as a hand grip when the assembly is being handled for delivering the mixture.

The dispenser may have a camera and/or one or more sensors such as accelerometers so as to automatically locate the area to which the mixture is applied, and so as to be able to automatically regulate the mattness/shine depending on the position, if appropriate.

A further subject of the invention is a method for applying makeup using an assembly as defined above, in which a mixture is sprayed onto the skin using the spray means, notably the airbrush.

The composition of the mixture can be modified as the airbrush is moved relative to the skin. A graduated effect can be achieved.

This aspect of the invention is based on the observation that the dispenser can be used to supply the spray system, notably the airbrush, while at the same time allowing the dispensing system to be responsive enough to allow a change in the mattness/shine of the mixture dispensed while the face is being made up, notably as the area to be made up changes.

It may be advantageous for the dispensing of products to be performed iteratively, notably with dispensing times that are not phase-shifted between the various products.

This may make it easier to vary the composition of the mixture dispensed over time.

The mixture may be created directly in the airbrush, with practically no troublesome dead volume, thus allowing the mixture sprayed to be changed in real time.

The depression created in the pickup chamber is strong enough to entrain the base products without in any way impeding the metering.

The depression which prevails in the pickup chamber is for example between 10 mbar and 200 mbar, better still between 50 and 150 mbar, even better still between 75 and 125 mbar.

The viscosity of the base products as measured at 1 atm and 25° C. with a CONTRAVES TV rotary viscometer fitted with an MS-r3 or MS-r4 measuring bar at a frequency of 60 Hz after 10 minutes of rotation of the measuring bar is, for example, between 0.05 Pa·s and 50 Pa·s.

The cross section of the passages along which the base products arrive in the chamber is, for example, between 1 and 3 mm$^2$, better still between 2 and 3 mm$^2$.

The product is preferably supplied continuously.

It is also possible to apply immiscible or reactive base products, such as an aqueous gel and an oily gel, simultaneously, and these will be deposited directly onto the skin in a pixelated manner, producing a kind of gel/gel in situ, reactive silicones, or colorants that react with one another. The ratios of base products can be adjusted depending on the particular result desired. For example, in the case of aqueous gels and oily gels, the ratio corresponding to the volume of the first base product to the volume of the second base product could be varied between 10/1 and 1/10, better still between 5/1 and 1/5.

Location or Auto-Location System

The dispensing system according to the invention may have a location or auto-location system.

A location system is the name given to a means via which the person inputs the area that she is to treat. This can be performed notably using systems that leave at least one hand free. Thus, an interface of a computer system such as a touch screen, a joystick, or voice recognition system can be used.

An auto-location system is the name given to a means for inputting the area that is to be treated without intervention on the part of the person. This can be achieved using one or more accelerometers which deduce, from the movements, the directions targeted by the person or by a camera and an image recognition system.

The dispensing system may be of the kind illustrated in the above-described figures. Therefore, the figures will not all be described again.

FIG. 29C illustrates a support having spaces disposed thereon substantially in the manner of the different areas of a face; each space may contain a mixture, the mattness/shine of which is suited to the corresponding part of the face. Thus it is easy for the user to know where to apply the mixture picked up from a given space.

The dispenser 11 can be used to deliver a mixture, the formulation of which changes over time, and to collect the mixture in a container that is movable with respect to the dispenser, such that the mixture is deposited in a location of the container that varies over time, in order to achieve a graduated effect.

For example, as illustrated in FIGS. 29A and 29B, the dispensing system has an outlet interface 110 having a part that is fixed relative to the dispenser and a moving part 252 that has a space 253 for receiving the mixture.

For example, the dispenser 11 is arranged in this case with the outlet orifices of the cartridges downward and is equipped with a blender such that the mixture falls into the space 253 under its own weight. A motor may move the moving part of the outlet interface relative to the dispenser, in a manner that is synchronized with the variation in characteristics of the mixture, such that a graduated effect is obtained all along the space 253, as illustrated in FIG. 29B.

As indicated above, the dispensing system 10 according to the invention preferably has a man-machine interface that allows the user to easily and intuitively operate the dispenser 11. This interface may form part of a computer system 100 which communicates with the dispenser 11.

FIGS. 31 to 37 show various examples of touch-sensitive interfaces that may allow the user to select the mattness/shine of the mixture resulting from the metered dispensing of the various base products.

This interface may have, as illustrated in FIG. 31, a mattness/shine selection area, for example in the form of a triangle, the vertices of which correspond to the mattness/shine of each of the base products contained in the cartridges.

The user can move a cursor 300, for example in the form of a ball, relative to the vertices A, B and C of the triangle.

The closer he brings the cursor 300 to one of the vertices, the larger the fraction of the corresponding base product relative to the total quantity of the various products dispensed.

The fraction of each product relative to the total quantity may be indicated at 301 by a numerical value on the interface.

The interface may allow the user to increment or decrease the quantity of each of the products, for example by operating control buttons 302, which allow precise adjustment of the quantity of each of the base products.

The surface of the triangle 310 may have a mattness/shine that varies locally so as to be indicative at each point of the mattness/shine of the mixture that results from the weighting of the various base products in the proportions corresponding to the relative coordinates at this point.

The interface may have a button 305 providing access to a specific menu for adjusting the volume of product dispensed for purging the dispenser.

The interface may also advantageously allow the flow rate of product to be adjusted using buttons 304 and 306 returning to a specific menu for adjusting the flow rate.

In the example in question, the interface affords the choice between a continuous dispensing mode, using the button 304, in which the products are dispensed for as long as the user is pressing the control button 12.

The corresponding dose can be transmitted to the interface and displayed.

The button 306 allows selection of a dose mode of operation, during which even a brief press of the button 12 triggers the dispensing of a predefined dose.

In order to vary the flow rate, the dispenser acts, for example, on the operating duty cycle of the motors.

The interface may be designed to allow the user to program or memorize the settings he or she prefers, using a menu 307 providing access to favorites.

The touch-sensitive interface illustrated in FIG. 32 shows on the screen three colored areas 400, each one corresponding to the mattness/shine of one of the base products contained in the dispenser 10, and a central area 410 which shows the mattness/shine of the resulting mixture.

The relative quantity of each of the base products can be adjusted using cursors 415 which move for example along lines joining each of the areas 400 to the central area 410.

During use of the interface, the latter may memorize a given setting and cause a button 420 of the mattness/shine of the mixture to appear on the screen. The user can then, simply by pressing this button 420, dispense a mixture of the corresponding mattness/shine.

In the example in FIG. 34, the interface displays, in an area 500, a given shade and offers the user, by virtue of control buttons 510 that are each for the mattness/shine of the corresponding base product, the opportunity to increase or decrease the proportion of this base product in the final mixture. The mattness/shine of the area 500 is recalculated depending on the actions on the control buttons 510.

In the variant in FIG. 35, the interface shows a color chart having several areas 530, each one corresponding to a particular proportion of the various base products.

The user may select one of these areas, for example by pressing it with his or her finger.

The interface may be designed to display the selected mattness/shine to a larger scale in an area 535. The programming of the dispenser 11 to dispense this mattness/shine is triggered for example by the pressing the area.

In the example in FIG. 36, the user may move a cursor 555 over a continuous color chart 550, causing the selected mattness/shine to be displayed in an area 558.

The user can then, for example by pressing the area 556, trigger the sending to the dispenser 11 of the necessary instructions for the dispenser to dispense a product in the selected mattness/shine.

It is apparent from FIG. 37 that the interface can memorize the various shades selected and then display them on the screen so as to allow the user, by pressing corresponding buttons 560, very easily to again select a shade that has already been chosen.

FIG. 38 shows an example of a user interface 1000 of a dispensing system comprising a dispenser, preferably as described above, and a computer system 100 to which the interface belongs.

The computer system comprises here, for example, a device such as a laptop computer, a tablet or a smartphone, that operates autonomously or is connected to a remote server.

In the example in question, the interface 1000 is defined by the touch screen of such a device. In a variant that has not been illustrated, the dispenser incorporates a touch screen or any other type of man-machine interface, and can be used without connection to another device.

The device runs an application, for example which has been downloaded beforehand and which displays on the screen a face 1035 and a series of buttons allowing the user to input information.

The face may comprise several areas Z1 to Z6 that can be selected by touch, for example the forehead, the nose, the cheeks, the eyelids, the chin, and the lips.

The buttons present on the screen may make it possible for example to input the name of the makeup or of the user, to display the selected area, to choose the mattness/shine, and to inform the computer system as to whether or not the result of the test carried out is acceptable, or even, as illustrated, to provide information regarding the assessment of the result relative to a test carried out previously, namely, for example, better or "not as good". The screen may also display a button allowing the choice of a mattness/shine and an area to be memorized after a test has been carried out with this mattness/shine on the area in question.

The choice of mattness/shine is made for example with a mattness/shine scale similar to the one described with reference to FIG. 36.

The computer system is designed to memorize the data in the form of a look-up table for example, so as to associate an area of the face with the parameters that allow the mixture dispensed during the test to be reproduced. These parameters include, for example, the relative contents of each of the base products of the dispenser in the mixture, the quantity Q dispensed, and additional data such as, for example, the name of the area, the date the mixture was dispensed and/or any other mixture identifier, identifiers of the base products, the period of the year, notably the season, the age of the user, his or her sex, his or her given or family name, the name of an event associated with the makeup, for example a birthday, amongst other data, and the quantity of product suitable for the area. The ancillary data may allow the user to reproduce more easily a makeup look considered suitable for a time of year or recalling a life event, or to give a rejuvenating effect.

These data may be memorized in the computer system 100, for example in the abovementioned device and/or on a remote server with which the device is in communication, or alternatively in an electronic memory incorporated into the dispenser 11.

Thus, according to the invention, the user may make the dispenser deliver a first colored substance, and apply it to a first area of the face, then judge whether or not it is suitable. If the result is satisfactory, the user may record it, indexing it to the area; if the result is unsatisfactory, the user may command a new mattness/shine in order to repeat the above operations.

The computer system can be used in this context in various ways.

For example, as illustrated in FIG. 40, in a step 1010, the user has selected a mattness/shine to test, using for example the mattness/shine scale 1011 displayed on the screen, by moving the adjusting button 1012.

Next, the choice of mattness/shine is transmitted to the dispenser 11, in step 1015.

For example, the device transmits the quantities of each of the base products to be dispensed and the electronic circuit 81 takes charge of operating the motors accordingly.

In step 1016, the user presses the control button 12 of the dispenser 11, this causing, for example, a dose of the mixture, with the mattness/shine selected by the user, to be dispensed.

The mixture is, for example, dispensed into the cup 115, then picked up and applied by the user to the cheeks or any other area instructed on the interface, in step 1020.

In variants, the product is applied using an airbrush or by any other means as described above.

The user then, in step 1022, informs the computer system of the result using the buttons 1021.

If the user indicates that the result is satisfactory, the system suggests for example that he/she validate the parameters of the test using a button so as to memorize these parameters in step 1031.

If the user does not consider the result to be satisfactory and makes this known using the button 1032, the result can nevertheless be automatically saved in step 1034.

Thus, each area can be indexed not only with the suitable mattness(es)/shine(s), but also with the mattness(es)/shine(s) that is/are not at all suited to this area.

The user can then perform a further test on the same area by returning to step 1010.

If the user is satisfied with the result, he or she may also wish to carry out a further test, for example on a different area of the face.

If appropriate, if the user is not satisfied, the interface may suggest that the user indicate whether the result is considered better than or not as good as the previous test, using corresponding buttons 1040 and 1041.

In that case, the computer system may be designed to determine whether, in light of the information input by the user, a proposal can be automatically made as to what mattness/shine to test next.

If appropriate, a questionnaire may be displayed to assist the computer system in proposing a mattness/shine in light of the tests carried out and the way in which the user or a professional assisting the user has assessed these tests.

For example, if the mattness/shine is considered "unsuitable", the system may receive from the user additional information, for example "too matt", "too shiny", which will assist the system in proposing a new mattness/shine better suited to the user's expectations.

It may be advantageous for the computer system to be able to receive information comparing the result against the previous tests, for example "it's better" or "it's not as good" and, from there, for the system to be capable of deducing what new mattness/shine to propose.

Another option is for the computer system to be able to receive comparison information regarding a comparison against a target, for example "it's almost ideal" and, from there, for the system to be capable of automatically adjusting its mattness/shine modifications.

In this particular instance, if it receives the information that the desired result has almost been achieved, the system can adopt small levels of mattness/shine change and revise the reflection scale of adjustment accordingly.

If the dispensing system itself proposes the colored mixtures to be tested, these may be based on preprogrammed test scenarios and the system may alter how the scenario is followed through according to the successes or failures of the assessment. Thus, for example if, from the third application of product, it receives information that the mattness/shine is almost ideal for the user, the dispensing system may exit the program and thereafter allow itself to be guided by instructions from the operator.

In general, the user may be assisted by an expert system in the choice of mattness(es)/shine(s) to test.

This expert system is, for example, a program run on the device with which the dispenser communicates or on the dispenser itself, and which is based on the answers to a questionnaire and/or on measurements, for example of the mattness/shine of the skin, taken by a specific sensor or by a camera. The user can thus get assistance from an instrumented evaluation, for example a mattness/shine sensor. The expert system can even be implemented on a remote server with which the device or the dispenser exchanges information. The operator may even send an image of his or her face to a specialist, who can preprogram the starting mattness/shine choice. In another exemplary embodiment, the user presents the computer system with a photo of his or her face, and the computer system is designed to analyze this and create a program defining the areas to be tested and the first products to be delivered, both in terms of mattness/shine and in terms of quantity. For example, the computer system may be designed to automatically select the mattness(es)/shine(s) of makeup to propose to the user by capturing a photograph in step 1070, as illustrated in FIG. 42. For example, the device which communicates with the dispenser 11 is equipped with a camera, and the user takes a photograph of his or her face. The image is then analyzed in step 1071, and mattness(es)/shine(s) are proposed for each area of the face in step 1072, for example in accordance with predefined mattness/shine combination rules.

The dispensing system may be oriented by the user to decide on the mattness/shine and also on the quantity of product to be delivered. For example, the user may indicate "nose" or "blemish" and the dispensing system is designed to adapt the dose dispensed according to a memorized map of doses to be dispensed depending on the areas to be treated.

The computer system may guide the user in the choice of mattnesses/shines in the mixture to be tested, so as to limit the number of tests needed until the user obtains a result that pleases him or her.

It is thus possible, as illustrated in FIG. 41, that after a mixture dispensed by the dispenser has been applied to a given area of the face in step 1060, the computer system will ask the user whether or not the result is satisfactory and will, of its own accord, if the result is considered to be unsatisfactory, make a change 1061 to the dispenser parameters in order to modify the mixture dispensed.

The user then only has to perform a new test with the modified mixture.

When a mixture is indicated as being satisfactory, the computer system can memorize the corresponding parameters so as to allow the mixture to be recreated at a later date.

The system can then begin the above steps afresh for a new application area.

During the successive tests, the operator does not need to treat the entire face. He or she may for example choose between 3 and 8, for example 5, small areas. The dispensing system is then advantageously designed to interpolate and/or extrapolate the data regarding the mattnesses/shines considered to be suitable, so as to calculate the mattnesses/shines that ought to be considered suitable for areas for which the exercise has not been conducted.

At the end of the learning stage, the system may generate a display of the suitable mattnesses/shines on the various areas, tested or calculated.

The dispensing system may be designed to indicate whether certain mattnesses/shines appear to be incorrect, doing so on the strength of a comparison against standard maps it has in memory. Thus, it may propose that the user repeat all or some of the mapping exercise.

Once the computer system has completed its learning, i.e. once the mattnesses/shines of mixtures have been identified as being agreeable to the user for making-up certain areas, the user wishing to apply makeup only has to call up the area that is to be made up, in step 1080 of FIG. 43, and the system will be able to automatically propose a suitable mattness/shine of mixture to the user in step 1081.

In the variant illustrated in FIG. 44, the user selects a mattness/shine in step 1090 and the computer system proposes, in step 1091, an area in which to apply a mixture of this mattness/shine, on the basis of information previously collected on the basis of the tests performed.

The area proposed is, for example, the area in which an identical or very similar mattness/shine has already been applied and the result considered acceptable by the user.

FIG. 46 illustrates an example of an implementation of the invention in which, having carried out tests on various zones in step 2010, the user informs the system of the mixture(s) he or she considers to afford the best result, this allowing the system to know the corresponding parameters in step 2012. Next, in step 2014, the system may propose to the user references of commercial products that have the same properties or very similar properties.

In one variant, the system sends the parameters to a remote manufacturing center so that a composition that has the same formulation or the same properties as that of the mixture that the user has tested and found to be satisfactory can be produced.

FIG. 45 illustrates the possibility of using the dispenser to dispense several doses 2020a to 2020d of different mixtures, next to one another on a support 2021, so as to allow these to be applied to adjacent distinct regions of the same area.

The user can, in a single hit, apply a series of mattnesses/shines in order rapidly to home in on the appropriate mattness/shine. The colored substances present on the support 2021 may have been chosen by the operator him- or herself or proposed by the dispensing system.

The support 2021 is, for example, movable with respect to the housing of the dispenser and is moved sequentially to deposit the corresponding mixtures in the various areas 2020a to 2020d, being for example similar to the supports described with reference to FIG. 29 or 29A. The user can thus easily compare the results between the various regions and inform the system of which mixture produces the best effect.

FIG. 47 illustrates a system that assists the user in applying makeup, notably in choosing the correct colorings.

This system makes it possible to establish a video link, for example over the Internet, between a camera 2060 at a first site 2061 and a second site 2062.

The camera 2060 is, for example, built into a tablet or a smartphone that constitutes the computer system 100.

The second site 2062 is allowed to operate the dispenser 11 present at the first site 2061 either directly or indirectly.

Thus, the person present at the first site can apply the mixture dispensed and send to the second site 2062 a corresponding image, and in return receive information relating to the makeup result.

The second site 2062 may have a display screen 2064 that allows an adviser sitting at this screen to see the result of the makeup with the mixture dispensed by the dispenser and advise the person who has applied the makeup. This adviser may in return influence the dispenser 11 to alter the mattness/shine of the mixture and adapt it to best suit the face of the person present at the first site. The protocol for the exchange of data between the two sites thus allows command instructions to be sent to the dispenser 11, either directly or via the computer system 100 present at the first site. Thus, the person present at the second site controls the mixture delivered by the dispenser 11. The first person may make herself up under the gaze of the second. The second person sees the result of the test on their screen and can thus correct the mixture that this second person will control remotely until the ideal makeup is obtained.

Preferably, the video link between the two sites is a two-way link, such that the user present at the first site can see an image of the adviser on the screen of the computer system. This adviser can send the user present at the first site a tutorial if need be.

The memorizing of the setting parameters of the dispenser 11, once a given mixture has been considered satisfactory, may be commanded from the second site.

Advantageously, the dispensing system 10 is designed to be able to modify all the mattnesses/shines esthetically for each area if the person wishes to change the mattness/shine of his or her face. The dispensing system may be designed in such a way that the user only has to modify a single mattness/shine in one area for the system to modify all the others. To this end, the dispensing system can use translations, for example by recording the mattness/shine saturation or shifting the shade.

The dispensing system may be designed to receive the map of somebody else, real or virtual. It may also combine the map of the person with the map of another, in order to sublimate the makeup without losing the inherent characteristics.

The interface may be used to define makeup programs in which the order of the areas to make up or the order of the mattnesses/shines to propose is defined.

Examples

A dispenser 11 like that illustrated in FIG. 3 and described above is created. The dispenser is designed to communicate with a tablet 100 such as an iPad. This computer system runs an application known as "µMix" developed in the specific Apple environment (XCode 4 and iOS simulator) in the Objective C language.

It uses Foundation, UTKit and CoreGraphics basic frameworks which supply the tools for manipulating the data structures, computation tools and functionalities associated with the user graphics interface.

The application also uses the CoreBluetooth framework providing access to the Bluetooth 4 Low Energy peripherals, with the following main tasks:
  looking for Bluetooth 4.0 Low Energy peripherals,
  connection/disconnection and management of connection parameters,
  communication in read and/or write mode based on the GATT (Generic Attribute Profile) architecture.

The application proposes the following functionalities:
  definition of the fractions of base products,
  choice of mode of operation when pressing the control button 12, namely continuous, purge or dose,
  display of a triangle of volumetric fraction as illustrated in FIG. 30 with management of the volumetric fraction by tactile touch on the triangle or using the +/−buttons associated with each product, Bluetooth connection/disconnection and real-time transfer of instructions to the dispenser, settings of flow rates in continuous mode, and of quantities in dose mode, calculation, display and transfer to the dispenser of the volumetric fractions of products in real time, depending on the instruction, with the sum of the fractions always equal to 100%, collection and display of the torques of the three motors in real time, and saving of the key parameters in a configuration file.

The continuous mode is a dispensing mode in which the mixture of the three base products is dispensed for as long as the user presses the dispensing button 12. The product is dispensed at a flow rate, an estimate of which is displayed above the "Continuous" button 304. The choice of flow rate is made in a "Settings" menu.

The "dose" mode is a mode of dispensing the mixture in doses, in which the dose is delivered after the user presses the dispensing button 12. One press is enough and the user can then release the button. The overall dose of product dispensed is that indicated above the "Dose" button 306, for example 0.1 ml. This volume can be altered in the "Settings" menu.

The "purge" mode is a dispensing mode in which a dose of mixture with equal volumetric fractions (33%) is delivered as soon as the user has pressed the dispensing button 12, as in the "dose" mode. One press is enough and the user can then release the button. When the dose has been dispensed in full, the button may be released. If the button is released before the end, dispensing stops, even if the specified volume has not been achieved. The overall dose of product dispensed is that indicated above a "Purge" button 305, for example 3 ml. This volume can be altered in the Settings menu.

The user determines the desired mattness/shine with the application which is run on the tablet and which calculates the fractions of the various products. The tablet communicates this value to the dispenser by a Bluetooth connection.

The electronics built into the dispenser 11 collects the information and automatically adjusts the flow rates of the three cartridges so as to obtain a mixture of the desired mattness/shine.

When the user wishes to use the product, he or she presses the button 12 of the dispenser in order to cause the product to be expelled. He or she presses for as long as he or she wants product, in "continuous" mode. In "dose" mode, the user presses the button 12 once and the predefined dose is delivered.

Dispensing may be performed continuously, namely with the motors operating continuously, the entire volume being dispensed in one hit, or iteratively, the motors then operating in a pulsed fashion; in that case, the time interval between two pulses makes it possible to vary the flow rate. Small volumes are delivered one after another in several stages.

The pulses may be separated for example by intervals of 50 ms, 100 ms or 200 ms. The duration of a pulse during which the motor is turning will be from 50 to 150 ms, for example.

The main page of the "µMix" application comprises in this example the following elements, as can be seen notably in FIG. 31:

status bar at the top of the screen: indicates the status of the Bluetooth connection or µMix if there is no Bluetooth connection;

thumbnails at the bottom of the screen: for selecting the active page: main page, Settings, Bluetooth, Products and Favorites;

Continuous button 304 for selecting the mode in which products are dispensed continuously;

Purge button 305 for selecting the Purge mode;

Dose button 306 for selecting the mode in which dispensing is in doses with the volume of the dose associated with the Dose button;

a blue ball 300 that the user can move around inside the volumetric triangle either by dragging it or using a double tap;

"−" buttons 302 for each product A, B and C: reduces the fraction of product selected when moving along the straight line connecting the point to the vertex of the product selected;

"+" buttons 302 for each product A, B and C: increases the fraction of product selected when moving along the straight line connecting the point to the vertex of the product selected;

volumetric fraction of each product as a percentage: modifiable by the user and updated in real time according to the instruction from the + and − buttons 302 and the position of the ball 300.

While the volumetric fractions are being modified by moving the ball or using the + and − buttons, the values of the volumetric fractions of the products A, B and C are updated automatically. When the volumetric fractions are modified using the + and − buttons, the ball 300 is moved automatically into the corresponding position in the triangle.

When the application run on the tablet is started up, it automatically connects to the dispenser 11 if it is detected. When the dispenser is switched off or the Bluetooth connection is broken, the tablet disconnects. When the user moves the cursors that adjust the proportions of the products A and B, the values are transmitted in real time to the dispenser 11.

The Settings page of the application contains the following elements:

status bar at the top of the screen: indicates the status of the Bluetooth connection or µMix if there is no Bluetooth connection;

thumbnails at the bottom of the screen: for selecting the active page:

main page, Settings, Bluetooth, or Info;

"Volumes" part with a text field to be filled in by the user to define the volume of the dose, in ml (2 ml for example), and a field for the purge volume, in ml (3 ml for example). The minimum doses in this example are 0.023 ml and the maximum doses are 9.90 ml (3×3.3 ml);

"Flow rate" part with selection of the flow rate: fast (»0.03 ml/s), medium (»0.02 ml/s) or slow (»0.01 ml/s);

"Dose" part with iterative choice of the mixture, for dispensing a mixture of products with small volumes delivered one after another in several stages; In the contrary case, the total volume of each product is dispensed in one hit;

"Triangle image" part for selecting the image of the triangle that will be displayed on the main page in order to be able to display a triangle with the mattnesses/shines delivered by the dispenser 11. By using a "Choose image" button on the "Settings" page, an album can be accessed.

The "Products" page of the application has, in the example in question, the following elements:

a choice of the value of each product in code step units from 0 to 1414.

Each unit corresponds to a delivered product volume of 2.33 µl, which is the smallest quantity that the dispenser in this example can deliver; when this page is displayed, it is the values of products on this page that are transmitted in real time to the dispenser. As soon as the page is no longer displayed, the values sent to the dispenser are those of the main page with the triangle;

display of the motor torques for A, B and C in real time refreshed every 45 values.

The mode in which the products are delivered is the iterative or direct dose mode, according to the option chosen on the Settings page.

The "Favorites" page allows configurations to be saved in a file. It provides access in the example in question to 10 files, namely "Configuration 1" to "Configuration 10" in addition to the default file. These files record for example the following parameters:

fractions of products A, B and C,
Purge volume,
Dose volume,
fast, medium or slow flow rate,
Dose, Purge or Continuous mode,
continuous or iterative dispensing.

Example (Seventh Aspect of the Invention)

Several base products are created (the proportions are by mass)

The formulations F1 and F2 are rich in fillers (and are different colors). The formulation F3 is rich in nacre (bismuth oxychloride).

| | F1 mass % | F2 mass % | F3 mass % |
|---|---|---|---|
| Dimethicone copolyol sold under the reference KF 6017 by the company Shin-Etsu | 2 | 2 | 1.8 |
| Etsu Bis PEG/PPG-14/14 dimethicone + Cyclopentasiloxane sold under the reference Abil EM 97 by the company Goldschmidt | 1 | 1 | 0.9 |
| Cyclopentasiloxane | 17.65 | 17.65 | 15.92 |
| Phenyl trimethicone sold under the reference DC556 by the company Dow Corning | 2 | 2 | 1.8 |
| Ethyl hexyl methoxycinnamate | 3 | 3 | 2.7 |
| Squalane | 1 | 1 | 0.9 |
| Dispersion of bismuth oxychloride in 2-ethylhexyl hydroxystearate (70:30) (Timiron Liquid Silver ® from Merck) | 0 | 0 | 10 |
| Cyclopentasiloxane | 7 | 7 | 6.29 |
| Yellow iron oxide coated with aluminum stearoyl glutamate NAI-C33-9001-10 from the company Miyoshi Kasei | 1.62 | 1.1 | 1.45 |
| Red iron oxide coated with aluminum stearoyl glutamate NAI-C33-8001-10 from the company Miyoshi Kasei | 0.29 | 0.6 | 0.26 |
| Black iron oxide coated with aluminum stearoyl glutamate NAI-C33-7001-10 from the company Miyoshi Kasei | 0.13 | 0.13 | 0.12 |
| Titanium dioxide (anatase) coated with aluminum stearoyl glutamate NAI-TAO-77891 from the company Miyoshi Kasei | 9.96 | 10.17 | 8.95 |
| Talc sold under the reference Micro Ace P3 by the company Nippon Talc | 0.5 | 0.5 | 0.45 |
| Nylon 12 powder sold under the reference SP 500 by the company Toray Industries | 0.5 | 0.5 | 0.45 |
| Demineralized water | 36.15 | 36.15 | 32.53 |
| 1,3-Butylene glycol | 3 | 3 | 2.7 |
| Magnesium sulfate | 0.7 | 0.7 | 0.63 |
| Hydrogenated maltose solution | 0.5 | 0.5 | 0.45 |
| Denatured 96° ethyl alcohol | 13 | 13 | 11.7 |
| TOTAL | 100 | 100 | 100 |

Procedure

The constituents of phase A are weighed out in the main beaker and are stirred with a Moritz blender (1000 rpm) while maintaining at room temperature. Phase B is prepared separately by milling three times in a three-roll mill the mixture of pigments and of cyclopentasiloxane. This phase B is then added, with continued stirring, along with the fillers (phase C).

The aqueous phase D is also prepared separately, by weighing out in a beaker the butylene glycol, the magnesium sulfate, the hydrogenated maltose solution, and water at room temperature. The aqueous phase D is stirred using a magnetic bar until homogenized. C D E The emulsion is made at room temperature: the aqueous phase D is poured into the fatty phase while gradually increasing the stirring speed (Moritz blender) up to 4000 rpm. Stirring is continued for 7 minutes. Finally, phase E (ethyl alcohol) is added for the last 3 minutes of 5 the emulsification.

Test

The system was tested with:
F1 in compartment A
F2 in compartment B
F3 in compartment C
M1 (the proportions in the mixture dispensed are volumetric): A 30%, B 20%, C 50%
M2: A 30%, B 50%, C 20%
M3: A 30%, B 30%, C 40%
M1, M2, M3 are applied to different areas of the face. Different colors are obtained, and different mattness/shine results.

G) System for Customizing One's Foundation Depending on the State of One's Skin

The present invention relates to methods and systems for dispensing, notably a makeup product.

Many people wish to make themselves up in order to enhance their appearance, particularly their face.

There are two types of reason why these people may wish to do this:

to conceal certain imperfections, such as blemishes, wrinkles or pores,
to enhance the look of the face by changes of color.

In these different cases, the operation involves supplying a colored substance and covering the skin or an area of skin therewith.

In order to obtain an attractive effect, the person needs to make the correct choice of colored substance.

In the first of the cases given above, the operation may be complicated because the face comprises a whole range of colors.

Thus, if the person wishes to cover only a few areas of the face, by attempting to make the color added coincide with the natural color of the surrounding skin, he or she needs to find the color suited to each area of the face, a task rendered all the more difficult by the fact that the coverage of the product and the thickness of the layer applied, together with the color and surface condition of the underlying skin or the greasiness thereof may influence the result.

Bearing these difficulties in mind, people seeking to conceal imperfections on their face adopt the habit of covering the entire face. This then gets around the problem of choosing the colored substance depending on the area of the face.

However, because of the uniformity it brings, the result detracts from the natural appearance of the face.

In the second case, the operation is not simple either because it is difficult to find a colored substance which best suits the appearance of the face. In particular, it is difficult to find the color of one's coloring, particularly if looking for a bold color different from one's natural coloring. Some people would like to choose sun-kissed colors or other shades of different coloring, but do not do so out of fear that the color will not suit them. And if they do, they often give up, disappointed. When not disappointed by the result, they no longer dare change color.

The same goes for makeup applied to the lips, cheeks and eyelids.

Users also need to be able to alter the quality, durability and comfort of their makeup depending on the time, the weather or season, but also the location on the face. Usually, by using a product with a high filler content, the makeup is suited to relatively greasy areas in order to confer mattness thereon throughout the day. However, this solution is not satisfactory, since it can lead to discomfort problems in other areas of the skin, and it tends to generate an unattractive makeup result in dry areas. The use of composition rich in moisturizing agent such as glycols, for example glycerol, makes it possible to make up the entire face, including the driest areas. However, this solution is not very satisfactory for other areas of the face. The example of the area around the nose is a typical example. The area under the nose is often dry, thus requiring the application of a formulation containing a moisturizing agent. A few centimeters away, the sides of the nose are often greasy and are poorly suited to the application of a moisturizing product, causing shininess and discomfort, thus requiring the application of a formulation containing fillers for conferring mattness throughout the day.

Changes in the weather (from day to day and during the year) complicate the problem.

The simplest possible solution is sought to solve this problem.

Moreover, there is a desire to be able to control the color or the coverage of the products.

This complicates the situation.

It is possible to use several products of different colors and/or coverage, but these generally have unsuitable levels of comfort and quality of the makeup. Thus, even if a single area becomes uncomfortable, on account of the comfort being poorly adapted to the area, the comfort as a whole becomes a source of concern, even resulting in the makeup being abandoned. Similarly, if a single area has a defect in the quality of the makeup, on account of being poorly adapted to the area, the quality of the makeup as a whole becomes a source of concern, even resulting in the makeup being abandoned.

A solution is required for giving access to an entire range of colors and covering levels, which can be applied to one and the same face without causing problems with comfort and quality of the makeup.

There are very few solutions for solving these problems.

A first approach is to buy numerous products and try them all out. This approach is costly and often gives rise to waste insofar as only a small number of the colored substances tried are generally kept.

A second approach is to test out various products in store. That is not always suitable, because it is very difficult to get a feeling for the results in just a few moments and at a location missing the usual landmarks. In particular, in order to fully assess the makeup effect in store, it would be necessary to be able to have the same lighting as will be found in future conditions of use, and this is something that is rarely possible. In general, it is only by testing out makeup over the course of a day that one can determine whether or not it is suitable in terms of the result and comfort. In addition, while certain stores have advisers and allow testing, this is not the case for a large number of other sales outlets and Internet sales.

Another approach has been tested but not developed. This is to create one's products by hand by mixing several coloured products. This may prove relatively difficult to do because it is not very easy to reproduce the same mixture exactly a number of times over, and it is awkward to quickly create the mixtures one needs at the moment of applying the makeup.

Dispensers for dispensing a cosmetic composition of variable color are also known.

Of the tests that have been able to be attempted for automating the manufacture of a customized cosmetic composition, many are those in which the proposed solutions allow mixtures to be created in quantities of around 100 g or sometimes less, but not in the very small proportions generally needed by a person applying makeup, namely in the region of one gram or much less.

In order to illustrate this problem, consider the case of somebody wishing to hide two imperfections in the region of one cm2 on her face. For the first area, she needs to find the corresponding mixture, then deliver a very small quantity, for example around 10 mg, thereof. For the second, she needs to change the setting of the dispenser, then, once again, deliver a very small quantity.

Therefore, for a great many people, choosing the colored substances that will yield the best results remains a difficult matter.

There is therefore a need to make searching for a makeup product that meets the expectations of a consumer and that allows this consumer to create mixtures under reliable conditions and in various quantities easier.

Therefore, according to certain aspects, the invention seeks to make it easier to make up the face, and notably to find the products best suited to the various areas thereof in terms of comfort and quality of the makeup.

There is also a need to improve the dispensing systems for delivering products of variable color, in order notably to make these easier to use and improve the quality of the makeup.

There is also a need to apply to the same face several products with ingredient contents chosen to suit the state of the skin.

In particular, people can have areas of the face that are marked to a greater or lesser extent and thus require different concealing strengths. It is therefore advantageous to be able to have a means for producing formulations with different types of ingredients in order to optimize the comfort and the quality of the makeup with regard to the characteristics of the area.

There is therefore a need to improve the dispensing systems for delivering products of variable color while regulating the ingredients, in order notably to optimize the comfort and the quality of the makeup with regard to characteristics of the area.

According to its eighth aspect, the invention is based upon a dispensing system that allows mixtures to be generated from base products. These base products may be of different colors, such that the color of the mixture can be varied. The base products may even make it possible to vary the proportions of fillers and moisturizing agent in the mixture, such that the comfort and the quality of the makeup resulting from applying the mixture to human keratin materials varies, being fairly close to that of said materials. The base products may also vary the color and the coverage. Thus, the idea of color is to be understood in a broad sense and encompasses mixtures of which the color varies after application as a result of variations in their level of coverage and in the color of the underlying skin.

According to an eighth of its aspects, the subject of the invention is a system for dispensing a product, comprising a dispenser that receives at least two cartridges that each have a reservoir containing first and second base products, respectively, the first base product comprising a moisturizing agent, the second base product comprising a filler, the dispenser making it possible to deliver at least these two base products in adjustable proportions.

According to this eighth aspect, the invention may have one or more of the following features:

the moisturizing agent is chosen from polyols, urea and derivatives thereof, such as notably hydroxyalkyl urea, in particular hydroxyethylurea, hyaluronic acid, glycine, β-alanine, taurine, trimethyl glycine, and mixtures thereof, preferably chosen from polyols such as ethylene glycol, pentaerythritol, trimethylolpropane, propylene glycol, glycerol, polyglycerols, polyethylene glycols, and mixtures thereof, and more preferably chosen from propylene glycol and glycerol, the particle size D50 by volume of the particles of the filler is between 100 nm and 1 mm, better still between 1 micron and 100 microns, even better still between 2 microns and 50 microns, the filler is chosen from talc, mica, silica, kaolin, poly-β-alanine powder and polyethylene powder, tetrafluoroethylene polymer powders, nylon powders, polymethyl methacrylate powders, lauroyllysine, starch, boron nitride, hollow polymer microspheres such as those of polyvinylidene chloride/acrylonitrile, acrylic acid copolymer microspheres, silicone resin microbeads, polyorganosiloxane elastomer particles, precipitated calcium carbonate, magnesium carbonate, magnesium hydrogen carbonate, hydroxyapatite, barium sulfate, aluminum oxides, polyurethane powders, composite fillers, hollow silica microspheres, and glass or ceramic microcapsules, the particles that are in the form of hollow sphere portions, and mixtures thereof, and is preferably chosen from talc, mica, silica, nylon powders, polymethyl methacrylate powders, and mixtures thereof, and is even more preferably talc, the filler may have a coating comprising at least one lipophilic or hydrophobic compound, the first base product and the second base product comprise an inverse emulsion, the mass content of filler in the second base product is greater than or equal to 0.5% by mass relative to the mass of the second product, and preferably greater than 1% by mass relative to the mass of the second product, the dispensing system comprises a third cartridge with a third base product, the cartridges are received in a removable manner in the dispenser, each product leaves the cartridge through an outlet passage of the cartridge, the outlet passage being defined by a dispensing end piece of the cartridge, said end piece being driven in rotation relative to a body of the cartridge by a drive mechanism of the dispenser in order to dispense the base product contained in the cartridge.

According to this eighth aspect, a subject of the invention is also a method for applying a cosmetic, makeup and/or care, product to human keratin materials, comprising the setting of the dispenser depending on the area to be treated, and the dispensing of the product by base products being picked up from the cartridges in the proportions corresponding to the setting of the dispenser.

According to its eighth aspect, the invention is based on a dispensing system having compartments containing at least two different formulations. They may contain different inverse emulsions, one with a concentration of fillers, the other with a concentration of moisturizing agent such as glycols, for example glycerol.

The system may be programmed to deliver, for each location on the face, the best mixture in terms of mattness, color, coverage and comfort (containing neither too much or too little in the way of fillers, nor too much or tool little in the way of moisturizing agent). The system may also be used to vary the level of fillers and moisturizing agent depending on the state of the time or the state of the present or future weather (for example more moisturizing for winter, comprising more fillers for summer).

Dispensing System

The dispensing system may consist of a single device operating autonomously, preferably able to be manipulated in one hand, or of a device that operates in interaction with other components or devices. It may for example entail various outlet interfaces which are mounted on the dispenser depending on the type of makeup to be created, as will be specified below. It may also entail a computer system which exchanges information with the dispenser in order to operate the latter, this computer system comprising, for example, a portable terminal such as a smartphone, a camera phone, a tablet, a laptop computer or a dedicated terminal.

Preferably, the dispenser is designed to pressurize one or more compartments containing the base product(s), via volumetric metering devices, preferably a motor causing a piston to move in the corresponding compartment.

The dispenser may be formed of a housing and of at least two or three compartments, and preferably an identical number of motors. For example, the rotation of the motors drives endless screws which push the pistons of each compartment. The advancing movement of the pistons is, for example, controlled by the number of command pulses sent to the motors and/or by the length of time for which the latter are operating. The motors may be powered in sequence or preferably simultaneously.

For example, the motors are powered during an elementary operating cycle for a short duration one after the other or at the same time as one another, so as to dispense corresponding microdoses.

The elementary cycles are repeated, possibly with a pause between them, giving the base products time to flow out of the compartments.

The compartments may be defined by cartridges, which are removed when they become empty. As an alternative, the compartments are permanently present and refilled once they become empty.

Each cartridge may be closed by a stopper that can be removed to allow the cartridge to be cleaned.

Preferably, the housing of the dispenser is of elongate shape along a longitudinal axis, making it easier to handle, and the cartridges are disposed about this axis, inside the housing.

Preferably, the cartridges are inserted from the rear and the mixture is delivered from the front. The cartridges may be inserted individually or, as an alternative, the cartridges constitute a one-piece assembly as they are inserted.

The cartridges may each have a volumetric metering mechanism comprising a piston moved by a drive mechanism of the dispenser in a direction accompanied by a reduction in the internal volume containing the base product and the expulsion of some product. It may be advantageous for the cartridges to have at least a region of their wall that is transparent so that the color of the product contained therein can be seen.

The drive mechanism may have a motorization system formed of motors coupled to gearboxes, of elongate shape parallel to the longitudinal axis of the dispenser, and positioned between the cartridges. Positioning the motors and cartridges in this way makes the dispenser particularly compact.

The base product can leave the corresponding cartridge in a sealed manner, then flow along a passage provided for this purpose in the housing of the dispenser, before leaving the latter.

The cartridges advantageously end in an end piece produced in such a way that, once the cartridge has been inserted into the housing of the dispenser, the end of the end piece terminates flush with the housing. As an alternative, the end piece is long enough to protrude beyond the housing and thus connect various outlet interfaces that can be attached to the housing of the dispenser.

By virtue of the drive mechanism having motors for causing the pistons to advance, it is possible to precisely deliver mixtures in very small quantities. Thus, the drive mechanism can deliver the base products with a minimum flow rate less than or equal to 50 L/s, better still less than or equal to 20 μL/s, even better still less than or equal to 10 μL/s. Preferably, the drive mechanism delivers flow rates of between 20 and 100 μL/s, better still between 40 μL/s and 60 μL/s. It is thus possible to easily create a mixture of around 10 mg. Such a dispensing system is therefore ideal for achieving small touches of makeup, for covering an area of 1 cm², better still an area of 0.5 cm², for example.

It is also possible to create larger quantities of mixture such as the quantities needed to make up a cheek or a face. These quantities remain relatively low, however, for example a quantity of between 100 and 500 mg, better still between 150 and 250 mg.

Preferably, the cartridge has a dispensing end piece through which the product exits, and this dispensing end piece is driven in rotation by the drive mechanism for moving the piston. The end piece may have at least one rotation-proofing relief, better still two diametrically opposed rotation-proofing studs.

The end piece may bear a seal, notably an O-ring seal. Thus, when changing the cartridge, the seal is also changed, making it possible to get around the problem of seal wear.

The dispenser may have an electronic board for controlling the motorized drive mechanism, this electronic board having the end piece(s) passing through it. This may make it possible to produce a board extending across substantially the entire cross section of the dispenser so that all the electronic components of the dispenser can be grouped together on a single board, thus improving compactness and reliability. The board may extend substantially perpendicularly to the longitudinal axis of the housing. The board may bear a switch for controlling operation of the dispenser.

The dispensing system may be designed to operate in at least two dispensing modes.

In a first mode, referred to as "continuous", the mixture is dispensed as long as pressure is applied to the control switch.

In a second mode, referred to as "dose", a predefined quantity of the mixture is dispensed for each press of the switch.

The end piece(s) may terminate at one end of the housing. This may make it possible to reduce the dead volume, as will be explained in detail below.

The end piece(s) may have at their end a shutoff system for preventing the products from drying out in the duct, for example a self-healing membrane.

The cartridge may have a hollow screw onto which the piston is screwed, the piston being able to move axially along the screw as the latter turns; the piston is prevented from turning in the body of the cartridge. For example, the friction of the piston against the body of the cartridge may be enough to prevent it from turning when the screw turns.

Preferably, rotation is rendered impossible with a cartridge body of non-circular cross section and a piston that is not deformable.

The torque of the motors may be determined electronically depending on the current drawn, and may be used for example to detect that the piston has reached the end of its travel. Information regarding the torque may be transmitted remotely to a computer system that has a man-machine interface, in order that correct operation of the dispenser can be monitored.

In order to adjust the shade, the dispensing system according to the invention has to allow the user to vary the volume delivered from each compartment.

Preferably, the dispenser is operated by a computer system built into the dispenser or external thereto, the dispenser then being able to exchange information with the computer system using a wireless or wired protocol.

The dispenser may thus be operated so as to allow the shade to be adjusted by controlled simultaneous or sequential dispensing of several base products with different proportions of fillers and moisturizing agent.

The dispensing of the base products may be continuous; in such a case, the volumes of each of the base products are dispensed in a single shot, simultaneously or in succession.

In the case of simultaneous dispensing, it is beneficial to be able to adjust the respective flow rates of the various base products in order for the dispensed mixture to correspond to the desired mixture at all times. Such a dispensing mode may be suitable in particular when dispensing the mixture by spraying, using an airbrush. To adjust the flow rates it is possible, for example, to alter the speed at which the pistons move, for example in the case where the pistons are driven by an endless screw, by varying the rotational speed of the motors that drive the screw. The products may also be dispensed in a pulsed manner with a dispensing time and a pause in each cycle. By altering the duty cycle it is possible to alter the flow rate.

All the products may be delivered simultaneously during the dispensing time or, as an alternative, the cycles of the various products are phase-shifted from one another so that one product is dispensed while the other products are paused.

In one particular embodiment of the invention, the mixture is delivered into a cavity of a container which may close hermetically or not, for example in the form of a cup, into which an applicator, particularly a stylus or a brush may be slipped. Such a dispensing system is especially suited to liners, glosses and other formulations applied without direct contact with the hands. This container may be removable.

For example, it is used as a lip-color dispenser and has a dispensing system, for example using a screw. When it is not removable, the container may be produced with the body of the dispenser. When it is removable, it may constitute one output interface among others that can be mounted on the dispenser.

The compartments, and in particular the cartridges, may contain all or part of the drive mechanism and, for example, the motorizing system or, better still, part of the motorizing system, the purpose of this being to reduce the number of moving parts in the body of the dispenser outside the cartridges. For example, the cartridges contain the rotor of the motor. Once the cartridges have been installed in the body of the dispenser, the rotors are made to interact with the stators.

The dispensing system is advantageously arranged in such a way as to allow the running of preprogrammed sequences in which the mixture delivered by the system is modified continuously or discontinuously. A "graduated" mode makes it possible for example to progress gradually from a mixture A to a mixture B. In the case where the application is by spraying, notably using an airbrush, this makes it possible for graduations to be achieved simply. An "alternate" mode makes it possible for example to switch quickly from a mixture A to a mixture B several times in succession. In the case of application by spraying, a multilayer application can thus be achieved, with different formulations for two superposed adjacent coats. Another mode makes it possible for example to offer several preprogrammed successive mixtures, the computer system each time indicating to the user how these should be used, for example by display on a screen.

In the case of manual application, the mixtures are dispensed for example into a cup. The person applies the makeup to the recommended place with a corresponding mixture taken from the cup, then, if necessary, cleans out the cup and commands delivery of a new mixture; the operation is repeated as many times as necessary until the person is fully made up.

The mixtures dispensed can be homogenized in various ways depending on the type of use. In the case of manual application, it can be done directly on the application area at the time of application or in the cup before the mixture is picked up; in the case of an airbrush application, the pipe of the airbrush is used as a mixing chamber; if the mixture is dispensed into a container for later use, homogenization can be performed by hand or by passing the dispensed products through a mixing chamber situated between the dispenser and the container or incorporated directly into the container, as described in detail below.

The product may be delivered by the dispensing system and used extemporaneously. As an alternative, the product delivered by the dispensing system is packaged and used later, for example on several occasions, with, for example, at least one day's interval between two uses.

According to its eighth aspect, the invention is based on a dispensing system having compartments containing at least two different formulations. They may contain different inverse emulsions. One with a concentration of fillers. The other with a concentration of moisturizing agent.

Fillers

These fillers are colorless or white solid particles of any form, which are in a form that is insoluble and dispersed in the medium of the composition.

As illustrations of these fillers, mention may be made of talc, mica, silica, kaolin, poly-β-alanine powder and polyethylene powder, tetrafluoroethylene polymer powders (Teflon®), nylon powders, polymethyl methacrylate powders, lauroyllysine, starch, boron nitride, hollow polymer microspheres such as those of polyvinylidene chloride/acrylonitrile, for instance Expancel® (Nobel Industrie), acrylic acid copolymer microspheres, silicone resin microbeads (for example Tospearls® from Toshiba), polyorganosiloxane elastomer particles, precipitated calcium carbonate, magnesium carbonate, magnesium hydrogen carbonate, hydroxyapatite, barium sulfate, aluminum oxides, polyurethane powders, composite fillers, hollow silica microspheres, and glass or ceramic microcapsules. Use may also be made of particles that are in the form of hollow sphere portions, as described in the patent applications JP-2003 128 788 and JP-2000 191 789.

The fillers may have a coating comprising at least one lipophilic or hydrophobic compound.

The filler is other than a colored pigment conferring a color on the composition, such as a nacre or an iron oxide.

Moisturizing Agent

A "moisturizing agent" is understood, according to the present invention, to be any compound capable of penetrating into the stratum corneum and of keeping the latter moisturized.

The moisturizing agents that are usable according to the invention are notably chosen from polyols, urea and its derivatives, such as notably hydroxyalkyl urea, in particular hydroxyethylurea such as the product sold under the trade name Hydrovance® by the company Akzo Nobel, hyaluronic acid, glycine, β-alanine, taurine, trimethyl glycine, and mixtures thereof.

Within the meaning of the present invention, a "polyol" is understood to be any organic molecule comprising at least two free hydroxyl groups.

According to one particular form, the polyol may be chosen from sugars such as trehalose, mannitol, xylitol, sorbitol, and mixtures thereof.

Preferably, a polyol according to the present invention is present in liquid form at room temperature.

A polyol that is suitable for use in the invention may be a compound of linear, branched or cyclic, saturated or unsaturated alkyl type, bearing on the alkyl chain at least two —OH functions, in particular at least three —OH functions and more particularly at least four —OH functions.

The polyols that are advantageously suitable for formulating a composition according to the present invention are those especially containing from 2 to 32 carbon atoms and preferably 3 to 16 carbon atoms.

Advantageously, the polyol may be chosen, for example, from ethylene glycol, pentaerythritol, trimethylolpropane, propylene glycol, 1,3-propanediol, butylene glycol, isoprene glycol, pentylene glycol, hexylene glycol, glycerol, polyglycerols, such as glycerol oligomers, for instance diglycerol, and polyethylene glycols, and mixtures thereof According to a preferred embodiment of the invention, said polyol is chosen from ethylene glycol, pentaerythritol, trimethylolpropane, propylene glycol, glycerol, polyglycerols, polyethylene glycols and mixtures thereof.

According to a particular mode, the composition of the invention may comprise at least propylene glycol and/or glycerol.

Inverse Emulsions/Anhydrous Compositions

According to the invention, when a composition is said to be in the form of an inverse emulsion, it will be understood that it can also alternately be in another form depending on the composition in question.

A base product may be in the form of an emulsion, for example an O/W, W/O, O/W/O or W/O/W emulsion, and preferably a W/O inverse emulsion, or in the form of an anhydrous composition, comprising notably carbon-based compounds and/or silicone compounds, such as hydrocarbon-based oils and/or silicone oils.

The emulsions according to the eighth aspect of the invention are preferably water-in-oil (W/O) emulsions, also known as inverse emulsions, namely constituted of an oily continuous phase in which the aqueous phase is dispersed in the form of droplets so as to observe a mixture that is macroscopically homogeneous to the naked eye.

Use for Making Up One or More Precise Areas of the Skin

The dispensing system allows makeup to be applied, day after day, with only the areas that need to be hidden being treated. To this end, small doses of makeup are delivered, and are applied specifically and sequentially to the corresponding areas. Each small dose is created using the mixture suited to the area.

In one preferred embodiment of the invention, the dispensing system waits for information regarding which area is to be treated and then delivers the corresponding mixture. It may use a preprogrammed look-up table for that purpose, this table being the result for example of a learning process as defined below. As an alternative, the dispensing system informs the person, when delivering a mixture, of the area to which the person is to apply the mixture. Thus, the dispensing system may follow an application program in which it delivers, in a given order, the various mixtures that are to be applied.

In one particular embodiment of the invention, the dispensing system is informed as to the quantities to be delivered. For that, it memorizes the relationship between the color, the area of the face and the quantity needed, thereby making it possible to reduce costs and wastage of product, and to cover the skin only lightly, thus avoiding occlusion effects. In so doing, it is possible to use products that have a high covering capability and provide too much cover to be applied to the whole of the face. Thus, it is possible to obtain makeup of natural or even undetectable appearance.

The dispensing system may also make it possible, by facilitating the dispensing of small quantities and rapid use thereof, to reduce the time for which the products are kept, thus making it possible to reduce the risks of the products changing and/or to reduce the amounts of preservative to be used.

The dispensing system is suited to treating the areas that are to be concealed, without having to conceal the entire face.

It may also be used to conceal one or more marks, while adapting the product for the best comfort and the best quality of the makeup with regard to the area.

In an especially advantageous variant, the system may be used to apply to the base of the face a formulation with little concealing effect and then one or two applications to precise areas of the face of formulations that are more concealing, all with the best comfort and the best quality of the makeup with regard to each area. It is also possible to start with applications to the precise areas of the face of concealing formulations and then to apply to the base of the face an application of a formulation that is less concealing.

In the second case, time is taken, before applying the second layer, to wait for the film produced by the application to the precise areas to become sufficiently cohesive so that the second layer does not remove the first layer.

Alternatively, the second layer is applied without rubbing (spray for example, or sponge).

When the user is looking for the color to apply to an area of the face, it is advantageous to memorize the color best suited to each area, and the dispensing system is thus advantageously designed to memorize this color and the corresponding area. Thus, by using the memorized information, on each use, the same mixture can be delivered for each area or, if several areas are being treated, the same series of mixtures can be delivered for the same series of areas.

The dispensing system may also be designed to allow an area to be treated by varying the colors application after application. Thus, the person may make up her lips using different colors that she chooses on a day-by-day basis to suit her tastes. This approach is also suitable for the eyelids or eyelashes, and for face makeup because the person may fancy a change of foundation color. For example, on weekdays, the person applies a pale colored foundation, with a more tanned foundation color at the weekends, or may have eye makeup in one color one day and another color another day. Idem for variations in the proportions of fillers and moisturizing agent in order to have the best comfort and the best quality of the makeup for each area.

The dispensing system may be designed to allow the user to change color to suit her tastes according to the day, the time, what she is wearing, and the weather. Thus, a system to assist with decision making is advantageously provided to guide the user in her choices of color (broadly speaking) and the proportions of fillers and moisturizing agent.

An assistance system may also be provided for balancing the colors on the same face and contribute toward a successful overall makeup look, all with an ideal makeup result and comfort for each area and thus an optimal makeup result and comfort over the entire face.

It may be desirable for several people in the same group, for example a family, to be able to use the dispensing system, thus reducing costs and minimizing the space taken up. This solution is particularly suited to travel or hotels, campsites, airplanes, campervans, boutiques, schools, etc. For that, provision may be made for the dispensing system to be able to be informed as to which person is using it, so as to access pre-stored personal data.

Continuous Use for Makeup with Graduated Moisturizing/Matting

In this application, the dispensing system changes the formulation of the mixture while it is delivering the product. In addition, the outlet for the base products or for the mixture is moved relative to a container or a support defining an application surface. In one particular embodiment of the invention, the dispensing system is designed to calculate the way in which the mixture evolves as a function of the moisturizing/matting $C_1$ of one area to be treated and of the moisturizing/matting $C_2$ of another area to be treated. For example, with the knowledge that the chin requires a moisturizing/matting C1 and that the cheek requires a moisturizing/matting C2, the dispensing system may vary the formulation of the mixture while it is delivering it in order to carry out a treatment between these two points. This makes it possible for example to better conceal imperfections of the face while ensuring that the end result is comfortable and that the makeup is of quality, even if areas of skin with different states are covered. The dispensing system may also be designed such that the user can command a variation in moisturizing/matting of the mixture dispensed without the start and/or end moisturizing/matting having been set beforehand. To do that, the dispensing system may possess a location or auto-location system and deduce from a look-up table the moisturizing/matting C1 and the moisturizing/matting C2 that it is to create and therefore the changes in the mixture that it has to make.

The dispensing system may have an outlet head, in particular in the case of an airbrush, which is mobile and steered. This option then makes it possible to achieve graduated effects without moving the rest of the dispensing system. For example, the dispensing system is located near to the cheek, then a control system is triggered that will automatically steer the variation in formulation of the mixture and the movement of the outlet head so as, for example, to make the center of the cheek redder than the periphery thereof, with a graduation between the two.

The dispensing system may even be used to create tailor-made products that are kept for several applications.

It is also possible to produce solid or semi-solid products.

Manufacture of "Bespoke" Compacts or Other Solid or Semi-Solid Products

The dispensing system may be designed to allow a mixture to be chosen and delivered to a container such as a cup. The mixture preferably comprises compounds which are such that the mixture can set solid.

More preferably, use is made of compounds that make the setting especially rapid. These compounds are either deposited in the container before or after it is filled with the other ingredients, or are provided in the compartments of the dispenser with the other constituents of the base products, or are contained in the dispenser in a compartment especially designed to contain them.

Specific compositions which may harden quickly by chemical, biochemical or physicochemical reaction after discharge may thus be dispensed.

These compositions are especially designed for the creation of compacts, namely they:
 set solid,
 yield a material that can crumble if rubbed, and are preferably colored.

Preferably, these compositions are very rich in solid particles, with for example more than 10% by mass of solid particles relative to the total mass of the composition, better still more than 20% by mass of solid particles relative to the total mass of the composition, even better still more than 30% by mass of solid particles relative to the total mass of the composition, preferably between 10 and 40% by mass of solid particles relative to the total mass of the composition.

These compositions may contain absorbent particles or reactive compounds, such as those that react in contact with the air, for example cyanoacrylate or alpha-silanes or those which react to light, notably UV.

The container into which the mixture is dispensed may contain a compound A and the dispensed compositions may contain a compound B, A and B being chosen to react with one another and solidify the mixture.

In one particular embodiment of the invention, the dispensing system incorporates a heating means, for example with an electrical resistor, to create lipsticks or other waxy products. In that case, the base products are heated before being delivered.

The dispensing system may also comprise a means for supplying heat and/or light energy, after the mixture has been dispensed into a container, for example an electrical resistor or an LED, notably UV. This energy may accelerate the setting-solid of the dispensed mixture.

Preferably, the mixture is homogenized before it sets solid.

The products, of different coverage, will exhibit different moisturizing/matting, suitable for the different states of the skin.

Creation of Color Palettes

The dispensing system may have a support, having several regions, and may be designed to automatically generate several mixtures deposited in said regions, for example a series of colors suited to various parts of the face.

The support may define several cavities to receive the mixtures or may bear several containers, for example in the form of cups, potentially cups that are separable from the support.

In one particular case, the support adopts the shape of a face with regions for receiving the mixtures for targeted application areas.

The support may be able to move, notably to rotate, with respect to the body of the dispenser and, for example, may be driven in its movement by the dispenser so that various spaces or containers can be filled in succession.

The products in the palette may exhibit different moisturizing/matting.

Cup-Type Dispenser

There is a benefit to having a dispensing system capable of delivering a mixture that the user can easily pick up. Moreover, in cases in which the base products delivered by the dispensing system are not already blended, there is a need to allow the user to perform the mixing easily.

Preferably, the dispensing system has a cup and a dispenser for filling the cup with at least one product, the cup being secured to the dispenser at least while it is being filled.

The cup is sometimes also known as a "crucible" and that term should be understood in its broadest sense.

A "cup secured to the dispenser" should be understood as meaning that the cup is held, notably immobilized, at least temporarily, on the dispenser, being for example fixed to the latter by screws, magnetic attraction, clip-fastening, bayonet locking, clamping, or produced with a part of the dispenser body by material molding. When it is secured to the dispenser, the cup allows the latter to be manipulated in one hand, the cup remaining in place on the dispenser while the latter is being moved around.

The dispenser may be offered to the user with the cup already in place.

As an alternative, the cup is installed by the user the first time the dispensing system is used.

The cup is preferably less deep than it is wide, making access to it easier and allowing the product, notably the mixture, to be picked up with an applicator or a finger.

Preferably, the cup is separable from the dispenser and constitutes one outlet interface that can be chosen from a collection of outlet interfaces that can be mounted on the dispenser, at the choice of the user and according to the making up to be performed, as described in detail below.

Preferably, the dispensing system comprises several filling orifices for filling with different base products, opening into the cup. Thus, the mixing of these products may take place in the cup.

The cup preferably has a bottom that is concave toward the outside, making it easier for the user to clean it between two uses.

In addition, this may make the product easier for the user to pick up and the base products easier to mix.

Preferably, the dispenser allows at least two base products to be delivered into the cup, in adjustable proportions, and better still at least three products.

In one exemplary embodiment, the dispensing system has at least two cups that can be selectively fed by the dispenser. This may allow the user to fill these two cups quickly with mixtures with different characteristics. This may facilitate the testing of colored substances and/or allow the preparation of several different moisturizing/matting mixtures intended for making up respective areas of the face. The cups may be associated with identifiers that remind the user of the area of the face for which a mixture contained in a given cup is intended.

The cups may be able to move relative to the dispenser, being for example borne by a mobile support such as a turret that is rotatable with respect to the dispenser or by a slide capable of translational movement with respect to the dispenser.

The dispensing system may comprise a lid for closing the cup. This closure lid is preferably transparent so that the user can see the color of the mixture contained inside.

When the cup is separable from the dispenser it may if necessary be introduced into a housing that allows it to be transported more easily, this housing being able, if necessary, to contain a mirror and/or an applicator. The lid of the housing may in this case act as a lid for the cup.

The volume of the cup may be between 2 and 1000 $mm^3$, better still between 100 and 1000 $mm^3$, even better still between 250 and 750 $mm^3$.

The base product(s) delivered into the cup are preferably foundations, but as an alternative may be makeup products for the lips or eyelids.

The cup preferably has a shape that exhibits symmetry of revolution. As an alternative, it has a polygonal or some other contour. Its largest inside diameter, or that of the inscribed circle in the case of a noncircular contour, is preferably between 2 and 100 mm, preferentially between 5 and 40 mm. Its depth is preferably between 1 and 10 mm, better still between 3 and 8 mm. Preferably, the size and shape of the cup either allow direct application of the mixture to the skin or allow the mixture to be picked up on a finger or using an applicator. The cup may be made of an elastically deformable material, making it possible for example to turn the concavity of the bottom of the cup inside out and empty it more easily or use it to apply the product.

The cup may have no blender; in that case, the base products may arrive in the cup from the dispenser in the unmixed state, via distinct respective dispensing orifices. As an alternative, the dispenser incorporates a blender and the base products arrive in the cup already blended.

The cup may also incorporate a static blender as described in detail below, which is fed via distinct filling orifices of the dispenser and which preferably delivers the mixture into a cavity of the cup situated above the blender.

A further subject of the invention is a method for preparing a makeup product, comprising the step of filling a cup of a dispensing system as defined above with at least one base product from the dispenser.

The products, with different coverage, will have equivalent mattness/shine effects.

Several products may be delivered into the bottom of the cup, then blended using a finger or an applicator, or a static blender incorporated into the cup.

The cup is preferably filled from beneath. Dispensing systems using a sonotrode have been proposed in the past.

The cup according to the invention is not intended to vibrate in order to dispense the product(s) conveyed by the feed passage(s) supplying it. It differs from a sonotrode.

Preferably, the cup is made of plastic.

Blender Incorporated into the Outlet Interface

There is a benefit in having a dispensing system capable of delivering a mixture that can easily be used, notably picked up by the user, without the need for an additional mixing action on the part of the user.

One subject of the invention is a dispensing system having a dispenser having outlet passages for base products and an outlet interface that is separable from the dispenser, this interface having a static blender that preferably delivers the mixture into a cavity where it can be picked up.

The static blender may be situated under the abovementioned cavity. The dispensing system is then particularly suited to the creation of compacts, using cups with an in-built static blender as outlet interfaces. In that case, the cavity of the cup is filled with product from beneath. After passing into the static blender, the blended base products cover the blender.

According to this aspect of the invention, it is possible to use several outlet interfaces and to fill them with different respective mixtures, without the need to purge the blender, thereby reducing losses of product. The outlet interface may be a single-use interface, if necessary.

Preferably, the static blender has a central chamber communicating with base product intake ducts. This central chamber may communicate with a peripheral chamber having a series of partitions which act as deflectors for the mixture and create shearing thereof.

The peripheral chamber may have a perforated annular partition defining perforations through which the mixture passes as it circulates in the peripheral chamber. The central and peripheral chambers may be closed at the top by a wall which defines the end wall of the cavity receiving the mixture.

The end wall of the peripheral chamber may be of helical shape about the axis of the cup and of a height that decreases in the direction toward the outlet. The latter may open ahead of a connecting ramp connecting the end wall of the peripheral chamber and the top wall of the blender, this connecting ramp preferably being a portion of a helix extending the helix formed by the end wall of the peripheral chamber.

Preferably, the peripheral chamber comprises the abovementioned annular partition and radial partitions that force the mixture to circulate alternately between upper and lower regions of the peripheral chamber and between radially inner and outer regions, the mixture circulating for example from an upper and radially outer region to a lower and radially outer region by passing through the abovementioned annular partition.

The blender may have an outer body in which a component forming the core of the blender is housed, the outer body radially closing the peripheral chamber on the outside and comprising an upright that separates the central and peripheral chambers.

The outer body of the blender and the core of the blender may each be produced as a single piece by injection molding.

Reduced Dead Volume

There is benefit to be had in reducing the losses of product when changing the formulation of the mixture and in allowing the color or moisturizing/matting of the mixture to be varied as quickly as possible during application, particularly when the dispenser is coupled to an airbrush.

A further subject of the invention is a system for dispensing a makeup product, having a dispenser that receives at least two cartridges that each have a reservoir containing a base product, the latter leaving the cartridge through an outlet passage of the cartridge, this outlet passage opening to outside of the dispenser or near the external surface thereof.

The outlet passage may notably open into an area in which the mixture is picked up or close to this area, notably less than 5 mm away, better still less than 3 mm away, better still less than 1 mm away, or even better still flush therewith.

The cross section of the outlet passage is, for example, between 1 and 3 mm$^2$.

Thus, each base product coming from a cartridge can leave the dispenser without mixing with a base product from another cartridge and the dead volume that cannot be picked up and is likely to increase the inertia of the system is minimized. The product is more quickly available without having to circulate through special passages in the housing of the dispenser, thereby avoiding a painstaking purging step in the event of a cartridge change.

The outside of the dispenser may be the product pickup area, notably when the dispenser is produced with a cup that is not designed to be removed, into which the mixture is dispensed, or a dispensing area intended for the mounting of a removable outlet interface, which defines the pickup area. This outlet interface may have a cup as defined above. This mounting area corresponds for example to the outside of the housing of the dispenser in the absence of an outlet interface. The mounting area may be substantially planar and perpendicular to the longitudinal axis of the dispenser housing.

The dispenser may have three cartridges of base products.

The dispenser may have housings for receiving the cartridges, which are preferably received removably in the dispenser. The latter may comprise passages for ducts for the cartridges defining the outlet passages.

The length of these ducts is preferably such that the ducts are set back slightly from the end or lie flush with the cavity used for picking up the product or, as an alternative, are set back slightly from or lie flush with the end face of the housing of the dispenser that defines the mounting area.

These ducts of the cartridges may be end pieces used for causing the pistons to move within the cartridges, as described in detail above.

Multiple Outlet Interfaces

There is a need to be able, using the same dispensing system, to achieve different makeup looks easily and be able, if so desired, to make up areas as different as the skin, the lips, the eyelashes or eyebrows.

In one of its aspects, independently of or in combination with the other aspects thereof, and notably with the foregoing, one subject of the invention is a dispensing system comprising an assembly comprising a dispenser of at least one cosmetic, notably makeup, product and at least two outlet interfaces, each of which can be mounted removably on the dispenser, these outlet interfaces which are able to receive the product or products delivered by the dispenser preferably being chosen from among the following:

an outlet interface having a container, notably a cup, allowing the product to be picked up using a finger or using an applicator, an outlet interface allowing the product to be delivered to a spray system, notably an airbrush, an outlet interface having several regions for receiving the product, which can move relative to the dispenser, an outlet interface that allows the product to be delivered to a dispensing end piece.

Preferably, the assembly comprises at least three of said outlet interfaces, or better still the four outlet interfaces.

The dispenser may comprise at least two different base products and allow these to be delivered in variable proportions and, preferably, the dispenser comprises three different base products and allows these to be delivered in variable proportions.

Each outlet interface may have a base allowing it to be fixed to the dispenser. This fixing may be done using screws for example, but preferably the base is designed to allow an outlet interface to be removed and replaced without the need for tools. It is, for example, a quarter-turn fixing or a fixing using an external locking ring.

The outlet interface and/or the housing of the dispenser may comprise seals allowing sealed communication between the housing of the dispenser and the outlet interface. If appropriate, the dispenser is designed to recognize the outlet interface mounted above, for example by virtue of the outlet interface having identifiers in the form of specific reliefs which are detected by the dispenser, or in the form of an electronic chip that the dispenser recognizes. That may allow the operation of the dispenser to be adapted to the outlet interface mounted above. The dispenser may communicate information about the outlet interface it is bearing to a computer system, and the computer system may, on the basis of this information, display a specific screen and/or run a specific program for controlling the operating parameters of the dispenser so as, for example, to adapt the dose dispensed and/or the flow rate to the type of outlet interface.

The user may be initially offered several outlet interfaces with a common dispenser within one and the same package, for example a case or a cardboard box.

A further subject of the invention is a makeup method involving the step of selecting an outlet interface, mounting it on the dispenser, and delivering the product(s) contained in the dispenser to the interface.

Mapping and Learning

The term "mapping" should be understood here as meaning a process of indexing moisturizing/matting with an area, with recording.

It may be the case that a person requires several levels of moisturizing/matting with a single color and/or coverage for all areas.

It may also be the case that she requires several levels of coverage with one level of moisturizing/matting on one part of the face and another level of moisturizing/matting for another area. For example, she has several marks on the forehead and several marks on the cheeks. Thus, she may want to create several levels of coverage for the forehead with a given level of moisturizing/matting for this surface. She may want to create several levels of coverage for the cheeks with one level of moisturizing/matting for this surface.

The mapping may relate to applications to areas smaller than 1 cm$^2$. However, the naked eye then has difficulty in discerning whether the result obtained is adequate, and it is preferable to substitute an instrumented evaluation with magnification for evaluation by the naked eye. Small quantities of colored substance may be applied with a finger, using conventional tools such as brushes, or using specialist applicators.

The map may be generated during a learning period in which the user carries out tests with mixtures on different areas of the face; once created, the map can then be used for everyday makeup.

Specific graphic interfaces can be used during the learning period and during the period of use of the map.

In particular, the dispensing system may be used with a graphic interface in which the operator sees the face, which is for example a schematic, figurative or accurate representation such as a photograph or a 3D simulation. In that case, the operator can point at part of the face on the screen to show and/or deliver the appropriate moisturizing/matting.

The graphic interface may also show the other areas of the face where use of that same moisturizing/matting is appropriate.

To create the map, the operator applies moisturizing/matting, then makes an assessment.

The areas of the face can be treated one after the other; for example, the exercise is carried out on part of the cheek, then on the nose, etc.

Another option is to create a given mixture and apply this same mixture to several areas. The operator then needs to look for the area of the face to which the moisturizing/matting is suited. The mixture is then indexed in the computer system which attributes it to the area(s) of the face for which it is suitable.

A subject of the invention is also a learning process for a dispensing system, comprising a dispenser for dispensing a mixture of variable moisturizing/matting, and a computer system for selecting moisturizing/matting and for storing data, comprising the steps of.
- a) selecting at least one moisturizing/matting with the aid of an interface of the computer system,
- b) delivering, with the aid of the dispenser, at least one mixture with the selected moisturizing/matting,
- c) evaluating the mixture(s) dispensed following the application thereof to at least one area of the face,
- d) memorizing the characteristics of at least one mixture, notably a mixture that the user wishes to be able to recall, and of at least one area on which it has been tested.

This memorizing can be carried out notably with a view to subsequent dispensing of this mixture for making up said area.

Preferably, the computer system is designed to allow the user to indicate whether or not the result of the test is satisfactory, or even to inform same of the comparison with a test carried out earlier.

It is also possible to create a given mixture and to look for the area of the face for which it is suitable. The mixture is then recorded, being attributed to the area(s) of the face for which it is suitable, in a look-up table that will be used subsequently in order to deduce which mixture to use on the basis of an area of the skin.

The same procedure can be adopted with other mixtures in order to create a map of the entire face and thus have a complete look-up table for the face.

It is also possible to create a given mixture, apply it to a given area, and then vary the mixture until the most suitable mixture is obtained. The mixture is then recorded, being attributed to the area(s) of the face for which it is suitable, in a look-up table that will be used subsequently in order to deduce which mixture to use on the basis of an area of the skin.

Preferably, the computer system evaluates and memorizes the quantities used area by area. Such a method, which uses "test patches" makes it possible to identify the product(s) required by the person wishing to apply makeup. Thus, the dispensing system can be used at sales outlets to advise people wishing to apply makeup or at home in order to define correctly which products to order.

The interface of the computer system preferably has a touch screen displaying the moisturizing/matting of the mixture when it is selected.

The interface may display a face and allow the computer system to be informed by selecting the area on the face displayed.

The computer system is preferably designed to allow an area, mixture reconstruction parameters, and the date of the test and/or any other identifier of the mixture to be associated with one another.

The computer system is preferably also designed to allow at least one of the following data: the name of the area, the period of the year, the name of an event, a user identifier and the age of the user, to additionally be associated with said area, with the mixture reconstruction parameters, and with the date or identifier of the mixture.

Steps a) to c) may be repeated at least once before the characteristics of the mixture are memorized in step d).

The computer system may be designed to search a database for a reference of a commercial product on the basis of the characteristics of the mixture identified as being suitable for at least one given area, and to relay this information to the user.

The selection in step a) may be carried out using an expert system, which may or may not be external to the computer system.

The expert system may analyze an image of the user in order to propose a mixture moisturizing/matting at least on the basis of the image analyzed.

Step a) may be preceded by the computer system proposing to the user a moisturizing/matting and an area to be tested with a mixture of this moisturizing/matting.

The computer system may be designed to allow the user to inform same of his or her assessment of the result of the test in step c) and to generate a proposal to modify the mixture to be selected upon return to step a).

The computer system may be designed to propose at least one moisturizing/matting of mixture in step a) depending on an application area of which it has been informed by the user.

The computer system may be designed to propose at least one application area in step a), on the basis of a moisturizing/matting of which it has been informed by the user.

The dispenser may deliver, in step b), at least two mixtures of different moisturizing/matting, preferably separate, so that they can be applied simultaneously to the test area.

This may allow time to be saved and make it easier to compare the results.

A further subject of the invention is a method of making up using a dispensing system according to this aspect of the invention, in which:
- a) the user sends the computer system a request regarding a need for makeup,
- b) in return, the computer system generates a proposed moisturizing/matting for making up an associated zone, on the basis of the learning performed beforehand, and
- c) the computer system operates the dispenser to produce the mixture of the proposed moisturizing/matting, notably if this is validated by the user.

Such a method may use a map previously established with the user.

A further subject of the invention is a computer program product containing code instructions which, when run in a computer system, allow the computer system to be made to:
- allow the user to select at least one moisturizing/matting and/or one application area, notably using an interface such as a touch screen,
- operate a dispenser in such a way as to deliver a mixture of moisturizing/matting selected by the user,
- allow the user to trigger the memorizing of the moisturizing/matting of the mixture and of an associated application area, notably with a view to subsequently dispensing the same mixture, notably on the same area.

The computer program product may comprise code instructions which, when run in a computer system, allow the computer system to be made to:
- receive a request from the user regarding a need for makeup, notably using an interface such as a touch screen,
- propose, on the basis at least of data generated by the learning process as defined above, at least one moisturizing/matting and/or one application area,
- operate a dispenser to produce the mixture of the proposed moisturizing/matting, notably if this is validated by the user.

The person may incorporate into the map the level of mattness/shine that she desires for each area of the face, area by area or set of areas by set of areas. The system will then interpret the mixtures it needs to create to ensure the moisturizing/matting and coverage desired and the wanted mattness/shine.

The map may subsequently be modified. Thus, it is possible to create the map in terms of the colors in the first instance, and then refine the map by subsequently defining the levels of moisturizing/matting.

Remote Assistance

It is desirable to be able to assist the user in applying makeup, notably in choosing the correct colorings.

In one of its aspects, independently of or in combination with the other aspects thereof, and notably with the foregoing, one subject of the invention is thus a method of applying makeup involving the steps of:
- allowing a video link to be established, for example over the Internet, between a camera on a first site and a second site,
- allowing the second site to directly or indirectly operate a dispenser present at the first site, this dispenser making it possible to vary the moisturizing/matting of a mixture dispensed,
- allowing a person present at the first site to apply the mixture dispensed and to send a corresponding image to the second site, so as to receive in return information relating to the makeup result.

The second site may notably have a viewing screen which allows an adviser sitting at this screen to see the makeup result with the product dispensed by the dispenser and advise the person who has applied the makeup. This adviser may in return influence the dispenser to alter the moisturizing/matting of the mixture and adapt it to best suit the face of the person present at the first site. Thus, this person controls the mixture delivered by the dispenser. The first person may make herself up under the gaze of the second. The second person sees the result of the test on their screen and can thus correct the mixture that this second person will control remotely until the ideal makeup is obtained.

If appropriate, the video acquisition can be calibrated using a test pattern or with the mixture dispensed by the dispenser onto a reference surface. That then allows a more faithful display of the makeup applied at the first site.

Preferably, the video link between the two sites is a two-way link.

The first site may receive a tutorial from the second site, if appropriate.

Identifiers of the base products may be communicated to the second site; this may make it possible to precisely determine the moisturizing/matting of each of the base products.

The method may involve memorizing the dispenser setting parameters once a given mixture is considered to be satisfactory. Preferably, this memory storage may be commanded from the second site. The memory storage may be in the computer system present at the first site and/or on an external server.

One alternative may be to have one person working to help several apply makeup. This embodiment makes it possible to develop makeup artists and their work, either within an institute or over the Internet. It also allows people with limited capabilities, such as people with poor eyesight, or people who have difficulty discerning moisturizing/matting, or the elderly, or those lacking in self-confidence to apply makeup.

Operation Via Touch-Sensitive Interface

There is a need to make it easier to control the dispensing system and notably the choice of the moisturizing/matting of the mixture dispensed.

A further subject of the invention is a dispensing system having a dispenser and a computer system for operating the dispenser, this computer system having a touch screen on which the moisturizing/matting of the mixture can be displayed, and a selection means movable on the screen, in order to vary the moisturizing/matting of the dispensed mixture.

Preferably, the screen displays moisturizing/matting end points between which the moisturizing/matting of the mixture can be selected by moving the selection means between these moisturizing/matting end points.

The screen may display a scale of moisturizing/matting between at least two levels, or an area, notably of triangular outline, within which the selection means can be moved. This area may locally show the moisturizing/matting of the mixture depending for example on the distance from each of the vertices, each one embodying a pure base product.

The computer system may perform some of the calculations necessary to determine the fractions of each of the base products that lead to a mixture of the desired moisturizing/matting.

The computer system may be a smartphone, a camera phone, a tablet, or a personal computer. As an alternative, it is incorporated into the housing of the dispenser.

The computer system may have a camera. The latter can be used notably for capturing an image of the user and/or of the mixture.

The computer system may be designed to display an image of a face, in order to make it easier to identify the areas to which the mixture is to be applied.

Coupling of the Dispensing System to a Spray Means

The dispensing system may have or be connected to a means of spraying the mixture, preferably an airbrush.

A subject of the invention is also an assembly comprising:
- a spray means, preferably an airbrush having a pickup chamber subjected to a stream of entrainment air, a dispenser having at least two compartments containing different base products, the products being delivered to the spray means preferably via distinct distribution orifices.

The dispenser may have three cartridges containing makeup products of different moisturizing/matting.

The airbrush may have a stylus defining the pickup chamber, the stylus being fixed to the dispenser or to an outlet interface fixed to the dispenser, or forming an integral part of this outlet interface.

The dispensing system may have a circuit controlling operation of the dispenser, allowing the proportion of base products delivered to the pickup chamber to be varied while the airbrush is in operation. The proportions may be modified depending on the movement of the airbrush relative to the surface onto which the mixture is sprayed. This movement may be mechanized, if appropriate.

This control circuit may have or be constituted by a computer system as defined above.

The housing of the dispenser may act as a hand grip when the assembly is being handled for delivering the mixture.

The dispenser may have a camera and/or one or more sensors such as accelerometers so as to automatically locate the area to which the mixture is applied, and so as to be able to automatically regulate the moisturizing/matting depending on the position, if appropriate.

A further subject of the invention is a method for applying makeup using an assembly as defined above, in which a mixture is sprayed onto the skin using the spray means, notably the airbrush.

The composition of the mixture can be modified as the airbrush is moved relative to the skin. A graduated effect can be achieved.

This aspect of the invention is based on the observation that the dispenser can be used to supply the spray system, notably the airbrush, while at the same time allowing the dispensing system to be responsive enough to allow a change in the moisturizing/matting of the mixture dispensed while the face is being made up, notably as the area to be made up changes.

It may be advantageous for the dispensing of products to be performed iteratively, notably with dispensing times that are not phase-shifted between the various products.

This may make it easier to vary the composition of the mixture dispensed over time.

The mixture may be created directly in the airbrush, with practically no troublesome dead volume, thus allowing the mixture sprayed to be changed in real time.

The depression created in the pickup chamber is strong enough to entrain the base products without in any way impeding the metering.

The depression which prevails in the pickup chamber is for example between 10 mbar and 200 mbar, better still between 50 and 150 mbar, even better still between 75 and 125 mbar.

The viscosity of the base products as measured at 1 atm and 25° C. with a CONTRAVES TV rotary viscometer fitted with an MS-r3 or MS-r4 measuring bar at a frequency of 60 Hz after 10 minutes of rotation of the measuring bar is, for example, between 0.05 Pa·s and 50 Pa·s.

The cross section of the passages along which the base products arrive in the chamber is, for example, between 1 and 3 mm$^2$, better still between 2 and 3 mm$^2$.

The product is preferably supplied continuously.

It is also possible to apply immiscible or reactive base products, such as an aqueous gel and an oily gel, simultaneously, and these will be deposited directly onto the skin in a pixelated manner, producing a kind of gel/gel in situ, reactive silicones, or colorants that react with one another. The ratios of base products can be adjusted depending on the particular result desired. For example, in the case of aqueous gels and oily gels, the ratio corresponding to the volume of the first base product to the volume of the second base product could be varied between 10/1 and 1/10, better still between 5/1 and 1/5.

Location or Auto-Location System

The dispensing system according to the invention may have a location or auto-location system.

A location system is the name given to a means via which the person inputs the area that she is to treat. This can be performed notably using systems that leave at least one hand free. Thus, an interface of a computer system such as a touch screen, a joystick, or voice recognition system can be used.

An auto-location system is the name given to a means for inputting the area that is to be treated without intervention on the part of the person. This can be achieved using one or more accelerometers which deduce, from the movements, the directions targeted by the person or by a camera and an image recognition system.

Examples of dispensing systems suitable for implementing the invention according to its eighth aspect are shown in the above-described figures, which therefore will not all be described in detail again.

FIG. 29C illustrates a support having spaces disposed thereon substantially in the manner of the different areas of a face; each space may contain a mixture, the moisturizing/matting of which is suited to the corresponding part of the face. Thus it is easy for the user to know where to apply the mixture picked up from a given space.

The dispenser 11 can be used to deliver a mixture, the formulation of which changes over time, and to collect the mixture in a container that is movable with respect to the dispenser, such that the mixture is deposited in a location of the container that varies over time, in order to achieve a graduated effect.

For example, as illustrated in FIGS. 29A and 29B, the dispensing system has an outlet interface 110 having a part that is fixed relative to the dispenser and a moving part 252 that has a space 253 for receiving the mixture.

For example, the dispenser 11 is arranged in this case with the outlet orifices of the cartridges downward and is equipped with a blender such that the mixture falls into the space 253 under its own weight. A motor may move the moving part of the outlet interface relative to the dispenser, in a manner that is synchronized with the variation in characteristics of the mixture, such that a graduated effect is obtained all along the space 253, as illustrated in FIG. 29B.

The dispensing system may have a stand 254 which keeps the dispenser head down.

The outlet interface 110, notably when it comprises a cup, may have a static blender which mixes the base products.

FIGS. 17 to 21 show an outlet interface 110 having such a static blender.

This outlet interface 110 may have an exterior body 260 which is fixed to the housing of the dispenser 11 and has an exterior tubular upright 270.

The body 260 has passages 261 for admitting the various base products. These passages 261 open into a central chamber 262 delimited by an interior tubular upright 263.

This upright 263 has an opening 264 passing through it, which opens into an annular space 265 between the interior upright 263 and the exterior upright 270.

FIGS. 31 to 37 show various examples of touch-sensitive interfaces that may allow the user to select the moisturizing/matting of the mixture resulting from the metered dispensing of the various base products.

This interface may have, as illustrated in FIG. 31, a moisturizing/matting selection area, for example in the form of a triangle, the vertices of which correspond to the moisturizing/matting of each of the base products contained in the cartridges.

The user can move a cursor 300, for example in the form of a ball, relative to the vertices A, B and C of the triangle.

The closer he brings the cursor 300 to one of the vertices, the larger the fraction of the corresponding base product relative to the total quantity of the various products dispensed.

The fraction of each product relative to the total quantity may be indicated at 301 by a numerical value on the interface.

The interface may allow the user to increment or decrease the quantity of each of the products, for example by operating control buttons 302, which allow precise adjustment of the quantity of each of the base products.

The surface of the triangle 310 may have a moisturizing/matting that varies locally so as to be indicative at each point of the moisturizing/matting of the mixture that results from the weighting of the various base products in the proportions corresponding to the relative coordinates at this point.

The interface may have a button 305 providing access to a specific menu for adjusting the volume of product dispensed for purging the dispenser.

The interface may also advantageously allow the flow rate of product to be adjusted using buttons 304 and 306 returning to a specific menu for adjusting the flow rate.

In the example in question, the interface affords the choice between a continuous dispensing mode, using the button 304, in which the products are dispensed for as long as the user is pressing the control button 12.

The corresponding dose can be transmitted to the interface and displayed.

The button 306 allows selection of a dose mode of operation, during which even a brief press of the button 12 triggers the dispensing of a predefined dose.

In order to vary the flow rate, the dispenser acts, for example, on the operating duty cycle of the motors.

The interface may be designed to allow the user to program or memorize the settings he or she prefers, using a menu 307 providing access to favorites.

The touch-sensitive interface illustrated in FIG. 32 shows on the screen three colored areas 400, each one corresponding to the moisturizing/matting of one of the base products contained in the dispenser 10, and a central area 410 which shows the moisturizing/matting of the resulting mixture.

The relative quantity of each of the base products can be adjusted using cursors 415 which move for example along lines joining each of the areas 400 to the central area 410.

During use of the interface, the latter may memorize a given setting and cause a button 420 of the moisturizing/matting of the mixture to appear on the screen. The user can then, simply by pressing this button 420, dispense a mixture of the corresponding moisturizing/matting.

In the example in FIG. 34, the interface displays, in an area 500, a given shade and offers the user, by virtue of control buttons 510 that are each for the moisturizing/matting of the corresponding base product, the opportunity to increase or decrease the proportion of this base product in the final mixture. The moisturizing/matting of the area 500 is recalculated depending on the actions on the control buttons 510.

In the variant in FIG. 35, the interface shows a color chart having several areas 530, each one corresponding to a particular proportion of the various base products.

The user may select one of these areas, for example by pressing it with his or her finger.

The interface may be designed to display the selected moisturizing/matting to a larger scale in an area 535. The programming of the dispenser 11 to dispense this moisturizing/matting is triggered for example by pressing the area.

In the example in FIG. 36, the user may move a cursor 555 over a continuous moisturizing/matting chart 550, causing the selected moisturizing/matting to be displayed in an area 558.

The user can then, for example by pressing the area 556, trigger the sending to the dispenser 11 of the necessary instructions for the dispenser to dispense a product in the selected moisturizing/matting.

It is apparent from FIG. 37 that the interface can memorize the various shades selected and then display them on the screen so as to allow the user, by pressing corresponding buttons 560, very easily to again select a shade that has already been chosen.

FIG. 38 shows an example of a user interface 1000 of a dispensing system comprising a dispenser, preferably as described above, and a computer system 100 to which the interface belongs.

The computer system comprises here, for example, a device such as a laptop computer, a tablet or a smartphone, that operates autonomously or is connected to a remote server.

In the example in question, the interface 1000 is defined by the touch screen of such a device. In a variant that has not been illustrated, the dispenser incorporates a touch screen or any other type of man-machine interface, and can be used without connection to another device.

The device runs an application, for example which has been downloaded beforehand and which displays on the screen a face 1035 and a series of buttons allowing the user to input information.

The face may comprise several areas Z1 to Z6 that can be selected by touch, for example the forehead, the nose, the cheeks, the eyelids, the chin, and the lips.

The buttons present on the screen may make it possible for example to input the name of the makeup or of the user, to display the selected area, to choose the moisturizing/matting, and to inform the computer system as to whether or not the result of the test carried out is acceptable, or even, as illustrated, to provide information regarding the assessment of the result relative to a test carried out previously, namely, for example, better or "not as good". The screen may also display a button allowing the choice of a moisturizing/matting and an area to be memorized after a test has been carried out with this moisturizing/matting on the area in question.

The choice of moisturizing/matting is made for example with a moisturizing/matting scale similar to the one described with reference to FIG. 36.

The computer system is designed to memorize the data in the form of a look-up table for example, so as to associate an area of the face with the parameters that allow the mixture dispensed during the test to be reproduced. These parameters include, for example, the relative contents of each of the base products of the dispenser in the mixture, the quantity Q dispensed, and additional data such as, for example, the name of the area, the date the mixture was dispensed and/or any other mixture identifier, identifiers of the base products, the period of the year, notably the season, the age of the user, his or her sex, his or her given or family name, the name of an event associated with the makeup, for example a birthday, amongst other data, and the quantity of product suitable for the area. The ancillary data may allow the user to reproduce more easily a makeup look considered suitable for a time of year or recalling a life event, or to give a rejuvenating effect.

These data may be memorized in the computer system 100, for example in the abovementioned device and/or on a remote server with which the device is in communication, or alternatively in an electronic memory incorporated into the dispenser 11.

Thus, according to the invention, the user may make the dispenser deliver a first colored substance, and apply it to a first area of the face, then judge whether or not it is suitable. If the result is satisfactory, the user may record it, indexing it to the area; if the result is unsatisfactory, the user may command new moisturizing/matting in order to repeat the above operations.

The computer system can be used in this context in various ways.

For example, as illustrated in FIG. 40, in a step 1010, the user has selected moisturizing/matting to test, using for example the moisturizing/matting scale 1011 displayed on the screen, by moving the adjusting button 1012.

Next, the choice of moisturizing/matting is transmitted to the dispenser 11, in step 1015.

For example, the device transmits the quantities of each of the base products to be dispensed and the electronic circuit 81 takes charge of operating the motors accordingly.

In step 1016, the user presses the control button 12 of the dispenser 11, this causing, for example, a dose of the mixture, with the moisturizing/matting selected by the user, to be dispensed.

The mixture is, for example, dispensed into the cup 115 then picked up and applied by the user to the cheeks or any other area instructed on the interface, in step 1020.

In variants, the product is applied using an airbrush or by any other means as described above.

The user then, in step 1022, informs the computer system of the result using the buttons 1021.

If the user indicates that the result is satisfactory, the system suggests for example that he/she validate the parameters of the test using a button so as to memorize these parameters in step 1031.

If the user does not consider the result to be satisfactory and makes this known using the button 1032, the result can nevertheless be automatically saved in step 1034.

Thus, each area can be indexed not only with the suitable moisturizing/matting, but also with the moisturizing/matting that is not at all suited to this area.

The user can then perform a further test on the same area by returning to step 1010.

If the user is satisfied with the result, he or she may also wish to carry out a further test, for example on a different area of the face.

If appropriate, if the user is not satisfied, the interface may suggest that the user indicate whether the result is considered better than or not as good as the previous test, using corresponding buttons 1040 and 1041.

In that case, the computer system may be designed to determine whether, in light of the information input by the user, a proposal can be automatically made as to what moisturizing/matting to test next.

If appropriate, a questionnaire may be displayed to assist the computer system in proposing moisturizing/matting in light of the tests carried out and the way in which the user or a professional assisting the user has assessed these tests.

For example, if the moisturizing/matting is considered "unsuitable", the system may receive from the user additional information, for example "too greasy" or "too dry", which will assist the system in proposing new moisturizing/matting better suited to the user's expectations.

It may be advantageous for the computer system to be able to receive information comparing the result against the previous tests, for example "it's better" or "it's not as good" and, from there, for the system to be capable of deducing what new moisturizing/matting to propose.

Another option is for the computer system to be able to receive comparison information regarding a comparison against a target, for example "it's almost ideal" and, from there, for the system to be capable of automatically adjusting its moisturizing/matting modifications.

In this particular instance, if it receives the information that the desired result has almost been achieved, the system can adopt small levels of moisturizing/matting change and revise the moisturizing scale of adjustment accordingly.

If the dispensing system itself proposes the colored mixtures to be tested, these may be based on preprogrammed test scenarios and the system may alter how the scenario is followed through according to the successes or failures of the assessment. Thus, for example if, from the third application of product, it receives information that the moisturizing/matting is almost ideal for the user, the dispensing system may exit the program and thereafter allow itself to be guided by instructions from the operator.

In general, the user may be assisted by an expert system in the choice of moisturizing/matting to test.

This expert system is, for example, a program run on the device with which the dispenser communicates or on the dispenser itself, and which is based on the answers to a questionnaire and/or on measurements, for example of the moisturizing/matting of the skin, taken by a specific sensor or by a camera. The user can thus get assistance from an instrumented evaluation, for example a sensor of the state of dryness of the skin or greasiness of the skin. The expert system can even be implemented on a remote server with which the device or the dispenser exchanges information. The operator may even send an image of his or her face to a specialist, who can preprogram the starting moisturizing/matting choice. In another exemplary embodiment, the user presents the computer system with a photo of his or her face, and the computer system is designed to analyze this and create a program defining the areas to be tested and the first products to be delivered, both in terms of moisturizing/matting and in terms of quantity. For example, the computer system may be designed to automatically select the moisturizing/matting of makeup to propose to the user by capturing a photograph in step 1070, as illustrated in FIG. 42. For example, the device which communicates with the dispenser 11 is equipped with a camera, and the user takes a photograph of his or her face. The image is then analyzed in step 1071, and moisturizing/matting is proposed for each area of the face in step 1072, for example in accordance with predefined moisturizing/matting combination rules.

The dispensing system may be oriented by the user to decide on the moisturizing/matting and also on the quantity of product to be delivered. For example, the user may indicate "nose" or "blemish" and the dispensing system is designed to adapt the dose dispensed according to a memorized map of doses to be dispensed depending on the areas to be treated.

The computer system may guide the user in the choice of colors in the mixture to be tested, so as to limit the number of tests needed until the user obtains a result that pleases him or her.

It is thus possible, as illustrated in FIG. 41, that after a mixture dispensed by the dispenser has been applied to a given area of the face in step 1060, the computer system will ask the user whether or not the result is satisfactory and will, of its own accord, if the result is considered to be unsatisfactory, make a change 1061 to the dispenser parameters in order to modify the mixture dispensed.

The user then only has to perform a new test with the modified mixture.

When a mixture is indicated as being satisfactory, the computer system can memorize the corresponding parameters so as to allow the mixture to be recreated at a later date.

The system can then begin the above steps afresh for a new application area.

During the successive tests, the operator does not need to treat the entire face. He or she may for example choose between 3 and 8, for example 5, small areas. The dispensing system is then advantageously designed to interpolate and/or extrapolate the data regarding the moisturizing/matting considered to be suitable, so as to calculate the moisturizing/matting that ought to be considered suitable for areas for which the exercise has not been conducted.

At the end of the learning stage, the system may generate a display of the suitable moisturizing/matting on the various areas, tested or calculated.

The dispensing system may be designed to indicate whether certain moisturizing/matting levels appear to be incorrect, doing so on the strength of a comparison against standard maps it has in memory. Thus, it may propose that the user repeat all or some of the mapping exercise.

Once the computer system has completed its learning, i.e. once the moisturizing/matting levels of mixtures have been identified as being agreeable to the user for making-up certain areas, the user wishing to apply makeup only has to call up the area that is to be made up, in step 1080 of FIG. 43, and the system will be able to automatically propose a suitable moisturizing/matting of mixture to the user in step 1081.

In the variant illustrated in FIG. 44, the user selects moisturizing/matting in step 1090 and the computer system proposes, in step 1091, an area in which to apply a mixture of this moisturizing/matting, on the basis of information previously collected on the basis of the tests performed.

The area proposed is, for example, the area in which identical or very similar moisturizing/matting has already been applied and the result considered acceptable by the user.

FIG. 46 illustrates an example of an implementation of the invention in which, having carried out tests on various zones in step 2010, the user informs the system of the mixture(s) he or she considers to afford the best result, this allowing the system to know the corresponding parameters in step 2012. Next, in step 2014, the system may propose to the user references of commercial products that have the same properties or very similar properties.

In one variant, the system sends the parameters to a remote manufacturing center so that a composition that has the same formulation or the same properties as that of the mixture that the user has tested and found to be satisfactory can be produced.

FIG. 45 illustrates the possibility of using the dispenser to dispense several doses 2020a to 2020d of different mixtures, next to one another on a support 2021, so as to allow these to be applied to adjacent distinct regions of the same area.

The user can, in a single hit, apply a series of moisturizing/matting levels in order rapidly to home in on the appropriate moisturizing/matting level. The colored substances present on the support 2021 may have been chosen by the operator him- or herself or proposed by the dispensing system.

The support 2021 is, for example, movable with respect to the housing of the dispenser and is moved sequentially to deposit the corresponding mixtures in the various areas 2020a to 2020d, being for example similar to the supports described with reference to FIG. 29 or 29A. The user can thus easily compare the results between the various regions and inform the system of which mixture produces the best effect.

FIG. 47 illustrates a system that assists the user in applying makeup, notably in choosing the correct colorings.

This system makes it possible to establish a video link, for example over the Internet, between a camera 2060 at a first site 2061 and a second site 2062.

The camera 2060 is, for example, built into a tablet or a smartphone that constitutes the computer system 100.

The second site 2062 is allowed to operate the dispenser 11 present at the first site 2061 either directly or indirectly.

Thus, the person present at the first site can apply the mixture dispensed and send to the second site 2062 a corresponding image, and in return receive information relating to the makeup result.

The second site 2062 may have a display screen 2064 that allows an adviser sitting at this screen to see the result of the makeup with the mixture dispensed by the dispenser and advise the person who has applied the makeup. This adviser may in return influence the dispenser 11 to alter the moisturizing/matting of the mixture and adapt it to best suit the face of the person present at the first site. The protocol for the exchange of data between the two sites thus allows command instructions to be sent to the dispenser 11, either directly or via the computer system 100 present at the first site. Thus, the person present at the second site controls the mixture delivered by the dispenser 11. The first person may make herself up under the gaze of the second. The second person sees the result of the test on their screen and can thus correct the mixture that this second person will control remotely until the ideal makeup is obtained.

Preferably, the video link between the two sites is a two-way link, such that the user present at the first site can see an image of the adviser on the screen of the computer system. This adviser can send the user present at the first site a tutorial if need be.

The memorizing of the setting parameters of the dispenser 11, once a given mixture has been considered satisfactory, may be commanded from the second site.

The dispensing system may be designed to receive the map of somebody else, real or virtual. It may also combine the map of the person with the map of another, in order to sublimate the makeup without losing the inherent characteristics.

The interface may be used to define makeup programs in which the order of the areas to make up or the order of the moisturizing/matting states to propose is defined.

Examples (Eighth Aspect of the Invention)

A dispenser 11 like that illustrated in FIG. 3 is created. The dispenser is designed to communicate with a tablet 100 such as an iPad. This computer system runs an application known as "µMix" developed in the specific Apple environment (XCode 4 and iOS simulator) in the Objective C language.

It uses Foundation, UIKit and CoreGraphics basic frameworks which supply the tools for manipulating the data structures, computation tools and functionalities associated with the user graphics interface.

The application also uses the CoreBluetooth framework providing access to the Bluetooth 4 Low Energy peripherals, with the following main tasks:
- looking for Bluetooth 4.0 Low Energy peripherals,
- connection/disconnection and management of connection parameters,
- communication in read and/or write mode based on the GATT (Generic Attribute Profile) architecture.

The application proposes the following functionalities:
- definition of the fractions of base products,
- choice of mode of operation when pressing the control button 12, namely continuous, purge or dose,
- display of a triangle of volumetric fraction as illustrated in FIG. 30 with management of the volumetric fraction by tactile touch on the triangle or using the +/−buttons associated with each product,
- Bluetooth connection/disconnection and real-time transfer of instructions to the dispenser,
- settings of flow rates in continuous mode, and of quantities in dose mode,
- calculation, display and transfer to the dispenser of the volumetric fractions of products in real time, depending on the instruction, with the sum of the fractions always equal to 100%,
- collection and display of the torques of the three motors in real time, and
- saving of the key parameters in a configuration file.

The continuous mode is a dispensing mode in which the mixture of the three base products is dispensed for as long as the user presses the dispensing button 12. The product is dispensed at a flow rate, an estimate of which is displayed above the "Continuous" button 304. The choice of flow rate is made in a "Settings" menu.

The "dose" mode is a mode of dispensing the mixture in doses, in which the dose is delivered after the user presses the dispensing button 12. One press is enough and the user can then release the button. The overall dose of product dispensed is that indicated above the "Dose" button 306, for example 0.1 ml. This volume can be altered in the "Settings" menu.

The "purge" mode is a dispensing mode in which a dose of mixture with equal volumetric fractions (33%) is delivered as soon as the user has pressed the dispensing button 12, as in the "dose" mode. One press is enough and the user can then release the button. When the dose has been dispensed in full, the button may be released. If the button is released before the end, dispensing stops, even if the specified volume has not been achieved. The overall dose of product dispensed is that indicated above a "Purge" button 305, for example 3 ml. This volume can be altered in the Settings menu.

The user determines the desired moisturizing/matting with the application which is run on the tablet and which calculates the fractions of the various products. The tablet communicates this value to the dispenser by a Bluetooth connection.

The electronics built into the dispenser 11 collects the information and automatically adjusts the flow rates of the three cartridges so as to obtain a mixture of the desired moisturizing/matting.

When the user wishes to use the product, he or she presses the button 12 of the dispenser in order to cause the product to be expelled. He or she presses for as long as he or she wants product, in "continuous" mode. In "dose" mode, the user presses the button 12 once and the predefined dose is delivered.

Dispensing may be performed continuously, namely with the motors operating continuously, the entire volume being dispensed in one hit, or iteratively, the motors then operating in a pulsed fashion; in that case, the time interval between two pulses makes it possible to vary the flow rate. Small volumes are delivered one after another in several stages.

The pulses may be separated for example by intervals of 50 ms, 100 ms or 200 ms. The duration of a pulse during which the motor is turning will be from 50 to 150 ms, for example.

The main page of the "µMix" application comprises in this example the following elements, as can be seen notably in FIG. 31:
- status bar at the top of the screen: indicates the status of the Bluetooth connection or µMix if there is no Bluetooth connection;
- thumbnails at the bottom of the screen: for selecting the active page: main page, Settings, Bluetooth, Products and Favorites;
- Continuous button 304 for selecting the mode in which products are dispensed continuously;
- Purge button 305 for selecting the Purge mode;
- Dose button 306 for selecting the mode in which dispensing is in doses with the volume of the dose associated with the Dose button;
- a blue ball 300 that the user can move around inside the volumetric triangle either by dragging it or using a double tap;
- "−" buttons 302 for each product A, B and C: reduces the fraction of product selected when moving along the straight line connecting the point to the vertex of the product selected;
- "+" buttons 302 for each product A, B and C: increases the fraction of product selected when moving along the straight line connecting the point to the vertex of the product selected;
- volumetric fraction of each product as a percentage: modifiable by the user and updated in real time according to the instruction from the + and − buttons 302 and the position of the ball 300.

While the volumetric fractions are being modified by moving the ball or using the + and − buttons, the values of the volumetric fractions of the products A, B and C are updated automatically. When the volumetric fractions are modified using the + and − buttons, the ball 300 is moved automatically into the corresponding position in the triangle.

When the application run on the tablet is started up, it automatically connects to the dispenser 11 if it is detected. When the dispenser is switched off or the Bluetooth connection is broken, the tablet disconnects. When the user moves the cursors that adjust the proportions of the products A and B, the values are transmitted in real time to the dispenser 11.

The Settings page of the application contains the following elements:

status bar at the top of the screen: indicates the status of the Bluetooth connection or μMix if there is no Bluetooth connection;

thumbnails at the bottom of the screen: for selecting the active page:

main page, Settings, Bluetooth, or Info;

"Volumes" part with a text field to be filled in by the user to define the volume of the dose, in ml (2 ml for example), and a field for the purge volume, in ml (3 ml for example). The minimum doses in this example are 0.023 ml and the maximum doses are 9.90 ml (3×3.3 ml);

"Flow rate" part with selection of the flow rate: fast (»0.03 ml/s), medium (»0.02 ml/s) or slow (»0.01 ml/s);

"Dose" part with iterative choice of the mixture, for dispensing a mixture of products with small volumes delivered one after another in several stages;

In the contrary case, the total volume of each product is dispensed in one hit;

"Triangle image" part for selecting the image of the triangle that will be displayed on the main page in order to be able to display a triangle with the moisturizing/matting levels delivered by the dispenser 11. By using a "Choose image" button on the "Settings" page, an album can be accessed.

The "Products" page of the application has, in the example in question, the following elements:

a choice of the value of each product in code step units from 0 to 1414.

Each unit corresponds to a delivered product volume of 2.33 μl, which is the smallest quantity that the dispenser in this example can deliver; when this page is displayed, it is the values of products on this page that are transmitted in real time to the dispenser. As soon as the page is no longer displayed, the values sent to the dispenser are those of the main page with the triangle;

display of the motor torques for A, B and C in real time refreshed every 45 values.

The mode in which the products are delivered is the iterative or direct dose mode, according to the option chosen on the Settings page.

The "Favorites" page allows configurations to be saved in a file. It provides access in the example in question to 10 files, namely "Configuration 1" to "Configuration 10" in addition to the default file. These files record for example the following parameters:

fractions of products A, B and C,
Purge volume,
Dose volume,
fast, medium or slow flow rate,
Dose, Purge or Continuous mode,
continuous or iterative dispensing.

Several base products are created (the proportions are by mass)

The formulations F1 and F2 are rich in fillers (and are different colors). The formulation F3 is rich in moisturizing agent.

| | F1 mass % | F2 mass % | F3 mass % |
|---|---|---|---|
| Dimethicone copolyol sold under the reference KF 6017 by the company Shin-Etsu | 2 | 2 | 2 |
| Etsu Bis PEG/PPG-14/14 dimethicone + Cyclopentasiloxane sold under the reference Abil EM 97 by the company Goldschmidt | 1 | 1 | 1 |
| Cyclopentasiloxane | 17.65 | 17.65 | 17.65 |
| Phenyl trimethicone sold under the reference DC556 by the company Dow Corning | 2 | 2 | 2 |
| Ethyl hexyl methoxycinnamate | 3 | 3 | 3 |
| Squalane | 1 | 1 | 1 |
| Dispersion of bismuth oxychloride in 2-ethylhexyl hydroxy stearate (70:30) (Timiron Liquid Silver ® from Merck) | 0 | 0 | 0 |
| Cyclopentasiloxane | 7 | 7 | 7 |
| Yellow iron oxide coated with aluminum stearoyl glutamate NAI-C33-9001-10 from the company Miyoshi Kasei | 1.65 | 1.25 | 1.45 |
| Red iron oxide coated with aluminum stearoyl glutamate NAI-C33-8001-10 from the company Miyoshi Kasei | 0.3 | 0.5 | 0.4 |
| Black iron oxide coated with aluminum stearoyl glutamate NAI-C33-7001-10 from the company Miyoshi Kasei | 0.15 | 0.15 | 0.15 |
| Titanium dioxide (anatase) coated with aluminum stearoyl glutamate NAI-TAO-77891 from the company Miyoshi Kasei | 9.9 | 10.1 | 10 |
| Talc sold under the reference Micro Ace P3 by the company Nippon Talc | 0.5 | 0.5 | 0.25 |
| Nylon 12 powder sold under the reference SP 500 by the company Toray Industries | 0.5 | 0.5 | 0.25 |
| Demineralized water | 36.15 | 36.15 | 34.65 |
| Glycerol | 0 | 0 | 5 |
| 1,3-Butylene glycol | 3 | 3 | 3 |
| Magnesium sulfate | 0.7 | 0.7 | 0.7 |
| Hydrogenated maltose solution | 0.5 | 0.5 | 0.5 |
| Denatured 96 ® ethyl alcohol | 13 | 13 | 10 |
| TOTAL | 100 | 100 | 100 |

Procedure

The constituents of phase A are weighed out in the main beaker and are stirred with a Moritz blender (1000 rpm) while maintaining at room temperature. Phase B is prepared separately by milling three times in a three-roll mill the mixture of pigments and of cyclopentasiloxane. This phase B is then added, with continued stirring, along with the fillers (phase C).

The aqueous phase D is also prepared separately, by weighing out in a beaker the glycerol, the butylene glycol, the magnesium sulfate, the hydrogenated maltose solution, and water at room temperature. The aqueous phase D is stirred using a magnetic bar until homogenized. C D E The emulsion is made at room temperature: the aqueous phase D is poured into the fatty phase while gradually increasing the stirring speed (Moritz blender) up to 4000 rpm. Stirring is continued for 7 minutes. Finally, phase E (ethyl alcohol) is added for the last 3 minutes of 5 the emulsification.

Test 1

The system was tested with:

F1 in compartment A

F2 in compartment B

F3 in compartment C

The system was used to create several mixtures:
M1: A 30%, B 0%, C 70%
M2: A 70%, B 0%, C 30%
M3: A 50%, B 0%, C 50%

M1, M2, M3 were applied to different areas of the face: M1 to dry areas such as the cheeks, M2 to greasy areas such as the forehead, and M3 to intermediate areas such as the chin.

Test 2

The system was used to create several mixtures:
M1: A 80%, B 10%, C 10%
M2: A 35%, B 35%, C 30%
M3: A 20%, B 20%, C 60%

M1 and M2 are intended for greasy areas. M1, fairly yellow, is applied to the bags. M1, more pink, is applied to the sides of the nose.

M3 is applied to very dry areas such as the area above the mouth.

I) System for Creating Tailor-Made Mixtures Based on Alcoholic Formulation

According to this ninth aspect, the invention relates more particularly to methods and systems for dispensing products with a high concentration of alcohol.

It relates more particularly to the production of perfumes (concentrated, eaux de parfums, eaux de toilettes, etc.), fragrancing products and deodorants.

These products are used for perfuming oneself to enjoy the odor or to conceal disagreeable (body) odors.

Users wish to have numerous perfumes, with different notes and strengths. For that, professionals create and market mixtures of different ingredients, in the process creating notes which are pleasant to a large number of people. However, the evolution of society has led to people wanting to have their own specific perfume, with notes and strengths that are tailor-made. Users may make tailor-made mixtures, but this does not meet the need for regular change well. Moreover, there is a desire to be able to propose an entire choice of types of fragrance. However, it is apparent that when a mixture is tailor-made, using alcoholic compositions, there is a risk of the mixture not corresponding to the programmed odor if the different ingredients or preparations of ingredients are not properly metered. An error in the proportions can cause a notable, or even unacceptable, difference in smell.

An error is even less acceptable given that the person has had to pay a fairly large amount for the preparation of his tailor-made perfume (or spend time if he has wanted to make it himself) and is thus disappointed that the odor does not correspond to the intended odor. For example, if he has an old preparation, he will very quickly realize the difference on making a comparison. As is known, this problem does not arise each time a mixture is created, but there is always the risk of ending up with dissatisfied customers. Large-volume productions could limit these risks, but they are neither economical nor sensible given that the quantities used are often limited (for example 200 mg per day), since users like to change recipe upon each use or frequently.

This problem is all the greater given that the ingredients or ingredient bases used often differ from one another (in terms of odor).

It may be possible to limit oneself to mixing ingredients or ingredient bases that are similar (in terms of smell), but this greatly reduces the range of perfumes possible.

Thus, none of the existing solutions is satisfactory, to this day limiting the development of tailor-made perfumes.

The invention seeks, according to its ninth aspect, to respond to this problem, and one subject thereof is a system for dispensing a perfumed product, comprising a dispenser that receives at least two cartridges containing first and second base products, respectively, the first base product comprising a composition containing at least one alcohol and at least one cellulose derivative acting as a thickener, the dispenser making it possible to deliver at least these two base products in adjustable proportions.

The invention according to this ninth aspect may have one or more of the following features:
  each base product comprises a composition containing at least one alcohol and at least one cellulose derivative,
  the first base product or each base product has a mass concentration of alcohol relative to the other, non-alcoholic compound(s) of the first product of at least 80/20, better still 85/15 and even better still 90/10,
  the first base product or each base product contains at least 50% by mass of ethanol in its solvent phase, better still at least 80% by mass of ethanol in its solvent phase, even better still at least 85% by mass of ethanol in its solvent phase,
  the first base product or each base product contains at least one odorous compound, preferably chosen from esters, carbonates, acids, anhydrides, aldehydes, alcohols, aliphatic compounds without functions other than alkanes and alkenes, and mixtures thereof,
  the odorous compound(s) is/are chosen from hexanal, octanal, nonanal, decanal, undecanal, dodecanal, tridecanal, 2-methyldecanal, 2-methylundecanal, trans-2-hexenal, cis-4-heptanal, 2,6-dimethyl-5-hepten-1-al, E-4-decenal, 10-undecenal, 2-dodecenal, 1,1-dimethoxy-2,2,5-trimethyl-4-hexene, 2-methyl-2-pentenoic acid, (S)-(+)-2-methylbutanoic acid, ethyl formate, cis-3-hexenyl formate, ethyl acetate, butyl acetate, isoamyl acetate, hexyl acetate, 3,5,5-trimethylhexyl acetate, trans-2-hexenyl acetate, cis-3-hexenyl acetate, ethyl propionate, ethyl butyrate, butyl butyrate, isoamyl butyrate, hexyl butyrate, cis-3-hexenyl isobutyrate, ethyl isovalerate, ethyl-2-methyl butyrate, ethyl hexanoate, ethyl 2-methyl pentanoate, 2-propenyl hexanoate, ethyl heptanoate, 2-propenyl heptanoate, ethyl octanoate, methyl 2-nonenoate, ethyl 2-trans-4-cis-decadienoate, methyl 2-octynoate, methyl 2-nonynoate, ethyl 3-octobutanoate, allyl amyl glycolate, Z-3-hexenyl methyl carbonate, 3-octanol; 2,6-dimethyl-2-heptanol, trans-2-hexen-1 ol; 3-hexen-1-ol; 1-octen-3-ol; 9-decen-1-ol; 10-undecen-1-ol; 2-trans-6-cis-nonadien-1-ol; 4-methyl-3-decen-5-ol, myrcene, ocimene, beta-Farnesene, citral, citral diethyl acetate, citronellal, methoxydihydrocitronellal, 2,6,10-trimethyl-9-undecanal, cis-geranic acid, citronellic acid, geranyl ester (formate, acetate, propionate, isobutyrate, isovalerate), neryl acetate, linalyl esters (formate, acetate, propionate, isobutyrate), citronellyl esters (formate, acetate, propionate, isobutyrate, isovalerate, tiglate) and esters of myrcenol, geraniol, nerol, linalool, myrcenol, lavendulol, citronellol, trans,trans-farnesol, trans-nerolidol, tetrahydrogeraniol, tetrahydrolinalool, avendulol, trans,trans-farnesol, trans-nerolidol, tetrahydrogeraniol, tetrahydrolinalool, limonene, terpinene, terpinolene, phellandrene, camphene, 3-carene, menthyl ester (acetate, lactate), alpha-terpinyl esters (acetate), noryl esters (acetate), bornyl esters (acetate), isobornyl esters (acetate), cedryl esters (acetate), 2,4-dimethyl-3-cyclohexene carboxaldehyde, 4-(4-hydroxy-4-methylpentyl)-3 cyclohexene carboxaldehyde, 1-(4-isopropycyclohexyl)ethanol, 2-methyl-4-(2,2,3-trimethyl-3-cyclopenten-1-yl)butanol, 2-methyl-4-(2,2,3-trimethyl-3-cyclopenten-1-yl)butenol, 3-methyl-5-(2,2,3-trimethyl-3-cyclopenten-1-yl)-4-penten-2-ol, 3,3-dimethyl-5-(2,2,3-trimethyl-3-cyclopenten-1-yl)-4-penten-2-ol, indole, p-cymene, diphenylmethane, benzaldehyde, phenylacetaldehyde, phenylacetaldehyde dimethyl acetal, dihydrocinnamaldehyde, 2-phenylpropanal, cyclamen aldehyde, 2-methyl-3-(4-tert-butyl-phenyl)propanal, cinnamaldehyde, heliotropin, furfuraldehyde, benzyl esters (acetate, propionate, isovalerate), phenethyl esters (acetate, isobutyrate, isovalerate), alpha-trichloromethylbenzyl ester (acetate), cinnamyl acetate, benzoate ester (acetate, hexyl, benzyl), phenylacetate ethyl, phenylacetate geranyl, methyl cinnamate, benzyl cinnamate, phenyl ethyl cinnamate, eugenol acetate, phenylacetic acid, benzyl alcohol, 2-phenyl ethyl alcohol, styrallyl alcohol, 2,2-dimethyl-3-(3-methylphenyl)propanol, cinnamyl alcohol, 3-methyl-5-phenylpentanol, thymol, anethole, isoeugenol, eugenol, anise alcohol, raspberry ketone, ethylmaltol, 2,6-dimethoxyphenol, 2-propylphenol, 2-(methylthio)phenol, ortho-guaiacol, 4-methyl guaiacol, abietic anhydride, citraconic anhydride, the cellulose derivative is chosen from derivatives of cellulose obtained by reacting basified cellulose with propylene oxide or ethylene oxide, the cellulose derivative is hydroxypropylcellulose, the molecular weight size of the cellulose derivative is greater than or equal to 10 000, better still between around 850 000 and around 1 150 000, the total mass content of cellulose compound(s) varies between 0.1% and 20%, better still between 0.5% and 5%, even better still between 0.7% and 2%, the percentage being expressed relative to the mass of the base product, the system comprises a third cartridge with a third base product, the cartridges are received in a removable manner in the dispenser, each product leaves the cartridge through an outlet passage of the cartridge, the outlet passage being defined by a dispensing end piece of the cartridge, said end piece being driven in rotation relative to a body of the cartridge by a drive mechanism of the dispenser in order to dispense the base product contained in the cartridge, the dispensing system has an electronic memory for recording, in association with a dispensed product, the respective proportions of each of the base products of this product, in order to be able to automatically dispense this product again later.

A further subject of the invention, according to its ninth aspect, is a method for generating a perfumed product with aid of a system as claimed in any one of the preceding claims, wherein one or more base products contained in respective cartridges of the dispenser is/are selected, and the base products selected are dispensed in chosen quantities.

It is also possible to memorize the proportions of the different base products making up the dispensed product.

1) Thus, according to its ninth aspect, the invention is preferably based on a dispensing system comprising a programmable dispenser with several compartments.

2) Which is able to deliver very small quantities from each compartment with precision.

3) At least one composition contains alcohol (in particular ethanol), with or without odorous compounds, and an agent of the cellulose derivative type of the "hydroxypropylcellulose" type.

4) There may optionally be other compartments containing compositions which are not alcoholic.

By virtue of the invention according to this ninth aspect, the person may:

a) Design and record perfumes b) Produce a small quantity for use, without any risk of differing from the intended odor c) specifically using the full panorama of olfactory ingredients.

Even if the reservoirs are used up, or have even gone off, the person could refill the compartments with new cartridges and then create a small quantity for use.

The person could also share their perfume with others, even remotely.

This system could furthermore be used to create larger quantities, it being understood that these quantities should be considered, once created, to have a limited life (usually between 1 month and 48 months).

Dispensing System

The dispensing system may consist of a single device operating autonomously, preferably able to be manipulated in one hand, or of a device that operates in interaction with other components or devices. It may for example entail various outlet interfaces which are mounted on the dispenser depending on the type of note to be created, as will be specified below. It may also entail a computer system which exchanges information with the dispenser in order to operate the latter, this computer system comprising, for example, a portable terminal such as a smartphone, a camera phone, a tablet, a laptop computer or a dedicated terminal.

Preferably, the dispenser is designed to pressurize one or more compartments containing the base product(s), via volumetric metering devices, preferably a motor causing a piston to move in the corresponding compartment.

The dispenser may be formed of a housing and of at least two or three compartments, and preferably an identical number of motors. For example, the rotation of the motors drives endless screws which push the pistons of each compartment. The advancing movement of the pistons is, for example, controlled by the number of command pulses sent to the motors and/or by the length of time for which the latter are operating. The motors may be powered in sequence or preferably simultaneously.

For example, the motors are powered during an elementary operating cycle for a short duration one after the other or at the same time as one another, so as to dispense corresponding microdoses.

The elementary cycles are repeated, possibly with a pause between them, giving the base products time to flow out of the compartments.

The compartments may be defined by cartridges, which are removed when they become empty. As an alternative, the compartments are permanently present and refilled once they become empty.

Each cartridge may be closed by a stopper that can be removed to allow the cartridge to be cleaned.

Preferably, the housing of the dispenser is of elongate shape along a longitudinal axis, making it easier to handle, and the cartridges are disposed about this axis, inside the housing.

Preferably, the cartridges are inserted from the rear and the mixture is delivered from the front. The cartridges may be inserted individually or, as an alternative, the cartridges constitute a one-piece assembly as they are inserted.

The cartridges may each have a volumetric metering mechanism comprising a piston moved by a drive mechanism of the dispenser in a direction accompanied by a reduction in the internal volume containing the base product and the expulsion of some product. It may be advantageous for the cartridges to have at least a region of their wall that is transparent so that the color of the product contained therein can be seen.

The drive mechanism may have a motorization system formed of motors coupled to gearboxes, of elongate shape parallel to the longitudinal axis of the dispenser, and positioned between the cartridges. Positioning the motors and cartridges in this way makes the dispenser particularly compact.

The base product can leave the corresponding cartridge in a sealed manner, then flow along a passage provided for this purpose in the housing of the dispenser, before leaving the latter.

The cartridges advantageously end in an end piece produced in such a way that, once the cartridge has been inserted into the housing of the dispenser, the end of the end piece terminates flush with the housing. As an alternative, the end piece is long enough to protrude beyond the housing and thus connect various outlet interfaces that can be attached to the housing of the dispenser.

By virtue of the drive mechanism having motors for causing the pistons to advance, it is possible to precisely deliver mixtures in very small quantities. Thus, the drive mechanism can deliver the base products with a minimum flow rate less than or equal to 50 µL/s, better still less than or equal to 20 µL/s, even better still less than or equal to 10 µL/s. Preferably, the drive mechanism delivers flow rates of between 20 and 100 µL/s, better still between 40 µL/s and 60 µL/s. It is thus possible to easily create a mixture of around 10 mg. Such a dispensing system is thus ideal for creating small fragrant touches.

It is also possible to create larger quantities of mixture such as the quantities needed for fragrancing for one or more days. These quantities remain relatively low, however, at less than 1000 mg, for example a quantity of between 10 and 500 mg, better still between 40 and 250 mg.

Thus, one subject of the invention, according to one aspect thereof, is a dispensing system comprising a dispenser having a housing, and at least one cartridge received in the housing of the dispenser, this cartridge having a body and a piston capable of moving in the body, the housing comprising a motorized drive mechanism for moving the piston of the cartridge.

Preferably, the cartridge has a dispensing end piece through which the product exits, and this dispensing end piece is driven in rotation by the drive mechanism for moving the piston. The end piece may have at least one rotation-proofing relief, better still two diametrically opposed rotation-proofing studs.

The end piece may bear a seal, notably an O-ring seal. Thus, when changing the cartridge, the seal is also changed, making it possible to get around the problem of seal wear.

The dispenser may have an electronic board for controlling the motorized drive mechanism, this electronic board having the end piece(s) passing through it. This may make it possible to produce a board extending across substantially the entire cross section of the dispenser so that all the electronic components of the dispenser can be grouped together on a single board, thus improving compactness and reliability. The board may extend substantially perpendicularly to the longitudinal axis of the housing. The board may bear a switch for controlling operation of the dispenser.

The dispensing system may be designed to operate in at least two dispensing modes.

In a first mode, referred to as "continuous", the mixture is dispensed as long as pressure is applied to the control switch.

In a second mode, referred to as "dose", a predefined quantity of the mixture is dispensed for each press of the switch.

The end piece(s) may terminate at one end of the housing. This may make it possible to reduce the dead volume, as will be explained in detail below.

The end piece(s) may have at their end a shutoff system for preventing the products from drying out in the duct, for example a self-healing membrane.

The cartridge may have a hollow screw onto which the piston is screwed, the piston being able to move axially along the screw as the latter turns; the piston is prevented from turning in the body of the cartridge. For example, the friction of the piston against the body of the cartridge may be enough to prevent it from turning when the screw turns.

Preferably, rotation is rendered impossible with a cartridge body of non-circular cross section and a piston that is not deformable.

The torque of the motors may be determined electronically depending on the current drawn, and may be used for example to detect that the piston has reached the end of its travel. Information regarding the torque may be transmitted remotely to a computer system that has a man-machine interface, in order that correct operation of the dispenser can be monitored.

In order to adjust the note, the dispensing system according to the invention has to allow the user to vary the volume delivered from each compartment.

Preferably, the dispenser is operated by a computer system built into the dispenser or external thereto, the dispenser then being able to exchange information with the computer system using a wireless or wired protocol.

The dispenser may thus be operated so as to allow the note to be adjusted by controlled simultaneous or sequential dispensing of several different odorous base products.

The dispensing of the base products may be continuous; in such a case, the volumes of each of the base products are dispensed in a single shot, simultaneously or in succession.

In the case of simultaneous dispensing, it is beneficial to be able to adjust the respective flow rates of the various base products in order for the dispensed mixture to correspond to the desired mixture at all times. Such a dispensing mode may be suitable in particular when dispensing the mixture by spraying, using an airbrush. To adjust the flow rates it is possible, for example, to alter the speed at which the pistons move, for example in the case where the pistons are driven by an endless screw, by varying the rotational speed of the motors that drive the screw. The products may also be dispensed in a pulsed manner with a dispensing time and a pause in each cycle. By altering the duty cycle it is possible to alter the flow rate.

All the products may be delivered simultaneously during the dispensing time or, as an alternative, the cycles of the various products are phase-shifted from one another so that one product is dispensed while the other products are paused.

In one particular embodiment of the invention, the mixture is delivered into a cavity of a container which may close hermetically or not, for example in the form of a cup, into which an applicator, particularly a stylus or a brush may be slipped. Such a dispensing system is especially suited to formulations that are intended to be applied without direct contact with the hands. This container may be removable.

When it is not removable, the container may be produced with the body of the dispenser. When it is removable, it may constitute one output interface among others that can be mounted on the dispenser.

The compartments, and in particular the cartridges, may contain all or part of the drive mechanism and, for example, the motorizing system or, better still, part of the motorizing system, the purpose of this being to reduce the number of moving parts in the body of the dispenser outside the cartridges. For example, the cartridges contain the rotor of the motor. Once the cartridges have been installed in the body of the dispenser, the rotors are made to interact with the stators.

The dispensing system is advantageously arranged in such a way as to allow the running of preprogrammed sequences in which the mixture delivered by the system is modified continuously or discontinuously. A "graduated" mode makes it possible for example to progress gradually from a mixture A to a mixture B. In the case where the application is by spraying, notably using an airbrush, this makes it possible for odor graduations to be achieved simply. An "alternate" mode makes it possible for example to switch quickly from a mixture A to a mixture B several times in succession. In the case of application by spraying, a multilayer application can thus be achieved, with different formulations for two superposed adjacent coats. Another mode makes it possible for example to offer several preprogrammed successive mixtures, the computer system each time indicating to the user how these should be used, for example by display on a screen.

In the case of manual application, the mixtures are dispensed for example into a cup. The person applies the mixture to the recommended place with a corresponding mixture taken from the cup, then, if necessary, cleans out the cup and commands delivery of a new mixture; the operation is repeated as many times as necessary until the person has perfumed themselves fully.

The mixtures dispensed can be homogenized in various ways depending on the type of use. In the case of manual application, it can be done directly on the application area at the time of application or in the cup before the mixture is picked up; in the case of an airbrush application, the pipe of the airbrush is used as a mixing chamber; if the mixture is dispensed into a container for later use, homogenization can be performed by hand or by passing the dispensed products through a mixing chamber situated between the dispenser and the container or incorporated directly into the container, as described in detail below.

The product may be delivered by the dispensing system and used extemporaneously. As an alternative, the product delivered by the dispensing system is packaged and used later, for example on several occasions, with, for example, at least one day's interval between two uses.

Solvents of the Compositions

The alcoholic composition(s) contain(s) primary or non-primary alcohols, at a concentration relative to water or other non-alcoholic solvents of at least 80/20, preferably at least 85/15, even more preferably at least 90/10. The alcohols preferably contain at least 50% by mass of ethanol relative to the mass of the other alcohols, preferably at least 80% by mass of ethanol relative to the mass of the other alcohols, even better still at least 85% by mass of ethanol relative to the mass of the other alcohols. The other alcohols are typically glycols and/or alcohols of type C3 or more, in particular isopropanol.

The other non-alcohol solvents are typically acetone or ethers, such as glycol ethers.

Preferably, the composition contains, in its solvent phase: At least 80% by mass of ethanol, and between 0 and 10% by mass of water and between 0% and 20% by mass of another non-alcoholic organic solvent.

The alcoholic composition(s) contain(s) or do(es) not contain other compounds considered to be "nonsolvents".

Odorous compounds

Care compounds such as screening agents, biological agents

Dyes

Polymers

Odorous Compounds

An "odorous compound" is understood to include odorous molecules and those which have a (stimulating, modifying) effect on the odorous molecules. They are also understood to include steroids, which can then act on the final odor of the mixture.

Consideration is given to two types of odorous compounds.

Esters

Carbonates

Acids

Anhydrides

Aldehydes

Alcohols

Aliphatic compounds without functions other than alkanes and alkenes

More Specifically, the Compounds are Aliphatic:

Alkanes and alkenes (E,Z)-1,3,5-undecatriene

Aldehydes

Hexanal, octanal, nonanal, decanal, undecanal, dodecanal, tridecanal, 2-methyldecanal, 2-methylundecanal, trans-2-hexenal, cis-4-heptanal, 2,6-dimethyl-5-hepten-1-al, E-4-decenal, 10-undecenal, 2-dodecenal, 1,1-dimethoxy-2,2,5-trimethyl-4-hexene Acids 2-Methyl-2-pentenoic acid, (S)-(+)-2-methylbutanoic acid Esters Ethyl formate, cis-3-hexenyl formate, ethyl acetate, butyl acetate, isoamyl acetate, hexyl acetate, 3,5,5-trimethyl hexyl acetate, trans-2-hexenyl acetate, cis-3-hexenyl acetate, ethyl propionate, ethyl butyrate, butyl butyrate, isoamyl butyrate, hexyl butyrate, cis-3-hexenyl isobutyrate, ethyl isovalerate, ethyl 2-methyl butyrate, ethyl hexanoate, ethyl 2-methyl pentanoate, 2-propenyl hexanoate, ethyl heptanoate, 2-propenyl heptanoate, ethyl octanoate, methyl 2-nonenoate, ethyl 2-trans-4-cis-decadienoate, methyl 2-octynoate, methyl 2-nonynoate, ethyl 3-octobutanoate, allyl amyl glycolate Carbonates Z-3-hexenyl methyl carbonate Alcohols 3-Octanol; 2,6-dimethyl-2-heptanol, trans-2-hexen-1-ol; 3-hexen-1-ol; 1-octen-3-ol; 9-decen-1-ol; 10-undecen-1-ol; 2-trans-6-cis-nonadien-1-ol; 4-methyl-3-decen-5-ol The Compounds are Noncyclic Derivatives of Terpene Alkanes and alkenes Myrcene, ocimene, beta-Farnesene Aldehydes and acetal derivatives Citral, citral diethyl acetate, citronellal, methoxydihydrocitronellal, 2,6,10-trimethyl-9-undecanal Acids cis-Geranic acid, citronellic acid Esters Geranyl ester (formate, acetate, propionate, isobutyrate, isovalerate), neryl acetate, linalyl esters (formate, acetate, propionate, isobutyrate), citronellyl esters (formate, acetate, propionate, isobutyrate, isovalerate, tiglate) and esters of myrcenol, lavendulol, trans,trans-farnesol, trans-nerolidol, tetrahydrogeraniol, tetrahydrolinalool Alcohols Geraniol, nerol, linalool, myrcenol, lavendulol, citronellol, trans,trans-farnesol, trans-nerolidol, tetrahydrogeraniol, tetrahydrolinalool The Compounds are Cyclic Derivatives of Terpene Alkanes and alkenes Limonene, terpinene, terpinolene, phellandrene, camphene, 3-carene Esters Menthyl ester (acetate, lactate), alpha-terpinyl esters (acetate), noryl esters (acetate), bornyl esters (acetate), isobornyl esters (acetate), cedryl esters (acetate)

Alcohols

Menthol and various diastereoisomers (neomenthol, isomenthol, neoisomenthol), pulegol, and various diastereoisomers, piperitone, terpineols and various isomers, borneol, The Compounds are Cyclic Derivatives not of Terpene Alkanes and alkenes Aldehydes and acetal derivatives 2,4-dimethyl-3-cyclohexene carboxaldehyde, 4-(4-hydroxy-4-methylpentyl)-3 cyclohexene carboxaldehyde Esters OTBCHA, PTBCHA, allyl 4-cyclohexyl propionate, allyl cyclohexyl oxyacetate, methyl jasmonate, methyl dihydrojasmonate, Alcohols 1-(4-isopropycyclohexyl)ethanol, 2-methyl-4-(2,2,3-trimethyl-3-cyclopenten-1-yl)butanol, 2-methyl-4-(2,2,3-trimethyl-3-cyclopenten-1-yl)butenol, 3-methyl-5-(2,2,3-trimethyl-3-cyclopenten-1-yl)-4-penten-2-ol, 3,3-dimethyl-5-(2,2,3-trimethyl-3-cyclopenten-1-yl)-4-penten-2-ol The Compounds are Aromatic (Benzene or Heterocyclic) Derivatives Aromatic (benzene or heterocyclic) rings without additional functions Indole, p-cymene, diphenylmethane Aldehydes and acetal derivatives Benzaldehyde, phenylacetaldehyde, phenylacetaldehyde dimethyl acetal, dihydrocinnamaldehyde, 2-phenylpropanal, cyclamen aldehyde, 2-methyl-3-(4-tert-butyl-phenyl)propanal, cinnamaldehyde, heliotropin, furfuraldehyde Esters Benzyl esters (acetate, propionate, isovalerate), phenethyl esters (acetate, isobutyrate, isovalerate), alpha-trichloromethylbenzyl ester (acetate), cinnamyl acetate, benzoate ester (acetate, hexyl, benzyl), phenylacetate ethyl, phenylacetate geranyl, methyl cinnamate, benzyl cinnamate, phenyl ethyl cinnamate, eugenol acetate Acids Phenylacetic acid Alcohols Benzyl alcohol, 2-phenyl ethyl alcohol, styrallyl alcohol, 2,2-dimethyl-3-(3-methylphenyl)propanol, cinnamyl alcohol, 3-methyl-5-phenylpentanol, thymol, anethole, isoeugenol, eugenol, anise alcohol, raspberry ketone, ethylmaltol, 2,6-dimethoxyphenol, 2-propylphenol, 2-(methylthio)phenol, ortho-guaiacol, 4-methyl guaiacol Others Abietic anhydride Citraconic anhydride Cellulose Derivative They are obtained by reacting basified cellulose with propylene oxide or ethylene oxide. The degree of substitution of the alkylene oxides with respect to hydroxyls of the cellulose is typically greater than 2, better still greater than 4.

The molecular weight sizes vary from 10 000 to several million, preferably from 70 000 to 1 500 000 determined by exclusion chromatography.

For example, the cellulose derivative is a Klucel® (Ashland) sold under the name:

H→1 150 000

M→850 000

G→370 000

J→140 000

L→95 000

E→80 000

All grades of purity are usable:

Industrial

F

CS

F pharm

Preferably, sizes with higher values such as M and H are employed.

The total mass content of cellulose compound(s) may vary between 0.1% and 20%, better still between 0.5% and 5%, even better still between 0.7% and 2%, the percentage being expressed relative to the mass of the base product.

Use for Treating One or More Precise Areas of the Skin

The dispensing system allows perfume to be applied, day after day, with only the precise areas being treated. To this end, small doses of product are delivered, and are applied specifically and sequentially to the corresponding areas. Each small dose is created using the mixture suited to the area.

In one preferred embodiment of the invention, the dispensing system waits for information regarding which area is to be treated and then delivers the corresponding mixture. It may use a preprogrammed look-up table for that purpose, this table being the result for example of a learning process as defined below. As an alternative, the dispensing system informs the person, when delivering a mixture, of the area to which the person is to apply the mixture. Thus, the dispensing system may follow an application program in which it delivers, in a given order, the various mixtures that are to be applied.

In one particular embodiment of the invention, the dispensing system is informed as to the quantities to be delivered. For that, it memorizes the relationship between the odor, the area of the face and the quantity needed, thereby making it possible to reduce costs and wastage of product, and to cover the skin only lightly, thus avoiding occlusion effects. The dispensing system may also allow mixtures to be created precisely, facilitating the dispensing of small quantities and the rapid use thereof.

When the user is looking for the product to apply to an area of the face, it is advantageous to memorize the mixture (ratio between the products in the compartments) best suited to each area, and the dispensing system is thus advantageously designed to memorize the effect, the ratios and the corresponding area. Thus, by using the memorized information, on each use, the same mixture can be delivered for each area or, if several areas are being treated, the same series of mixtures can be delivered for the same series of areas.

The dispensing system may also be designed to allow an area to be treated by varying the effects application after application. Thus, the person may perfume her skin with different notes that she chooses on a day-by-day basis to suit her tastes. For example, on weekdays, the person applies a given perfume, and at the weekend a different one.

The system is also designed to deliver touches depending on the result of the application of different touches. Thus, if it is apparent to the user that, following the application of several touches, there is something missing for perfecting the result, the system can deliver, on demand, a mixture for realizing a touch which will complete the result.

For example, in the case of perfumes, if the person applies a touch of perfume at one location and then another touch of different perfume to another area, the person may desire completing the olfactory impression by applying to the same areas or to a different area another touch of yet another, different perfume.

The system is thus provided to propose variations and an interface for translating simple orders into the production of a mixture.

The dispensing system may be designed to allow the user to change the ingredients to suit her tastes according to the day, the time, what she is wearing, and the weather. Thus, a system to assist with decision making is advantageously provided to guide the user in her choices of perfume notes.

It may be desirable for several people in the same group, for example a family, to be able to use the dispensing system, thus reducing costs and minimizing the space taken up. This solution is particularly suited to travel or hotels, campsites, airplanes, campervans, boutiques, schools, etc. For that, provision may be made for the dispensing system to be able to be informed as to which person is using it, so as to access pre-stored personal data.

Continuous Use for Graduated Treatment

In this application, the dispensing system changes the formulation of the mixture while it is delivering the product.

In addition, the outlet for the base products or for the mixture is moved relative to a container or a support defining an application surface. In one particular embodiment of the invention, the dispensing system is designed to calculate the way in which the mixture evolves as a function of the odor C1 of one area to be treated and of the odor C2 of another area to be treated. For example, with the knowledge that the neck requires an odor C1 and that the hair requires an odor C2, the dispensing system may vary the formulation of the mixture while it is delivering it in order to graduate the odor between these two odors. This makes it possible for example to better conceal imperfections of the face while ensuring that the end result is realistic, or allows the odor to be graduated to increase attractivity. The dispensing system may also be designed such that the user can command a variation in odor of the mixture dispensed without the start and/or end odors having been set beforehand. To do that, the dispensing system may possess a location or auto-location system and deduce from a look-up table the odors C1 and C2 that it has to create and therefore the changes in the mixture that it has to make.

For example, he may create a perfume graduation along the neck in order to share a richness of odor with an approaching person.

The same concept is applicable to protective compositions. The person could create graduations of protective indices, thereby creating, after being exposed to the sun, a tanning result that is itself graduated.

The dispensing system may have an outlet head, in particular in the case of an airbrush, which is mobile and steered. This option then makes it possible to achieve graduated effects without moving the rest of the dispensing system. For example, the dispensing system is located near to the cheek, then a control system is triggered that will automatically steer the variation in formulation of the mixture and the movement of the outlet head so as, for example, to have the neck perfumed with one odor and the ear with another, with a graduation between the two.

The dispensing system may even be used to create tailor-made products that are kept for several applications.

Manufacture of "Bespoke" Compacts or Other Solid or Semi-Solid Products

The dispensing system may be designed to allow a mixture to be chosen and delivered to a container such as a cup. The mixture preferably comprises compounds which are such that the mixture can set solid.

More preferably, use is made of compounds that make the setting especially rapid. These compounds are either deposited in the container before or after it is filled with the other ingredients, or are provided in the compartments of the dispenser with the other constituents of the base products, or are contained in the dispenser in a compartment especially designed to contain them.

Specific compositions which may harden quickly by chemical, biochemical or physicochemical reaction after discharge may thus be dispensed.

These compositions are especially designed for the creation of compacts, namely they:
set solid,
yield a material that can crumble if rubbed, and are preferably colored.

Preferably, these compositions are very rich in solid particles, with for example more than 10% by mass of solid particles relative to the weight to the total mass of the composition, better still more than 20% by mass of solid particles relative to the total mass of the composition, even better still more than 30% by mass of solid particles relative to the total mass of the composition, preferably between 10 and 40% by mass of solid particles relative to the total mass of the composition.

Preferably, one or more of the compositions introduced into the system contain oil, preferably in a content greater than or equal to 20%.

These compositions may contain absorbent particles or reactive compounds, such as those that react in contact with the air, for example cyanoacrylate or alpha-silanes or those which react to light, notably UV.

The container into which the mixture is dispensed may contain a compound A and the dispensed compositions may contain a compound B, A and B being chosen to react with one another and solidify the mixture.

In one particular embodiment of the invention, the dispensing system incorporates a heating means, for example with an electrical resistor, to create lipsticks or other waxy products. In that case, the base products are heated before being delivered.

The dispensing system may also comprise a means for supplying heat and/or light energy, after the mixture has been dispensed into a container, for example an electrical resistor or an LED, notably UV. This energy may accelerate the setting-solid of the dispensed mixture.

The system preferably contains large quantities of cellulose derivatives, such as greater than 5% and preferably greater than 10%.

Preferably, the mixture is homogenized before it sets solid.

Creation of Odor Palettes

The dispensing system may have a support, having several regions, and may be designed to automatically generate several mixtures of odors deposited in said regions, suited to various parts of the face.

The support may define several cavities to receive the mixtures or may bear several containers, for example in the form of cups, potentially cups that are separable from the support.

In one particular case, the support adopts the shape of a face with regions for receiving the mixtures for targeted application areas.

The support may be able to move, notably to rotate, with respect to the body of the dispenser and, for example, may be driven in its movement by the dispenser so that various spaces or containers can be filled in succession.

Cup-Type Dispenser

There is a benefit to having a dispensing system capable of delivering a mixture that the user can easily pick up. Moreover, in cases in which the base products delivered by the dispensing system are not already blended, there is a need to allow the user to perform the mixing easily.

In one of its aspects, independently of or in combination with the other aspects thereof, and notably with the foregoing, one subject of the invention is a system for dispensing at least one fragrancing product, having a cup and a dispenser for filling the cup with at least one product, the cup being secured to the dispenser at least while it is being filled.

The cup is sometimes also known as a "crucible" and that term should be understood in its broadest sense.

A "cup secured to the dispenser" should be understood as meaning that the cup is held, notably immobilized, at least temporarily, on the dispenser, being for example fixed to the latter by screws, magnetic attraction, clip-fastening, bayonet locking, clamping, or produced with a part of the dispenser body by material molding. When it is secured to the dispenser, the cup allows the latter to be manipulated in one hand, the cup remaining in place on the dispenser while the latter is being moved around.

The dispenser may be offered to the user with the cup already in place.

As an alternative, the cup is installed by the user the first time the dispensing system is used.

The cup is preferably less deep than it is wide, making access to it easier and allowing the product, notably the mixture, to be picked up with an applicator or a finger.

Preferably, the cup is separable from the dispenser and constitutes one outlet interface that can be chosen from a collection of outlet interfaces that can be mounted on the dispenser, at the choice of the user and according to the fragrancing to be performed, as described in detail below.

Preferably, the dispensing system comprises several filling orifices for filling with different base products, opening into the cup. Thus, the mixing of these products may take place in the cup.

The cup preferably has a bottom that is concave toward the outside, making it easier for the user to clean it between two uses.

In addition, this may make the product easier for the user to pick up.

Preferably, the dispenser allows at least two base products to be delivered into the cup, in adjustable proportions, and better still at least three products.

In one exemplary embodiment, the dispensing system has at least two cups that can be selectively fed by the dispenser. This may allow the user to fill these two cups quickly with mixtures with different characteristics. This may facilitate the testing of odors and/or allow the preparation of several different odor mixtures intended for fragrancing respective areas of the face. The cups may be associated with identifiers that remind the user of the area of the face for which a mixture contained in a given cup is intended.

The cups may be able to move relative to the dispenser, being for example borne by a mobile support such as a turret that is rotatable with respect to the dispenser or by a slide capable of translational movement with respect to the dispenser.

The dispensing system may comprise a lid for closing the cup. This closure lid is preferably transparent so that the user can see the color of the mixture contained inside.

When the cup is separable from the dispenser it may if necessary be introduced into a housing that allows it to be transported more easily, this housing being able, if necessary, to contain a mirror and/or an applicator. The lid of the housing may in this case act as a lid for the cup.

The volume of the cup may be between 2 and 1000 $mm^3$, better still between 100 and 1000 $mm^3$, even better still between 250 and 750 $mm^3$.

The cup preferably has a shape that exhibits symmetry of revolution. As an alternative, it has a polygonal or some other contour. Its largest inside diameter, or that of the inscribed circle in the case of a noncircular contour, is preferably between 2 and 100 mm, preferentially between 5 and 40 mm. Its depth is preferably between 1 and 10 mm, better still between 3 and 8 mm. Preferably, the size and shape of the cup either allow direct application of the mixture to the skin or allow the mixture to be picked up on a finger or an applicator. The cup may be made of an elastically deformable material, making it possible for example to turn the concavity of the bottom of the cup inside out and empty it more easily or use it to apply the product.

The cup may have no blender; in that case, the base products may arrive in the cup from the dispenser in the unmixed state, via distinct respective dispensing orifices. As an alternative, the dispenser incorporates a blender and the base products arrive in the cup already blended.

The cup may also incorporate a static blender as described in detail below, which is fed via distinct filling orifices of the dispenser and which preferably delivers the mixture into a cavity of the cup situated above the blender.

A further subject of the invention is a method for preparing a fragrancing product, comprising the step of filling a cup of a dispensing system as defined above with at least one base product from the dispenser.

Several products may be delivered into the bottom of the cup, then blended using a finger or an applicator, or a static blender incorporated into the cup.

The cup is preferably filled from beneath. Dispensing systems using a sonotrode have been proposed in the past.

The cup according to the invention is not intended to vibrate in order to dispense the product(s) conveyed by the feed passage(s) supplying it. It differs from a sonotrode. Preferably, the cup is made of plastic.

Blender Incorporated into the Outlet Interface

There is a benefit in having a dispensing system capable of delivering a mixture that can easily be used, notably picked up by the user, without the need for an additional mixing action on the part of the user.

The dispensing system may have a dispenser having outlet passages for base products and an outlet interface that is separable from the dispenser, this interface having a static blender that preferably delivers the mixture into a cavity where it can be picked up.

The static blender may be situated under the abovementioned cavity. The dispensing system is then particularly suited to the creation of compacts, using cups with an in-built static blender as outlet interfaces. In that case, the cavity of the cup is filled with product from beneath. After passing into the static blender, the blended base products cover the blender.

According to this aspect of the invention, it is possible to use several outlet interfaces and to fill them with different respective mixtures, without the need to purge the blender, thereby reducing losses of product. The outlet interface may be a single-use interface, if necessary.

Preferably, the static blender has a central chamber communicating with base product intake ducts. This central chamber may communicate with a peripheral chamber having a series of partitions which act as deflectors for the mixture and create shearing thereof.

The peripheral chamber may have a perforated annular partition defining perforations through which the mixture passes as it circulates in the peripheral chamber. The central and peripheral chambers may be closed at the top by a wall which defines the end wall of the cavity receiving the mixture.

The end wall of the peripheral chamber may be of helical shape about the axis of the cup and of a height that decreases in the direction toward the outlet. The latter may open ahead of a connecting ramp connecting the end wall of the peripheral chamber and the top wall of the blender, this connecting ramp preferably being a portion of a helix extending the helix formed by the end wall of the peripheral chamber.

Preferably, the peripheral chamber comprises the abovementioned annular partition and radial partitions that force the mixture to circulate alternately between upper and lower regions of the peripheral chamber and between radially inner and outer regions, the mixture circulating for example from an upper and radially outer region to a lower and radially outer region by passing through the abovementioned annular partition.

The blender may have an outer body in which a component forming the core of the blender is housed, the outer body radially closing the peripheral chamber on the outside and comprising an upright that separates the central and peripheral chambers.

The outer body of the blender and the core of the blender may each be produced as a single piece by injection molding.

Reduced Dead Volume

There is benefit to be had in reducing the losses of product when changing the formulation of the mixture and in allowing the odor of the mixture to be varied as quickly as possible during application, particularly when the dispenser is coupled to an airbrush.

A system for dispensing a fragrancing product according to this ninth aspect of the invention has a dispenser receiving at least two cartridges that each have a reservoir containing a base product, the latter being able to leave the cartridge through an outlet passage of the cartridge, this outlet passage opening out at the outside of the dispenser or near the external surface thereof.

The outlet passage may notably open into an area in which the mixture is picked up or close to this area, notably less than 5 mm away, better still less than 3 mm away, better still less than 1 mm away, or even better still flush therewith.

The cross section of the outlet passage is, for example, between 1 and 3 mm$^2$.

Thus, each base product coming from a cartridge can leave the dispenser without mixing with a base product from another cartridge and the dead volume that cannot be picked up and is likely to increase the inertia of the system is minimized. The product is more quickly available without having to circulate through special passages in the housing of the dispenser, thereby avoiding a painstaking purging step in the event of a cartridge change.

The outside of the dispenser may be the product pickup area, notably when the dispenser is produced with a cup that is not designed to be removed, into which the mixture is dispensed, or a dispensing area intended for the mounting of a removable outlet interface, which defines the pickup area. This outlet interface may have a cup as defined above. This mounting area corresponds for example to the outside of the housing of the dispenser in the absence of an outlet interface. The mounting area may be substantially planar and perpendicular to the longitudinal axis of the dispenser housing.

The dispenser may have three cartridges of base products.

The dispenser may have housings for receiving the cartridges, which are preferably received removably in the dispenser. The latter may comprise passages for ducts for the cartridges defining the outlet passages.

The length of these ducts is preferably such that the ducts are set back slightly from the end or lie flush with the cavity used for picking up the product or, as an alternative, are set back slightly from or lie flush with the end face of the housing of the dispenser that defines the mounting area.

These ducts of the cartridges may be end pieces used for causing the pistons to move within the cartridges, as described in detail above.

Multiple Outlet Interfaces

There is a need to be able, using the same dispensing system, to achieve different fragrancing effects easily and be able, if so desired, to fragrance areas as different as the skin, the lips, the neck, the eyebrows or the hair.

The dispensing system may comprise an assembly having a dispenser of at least one fragrancing product, and at least two outlet interfaces, each of which can be mounted removably on the dispenser, these outlet interfaces being able to receive the product(s) delivered by the dispenser, preferably being chosen from the following:

an outlet interface having a container, notably a cup, allowing the product to be picked up using a finger or using an applicator, an outlet interface allowing the product to be delivered to a spray system, notably an airbrush, an outlet interface having several regions for receiving the product, which can move relative to the dispenser, an outlet interface that allows the product to be delivered to a dispensing end piece.

Preferably, the assembly comprises at least three of said outlet interfaces, or better still the four outlet interfaces.

The dispenser may comprise at least two different base products and allow these to be delivered in variable proportions and, preferably, the dispenser comprises three different base products and allows these to be delivered in variable proportions.

Each outlet interface may have a base allowing it to be fixed to the dispenser. This fixing may be done using screws for example, but preferably the base is designed to allow an outlet interface to be removed and replaced without the need for tools. It is, for example, a quarter-turn fixing or a fixing using an external locking ring.

The outlet interface and/or the housing of the dispenser may comprise seals allowing sealed communication between the housing of the dispenser and the outlet interface. If appropriate, the dispenser is designed to recognize the outlet interface mounted above, for example by virtue of the outlet interface having identifiers in the form of specific reliefs which are detected by the dispenser, or in the form of an electronic chip that the dispenser recognizes. That may allow the operation of the dispenser to be adapted to the outlet interface mounted above. The dispenser may communicate information about the outlet interface it is bearing to a computer system, and the computer system may, on the basis of this information, display a specific screen and/or run a specific program for controlling the operating parameters of the dispenser so as, for example, to adapt the dose dispensed and/or the flow rate to the type of outlet interface.

The user may be initially offered several outlet interfaces with a common dispenser within one and the same package, for example a case or a cardboard box.

A further subject of the invention is a fragrancing method involving the step of selecting an outlet interface, mounting it on the dispenser, and delivering the product(s) contained in the dispenser to the interface.

Mapping and Learning

The term "mapping" should be understood here as meaning a process of indexing an odor with an area, with recording.

The mapping may relate to applications to areas smaller than 1 cm$^2$. However, the naked eye then has difficulty in discerning whether the result obtained is adequate, and it is preferable to substitute an instrumented evaluation with magnification for evaluation by the naked eye. Small quantities of substance may be applied with a finger, using conventional tools such as brushes, or using specialist applicators.

The map may be generated during a learning period in which the user carries out tests with mixtures on different areas of the face; once created, the map can then be used for everyday fragrancing.

Specific graphic interfaces can be used during the learning period and during the period of use of the map.

In particular, the dispensing system may be used with a graphic interface in which the operator sees the face, which is for example a schematic, figurative or accurate representation such as a photograph or a 3D simulation. In that case, the operator can point at part of the face on the screen to show and/or deliver the appropriate odor.

The graphic interface may also show the other areas of the face where use of that same odor is appropriate.

To create the map, the operator applies an odor, then makes an assessment.

The areas of the face can be treated one after the other; for example, the exercise is carried out on part of the neck, then on the ear, then the hair, etc.

Another option is to create a given mixture and apply this same mixture to several areas. The operator then needs to look for the area of the face to which the odor is suited. The mixture is then indexed in the computer system which attributes it to the area(s) of the face for which it is suitable.

In one of its aspects, independently of or in combination with the other aspects thereof, and notably with the foregoing, one subject of the invention is a learning process for a dispensing system comprising a dispenser for dispensing a mixture of variable odor, and a computer system for selecting a fragrancing effect and for storing data, comprising the steps of.

a) selecting at least one odor with the aid of an interface of the computer system,
b) delivering, with the aid of the dispenser, at least one mixture in order to approach the selected odor,
c) evaluating the mixture(s) dispensed following the application thereof to at least one area of the face, (odor)
d) memorizing the characteristics of at least one mixture, notably a mixture that the user wishes to be able to recall, and of at least one area on which it has been tested.

This memorizing can be carried out notably with a view to subsequent dispensing of this mixture for fragrancing said area.

Preferably, the computer system is designed to allow the user to indicate whether or not the result of the test is satisfactory, or even to inform same of the comparison with a test carried out earlier.

It is also possible to create a given mixture and to look for the area of the face for which it is suitable. The mixture is then recorded, being attributed to the area(s) of the face for which it is suitable, in a look-up table that will be used subsequently in order to deduce which mixture to use on the basis of an area of the skin.

The same procedure can be adopted with other mixtures in order to create a map of the entire face and thus have a complete look-up table for the face.

It is also possible to create a given mixture, apply it to a given area, and then vary the mixture until the most suitable mixture is obtained. The mixture is then recorded, being attributed to the area(s) of the face for which it is suitable, in a look-up table that will be used subsequently in order to deduce which mixture to use on the basis of an area of the skin.

Preferably, the computer system evaluates and memorizes the quantities used area by area. Such a method, which uses "test patches" makes it possible to identify the product(s) required by the person wishing to perfume themselves. Thus, the dispensing system can be used at sales outlets to advise people wishing to perfume themselves or at home in order to define correctly which products to order.

The interface of the computer system preferably has a touch screen displaying a reminder of the odor of the mixture when it is selected.

The interface may display a face and allow the computer system to be informed by selecting the area on the face displayed.

The computer system is preferably designed to allow an area, mixture reconstruction parameters, and the date of the test and/or any other identifier of the mixture to be associated with one another.

The computer system is preferably also designed to allow at least one of the following data: the name of the area, the period of the year, the name of an event, a user identifier and the age of the user, to additionally be associated with said area, with the mixture reconstruction parameters, and with the date or identifier of the mixture.

Steps a) to c) may be repeated at least once before the characteristics of the mixture are memorized in step d).

The computer system may be designed to search a database for a reference of a commercial product on the basis of the characteristics of the mixture identified as being suitable for at least one given area, and to relay this information to the user.

The selection in step a) may be carried out using an expert system, which may or may not be external to the computer system.

The expert system may analyze an image of the user in order to propose a mixture odor at least on the basis of the image analyzed.

The computer system may be designed to allow the user to inform same of his or her assessment of the result of the test in step c) and to generate a proposal to modify the mixture to be selected upon return to step a).

The dispenser may deliver, in step b), at least two different mixtures, preferably separate, so that they can be applied simultaneously to the test area.

This may allow time to be saved and make it easier to compare the results.

A further subject of the invention is a method of fragrancing using a dispensing system according to this aspect of the invention, in which:

a) the user sends the computer system a request regarding a need,
 b) in return, the computer system generates a proposal for treating an associated zone, on the basis of the learning performed beforehand, and
 c) the computer system operates the dispenser to produce the proposed mixture, notably if this is validated by the user.

Such a method may use a map previously established with the user.

A further subject of the invention is a computer program product containing code instructions which, when run in a computer system, allow the computer system to be made to:

allow the user to select at least one odor and/or one application area, notably using an interface such as a touch screen,
 operate a dispenser in such a way as to deliver a mixture selected by the user,
 allow the user to trigger the memorizing of the mixture and of an associated application area, notably with a view to subsequently dispensing the same mixture, notably on the same area.

The computer program product may comprise code instructions which, when run in a computer system, allow the computer system to be made to:

receive a request from the user regarding a need for fragrancing, notably using an interface such as a touch screen,
 propose, on the basis at least of data generated by the learning process as defined above, at least one odor and/or one application area,
 operate a dispenser to produce the proposed mixture, notably if this is validated by the user.

Remote Assistance

It is desirable to be able to assist the user in perfuming themselves, notably in choosing the correct olfactory notes.

In one of its aspects, independently of or in combination with the other aspects thereof, and notably with the foregoing, one subject of the invention is thus a fragrancing method involving the steps of:

allowing a video link to be established, for example over the Internet, between a camera on a first site and a second site,
 allowing the second site to directly or indirectly operate a dispenser present at the first site, this dispenser making it possible to vary the odor of a mixture dispensed,
 allowing a person present at the first site to apply the mixture dispensed and to send a corresponding image or comments to the second site, so as to receive in return information relating to the application result.

The second site may notably have a viewing screen which allows an adviser sitting at this screen to hear or read the comments about the fragrancing result with the product dispensed by the dispenser and advise the person who has perfumed themselves. This adviser may in return influence the dispenser to alter the odor of the mixture and adapt it to best suit the face of the person present at the first site. Thus, this person controls the mixture delivered by the dispenser. The first person may perfume herself under the gaze of the second. The second person sees the result of the test on their screen and can thus correct the mixture that this second person will control remotely until the ideal fragrance is obtained.

Preferably, the video link between the two sites is a two-way link.

The first site may receive a tutorial from the second site, if appropriate.

Identifiers of the base products may be communicated to the second site; this may make it possible to precisely determine the perception of the odors of each of the base products.

The method may involve memorizing the dispenser setting parameters once a given mixture is considered to be satisfactory. Preferably, this memory storage may be commanded from the second site. The memory storage may be in the computer system present at the first site and/or on an external server.

One alternative may be to have one person working to help several perfume themselves. This embodiment makes it possible to develop "fragrancing coaches" and their work, either within an institute or over the Internet. It also allows people with limited capabilities, such as people lacking in self-confidence to perfume themselves.

Operation Via Touch-Sensitive Interface

There is a need to make it easier to control the dispensing system and notably the choice of the effects of the mixture dispensed.

The dispensing system may have a dispenser and a computer system for operating the dispenser, this computer system having a touch screen on which the odor of the mixture or the expected effect can be displayed, and a selection means movable on the screen, in order to vary the odor of the dispensed mixture.

Preferably, the screen displays end-point effects between which the effect of the mixture can be selected by moving the selection means between these end points.

The screen may display a scale of effects in the form of a line or area (triangular contour).

The computer system may perform some of the calculations necessary to determine the fractions of each of the base products that lead to a mixture of the desired effect.

The computer system may be a smartphone, a camera phone, a tablet, or a personal computer. As an alternative, it is incorporated into the housing of the dispenser.

The computer system may have a camera. The latter can be used notably for capturing an image of the user and/or of the mixture.

The computer system may be designed to display an image of a face, in order to make it easier to identify the areas to which the mixture is to be applied.

Coupling of the Dispensing System to a Spray Means

The dispensing system may have or be connected to a means of spraying the mixture, preferably an airbrush.

The dispensing system may comprise a spray system, preferably an airbrush, and according to one of its aspects, independently of or in combination with the other aspects, and notably the foregoing, one subject of the invention is an assembly comprising:

a spray means, preferably an airbrush having a pickup chamber subjected to a stream of entrainment air, a dispenser having at least two compartments containing different base products, the products being delivered to the spray means preferably via distinct distribution orifices.

The dispenser may have three cartridges containing fragrancing products.

The airbrush may have a stylus defining the pickup chamber, the stylus being fixed to the dispenser or to an outlet interface fixed to the dispenser, or forming an integral part of this outlet interface.

The dispensing system may have a circuit controlling operation of the dispenser, allowing the proportion of base products delivered to the pickup chamber to be varied while the airbrush is in operation. The proportions may be modified depending on the movement of the airbrush relative to the surface onto which the mixture is sprayed. This movement may be mechanized, if appropriate.

This control circuit may have or be constituted by a computer system as defined above.

The housing of the dispenser may act as a hand grip when the assembly is being handled for delivering the mixture.

The dispenser may have a camera and/or one or more sensors such as accelerometers so as to automatically locate the area to which the mixture is applied, and so as to be able to automatically regulate the odor depending on the position, if appropriate.

A further subject of the invention is a method for fragrancing using an assembly as defined above, in which a mixture is sprayed onto the skin using the spray means, notably the airbrush.

The composition of the mixture can be modified as the airbrush is moved relative to the skin. A graduated odor can be achieved.

This aspect of the invention is based on the observation that the dispenser can be used to supply the spray system, notably the airbrush, while at the same time allowing the dispensing system to be responsive enough to allow a change in the odor of the mixture dispensed while the face is being treated.

It may be advantageous for the dispensing of products to be performed iteratively, notably with dispensing times that are not phase-shifted between the various products.

This may make it easier to vary the composition of the mixture dispensed over time.

The mixture may be created directly in the airbrush, with practically no troublesome dead volume, thus allowing the mixture sprayed to be changed in real time.

The depression created in the pickup chamber is strong enough to entrain the base products without in any way impeding the metering.

The depression which prevails in the pickup chamber is for example between 10 mbar and 200 mbar, better still between 50 and 150 mbar, even better still between 75 and 125 mbar.

The viscosity of the base products as measured at 1 atm and 25° C. with a CONTRAVES TV rotary viscometer fitted with an MS-r3 or MS-r4 measuring bar at a frequency of 60 Hz after 10 minutes of rotation of the measuring bar is, for example, between 0.02 Pa·s and 50 Pa·s, preferably from 0.2 Pa·s to 5 Pa·s.

The cross section of the passages along which the base products arrive in the chamber is, for example, between 1 and 3 mm$^2$, better still between 2 and 3 mm$^2$.

The product is preferably supplied continuously.

It is also possible to apply immiscible or reactive base products, such as an aqueous gel and a composition according to the invention (based on an organic solvent), simultaneously, and these will be deposited directly onto the skin in a pixelated manner, producing a kind of gel/gel in situ, reactive silicones. The ratios of base products can be adjusted depending on the particular result desired. For example, in the case of aqueous gels and oily gels, the ratio corresponding to the volume of the first base product to the volume of the second base product could be varied between 10/1 and 1/10, better still between 5/1 and 1/5.

Location or Auto-Location System

The dispensing system according to the invention may have a location or auto-location system.

A location system is the name given to a means via which the person inputs the area that she is to treat. This can be performed notably using systems that leave at least one hand free. Thus, an interface of a computer system such as a touch screen, a joystick, or voice recognition system can be used.

An auto-location system is the name given to a means for inputting the area that is to be treated without intervention on the part of the person. This can be achieved using one or more accelerometers which deduce, from the movements, the directions targeted by the person or by a camera and an image recognition system.

Examples of dispensing systems suitable for the invention according to its ninth aspect are shown in the figures, which will not all be described in detail again.

The housing of the dispenser 11, in the configuration thereof illustrated in FIG. 13, i.e. without the outlet interface 110, has the advantage that it can be coupled to various forms of other outlet interfaces, depending on the fragrancing that is to be performed and/or on the area to be treated.

FIG. 29C illustrates a support having spaces disposed thereon substantially in the manner of the different areas of a face; each space may contain a mixture, the odor of which is suited to the corresponding part of the face. Thus it is easy for the user to know where to apply the mixture picked up from a given space.

The dispenser 11 can be used to deliver a mixture, the formulation of which changes over time, and to collect the mixture in a container that is movable with respect to the dispenser, such that the mixture is deposited in a location of the container that varies over time, in order to achieve a graduated effect.

For example, as illustrated in FIGS. 29A and 29B, the dispensing system has an outlet interface 110 having a part that is fixed relative to the dispenser and a moving part 252 that has a space 253 for receiving the mixture.

For example, the dispenser 11 is arranged in this case with the outlet orifices of the cartridges downward and is equipped with a blender such that the mixture falls into the space 253 under its own weight. A motor may move the moving part of the outlet interface relative to the dispenser, in a manner that is synchronized with the variation in characteristics of the mixture, such that a graduated effect is obtained all along the space 253, as illustrated in FIG. 29B.

FIGS. 31 to 37 show various examples of touch-sensitive interfaces that may allow the user to select the odor of the mixture resulting from the metered dispensing of the various base products.

This interface may have, as illustrated in FIG. 31, an odor selection area, for example in the form of a triangle, the vertices of which correspond to the odors of each of the base products contained in the cartridges.

The user can move a cursor 300, for example in the form of a ball, relative to the vertices A, B and C of the triangle.

The closer he brings the cursor 300 to one of the vertices, the larger the fraction of the corresponding base product relative to the total quantity of the various products dispensed.

The fraction of each product relative to the total quantity may be indicated at 301 by a numerical value on the interface.

The interface may allow the user to increment or decrease the quantity of each of the products, for example by operating control buttons 302, which allow precise adjustment of the quantity of each of the base products.

The surface of the triangle 310 may have an odor that varies locally so as to be indicative at each point of the odor of the mixture that results from the weighting of the various base products in the proportions corresponding to the relative coordinates at this point.

The interface may have a button 305 providing access to a specific menu for adjusting the volume of product dispensed for purging the dispenser.

The interface may also advantageously allow the flow rate of product to be adjusted using buttons 304 and 306 returning to a specific menu for adjusting the flow rate.

In the example in question, the interface affords the choice between a continuous dispensing mode, using the button 304, in which the products are dispensed for as long as the user is pressing the control button 12.

The corresponding dose can be transmitted to the interface and displayed.

The button 306 allows selection of a dose mode of operation, during which even a brief press of the button 12 triggers the dispensing of a predefined dose.

In order to vary the flow rate, the dispenser acts, for example, on the operating duty cycle of the motors.

The interface may be designed to allow the user to program or memorize the settings he or she prefers, using a menu 307 providing access to favorites.

The touch-sensitive interface illustrated in FIG. 32 shows on the screen three colored areas 400, each one corresponding to the odor of one of the base products contained in the dispenser 10, and a central area 410 which shows the odor of the resulting mixture.

The relative quantity of each of the base products can be adjusted using cursors 415 which move for example along lines joining each of the areas 400 to the central area 410.

During use of the interface, the latter may memorize a given setting and cause a button 420 of the odor of the mixture to appear on the screen. The user can then, simply by pressing this button 420, dispense a mixture of the corresponding odor.

In the example in FIG. 34, the interface displays, in an area 500, a given odor and offers the user, by virtue of control buttons 510 that are each for the odor of the corresponding base product, the opportunity to increase or decrease the proportion of this base product in the final mixture. The odor of the area 500 is recalculated depending on the actions on the control buttons 510.

In the variant in FIG. 35, the interface shows a color chart having several areas 530, each one corresponding to a particular proportion of the various base products.

The user may select one of these areas, for example by pressing it with his or her finger.

The interface may be designed to display the selected odor to a larger scale in an area 535. The programming of the dispenser 11 to dispense this odor is triggered for example by pressing the area.

In the example in FIG. 36, the user may move a cursor 555 over a continuous odor chart 550, causing the selected odor to be displayed in an area 558.

The user can then, for example by pressing the area 556, trigger the sending to the dispenser 11 of the necessary instructions for the dispenser to dispense a product in the selected odor.

It is apparent from FIG. 37 that the interface can memorize the various shades selected and then display them on the screen so as to allow the user, by pressing corresponding buttons 560, very easily to again select a shade that has already been chosen.

FIG. 38 shows an example of a user interface 1000 of a dispensing system comprising a dispenser, preferably as described above, and a computer system 100 to which the interface belongs.

The computer system comprises here, for example, a device such as a laptop computer, a tablet or a smartphone, that operates autonomously or is connected to a remote server.

In the example in question, the interface 1000 is defined by the touch screen of such a device. In a variant that has not been illustrated, the dispenser incorporates a touch screen or any other type of man-machine interface, and can be used without connection to another device.

The device runs an application, for example which has been downloaded beforehand and which displays on the screen a face 1035 and a series of buttons allowing the user to input information.

The face may comprise several areas Z1 to Z6 that can be selected by touch, for example the forehead, the nose, the cheeks, the eyelids, the chin, and the lips.

The buttons present on the screen may make it possible for example to input the name of the fragrance or of the user, to display the selected area, to choose the odor, and to inform the computer system as to whether or not the result of the test carried out is acceptable, or even, as illustrated, to provide information regarding the assessment of the result relative to a test carried out previously, namely, for example, better or "not as good". The screen may also display a button allowing the choice of an odor and an area to be memorized after a test has been carried out with this odor on the area in question.

The choice of odor is made for example with a scale similar to the one described with reference to FIG. 36.

The computer system is designed to memorize the data in the form of a look-up table for example, so as to associate an area of the face with the parameters that allow the mixture dispensed during the test to be reproduced. These parameters include, for example, the relative contents of each of the base products of the dispenser in the mixture, the quantity Q dispensed, and additional data such as, for example, the name of the area, the date the mixture was dispensed and/or any other mixture identifier, identifiers of the base products, the period of the year, notably the season, the age of the user, his or her sex, his or her given or family name, the name of an event associated with the fragrancing, for example a birthday, amongst other data, and the quantity of product suitable for the area. The ancillary data may allow the user to reproduce more easily a fragrance considered suitable for a time of year or recalling a life event, or to give a rejuvenating effect.

These data may be memorized in the computer system 100, for example in the abovementioned device and/or on a remote server with which the device is in communication, or alternatively in an electronic memory incorporated into the dispenser 11.

Thus, according to the invention, the user may make the dispenser deliver a first fragrancing substance, and apply it to a first area of the face, then judge whether or not it is suitable. If the result is satisfactory, the user may record it, indexing it to the area; if the result is unsatisfactory, the user may command a new odor in order to repeat the above operations.

The computer system can be used in this context in various ways.

For example, as illustrated in FIG. 40, in a step 1010, the user has selected an odor to test, using for example the scale 1011 displayed on the screen, by moving the adjusting button 1012.

Next, the choice of odor is transmitted to the dispenser 11, in step 1015.

For example, the device transmits the quantities of each of the base products to be dispensed and the electronic circuit 81 takes charge of operating the motors accordingly.

In step 1016, the user presses the control button 12 of the dispenser 11, this causing, for example, a dose of the mixture, in the odor selected by the user, to be dispensed.

The mixture is, for example, dispensed into the cup 115 then picked up and applied by the user to the cheeks or any other area instructed on the interface, in step 1020.

In variants, the product is applied using an airbrush or by any other means as described above.

The user then, in step 1022, informs the computer system of the result using the buttons 1021.

If the user indicates that the result is satisfactory, the system suggests for example that he/she validate the parameters of the test using a button so as to memorize these parameters in step 1031.

If the user does not consider the result to be satisfactory and makes this known using the button 1032, the result can nevertheless be automatically saved in step 1034.

Thus, each area can be indexed not only with the suitable odor(s), but also with the odor(s) that is/are not at all suited to this area.

The user can then perform a further test on the same area by returning to step 1010.

If the user is satisfied with the result, he or she may also wish to carry out a further test, for example on a different area of the face.

If appropriate, if the user is not satisfied, the interface may suggest that the user indicate whether the result is considered better than or not as good as the previous test, using corresponding buttons 1040 and 1041.

In that case, the computer system may be designed to determine whether, in light of the information input by the user, a proposal can be automatically made as to what odor to test next.

If appropriate, a questionnaire may be displayed to assist the computer system in proposing an odor in light of the tests carried out and the way in which the user or a professional assisting the user has assessed these tests.

For example, if the odor is considered "unsuitable", the system may receive from the user additional information, for example "too fruity", which will assist the system in proposing a new odor better suited to the user's expectations.

It may be advantageous for the computer system to be able to receive information comparing the result against the previous tests, for example "it's better" or "it's not as good" and, from there, for the system to be capable of deducing what new odor to propose.

Another option is for the computer system to be able to receive comparison information regarding a comparison against a target, for example "it's almost ideal" and, from there, for the system to be capable of automatically adjusting its odor modifications.

In this particular instance, if it receives the information that the desired result has almost been achieved, the system can adopt small levels of odor change and revise the scale of adjustment accordingly.

If the dispensing system itself proposes the odorous mixtures to be tested, these may be based on preprogrammed test scenarios and the system may alter how the scenario is followed through according to the successes or failures of the assessment. Thus, for example if, from the third application of product, it receives information that the odor is almost ideal for the user, the dispensing system may exit the program and thereafter allow itself to be guided by instructions from the operator.

In general, the user may be assisted by an expert system in the choice of odors to test.

This expert system is, for example, a program run on the device with which the dispenser communicates or on the dispenser itself, and which is based on the answers to a questionnaire and/or on measurements, for example of the odor of the skin or body, taken by a specific sensor or by a camera. The user can thus get assistance from an instrumented evaluation, for example an odor sensor. The expert system can even be implemented on a remote server with which the device or the dispenser exchanges information. The operator may even send an image of his or her face to a specialist, who can preprogram the starting odor choice. In another exemplary embodiment, the user presents the computer system with a photo of his or her face, and the computer system is designed to analyze this and create a program defining the areas to be tested and the first products to be delivered, both in terms of odor and in terms of quantity. For example, the computer system may be designed to automatically select the odors to propose to the user by capturing a photograph in step 1070, as illustrated in FIG. 42. For example, the device which communicates with the dispenser 11 is equipped with a camera, and the user takes a photograph of his or her face. The image is then analyzed in step 1071, and odors are proposed for each area of the face in step 1072, for example in accordance with predefined odor combination rules.

The dispensing system may be oriented by the user to decide on the odor and also on the quantity of product to be delivered. For example, the user may indicate "neck" or "hair" and the dispensing system is designed to adapt the dose dispensed according to a memorized map of doses to be dispensed depending on the areas to be treated.

The computer system may guide the user in the choice of odors in the mixture to be tested, so as to limit the number of tests needed until the user obtains a result that pleases him or her.

It is thus possible, as illustrated in FIG. 41, that after a mixture dispensed by the dispenser has been applied to a given area of the face in step 1060, the computer system will ask the user whether or not the result is satisfactory and will, of its own accord, if the result is considered to be unsatisfactory, make a change 1061 to the dispenser parameters in order to modify the mixture dispensed.

The user then only has to perform a new test with the modified mixture.

When a mixture is notified as being satisfactory, the computer system can memorize the corresponding parameters so as to allow the mixture to be recreated at a later date.

The system can then begin the above steps afresh for a new application area.

During the successive tests, the operator does not need to treat the entire face. He or she may for example choose between 3 and 8, for example 5, small areas. The dispensing system is then advantageously designed to interpolate and/or extrapolate the data regarding the odors considered to be suitable, so as to calculate the odors that ought to be considered suitable for areas for which the exercise has not been conducted.

At the end of the learning stage, the system may generate a display of the suitable odors on the various areas, tested or calculated.

The dispensing system may be designed to indicate whether certain odors appear to be incorrect, doing so on the strength of a comparison against standard maps it has in memory. Thus, it may propose that the user repeat all or some of the mapping exercise.

Once the computer system has completed its learning, i.e. once the odors of mixtures have been identified as being agreeable to the user for fragrancing certain areas, the user wishing to perfume themselves only has to call up the area that is to be treated, in step 1080 of FIG. 43, and the system will be able to automatically propose a suitable mixture odor to the user in step 1081.

In the variant illustrated in FIG. 44, the user selects an odor in step 1090 and the computer system proposes, in step 1091, an area in which to apply a mixture of this odor, on the basis of information previously collected on the basis of the tests performed.

The area proposed is, for example, the area in which an identical or very similar odor has already been applied and the result considered acceptable by the user.

FIG. 46 illustrates an example of an implementation of the invention in which, having carried out tests on various zones in step 2010, the user informs the system of the mixture(s) he or she considers to afford the best result, this allowing the system to know the corresponding parameters in step 2012. Next, in step 2014, the system may propose to the user references of commercial products that have the same properties or very similar properties.

In one variant, the system sends the parameters to a remote manufacturing center so that a composition that has the same formulation or the same properties as that of the mixture that the user has tested and found to be satisfactory can be produced.

FIG. 45 illustrates the possibility of using the dispenser to dispense several doses 2020a to 2020d of different mixtures, next to one another on a support 2021, so as to allow these to be applied to adjacent distinct regions of the same area.

The user can, in a single hit, apply a series of odors in order rapidly to home in on the appropriate odor. The substances present on the support 2021 may have been chosen by the operator him- or herself or proposed by the dispensing system.

The support 2021 is, for example, able to move with respect to the housing of the dispenser and is moved sequentially to deposit the corresponding mixtures in the various zones 2020a to 2020d, being for example similar to the supports described with reference to FIG. 29 or 29A. The user can thus easily compare the results between the various regions and inform the system of which mixture produces the best effect.

FIG. 47 illustrates a system that assists the user in perfuming themselves, notably in choosing the correct odors.

This system makes it possible to establish a video link, for example over the Internet, between a camera 2060 at a first site 2061 and a second site 2062.

The camera 2060 is, for example, built into a tablet or a smartphone that constitutes the computer system 100.

The second site 2062 is allowed to operate the dispenser 11 present at the first site 2061 either directly or indirectly.

Thus, the person present at the first site can apply the mixture dispensed and send to the second site 2062 a corresponding image, and in return receive information relating to the result of the fragrancing.

The second site 2062 may have a display screen 2064 that allows an adviser sitting at this screen to understand, via the comments, the result with the mixture dispensed by the dispenser and advise the person fragrancing themselves. This adviser may in return influence the dispenser 11 to alter the odor of the mixture and adapt it to best suit the face of the person present at the first site. The protocol for the exchange of data between the two sites thus allows command instructions to be sent to the dispenser 11, either directly or via the computer system 100 present at the first site. Thus, the person present at the second site controls the mixture delivered by the dispenser 11. The first person may perfume herself under the gaze of the second. The second person sees the result of the test on their screen and can thus correct the mixture that this second person will control remotely until the ideal fragrance is obtained.

Preferably, the video link between the two sites is a two-way link, such that the user present at the first site can see an image of the adviser on the screen of the computer system. This adviser can send the user present at the first site a tutorial if need be.

The memorizing of the setting parameters of the dispenser 11, once a given mixture has been considered satisfactory, may be commanded from the second site.

The interface may be used to define fragrancing programs in which the order of the areas to treat or the order of the odors to propose is defined.

EXAMPLES

A dispenser 11 like that illustrated in FIG. 3 is created.

The user determines the desired odor with the application which is run on the tablet and which calculates the fractions of the various products. The tablet communicates this value to the dispenser by a Bluetooth connection.

The electronics built into the dispenser 11 collects the information and automatically adjusts the flow rates of the three cartridges so as to obtain a mixture of the desired odor.

When the user wishes to use the product, he or she presses the button 12 of the dispenser in order to cause the product to be expelled. He or she presses for as long as he or she wants product, in "continuous" mode. In "dose" mode, the user presses the button 12 once and the predefined dose is delivered.

Dispensing may be performed continuously, namely with the motors operating continuously, the entire volume being dispensed in one hit, or iteratively, the motors then operating in a pulsed fashion; in that case, the time interval between two pulses makes it possible to vary the flow rate. Small volumes are delivered one after another in several stages.

The pulses may be separated for example by intervals of 50 ms, 100 ms or 200 ms. The duration of a pulse during which the motor is turning will be from 50 to 150 ms, for example.

The main page of the "µMix" application comprises in this example the following elements, as can be seen notably in FIG. 31:

status bar at the top of the screen: indicates the status of the Bluetooth connection or µMix if there is no Bluetooth connection;

thumbnails at the bottom of the screen: for selecting the active page: main page, Settings, Bluetooth, Products and Favorites;

Continuous button 304 for selecting the mode in which products are dispensed continuously;

Purge button 305 for selecting the Purge mode;

Dose button 306 for selecting the mode in which dispensing is in doses with the volume of the dose associated with the Dose button;

a blue ball 300 that the user can move around inside the volumetric triangle either by dragging it or using a double tap;

"−" buttons 302 for each product A, B and C: reduces the fraction of product selected when moving along the straight line connecting the point to the vertex of the product selected;

"+" buttons 302 for each product A, B and C: increases the fraction of product selected when moving along the straight line connecting the point to the vertex of the product selected;

volumetric fraction of each product as a percentage: modifiable by the user and updated in real time according to the instruction from the + and − buttons 302 and the position of the ball 300.

While the volumetric fractions are being modified by moving the ball or using the + and − buttons, the values of the volumetric fractions of the products A, B and C are updated automatically. When the volumetric fractions are modified using the + and − buttons, the ball 300 is moved automatically into the corresponding position in the triangle.

When the application run on the tablet is started up, it automatically connects to the dispenser 11 if it is detected. When the dispenser is switched off or the Bluetooth connection is broken, the tablet disconnects. When the user moves the cursors that adjust the proportions of the products A and B, the values are transmitted in real time to the dispenser 11.

The Settings page of the application contains the following elements:

status bar at the top of the screen: indicates the status of the Bluetooth connection or µMix if there is no Bluetooth connection;

thumbnails at the bottom of the screen: for selecting the active page:

main page, Settings, Bluetooth, or Info;

"Volumes" part with a text field to be filled in by the user to define the volume of the dose, in ml (2 ml for example), and a field for the purge volume, in ml (3 ml for example). The minimum doses in this example are 0.023 ml and the maximum doses are 9.90 ml (3×3.3 ml);

"Flow rate" part with selection of the flow rate: fast (»0.03 ml/s), medium (»0.02 ml/s) or slow (»0.01 ml/s);

"Dose" part with iterative choice of the mixture, for dispensing a mixture of products with small volumes delivered one after another in several stages;

In the contrary case, the total volume of each product is dispensed in one hit;

"Triangle image" part for selecting the image of the triangle that will be displayed on the main page in order to be able to display a triangle with the odors delivered by the dispenser 11. By using a "Choose image" button on the "Settings" page, an album can be accessed.

The "Products" page of the application has, in the example in question, the following elements:

a choice of the value of each product in code step units from 0 to 1414.

Each unit corresponds to a delivered product volume of 2.33 µl, which is the smallest quantity that the dispenser in this example can deliver; when this page is displayed, it is the values of products on this page that are transmitted in real time to the dispenser. As soon as the page is no longer displayed, the values sent to the dispenser are those of the main page with the triangle;

display of the motor torques for A, B and C in real time refreshed every 45 values.

The mode in which the products are delivered is the iterative or direct dose mode, according to the option chosen on the Settings page.

The "Favorites" page allows configurations to be saved in a file. It provides access in the example in question to 10 files, namely "Configuration 1" to "Configuration 10" in addition to the default file. These files record for example the following parameters:

fractions of products A, B and C,

Purge volume,

Dose volume, fast, medium or slow flow rate,

Dose, Purge or Continuous mode, continuous or iterative dispensing.

Several tests are carried out with the dispensing system.

Example 1 (Ninth Aspect of the Invention)

A set of three base products was created:

| | |
|---|---|
| F1: (orange peel odor) | |
| n-decanal | 6% |
| n-octanal | 5% |
| Klucel H CS | 1% |
| Absolute ethanol qs | 100 |
| F2 (rose odor) | |
| Phenylethyl ethanol | 6% |
| Klucel H CS | 1% |
| Absolute ethanol qs | 100 |
| F3 (anise odor) | |
| Anethole | 2% |
| Klucel H CS | 1% |
| Absolute ethanol qs | 100 |

Each composition has a rheology ranging from 2 to 2.7 Pa·s.

The three cartridges were placed in the three compartments C1, C2 and C3.

Next, several mixtures (200 mg) were created:

Mixture 1: C1 0%, C2 50%, C3 50%

Mixture 2: C1 50%, C2 50%, C3 0%

Mixture 3: C1 50%, C2 0%, C3 50%

Mixture 4: C1 34%, C2 33%, C3 33%

The olfactory notes of these mixtures were compared with mixtures created by balance of precision on 9 g.

Example 2 (Ninth Aspect of the Invention)

The same mixtures as in example 1 were created with the following formulations:

| F1: (orange peel odor) | |
|---|---|
| n-decanal | 6% |
| n-octanal | 5% |
| Klucel M CS | 1% |
| Absolute ethanol qs | 100 |
| F2 (rose odor) | |
| Phenylethyl ethanol | 6% |
| Klucel M CS | 1% |
| Absolute ethanol qs | 100 |
| F3 (anise odor) | |
| Anethole | 2% |
| Klucel M CS | 1% |
| Absolute ethanol qs | 100 |

The olfactory notes of these mixtures were compared with mixtures created by balance of precision on 9 g.

Example 3 (Comparative)

The same mixtures as in example 1 were created with the following formulations:

| F1: (orange peel odor) | |
|---|---|
| n-decanal | 6% |
| n-octanal | 5% |
| Absolute ethanol qs | 100 |
| F2 (rose odor) | |
| Phenylethyl ethanol | 6% |
| Klucel M CS | 1% |
| Absolute ethanol qs | 100 |
| F3 (anise odor) | |
| Anethole | 2% |
| Klucel M CS | 1% |
| Absolute ethanol qs | 100 |

The viscosities were around 2 to 2.5 Pa·s for formulations F2 and F3 and <0.02 Pa·s for formulation F1.

The viscosity of the products was measured at 1 atm and 25° C. with a CONTRAVES TV rotary viscometer fitted with an MS-r3 or MS-r4 measuring bar at a frequency of 60 Hz after 10 minutes of rotation of the measuring bar.

The olfactory notes of these mixtures were compared with mixtures created by balance of precision on 9 g. An olfactory difference was noted in the case of mixtures 2, 3 and 4.
Mixture 2: C1 50%, C2 50%, C3 0%
Mixture 3: C1 50%, C2 0%, C3 50%
Mixture 4: C1 34%, C2 33%, C3 33%

Example 4 (Ninth Aspect of the Invention)

Two people, a specialist and a beginner in the world of perfumes, are speaking on the telephone.

The beginner has the device with the compositions of example 1.

The beginner wishes to develop an aniseed and flowery formulation.

Firstly, the specialist regulates the device to create a mixture (100 mg) M1: C1 20%, C2 0%, C3 80%, which she believes will satisfy the beginner.

The beginner says that she thinks the mixture is too sweet. The specialist interprets this explanation and proposes a mixture (100 mg) M2: C1 20%, C40%, C3 40%, which she believes goes in the direction of the beginner's wishes.

The beginner says that she still thinks the mixture is too sweet. The specialist interprets this explanation and proposes a mixture (100 mg) M3: C1 30%, C50%, C3 20%, which she believes goes in the direction of the beginner's wishes.

The beginner says that she thinks the mixture is almost perfect. The specialist interprets this explanation and proposes three mixtures (100 mg):
M4: C1 35%, C50%, C3 15%,
M5: C1 25%, C50%, C3 25%,
M6: C1 25%, C60%, C3 15%, The beginner chooses her preferred mixture: M5

Next, a large quantity of mixture M5 is produced by weighing (25 g). The beginner then has a perfume with the same olfactory quality as the one she had determined during the work session with the specialist.

The same test carried out with the formulations of example 3 is also possible.

However, there is a difference between the mixture selected during the work session with the specialist and the perfume produced in a large quantity by weighing.

J) Dispensing System with a Set of Cartridges for Customizing the Levels of Durability/Comfort The precision of the color obtained is a very important factor for obtaining a quality result. Users also want to be able to alter the durability and comfort of their makeup depending on the time, but also the location on the face. Usually, by using a product with good durability, the makeup is resistant, even in stressed areas. However, this solution is not satisfactory on account of the discomfort created. The use of a comfortable composition makes it possible to make up the entire face, including the most sensitive areas. However, this solution is not very satisfactory on account of the poor durability of the exposed areas.

It is desirable for the properties of the film to be able to be adapted to the different parts of the face or to the time in order to be able to make up the entire face with one and the same system, even if the different parts of the face require different levels of durability and comfort.

It is known that the treatment of the lips requires good durability. It is known that the treatment of the area around the eye requires a film that is more flexible and comfortable, possibly entailing more limited durability. It is also known that the treatment of the base requires a film that is more comfortable than resistant. Other areas, which are less mobile, may benefit from films that are resistant without causing discomfort (for example, the nose).

It is also desired that the properties of the film can be adapted to different times of the day or of the year in order to be able to apply makeup suited to the time with one and the same system.

Thus, it is known that, sometimes, a person may wish for their lipstick to be as durable as possible, for instance in the case of a performance or show. By contrast, on other occasions, it is comfort which takes priority, for example when socializing.

Usually, the solution consists in using a series of products created for such and such a part of the face. This approach, which is very widespread, presents the problem of the number of references to be provided in order to cover all the needs in terms of color.

In our case, given the desire to create several levels of durability/comfort, the approach would consist in multiplying the products.

Moreover, when there is a desire to be able to vary the concentrations of colored ingredients (in order that the user can have the most suitable color(s) for each area), it is even more difficult to provide an entire range of products, with different colors and different levels of durability/comfort.

One possibility is to provide users with a single system for varying durability/comfort that is mounted with an entire set of cartridges of product providing a variety of film qualities. In this case, depending on the area to be treated, the system will use such and such a product without the user needing the change the cartridges of product in the compartments of the system. However, this approach is not realistic since it requires the system to have a very large number of compartments, and cartridges, requiring complex and expensive technology.

We have thus sought to propose a simple system for regulating the concentration of colored ingredients and of film quality.

This system is especially advantageous for rapidly treating (without having to change systems or cartridges) all of the areas of the face, varying the color thereof, and ensuring suitable film qualities.

It also allows the user to test their colors and film qualities until the best performance in terms of visual effect and comfort has been achieved.

According to a tenth aspect, the invention seeks to solve this problem, and it achieves this aim by virtue of a system for dispensing a product, comprising a dispenser that receives at least two cartridges containing a first base product and a second base product, respectively, the dispenser making it possible to deliver at least these two base products in adjustable proportions, the first base product comprising a volatile solvent and a film-forming polymer, the second base product comprising a nonvolatile oil.

The invention, according to this tenth aspect, has one or more of the following features:
the first base product is in the form of a liquid anhydrous composition,
the second base product is in the form of an anhydrous liquid composition,
the first base product comprises an inverse emulsion,
the second base product comprises an inverse emulsion,
the film-forming polymer is hydrophobic,
the property of the film that varies is its flexibility,
the property of the film that varies is its oily nature,
the property of the film that varies is its tightening nature,
the two base products are chosen to react with one another to form a film,
the first base product comprises a reactive silicone and the second base product comprises a catalyst that brings about the crosslinking of the reactive silicone,
the reactive silicone comprises a mixture of telechelic polyorganosiloxane bearing a vinyl function at the two chain ends and polyhydrogenosiloxane,
the catalyst is platinum based,
the first base product comprises a film-forming polymer and the second base product comprises an oily compound that is liquid at room temperature,
the film-forming polymer has a glass transition temperature Tg greater than or equal to 30° C., better still greater than or equal to 60° C.,
the film-forming polymer is chosen from vinyl, notably acrylic, polymers or copolymers,
the film-forming polymer is lipsoluble,
the first and second base products contain different respective film-forming polymers,
the film-forming polymer of the first base product has a glass transition temperature $Tg1$ and the polymer of the second base product has a glass transition temperature $Tg2$ different than $Tg1$, wherein preferably $Tg1>60°$ C. and $Tg2<10°$ C.,
the first base product comprises a polymer or copolymer chosen from methacrylic polymers and copolymers, polyamides, alkyl celluloses, polymers and copolymers of vinylpyrrolidone, and silicone resins,
the second base product comprises a polymer or copolymer chosen from acrylic polymers and copolymers, vinyl polymers and copolymers and polycondensates such as polyesters and polyurethanes,
the first base product comprises an oily compound with a melting point $Mp1>20°$ C. and the second base product comprises an oily compound with a melting point $Mp2<20°$ C.

According to its tenth aspect, a subject of the invention is also a method for applying a cosmetic, makeup and/or care, product to human keratin materials, comprising the setting of the dispenser depending on the area to be treated, and the dispensing of the product by base products being picked up from the cartridges in the proportions corresponding to the setting of the dispenser.

According to its tenth aspect, the invention is thus based on:
A dispensing system
At least two compartments which preferably comprise different inverse emulsions. One with a volatile solvent and a film former. The other with a nonvolatile oil.
The system may be programmed to deliver, for each location on the face, the best mixture.

According to this tenth aspect, the invention makes it possible to treat one or more areas of the face and to obtain mixtures that are very precise in terms of color faithfulness and comfort and suitable durability for obtaining particularly effective effects. Hereinbelow, the term "area" is used to denote a defined part of the face, fairly small in surface area, covering between 1 cm2 and 100 cm2, better still ranging from 2 cm2 to 50 cm2.

This concept applies here for all treatments in which a film is deposited on the skin, said film being colored, concealing, or not. For example, the concept comprises the application of a protective film (with screening agents) or a treating film (with biological active agents) or a tightening film.

The system according to the invention can vary the film produced, producing an effect of good durability or good comfort, and effects in between. Thus, depending on the adjustments chosen, the durability/comfort properties of the film are not the same.

Dispensing System

The dispensing system may consist of a single device operating autonomously, preferably able to be manipulated in one hand, or of a device that operates in interaction with other components or devices. It may for example entail various outlet interfaces which are mounted on the dispenser depending on the type of makeup to be created, as will be specified below. It may also entail a computer system which exchanges information with the dispenser in order to operate the latter, this computer system comprising, for example, a portable terminal such as a smartphone, a camera phone, a tablet, a laptop computer or a dedicated terminal.

Preferably, the dispenser is designed to pressurize one or more compartments containing the base product(s), via volumetric metering devices, preferably a motor causing a piston to move in the corresponding compartment.

The dispenser may be formed of a housing and of at least two or three compartments, and preferably an identical number of motors. For example, the rotation of the motors drives endless screws which push the pistons of each compartment. The advancing movement of the pistons is, for example, controlled by the number of command pulses sent to the motors and/or by the length of time for which the latter are operating. The motors may be powered in sequence or preferably simultaneously.

For example, the motors are powered during an elementary operating cycle for a short duration one after the other or at the same time as one another, so as to dispense corresponding microdoses.

The elementary cycles are repeated, possibly with a pause between them, giving the base products time to flow out of the compartments.

The compartments may be defined by cartridges, which are removed when they become empty. As an alternative, the compartments are permanently present and refilled once they become empty.

Each cartridge may be closed by a stopper that can be removed to allow the cartridge to be cleaned.

Preferably, the housing of the dispenser is of elongate shape along a longitudinal axis, making it easier to handle, and the cartridges are disposed about this axis, inside the housing.

Preferably, the cartridges are inserted from the rear and the mixture is delivered from the front. The cartridges may be inserted individually or, as an alternative, the cartridges constitute a one-piece assembly as they are inserted.

The cartridges may each have a volumetric metering mechanism comprising a piston moved by a drive mechanism of the dispenser in a direction accompanied by a reduction in the internal volume containing the base product and the expulsion of some product. It may be advantageous for the cartridges to have at least a region of their wall that is transparent so that the color of the product contained therein can be seen.

The drive mechanism may have a motorization system formed of motors coupled to gearboxes, of elongate shape parallel to the longitudinal axis of the dispenser, and positioned between the cartridges. Positioning the motors and cartridges in this way makes the dispenser particularly compact.

The base product can leave the corresponding cartridge in a sealed manner, then flow along a passage provided for this purpose in the housing of the dispenser, before leaving the latter.

The cartridges advantageously end in an end piece produced in such a way that, once the cartridge has been inserted into the housing of the dispenser, the end of the end piece terminates flush with the housing. As an alternative, the end piece is long enough to protrude beyond the housing and thus connect various outlet interfaces that can be attached to the housing of the dispenser.

By virtue of the drive mechanism having motors for causing the pistons to advance, it is possible to precisely deliver mixtures in very small quantities. Thus, the drive mechanism can deliver the base products with a minimum flow rate less than or equal to 50 µL/s, better still less than or equal to 20 µL/s, even better still less than or equal to 10 µL/s. Preferably, the drive mechanism delivers flow rates of between 20 and 100 µL/s, better still between 40 µL/s and 60 µL/s. It is thus possible to easily create a mixture of around 10 mg. Such a dispensing system is therefore ideal for achieving small touches of makeup, for covering an area of 1 cm$^2$, better still an area of 0.5 cm$^2$, for example.

It is also possible to create larger quantities of mixture such as the quantities needed to make up a cheek or a face. These quantities remain relatively low, however, for example a quantity of between 100 and 500 mg, better still between 150 and 250 mg.

Preferably, the cartridge has a dispensing end piece through which the product exits, and this dispensing end piece is driven in rotation by the drive mechanism for moving the piston. The end piece may have at least one rotation-proofing relief, better still two diametrically opposed rotation-proofing studs.

The end piece may bear a seal, notably an O-ring seal. Thus, when changing the cartridge, the seal is also changed, making it possible to get around the problem of seal wear.

The dispenser may have an electronic board for controlling the motorized drive mechanism, this electronic board having the end piece(s) passing through it. This may make it possible to produce a board extending across substantially the entire cross section of the dispenser so that all the electronic components of the dispenser can be grouped together on a single board, thus improving compactness and reliability. The board may extend substantially perpendicularly to the longitudinal axis of the housing. The board may bear a switch for controlling operation of the dispenser.

The dispensing system may be designed to operate in at least two dispensing modes.

In a first mode, referred to as "continuous", the mixture is dispensed as long as pressure is applied to the control switch.

In a second mode, referred to as "dose", a predefined quantity of the mixture is dispensed for each press of the switch.

The end piece(s) may terminate at one end of the housing. This may make it possible to reduce the dead volume, as will be explained in detail below.

The end piece(s) may have at their end a shutoff system for preventing the products from drying out in the duct, for example a self-healing membrane.

The cartridge may have a hollow screw onto which the piston is screwed, the piston being able to move axially along the screw as the latter turns; the piston is prevented from turning in the body of the cartridge. For example, the friction of the piston against the body of the cartridge may be enough to prevent it from turning when the screw turns.

Preferably, rotation is rendered impossible with a cartridge body of non-circular cross section and a piston that is not deformable.

The torque of the motors may be determined electronically depending on the current drawn, and may be used for example to detect that the piston has reached the end of its travel. Information regarding the torque may be transmitted remotely to a computer system that has a man-machine interface, in order that correct operation of the dispenser can be monitored.

In order to adjust the shade, the dispensing system according to the invention has to allow the user to vary the volume delivered from each compartment.

Preferably, the dispenser is operated by a computer system built into the dispenser or external thereto, the dispenser then being able to exchange information with the computer system using a wireless or wired protocol.

The dispenser may thus be operated so as to allow the shade to be adjusted by controlled simultaneous or sequential dispensing of several base products of different colors.

The dispensing of the base products may be continuous; in such a case, the volumes of each of the base products are dispensed in a single shot, simultaneously or in succession.

In the case of simultaneous dispensing, it is beneficial to be able to adjust the respective flow rates of the various base products in order for the dispensed mixture to correspond to the desired mixture at all times. Such a dispensing mode may be suitable in particular when dispensing the mixture by spraying, using an airbrush. To adjust the flow rates it is possible, for example, to alter the speed at which the pistons move, for example in the case where the pistons are driven by an endless screw, by varying the rotational speed of the motors that drive the screw. The products may also be dispensed in a pulsed manner with a dispensing time and a pause in each cycle. By altering the duty cycle it is possible to alter the flow rate.

All the products may be delivered simultaneously during the dispensing time or, as an alternative, the cycles of the various products are phase-shifted from one another so that one product is dispensed while the other products are paused.

In one particular embodiment of the invention, the mixture is delivered into a cavity of a container which may close hermetically or not, for example in the form of a cup, into which an applicator, particularly a stylus or a brush may be slipped. Such a dispensing system is especially suited to liners, glosses and other formulations applied without direct contact with the hands. This container may be removable.

For example, it is used as a lip-color dispenser and has a dispensing system, for example using a screw. When it is not removable, the container may be produced with the body of the dispenser. When it is removable, it may constitute one output interface among others that can be mounted on the dispenser.

The compartments, and in particular the cartridges, may contain all or part of the drive mechanism and, for example, the motorizing system or, better still, part of the motorizing system, the purpose of this being to reduce the number of moving parts in the body of the dispenser outside the cartridges. For example, the cartridges contain the rotor of the motor. Once the cartridges have been installed in the body of the dispenser, the rotors are made to interact with the stators.

The dispensing system is advantageously arranged in such a way as to allow the running of preprogrammed sequences in which the mixture delivered by the system is modified continuously or discontinuously. A "graduated" mode makes it possible for example to progress gradually from a mixture A to a mixture B. In the case where the application is by spraying, notably using an airbrush, this makes it possible for graduations to be achieved simply. An "alternate" mode makes it possible for example to switch quickly from a mixture A to a mixture B several times in succession. In the case of application by spraying, a multilayer application can thus be achieved, with different formulations for two superposed adjacent coats. Another mode makes it possible for example to offer several preprogrammed successive mixtures, the computer system each time indicating to the user how these should be used, for example by display on a screen.

In the case of manual application, the mixtures are dispensed for example into a cup. The person applies the makeup to the recommended place with a corresponding mixture taken from the cup, then, if necessary, cleans out the cup and commands delivery of a new mixture; the operation is repeated as many times as necessary until the person is fully made up.

The mixtures dispensed can be homogenized in various ways depending on the type of use. In the case of manual application, it can be done directly on the application area at the time of application or in the cup before the mixture is picked up; in the case of an airbrush application, the pipe of the airbrush is used as a mixing chamber; if the mixture is dispensed into a container for later use, homogenization can be performed by hand or by passing the dispensed products through a mixing chamber situated between the dispenser and the container or incorporated directly into the container, as described in detail below.

The product may be delivered by the dispensing system and used extemporaneously. As an alternative, the product delivered by the dispensing system is packaged and used later, for example on several occasions, with, for example, at least one day's interval between two uses.

In preferred exemplary embodiments:

Compartment 1 contains a composition C1.

Compartment 2 contains a composition C2.

The contact between C1 and C2, at different ratios, brings about different film durability/comfort qualities.

Composition C1 preferably comprises a lipophilic continuous phase (inverse emulsion or liquid anhydrous composition) comprising a film-forming polymer and a volatile solvent.

Composition C2 preferably comprises a lipophilic continuous phase (inverse emulsion or liquid anhydrous composition) comprising a nonvolatile oil.

Film-Forming Polymer

This type of polymer is particularly advantageous insofar as it makes it possible to significantly increase the durability of the matt effect over time.

According to a particularly preferred form of the invention, the compositions according to the invention comprise at least one hydrophobic film-forming polymer.

Within the meaning of the invention, a "polymer" is understood to be a compound corresponding to the repetition of one or more units (these units resulting from compounds known as monomers). This or these unit(s) are repeated at least twice and preferably at least three times.

Within the meaning of the present invention, a "hydrophobic film-forming polymer" is understood to denote a film-forming polymer that has no affinity for water and, in this respect, does not lend itself to a formulation in the form of a solute in an aqueous medium. In particular, a hydrophobic polymer is understood to be a polymer which has a solubility in water at 25° C. of less than 1% by weight.

A "film-forming polymer" is understood to be a polymer that is capable of forming, by itself or in the presence of an auxiliary film-forming agent, a macroscopically continuous film on a support, especially on keratin materials, and preferably a cohesive film, and better still a film of which the cohesion and mechanical properties are such that said film may be able to be isolated and manipulable in isolation, for example when said film is prepared by pouring onto a non-stick surface, for instance a Teflon-coated or silicone-coated surface.

In particular, the hydrophobic film-forming polymer is a polymer chosen from the group comprising:

film-forming polymers that are soluble in an organic solvent medium, in particular liposoluble polymers; this means that the polymer is soluble or miscible in the organic medium and forms a single homogeneous phase when it is incorporated into the medium;

film-forming polymers that are dispersible in an organic solvent medium, which means that the polymer forms an insoluble phase in the organic medium, the polymer remaining stable and/or compatible once incorporated into this medium. In particular, such polymers may be in the form of non-aqueous dispersions of polymer particles, preferably dispersions in silicone oils or hydrocarbon-based oils; in one embodiment, the non-aqueous polymer dispersions comprise polymer particles stabilized on their surface with at least one stabilizing agent; these non-aqueous dispersions are often referred to as NADs;

film-forming polymers in the form of aqueous dispersions of polymer particles, which means that the polymer forms an insoluble phase in water, the polymer remaining stable and/or compatible once incorporated into the water, the polymer particles possibly being stabilized at their surface with at least one stabilizing agent. These polymer particles are often known as "latices".

Hydrophobic film-forming polymers that may notably be mentioned include homopolymers and copolymers of a compound bearing an ethylenic unit, acrylic polymers and copolymers, polyurethanes, polyesters, polyureas, cellulose-based polymers such as nitrocellulose, silicone polymers such as silicone resins, silicone polyamides, polymers bearing a non-silicone organic backbone grafted with monomers containing a polysiloxane, polyamide polymers and copolymers, and polyisoprenes.

In particular, said hydrophobic film-forming polymer(s) are present totally or partially, and preferably solely, in the gelled oily phase.

As hydrophobic film-forming polymers that are most particularly suitable for use in the invention, mention may be made notably of block ethylenic polymers, vinyl polymers comprising at least one carbosiloxane dendrimer derivative and silicone resins (T resin, MQ resin).

Volatile Solvent

Within the meaning of the invention, a "volatile solvent" is understood to be any oil that is capable of evaporating on contact with the skin in less than one hour, at room temperature and atmospheric pressure.

The volatile oil is a volatile cosmetic compound, which is liquid at room temperature, notably having a non-zero vapor pressure, at room temperature and atmospheric pressure, notably having a vapor pressure ranging from 0.13 Pa to 40 000 Pa ($10^3$ to 300 mmHg), in particular ranging from 1.3 Pa to 13 000 Pa (0.01 to 100 mmHg) and more particularly ranging from 1.3 Pa to 1300 Pa (0.01 to 10 mmHg).

The volatile oils may be hydrocarbon-based oils or silicone oils.

Among the volatile hydrocarbon-based oils containing from 8 to 16 carbon atoms, mention may be made notably of branched C8-C16 alkanes, for instance C8-C16 isoalkanes (also known as isoparaffins), isododecane, isodecane, isohexadecane and, for example, the oils sold under the trade names Isopar or Permethyl, branched C8-C16 esters, for instance isohexyl neopentanoate, and mixtures thereof. Preferably, the volatile hydrocarbon-based oil is chosen from volatile hydrocarbon-based oils containing from 8 to 16 carbon atoms, and mixtures thereof, in particular from isododecane, isodecane and isohexadecane, and is especially isohexadecane.

Mention may also be made of volatile linear alkanes comprising from 8 to 16 carbon atoms, in particular from 10 to 15 carbon atoms and more particularly from 11 to 13 carbon atoms, for instance n-dodecane (C12) and n-tetradecane (C14) sold by Sasol under the respective references Parafol 12-97® and Parafol 14-97®, and also mixtures thereof, the undecane-tridecane mixture, mixtures of n-undecane (C11) and of n-tridecane (C13) obtained in examples 1 and 2 of the application WO 2008/155 059 from the company Cognis, and mixtures thereof.

Volatile silicone oils that may be mentioned include linear volatile silicone oils such as hexamethyldisiloxane, octamethyltrisiloxane, decamethyltetrasiloxane, tetradecamethylhexasiloxane, hexadecamethylheptasiloxane and dodecamethylpentasiloxane.

Volatile cyclic silicone oils that may be mentioned include hexamethylcyclotrisiloxane, octamethylcyclotetrasiloxane, decamethylcyclopentasiloxane and dodecamethylcyclohexasiloxane.

Nonvolatile Oil

A "nonvolatile oil" is understood to be an oil that remains on the skin at ambient temperature and atmospheric pressure for at least several hours, and that in particular has a vapor pressure of less than 0.13 Pa (0.01 mmHg).

These nonvolatile oils may be hydrocarbon-based oils, notably of animal or plant origin, silicone oils, or mixtures thereof. A "hydrocarbon-based oil" is understood to be an oil mainly containing hydrogen and carbon atoms and possibly oxygen, nitrogen, sulfur and/or phosphorus atoms.

Nonvolatile hydrocarbon-based oils that may especially be mentioned include:

hydrocarbon-based oils of animal origin, hydrocarbon-based oils of plant origin such as triglycerides constituted by fatty acid esters of glycerol, the fatty acids of which may have chain lengths varying from C4 to C24, these chains possibly being linear or branched, and saturated or unsaturated; these oils are in particular heptanoic or octanoic acid triglycerides, or alternatively wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passion-flower oil and musk rose oil; shea butter; or else caprylic/capric acid triglycerides, synthetic ethers containing from 10 to 40 carbon atoms, linear or branched hydrocarbons of mineral or synthetic origin, such as petroleum jelly, polydecenes, hydrogenated polyisobutene, squalane and liquid paraffins, and mixtures thereof, synthetic esters such as oils of formula R1COOR2 in which R1 represents a linear or branched fatty acid residue containing from 1 to 40 carbon atoms and R2 represents a notably branched hydrocarbon-based chain containing from 1 to 40 carbon atoms, on the condition that R1+R2≥10, for instance purcellin oil (cetostearyl octanoate), isopropyl myristate, isopropyl palmitate, C12 to C15 alkyl benzoates, hexyl laurate, diisopropyl adipate, isononyl isononanoate, isodecyl neopentanoate, 2-ethylhexyl palmitate, isostearyl isostearate, 2-hexyldecyl laurate, 2-octyldecyl palmitate, 2-octyldodecyl myristate, alkyl or polyalkyl heptanoates, octanoates, decanoates or ricinoleates such as propylene glycol dioctanoate; hydroxylated esters such as isostearyl lactate, diisostearyl malate and 2-octyldodecyl lactate; polyol esters and pentaerythritol esters, fatty alcohols that are liquid at room temperature, with a branched and/or unsaturated carbon-based chain containing from 12 to 26 carbon atoms, for instance octyldodecanol, isostearyl alcohol, oleyl alcohol, 2-hexyldecanol, 2-butyloctanol and 2-undecylpentadecanol, higher fatty acids such as oleic acid, linoleic acid or linolenic acid, and mixtures thereof, The nonvolatile silicone oils that may be used in the composition according to the invention may be nonvolatile polydimethylsiloxanes (PDMSs), polydimethylsiloxanes comprising alkyl or alkoxy groups, that are pendent and/or at the end of a silicone chain, the groups each containing from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes, and mixtures thereof.

Preferably, the oily phase comprises at least one silicone oil, even more preferably chosen from:
volatile cyclic silicone oils having a viscosity at room temperature of less than 8 cSt and containing in particular from 4 to 7 silicon atoms, these silicones optionally comprising alkyl or alkoxy groups containing from 1 to 10 carbon atoms, in particular chosen from hexamethylcyclotrisiloxane, octamethylcyclotetrasiloxane, decamethylcyclopentasiloxane and dodecamethylcyclohexasiloxane (cyclohexasiloxane), and mixtures thereof:
volatile or nonvolatile polydimethylsiloxanes (PDMSs) (INCI name: Dimethicone);
phenylated silicones;
polydimethylsiloxanes comprising aliphatic groups, in particular alkyl groups, or alkoxy groups, which are pendent and/or at the end of the silicone chain; these groups each comprising from 6 to 24 carbon atoms, and more particularly caprylyl methicone, such as the commercial product Dow Corning FZ-3196® from the company Dow Corning;
mixtures thereof.

Optimization

It is very advantageous to have as few compartments as possible.

Thus, if the system is desired to be able to adjust the color, it will be necessary to provide two compartments in addition to the two intended for controlling the film quality.

Thus, it will be necessary to provide:
compartments 1 and 2 containing the ingredients for varying the quality of durability/comfort of the film, and
other compartments (3 or 4 for example), for placing the ingredients M for varying the color therein.

It is also possible to place the active agents M in compartments 1 or 2 or 1 and 2.

In this way, the total number of compartments is reduced to 3, or even 2, rather than 4.

For example, the active agents M are put in the products that are placed in compartments 1 and 2. In compartment 1, M is set at a high concentration, and in compartment 2, M is set at a low concentration.

The active agents that produce the film and regulate the durability/comfort properties thereof are thus placed in compartments 1 and 2. Specifically, in the example, a polymer+volatile solvent in compartment 2 and the nonvolatile solvent in compartment 1.

If the system is used with a majority setting in 1, a product with a concentration of nonvolatile solvent and active agent M is obtained.

The majority setting in 1 can then be used on foundation areas where extensive coverage and a comfortable film are desired.

The majority setting in 2 can be used on marked areas of the face. The low quantity of colored active agent M does not make it possible to obtain good concealing, but this concealing will last over time, thus compensating for the moderate concealing power. The discomfort in these areas, of limited area, is not considered bothersome.

It is possible to place an active agent M1 in a product intended for compartment 1 and an active agent M2 in a product intended for compartment 2. For example, M1 is a yellow pigment and M2 is a red pigment. The active agents that produce the film and regulate the durability/comfort properties thereof are thus placed in compartments 1 and 2. Specifically, in the example, a polymer+volatile solvent in compartment 2 and the nonvolatile oil in compartment 1.

The majority setting in 1 can then be used on foundation areas where a base color and a comfortable film are desired.

The majority setting in 2 can be used on areas such as the lips or the cheeks. A reddish color with good durability is obtained.

It is possible to place an active agent M1 in a product intended for compartment 1 and the same active agent M1 in a product intended for compartment 2. For example, M1 is a yellow pigment. The active agents that produce the film and regulate the durability/comfort properties thereof are thus placed in compartments 1 and 2. Specifically, in the example, a polymer+volatile solvent in compartment 2 and the nonvolatile oil in compartment 1.

The majority setting in 1 can then be used on foundation areas where a base color and a comfortable film are desired.

The majority setting in 2 can be used on contour areas such as the top of the forehead or the nose. Thus, the same color as the rest of the face is obtained, but with better durability, making it possible to resist movements and rubbing and movements of the hair and/or spectacles.

It is possible to place the active agents M in a compartment 3. For example, a yellow pigment is placed therein.

The active agents that produce the durability/comfort of the film and regulate the film properties are placed in compartments 1 and 2. Specifically, in the example, a polymer+volatile solvent in compartment 2 and the nonvolatile oil in compartment 1.

The invention according to this tenth aspect is not limited to active agents that provide coloring effects. It is possible to use care active agents such as anti-aging, antioxidant, anti-wrinkle, antiperspirant, mark-preventing, photoprotective and moisturizing active agents.

It is also possible to mix active agents that provide coloring effects and care effects.

Use for Making Up One or More Precise Areas of the Skin

The dispensing system allows makeup to be applied, day after day, with only the areas that need to be hidden being treated. To this end, small doses of makeup are delivered, and are applied specifically and sequentially to the corresponding areas. Each small dose is created using the mixture suited to the area.

In one preferred embodiment of the invention, the dispensing system waits for information regarding which area is to be treated and then delivers the corresponding mixture. It may use a preprogrammed look-up table for that purpose, this table being the result for example of a learning process as defined below.

In one particularly advantageous embodiment, the programming takes into account the resistance and comfort to be achieved in order to obtain optimum results. As an alternative, the dispensing system informs the person, when delivering a mixture, of the area to which the person is to apply the mixture. Thus, the dispensing system may follow an application program in which it delivers, in a given order, the various mixtures that are to be applied.

In one particular embodiment of the invention, the dispensing system is informed as to the quantities to be delivered. For that, it memorizes the relationship between the color, the area of the face and the quantity needed, thereby making it possible to reduce costs and wastage of product, and to cover the skin only lightly, thus avoiding occlusion effects. In so doing, it is possible to use products that have a high covering capability and provide too much cover to be applied to the whole of the face. Thus, it is possible to obtain makeup of natural or even undetectable appearance.

The dispensing system may also make it possible, by facilitating the dispensing of small quantities and rapid use thereof, to reduce the time for which the products are kept, thus making it possible to reduce the risks of the products changing and/or to reduce the amounts of preservative to be used.

The dispensing system is suited to treating the areas that are to be concealed, without having to conceal the entire face.

When the user is looking for the color to apply to an area of the face, it is advantageous to memorize the color best suited to each area, and the dispensing system is thus advantageously designed to memorize this color and the corresponding area. Thus, by using the memorized information, on each use, the same mixture can be delivered for each area or, if several areas are being treated, the same series of mixtures can be delivered for the same series of areas.

The dispensing system may also be designed to allow an area to be treated by varying the colors application after application. Thus, the person may make up her lips using different colors that she chooses on a day-by-day basis to suit her tastes. This approach is also suitable for the eyelids or eyelashes, and for face makeup because the person may fancy a change of foundation color. For example, on weekdays, the person applies a pale colored foundation, with a more tanned foundation color at the weekends, or may have eye makeup in one color one day and another color another day.

The dispensing system may be designed to allow the user to change color to suit her tastes according to the day, the time, what she is wearing, and the weather. Thus, a system to assist with decision making is advantageously provided to guide the user in her choices of color.

An assistance system may also be provided for balancing the colors on the same face and contribute toward a successful overall makeup look.

It may be desirable for several people in the same group, for example a family, to be able to use the dispensing system, thus reducing costs and minimizing the space taken up. This solution is particularly suited to travel or hotels, campsites, airplanes, campervans, boutiques, schools, etc. For that, provision may be made for the dispensing system to be able to be informed as to which person is using it, so as to access pre-stored personal data.

Continuous Use for Graduated Makeup

In this application, the dispensing system changes the formulation of the mixture while it is delivering the product. In addition, the outlet for the base products or for the mixture is moved relative to a container or a support defining an application surface. In one particular embodiment of the invention, the dispensing system is designed to calculate the way in which the mixture evolves as a function of the color C1 of one area to be treated and of the color C2 of another area to be treated. For example, with the knowledge that the chin requires a color C1 and that the cheek requires a color C2, the dispensing system may vary the formulation of the mixture while it is delivering it in order to graduate the color between these two colors. This makes it possible for example to better conceal imperfections of the face while ensuring that the end result is realistic, or allows color to be graduated for beautifying purposes. The dispensing system may also be designed such that the user can command a variation in color of the mixture dispensed without the start and/or end colors having been set beforehand. To do that, the dispensing system may possess a location or auto-location system and deduce from a look-up table the colors C1 and C2 that it has to create and therefore the changes in the mixture that it has to make.

The dispensing system may have an outlet head, in particular in the case of an airbrush, which is mobile and steered. This option then makes it possible to achieve graduated effects without moving the rest of the dispensing system. For example, the dispensing system is located near to the cheek, then a control system is triggered that will automatically steer the variation in formulation of the mixture and the movement of the outlet head so as, for example, to make the center of the cheek redder than the periphery thereof, with a graduation between the two.

The dispensing system may even be used to create tailor-made products that are kept for several applications.

It is also possible to produce solid or semi-solid products.

Manufacture of "Bespoke" Compacts or Other Solid or Semi-Solid Products

The dispensing system may be designed to allow a mixture to be chosen and delivered to a container such as a cup. The mixture preferably comprises compounds which are such that the mixture can set solid.

More preferably, use is made of compounds that make the setting especially rapid. These compounds are either deposited in the container before or after it is filled with the other ingredients, or are provided in the compartments of the dispenser with the other constituents of the base products, or are contained in the dispenser in a compartment especially designed to contain them.

Specific compositions which may harden quickly by chemical, biochemical or physicochemical reaction after discharge may thus be dispensed.

These compositions are especially designed for the creation of compacts, namely they:

set solid, yield a material that can crumble if rubbed, and are preferably colored.

Preferably, these compositions are very rich in solid particles, with for example more than 10% by mass of solid particles relative to the total mass of the composition, better still more than 20% by mass of solid particles relative to the total mass of the composition, even better still more than 30% by mass of solid particles relative to the total mass of the composition, preferably between 10 and 40% by mass of solid particles relative to the total mass of the composition. These compositions may contain absorbent particles or reactive compounds, such as those that react in contact with the air, for example cyanoacrylate or alpha-silanes or those which react to light, notably UV.

The container into which the mixture is dispensed may contain a compound A and the dispensed compositions may contain a compound B, A and B being chosen to react with one another and solidify the mixture.

In one particular embodiment of the invention, the dispensing system incorporates a heating means, for example with an electrical resistor, to create lipsticks or other waxy products. In that case, the base products are heated before being delivered.

The dispensing system may also comprise a means for supplying heat and/or light energy, after the mixture has been dispensed into a container, for example an electrical resistor or an LED, notably UV. This energy may accelerate the setting-solid of the dispensed mixture.

Preferably, the mixture is homogenized before it sets solid.

Creation of Color Palettes

The dispensing system may have a support, having several regions, and may be designed to automatically generate several mixtures deposited in said regions, for example a series of colors suited to various parts of the face.

The support may define several cavities to receive the mixtures or may bear several containers, for example in the form of cups, potentially cups that are separable from the support.

In one particular case, the support adopts the shape of a face with regions for receiving the mixtures for targeted application areas.

The support may be able to move, notably to rotate, with respect to the body of the dispenser and, for example, may be driven in its movement by the dispenser so that various spaces or containers can be filled in succession.

Cup-Type Dispenser

There is a benefit to having a dispensing system capable of delivering a mixture that the user can easily pick up. Moreover, in cases in which the base products delivered by the dispensing system are not already blended, there is a need to allow the user to perform the mixing easily.

The dispensing system may have a cup and a dispenser for filling the cup with at least one product, the cup being secured to the dispenser at least while it is being filled.

The cup is sometimes also known as a "crucible" and that term should be understood in its broadest sense.

A "cup secured to the dispenser" should be understood as meaning that the cup is held, notably immobilized, at least temporarily, on the dispenser, being for example fixed to the latter by screws, magnetic attraction, clip-fastening, bayonet locking, clamping, or produced with a part of the dispenser body by material molding. When it is secured to the dispenser, the cup allows the latter to be manipulated in one hand, the cup remaining in place on the dispenser while the latter is being moved around.

The dispenser may be offered to the user with the cup already in place.

As an alternative, the cup is installed by the user the first time the dispensing system is used.

The cup is preferably less deep than it is wide, making access to it easier and allowing the product, notably the mixture, to be picked up with an applicator or a finger.

Preferably, the cup is separable from the dispenser and constitutes one outlet interface that can be chosen from a collection of outlet interfaces that can be mounted on the dispenser, at the choice of the user and according to the making up to be performed, as described in detail below.

Preferably, the dispensing system comprises several filling orifices for filling with different base products, opening into the cup. Thus, the mixing of these products may take place in the cup.

The cup preferably has a bottom that is concave toward the outside, making it easier for the user to clean it between two uses.

In addition, this may make the product easier for the user to pick up and the base products easier to mix.

Preferably, the dispenser allows at least two base products to be delivered into the cup, in adjustable proportions, and better still at least three products.

In one exemplary embodiment, the dispensing system has at least two cups that can be selectively fed by the dispenser. This may allow the user to fill these two cups quickly with mixtures with different characteristics. This may facilitate the testing of colored substances and/or allow the preparation of several different color mixtures intended for making up respective areas of the face. The cups may be associated with identifiers that remind the user of the area of the face for which a mixture contained in a given cup is intended.

The cups may be able to move relative to the dispenser, being for example borne by a mobile support such as a turret that is rotatable with respect to the dispenser or by a slide capable of translational movement with respect to the dispenser.

The dispensing system may comprise a lid for closing the cup. This closure lid is preferably transparent so that the user can see the color of the mixture contained inside.

When the cup is separable from the dispenser it may if necessary be introduced into a housing that allows it to be transported more easily, this housing being able, if necessary, to contain a mirror and/or an applicator. The lid of the housing may in this case act as a lid for the cup.

The volume of the cup may be between 2 and 1000 mm$^3$, better still between 100 and 1000 mm$^3$, even better still between 250 and 750 mm$^3$.

The base product(s) delivered into the cup are preferably foundations, but as an alternative may be makeup products for the lips or eyelids.

The cup preferably has a shape that exhibits symmetry of revolution. As an alternative, it has a polygonal or some other contour. Its largest inside diameter, or that of the inscribed circle in the case of a noncircular contour, is preferably between 2 and 100 mm, preferentially between 5 and 40 mm. Its depth is preferably between 1 and 10 mm, better still between 3 and 8 mm. Preferably, the size and shape of the cup either allow direct application of the mixture to the skin or allow the mixture to be picked up on a finger or using an applicator. The cup may be made of an elastically deformable material, making it possible for example to turn the concavity of the bottom of the cup inside out and empty it more easily or use it to apply the product.

The cup may have no blender; in that case, the base products may arrive in the cup from the dispenser in the unmixed state, via distinct respective dispensing orifices. As an alternative, the dispenser incorporates a blender and the base products arrive in the cup already blended.

The cup may also incorporate a static blender as described in detail below, which is fed via distinct filling orifices of the dispenser and which preferably delivers the mixture into a cavity of the cup situated above the blender.

A further subject of the invention is a method for preparing a makeup product, comprising the step of filling a cup of a dispensing system as defined above with at least one base product from the dispenser.

Several products may be delivered into the bottom of the cup, then blended using a finger or an applicator, or a static blender incorporated into the cup.

The cup is preferably filled from beneath. Dispensing systems using a sonotrode have been proposed in the past.

The cup according to the invention is not intended to vibrate in order to dispense the product(s) conveyed by the feed passage(s) supplying it. It differs from a sonotrode. Preferably, the cup is made of plastic.

Blender Incorporated into the Outlet Interface

There is a benefit in having a dispensing system capable of delivering a mixture that can easily be used, notably picked up by the user, without the need for an additional mixing action on the part of the user.

The dispensing system may have a dispenser having outlet passages for base products and an outlet interface that is separable from the dispenser, this interface having a static blender that preferably delivers the mixture into a cavity where it can be picked up.

The static blender may be situated under the abovementioned cavity. The dispensing system is then particularly suited to the creation of compacts, using cups with an in-built static blender as outlet interfaces. In that case, the cavity of the cup is filled with product from beneath. After passing into the static blender, the blended base products cover the blender.

It is possible to use several outlet interfaces and to fill them with different respective mixtures, without the need to purge the blender, thereby reducing losses of product. The outlet interface may be a single-use interface, if necessary.

Preferably, the static blender has a central chamber communicating with base product intake ducts. This central chamber may communicate with a peripheral chamber having a series of partitions which act as deflectors for the mixture and create shearing thereof The peripheral chamber may have a perforated annular partition defining perforations through which the mixture passes as it circulates in the peripheral chamber. The central and peripheral chambers may be closed at the top by a wall which defines the end wall of the cavity receiving the mixture.

The end wall of the peripheral chamber may be of helical shape about the axis of the cup and of a height that decreases in the direction toward the outlet. The latter may open ahead of a connecting ramp connecting the end wall of the peripheral chamber and the top wall of the blender, this connecting ramp preferably being a portion of a helix extending the helix formed by the end wall of the peripheral chamber.

Preferably, the peripheral chamber comprises the abovementioned annular partition and radial partitions that force the mixture to circulate alternately between upper and lower regions of the peripheral chamber and between radially inner and outer regions, the mixture circulating for example from an upper and radially outer region to a lower and radially outer region by passing through the abovementioned annular partition.

The blender may have an outer body in which a component forming the core of the blender is housed, the outer body radially closing the peripheral chamber on the outside and comprising an upright that separates the central and peripheral chambers.

The outer body of the blender and the core of the blender may each be produced as a single piece by injection molding.

Reduced Dead Volume

There is benefit to be had in reducing the losses of product when changing the formulation of the mixture and in allowing the color of the mixture to be varied as quickly as possible during application, particularly when the dispenser is coupled to an airbrush.

The dispensing system may have a dispenser receiving at least two cartridges that each have a reservoir containing a base product, the latter leaving the cartridge through an outlet passage of the cartridge, this outlet passage opening out at the outside of the dispenser or near the external surface thereof.

The outlet passage may notably open into an area in which the mixture is picked up or close to this area, notably less than 5 mm away, better still less than 3 mm away, better still less than 1 mm away, or even better still flush therewith.

The cross section of the outlet passage is, for example, between 1 and 3 $mm^2$. Thus, each base product coming from a cartridge can leave the dispenser without mixing with a base product from another cartridge and the dead volume that cannot be picked up and is likely to increase the inertia of the system is minimized. The product is more quickly available without having to circulate through special passages in the housing of the dispenser, thereby avoiding a painstaking purging step in the event of a cartridge change.

The outside of the dispenser may be the product pickup area, notably when the dispenser is produced with a cup that is not designed to be removed, into which the mixture is dispensed, or a dispensing area intended for the mounting of a removable outlet interface, which defines the pickup area. This outlet interface may have a cup as defined above. This mounting area corresponds for example to the outside of the housing of the dispenser in the absence of the outlet interface. The mounting area may be substantially planar and perpendicular to the longitudinal axis of the dispenser housing.

The dispenser may have three cartridges of base products.

The dispenser may have housings for receiving the cartridges, which are preferably received removably in the dispenser. The latter may comprise passages for ducts for the cartridges defining the outlet passages.

The length of these ducts is preferably such that the ducts are set back slightly from the end or lie flush with the cavity used for picking up the product or, as an alternative, are set back slightly from or lie flush with the end face of the housing of the dispenser that defines the mounting area.

These ducts of the cartridges may be end pieces used for causing the pistons to move within the cartridges, as described in detail above.

Multiple Outlet Interfaces

There is a need to be able, using the same dispensing system, to achieve different makeup looks easily and be able, if so desired, to make up areas as different as the skin, the lips, the eyelashes or eyebrows.

The dispensing system may comprise an assembly having a dispenser of at least one cosmetic product, in particular makeup, and at least two outlet interfaces, each of which can be mounted removably on the dispenser, these outlet interfaces being able to receive the product(s) delivered by the dispenser, preferably being chosen from the following:
- an outlet interface having a container, notably a cup, allowing the product to be picked up using a finger or using an applicator,
- an outlet interface allowing the product to be delivered to a spray system, notably an airbrush,
- an outlet interface having several regions for receiving the product, which can move relative to the dispenser,
- an outlet interface that allows the product to be delivered to a dispensing end piece.

Preferably, the assembly comprises at least three of said outlet interfaces, or better still the four outlet interfaces.

The dispenser may comprise at least two different base products and allow these to be delivered in variable proportions and, preferably, the dispenser comprises three different base products and allows these to be delivered in variable proportions.

Each outlet interface may have a base allowing it to be fixed to the dispenser. This fixing may be done using screws for example, but preferably the base is designed to allow an outlet interface to be removed and replaced without the need for tools. It is, for example, a quarter-turn fixing or a fixing using an external locking ring.

The outlet interface and/or the housing of the dispenser may comprise seals allowing sealed communication between the housing of the dispenser and the outlet interface. If appropriate, the dispenser is designed to recognize the outlet interface mounted above, for example by virtue of the outlet interface having identifiers in the form of specific reliefs which are detected by the dispenser, or in the form of an electronic chip that the dispenser recognizes. That may allow the operation of the dispenser to be adapted to the outlet interface mounted above. The dispenser may communicate information about the outlet interface it is bearing to a computer system, and the computer system may, on the basis of this information, display a specific screen and/or run a specific program for controlling the operating parameters of the dispenser so as, for example, to adapt the dose dispensed and/or the flow rate to the type of outlet interface.

The user may be initially offered several outlet interfaces with a common dispenser within one and the same package, for example a case or a cardboard box.

A further subject of the invention is a makeup method involving the step of selecting an outlet interface, mounting it on the dispenser, and delivering the product(s) contained in the dispenser to the interface.

Mapping and Learning

The term "mapping" should be understood here as meaning a process of indexing a color with an area, with recording.

The mapping may relate to applications to areas smaller than 1 cm². However, the naked eye then has difficulty in discerning whether the result obtained is adequate, and it is preferable to substitute an instrumented evaluation with magnification for evaluation by the naked eye. Small quantities of colored substance may be applied with a finger, using conventional tools such as brushes, or using specialist applicators.

The map may be generated during a learning period in which the user carries out tests with mixtures on different areas of the face; once created, the map can then be used for everyday makeup. This learning period may take account of the resistance and the comfort. In the process, the user tests several adjustments and inputs the best adjustment obtained.

Specific graphic interfaces can be used during the learning period and during the period of use of the map.

In particular, the dispensing system may be used with a graphic interface in which the operator sees the face, which is for example a schematic, figurative or accurate representation such as a photograph or a 3D simulation. In that case, the operator can point at part of the face on the screen to show and/or deliver the appropriate color.

The graphic interface may also show the other areas of the face where use of that same color is appropriate.

To create the map, the operator applies a color, then makes an assessment.

The areas of the face can be treated one after the other; for example, the exercise is carried out on part of the cheek, then on the nose, etc.

Another option is to create a given mixture and apply this same mixture to several areas. The operator then needs to look for the area of the face to which the color is suited. The mixture is then indexed in the computer system which attributes it to the area(s) of the face for which it is suitable.

In one of its aspects, independently of or in combination with the other aspects thereof, and notably with the foregoing, one subject of the invention is a learning process for a dispensing system comprising a dispenser for dispensing a mixture of variable color, and a computer system for selecting a color and for storing data, comprising the steps of
  a) selecting at least one color with the aid of an interface of the computer system,
  b) delivering, with the aid of the dispenser, at least one mixture of the selected color,
  c) evaluating the mixture(s) dispensed following the application thereof to at least one area of the face,
  d) memorizing the characteristics of at least one mixture, notably a mixture that the user wishes to be able to recall, and of at least one area on which it has been tested.

This memorizing can be carried out notably with a view to subsequent dispensing of this mixture for making up said area.

Preferably, the computer system is designed to allow the user to indicate whether or not the result of the test is satisfactory, or even to inform same of the comparison with a test carried out earlier.

It is also possible to create a given mixture and to look for the area of the face for which it is suitable. The mixture is then recorded, being attributed to the area(s) of the face for which it is suitable, in a look-up table that will be used subsequently in order to deduce which mixture to use on the basis of an area of the skin.

The same procedure can be adopted with other mixtures in order to create a map of the entire face and thus have a complete look-up table for the face.

It is also possible to create a given mixture, apply it to a given area, and then vary the mixture until the most suitable mixture is obtained. The mixture is then recorded, being attributed to the area(s) of the face for which it is suitable, in a look-up table that will be used subsequently in order to deduce which mixture to use on the basis of an area of the skin.

Preferably, the computer system evaluates and memorizes the quantities used area by area. Such a method, which uses "test patches" makes it possible to identify the product(s) required by the person wishing to apply makeup. Thus, the dispensing system can be used at sales outlets to advise people wishing to apply makeup or at home in order to define correctly which products to order.

The interface of the computer system preferably has a touch screen displaying the color of the mixture when it is selected.

The interface may display a face and allow the computer system to be informed by selecting the area on the face displayed.

The computer system is preferably designed to allow an area, mixture reconstruction parameters, and the date of the test and/or any other identifier of the mixture to be associated with one another.

The computer system is preferably also designed to allow at least one of the following data: the name of the area, the period of the year, the name of an event, a user identifier and the age of the user, to additionally be associated with said area, with the mixture reconstruction parameters, and with the date or identifier of the mixture.

Steps a) to c) may be repeated at least once before the characteristics of the mixture are memorized in step d).

The computer system may be designed to search a database for a reference of a commercial product on the basis of the characteristics of the mixture identified as being suitable for at least one given area, and to relay this information to the user.

The selection in step a) may be carried out using an expert system, which may or may not be external to the computer system.

The expert system may analyze an image of the user in order to propose a mixture color at least on the basis of the image analyzed.

Step a) may be preceded by the computer system proposing to the user a color and an area to be tested with a mixture of this color.

The computer system may be designed to allow the user to inform same of his or her assessment of the result of the test in step c) and to generate a proposal to modify the mixture to be selected upon return to step a).

The computer system may be designed to propose at least one color of mixture in step a) depending on an application area of which it has been informed by the user.

The computer system may be designed to propose at least one application area in step a), on the basis of a color of which it has been informed by the user.

The dispenser may deliver, in step b), at least two mixtures of different colors, preferably separate, so that they can be applied simultaneously to the test area.

This may allow time to be saved and make it easier to compare the results.

A further subject of the invention is a method of making up using a dispensing system according to this aspect of the invention, in which:
- a) the user sends the computer system a request regarding a need for makeup,
- b) in return, the computer system generates a proposed color for making up an associated zone, on the basis of the learning performed beforehand, and
- c) the computer system operates the dispenser to produce the mixture of the proposed color, notably if this is validated by the user.

Such a method may use a map previously established with the user.

A further subject of the invention is a computer program product containing code instructions which, when run in a computer system, allow the computer system to be made to:
- allow the user to select at least one color and/or one application area, notably using an interface such as a touch screen,
- operate a dispenser in such a way as to deliver a mixture of the color selected by the user,
- allow the user to trigger the memorizing of the color of the mixture and of an associated application area, notably with a view to subsequently dispensing the same mixture, notably on the same area.

The computer program product may comprise code instructions which, when run in a computer system, allow the computer system to be made to:
- receive a request from the user regarding a need for makeup, notably using an interface such as a touch screen,
- propose, on the basis at least of data generated by the learning process as defined above, at least one color and/or one application area,
- operate a dispenser to produce the mixture of the proposed color, notably if this is validated by the user.

Remote Assistance

It is desirable to be able to assist the user in applying makeup, notably in choosing the correct colorings.

A further subject of the invention is thus a makeup method comprising the steps of:
- allowing a video link to be established, for example over the Internet, between a camera on a first site and a second site,
- allowing the second site to directly or indirectly operate a dispenser present at the first site, this dispenser making it possible to vary the color of a mixture dispensed,
- allowing a person present at the first site to apply the mixture dispensed and to send a corresponding image to the second site, so as to receive in return information relating to the makeup result.

The second site may notably have a viewing screen which allows an adviser sitting at this screen to see the makeup result with the product dispensed by the dispenser and advise the person who has applied the makeup. This adviser may in return influence the dispenser to alter the color of the mixture and adapt it to best suit the face of the person present at the first site. Thus, this person controls the mixture delivered by the dispenser. The first person may make herself up under the gaze of the second. The second person sees the result of the test on their screen and can thus correct the mixture that this second person will control remotely until the ideal makeup is obtained.

If appropriate, the video acquisition can be calibrated using a test pattern or with the mixture dispensed by the dispenser onto a reference surface. That then allows a more faithful display of the makeup applied at the first site.

Preferably, the video link between the two sites is a two-way link.

The first site may receive a tutorial from the second site, if appropriate.

Identifiers of the base products may be communicated to the second site; this may make it possible to precisely determine the color of each of the base products.

The method may involve memorizing the dispenser setting parameters once a given mixture is considered to be satisfactory. Preferably, this memory storage may be commanded from the second site. The memory storage may be in the computer system present at the first site and/or on an external server.

One alternative may be to have one person working to help several apply makeup. This embodiment makes it possible to develop makeup artists and their work, either within an institute or over the Internet. It also allows people with limited capabilities, such as people with poor eyesight, or people who have difficulty discerning colors, or the elderly, or those lacking in self-confidence to apply makeup.

Operation Via Touch-Sensitive Interface

There is a need to make it easier to control the dispensing system and notably the choice of the color of the mixture dispensed.

In another of its aspects, independently of or in combination with the other aspects thereof, and notably with the foregoing, one subject of the invention is thus a dispensing system comprising a dispenser and a computer system for operating the dispenser, this computer system comprising a touch screen on which the color of the mixture may be displayed and a selection means that can be moved over the screen in order to vary the color of the mixture dispensed.

Preferably, the screen displays end-point colors between which the color of the mixture can be selected by moving the selection means between these end-point colors.

The screen may display a scale of colors between at least two colors, or an area, notably of triangular outline, within which the selection means can be moved. This area may locally show the color of the mixture depending for example on the distance from each of the vertices, each one embodying a pure base product.

The computer system may perform some of the calculations necessary to determine the fractions of each of the base products that lead to a mixture of the desired color.

The computer system may be a smartphone, a camera phone, a tablet, or a personal computer. As an alternative, it is incorporated into the housing of the dispenser.

The computer system may have a camera. The latter can be used notably for capturing an image of the user and/or of the mixture.

The computer system may be designed to display an image of a face, in order to make it easier to identify the areas to which the mixture is to be applied.

Coupling of the Dispensing System to a Spray Means

The dispensing system may have or be connected to a means of spraying the mixture, preferably an airbrush.

Another of the aspects of the invention is to improve still further the dispensing systems that comprise a spray system, preferably an airbrush, and according to one of its aspects, independently of or in combination with the other aspects, and notably the foregoing, one subject of the invention is an assembly comprising:
- a spray means, preferably an airbrush having a pickup chamber subjected to a stream of entrainment air,
- a dispenser having at least two compartments containing different base products, the products being delivered to the spray means preferably via distinct distribution orifices.

The dispenser may have three cartridges containing makeup products of different colors.

The airbrush may have a stylus defining the pickup chamber, the stylus being fixed to the dispenser or to an outlet interface fixed to the dispenser, or forming an integral part of this outlet interface.

The dispensing system may have a circuit controlling operation of the dispenser, allowing the proportion of base products delivered to the pickup chamber to be varied while the airbrush is in operation. The proportions may be modified depending on the movement of the airbrush relative to the surface onto which the mixture is sprayed. This movement may be mechanized, if appropriate.

This control circuit may have or be constituted by a computer system as defined above.

The housing of the dispenser may act as a hand grip when the assembly is being handled for delivering the mixture.

The dispenser may have a camera and/or one or more sensors such as accelerometers so as to automatically locate the area to which the mixture is applied, and so as to be able to automatically regulate the color depending on the position, if appropriate.

A further subject of the invention is a method for applying makeup using an assembly as defined above, in which a mixture is sprayed onto the skin using the spray means, notably the airbrush.

The composition of the mixture can be modified as the airbrush is moved relative to the skin. A graduated effect can be achieved.

This aspect of the invention is based on the observation that the dispenser can be used to supply the spray system, notably the airbrush, while at the same time allowing the dispensing system to be responsive enough to allow a change in the color of the mixture dispensed while the face is being made up, notably as the area to be made up changes.

It may be advantageous for the dispensing of products to be performed iteratively, notably with dispensing times that are not phase-shifted between the various products.

This may make it easier to vary the composition of the mixture dispensed over time.

The mixture may be created directly in the airbrush, with practically no troublesome dead volume, thus allowing the mixture sprayed to be changed in real time.

The depression created in the pickup chamber is strong enough to entrain the base products without in any way impeding the metering.

The depression which prevails in the pickup chamber is for example between 10 mbar and 200 mbar, better still between 50 and 150 mbar, even better still between 75 and 125 mbar.

The viscosity of the base products as measured at 1 atm and 25° C. with a CONTRAVES TV rotary viscometer fitted with an MS-r3 or MS-r4 measuring bar at a frequency of 60 Hz after 10 minutes of rotation of the measuring bar is, for example, between 0.05 Pa·s and 50 Pa·s.

The cross section of the passages along which the base products arrive in the chamber is, for example, between 1 and 3 mm$^2$, better still between 2 and 3 mm$^2$.

The product is preferably supplied continuously.

It is also possible to apply immiscible or reactive base products, such as an aqueous gel and an oily gel, simultaneously, and these will be deposited directly onto the skin in a pixelated manner, producing a kind of gel/gel in situ, reactive silicones, or colorants that react with one another. The ratios of base products can be adjusted depending on the particular result desired. For example, in the case of aqueous gels and oily gels, the ratio corresponding to the volume of the first base product to the volume of the second base product could be varied between 10/1 and 1/10, better still between 5/1 and 1/5.

Location or Auto-Location System

The dispensing system according to the invention may have a location or auto-location system.

A location system is the name given to a means via which the person inputs the area that she is to treat. This can be performed notably using systems that leave at least one hand free. Thus, an interface of a computer system such as a touch screen, a joystick, or voice recognition system can be used.

An auto-location system is the name given to a means for inputting the area that is to be treated without intervention on the part of the person. This can be achieved using one or more accelerometers which deduce, from the movements, the directions targeted by the person or by a camera and an image recognition system.

Examples of dispensing systems suitable for the invention according to its tenth aspect are shown in the figures, which will not be described in detail again.

Example (Tenth Aspect of the Invention)

Several base products are created (the proportions are by mass)

The formulation F2 is rich in film-forming agent and volatile solvent. The formulations E1 and F3 are rich in nonvolatile oils (phenyl trimethicone et squalane) and are different colors.

|   |   | F1 mass % | F2 mass % | F3 mass % |
|---|---|---|---|---|
| 1 | Dimethicone copolyol sold under the reference KF 6017 by the company Shin-Etsu | 2 | 2 | 2 |
|   | Cetyl PEG/PPG-10/1 dimethicone sold under the reference Abil EM 90 by the company Goldschmidt | 0 | 1 | 0 |
|   | Bis PEG/PPG-14/14 dimethicone + Cyclopentasiloxane sold under the reference Abil EM 97 by the company Goldschmidt | 1 | 0 | 1 |
|   | Cyclopentasiloxane | 17.65 | 0 | 17.65 |
|   | Cyclohexasiloxane | 0 | 8.2 | 0 |
|   | Isododecane | 0 | 1 | 0 |
|   | Isohexadecane | 0 | 1.6 | 0 |

-continued

|   | | F1 mass % | F2 mass % | F3 mass % |
|---|---|---|---|---|
|   | Phenyl trimethicone sold under the reference DC556 by the company Dow Corning | 2 | 0 | 2 |
|   | Ethyl hexyl methoxycinnamate | 3 | 3 | 3 |
|   | Squalane | 1 | 0 | 1 |
| 2 | Butyl acrylate copolymer containing dendritic silicone side chains: Tris((trimethylsiloxy) siloxyethyldimethylsiloxy)silylpropyl methacrylate in isododecane (40/60) sold under the reference Dow Corning FA 4002 ID by Dow Corning | 0 | 10 | 0 |
|   | Cyclopentasiloxane | 7 | 0 | 7 |
| 3 | Cyclohexasiloxane | 0 | 7.5 | 0 |
|   | Yellow iron oxide coated with aluminum stearoyl glutamate NAI-C33-9001-10 from the company Miyoshi Kasei | 1.25 | 1.25 | 1.65 |
|   | Red iron oxide coated with aluminum stearoyl glutamate NAI-C33-8001-10 from the company Miyoshi Kasei | 0.5 | 0.5 | 0.3 |
|   | Black iron oxide coated with aluminum stearoyl glutamate NAI-C33-7001-10 from the company Miyoshi Kasei | 0.15 | 0.15 | 0.15 |
|   | Titanium dioxide (anatase) coated with aluminum stearoyl glutamate NAI-TAO-77891 from the company Miyoshi Kasei | 10.1 | 10.1 | 9.9 |
| 4 | Talc sold under the reference Micro Ace P3 by the company Nippon Talc | 0.5 | 0 | 0.5 |
|   | Nylon 12 powder sold under the reference SP 500 by the company Toray Industries | 0.5 | 0 | 0.5 |
|   | Nylon 12 powder sold under the reference Orgasol 2002 EXD NAT COS by the company Arkema | 0 | 3 | 0 |
|   | Silica microspheres sold under the reference SB 700 by the company Miyoshi Kasei | 0 | 1 | 0 |
|   | Perlite sold under the reference Optimat 2550 OR by the company World Minerals | 0 | 0.2 | 0 |
|   | Demineralized water | 36.15 | 34.8 | 36.15 |
|   | 1,3-Butylene glycol | 3 | 6 | 3 |
|   | Magnesium sulfate | 0.7 | 0.7 | 0.7 |
|   | Hydrogenated maltose solution | 0.5 | 0 | 0.5 |
|   | Denatured 96° ethyl alcohol | 13 | 8 | 13 |
|   | TOTAL | 100 | 100 | 100 |

Procedure Formulation F2

The constituents of phase A1 are weighed out in the main beaker and are stirred with a Moritz blender (1000 rpm) while maintaining at room temperature. Next, phase A2 is added at room temperature, by stirring using a Moritz blender (1000 rpm) until homogenized. Phase A3 is prepared separately by milling three times in a three-roll mill the mixture of pigments and of cyclohexasiloxane. This phase A3 is then added, with continued stirring, along with phases A4 and A5.

The aqueous phase B is also prepared separately, by weighing out in a beaker the butylene glycol and the magnesium sulfate, and by adding water preheated to 95° C. The aqueous phase is stirred using a magnetic bar until homogenized. The emulsion is made at room temperature: the aqueous phase B is poured into the fatty phase while gradually increasing the stirring speed (Moritz blender) up to 4000 rpm. Stirring is continued for 10 minutes. Phase C (ethanol) is finally added. The product obtained is stirred using a Rayneri blender (paddles) for 10 minutes between 50 and 60 rpm.

Procedure Formulations F1 and F3

The constituents of phase A1 are weighed out in the main beaker and are stirred with a Moritz blender (1000 rpm) while maintaining at room temperature. Phase A3 is prepared separately by milling three times in a three-roll mill the mixture of pigments and of cyclopentasiloxane. This phase A3 is then added, with continued stirring, along with the fillers (phase A4).

The aqueous phase B is also prepared separately, by weighing out in a beaker the glycerol, the butylene glycol, the magnesium sulfate, the hydrogenated maltose solution, and water at room temperature. The aqueous phase B is stirred using a magnetic bar until homogenized. A4 B C The emulsion is made at room temperature: the aqueous phase B is poured into the fatty phase while gradually increasing the stirring speed (Moritz blender) up to 4000 rpm. Stirring is continued for 7 minutes. Finally, phase C (ethyl alcohol) is added for the last 3 minutes of 5 the emulsification.

The system was tested with:
F1 → Compartment 1
F2 → Compartment 2
F3 → Compartment 3

Test 1

Mixtures are created (volumetric proportions):
(The system is used to deliver doses of 50 to 200 mg of product. The mixtures are then spread little by little, dose by dose).

50/40/10 for making up the cheekbones in order to give a rosy look for the cheekbones with average durability and moderate comfort.

10/80/10 for making up the marked areas of the cheekbones, these areas requiring good durability.

20/80/0 for making up the lips, with good durability.

30/20/50 for making up the eyelids with good comfort.

Test 2

One day it is cold but, being a weekday, the person has few occasions to be outside. Thus, she creates mixtures:
(The system is used to deliver doses of 50 to 200 mg of product. The mixtures are then spread little by little, dose by dose).

(volumetric proportions) 50/40/10 for making up the cheekbones in order to give a rosy look for the cheekbones with average durability and moderate comfort.

10/80/10 for making up the marked areas of the cheekbones, these areas requiring good durability.

Another day it is cold but, being at the weekend, the person has plenty of occasions to be outside. Thus, she creates mixtures:
(The system is used to deliver doses of 50 to 200 mg of product. The mixtures are then spread little by little, dose by dose).

50/30/10 for making up the cheekbones in order to give a red look for the cheekbones with average durability and moderate comfort.

30/60/10 for making up the marked areas of the cheekbones, these areas requiring good durability.

The visual effects are similar on both days, but the comfort has been altered in the case of the weekend day. Of course, the comfort has been improved at the expense of the durability, but by virtue of the quality of the adjustments, the durability remains optimal.

The invention is not limited to each of the ten aspects that have just been described. In particular, it is possible, as part of new variants, to combine features of the invention according to the various aspects thereof

SUMMARY i) (first aspect) System for dispensing a product, having a dispenser that receives at least two cartridges that each have a reservoir containing a base product, a first base product comprising at least 0.1% by mass of particles exhibiting a difference in density of at least 0.5 g/cm3 with the medium which contains them, notably particles having a density greater than or equal to 2 g/cm3, and a thickener, the dispenser making it possible to deliver at least two base products in adjustable proportions, the viscosity of the first base product being greater than 2 Pa·s and preferably greater than or equal to 4 Pa·s. The viscosity of the base products is measured at 1 atm and 25° C. with a CONTRAVES TV rotary viscometer fitted with an MS-r3 or MS-r4 measuring bar at a frequency of 60 Hz after 10 minutes of rotation of the measuring bar.
ii) System according to i), a second base product having a viscosity less than that of the first base product, notably less than or equal to 1 Pa·s, and preferably less than 2 Pa·s.
iii) System according to ii), the second base product having a viscosity less than or equal to 2 Pa·s.
iv) System according to i) to iv), the density of said particles being greater than or equal to 5 g/cm3.
v) System according to i) to iv), the particles comprising at least one of the materials chosen from the following list: bismuth oxychloride, cerium oxide, chromium oxide, zirconium oxide, iron oxide, titanium oxide, talc, calcium carbonate, silica, boron nitride, tungsten carbide.
vi) System according to i) to v), the second product having no particles with a density greater than or equal to 2 g/cm3.
vii) System according to i) to vi), comprising a third cartridge with a third base product.
viii) System according to vii), the third base product comprising a thickener.
ix) System according to i) to viii), the thickener being chosen from saccharide compounds of the rubber type, such as gum arabic, acacia gum, guar gum, gellan gum, karaya gum, carrageenan gum, cellulose-based compounds such as CMC, HMC, HPMC, synthetic polymers such as polyacrylic or polymethacrylic acids such as carbomers (Carbopol), or polyurethanes, polyvinyl acetate, polyvinyl alcohol, inverse or direct thick emulsions, combinations of non-aqueous solvents with thickening agents for oil, clays such as bentonite, attapulgite, organochelators, proteins such as casein or collagen, shear-thinning or thixotropic rheology agents.
x) System according to ix), the thickener being chosen from saccharide compounds of the rubber type, and its mass content being between 0.1% and 5% in the first base product, better still from 0.8% to 2.5%.
xi) System according to i) to x), the cartridges being received in a removable manner in the dispenser.
xii) System according to i) to xi), each product leaving the cartridge through an outlet passage of the cartridge, the outlet passage being defined by a dispensing end piece of the cartridge, said end piece being driven in rotation relative to a body of the cartridge by a drive mechanism of the dispenser in order to dispense the base product contained in the cartridge.
xiii) System according to i) to xiii), comprising a mechanism for homogenizing the first base product, notably a vibrating mechanism.
xiv) (second aspect) System for dispensing a product, optionally according to one of i) to xiii), comprising a dispenser that receives at least two cartridges that each have a reservoir containing a base product, a first base product comprising a thickener, a second base product comprising an agent for modulating the viscosity of the thickener, the dispenser making it possible to deliver at least these two base products in adjustable proportions.
xv) System according to xiv), and:
First case:
The first product comprises a pH-sensitive thickening active agent, having a viscosity greater than 2 Pa·s and preferably greater than 4 Pa·s, and the second product contains an acid agent that modifies the viscosity of the active agent of the first product upon contact between the two products. The thickening active agent of the first product is notably a gelling agent based on acrylate or methacrylate polymer or copolymer, such as a Carbomer, used between 0.8% and 2.5%, and the second product is an acidifying agent, such as a mineral or organic acid such as citric or lactic acid, used at 0.2% to 10%. The viscosity of the second product may be less than or greater than or equal to the viscosity of the first product. Preferably, the viscosity of the second product is between 1 and 3 Pa·s. The pH of the first product is greater than 6 and preferably greater than 7. The pH of the second product is less than 6 and preferably less than 5.
Second case:
The first product has a viscosity greater than 2 Pa·s and preferably greater than 4 Pa·s, and the second product has a low viscosity, between 0.01 and 2. Pa·s, preferably between 0.1 and 0.5 Pa·s. The first product and the second product contain notably a gelling agent based on acrylate or methacrylate polymer or copolymer, such as a Carbomer, or a polyose-based gelling agent, with concentrations of gelling agent (all the gelling agents) in the region of 0.8% to 2.5% for the first and 0% to 2.5% for the second.
Third case:
The first product comprises a pH-sensitive thickening active agent, having a viscosity less than 2 Pa·s and preferably less than 1 Pa·s, and the second product contains an alkaline agent that modifies the viscosity of the active agent of the first product upon contact between the two products. The thickening active agent of the first product is notably a thickening agent based on acrylate or methacrylate polymer or copolymer, such as a Carbomer, and the second product is a basifying agent, such as a mineral or organic base such as an amine or aqueous ammonia. The viscosity of the second product may be less than or greater than or equal to the viscosity of the first product. Preferably, the viscosity of the second product is between 1 and 3 Pa·s. The concentration of thickening active agent of the first product may vary from 0.8% to 5%, The pH of the first product is less than 6 and preferably less than 5. The pH of the second product is greater than 6 and preferably less than 7.
xvi) System according to xiv) to xv), the thickener having a viscosity dependent on the pH and the agent for modulating the viscosity being an acid or a base, notably chosen from aqueous ammonia, amines, sodium hydroxide, citric acid, lactic acid.
xvii) System according to xiv) to xvi), the agent for modulating the viscosity being a diluent, notable water, ethanol, an oil or a slightly thickened composition of these agents.
xviii) . . . .
xix) . . . .

xx) System according to xiv) to xix), the second base product having a viscosity substantially equal to that of the first base product.

xxi) System according to xiv) to xx), comprising a third cartridge with a third base product.

xxii) System according to xxi), the third base product comprising a thickener, notably with a different concentration than that of the first base product.

xxiii) System according to xiv) to xxii), the thickener being chosen from saccharide compounds of the rubber type, such as gum arabic, acacia gum, guar gum, gellan gum, karaya gum, carrageenan gum, cellulose-based compounds such as CMC, HMC, HPMC, synthetic polymers such as polyacrylic or polymethacrylic acids such as carbomers (Carbopol), or polyurethanes, polyvinyl acetate, polyvinyl alcohol, inverse or direct thick emulsions, combinations of non-aqueous solvents with thickening agents for oil, clays such as bentonite, attapulgite, organochelators, proteins such as casein or collagen, shear-thinning or thixotropic rheology agents.

xxiv) System according to claim xxiii), the thickener being a Carbopol gel, preferably in a neutral or alkaline medium, notably with a content of between 0.1% and 2.5% by mass.

xxv) System according to claim xxiii), the thickener being chosen from saccharide compounds of the rubber type, and its mass content being between 0.2% and 5% in the first base product, better still from 0.8% to 2.5%.

xxvi) System according to xiv) to xxv), the cartridges being received in a removable manner in the dispenser.

xxvii) System according to xiv) to xxvi), each product leaving the cartridge through an outlet passage of the cartridge, the outlet passage being defined by a dispensing end piece of the cartridge, said end piece being driven in rotation relative to a body of the cartridge by a drive mechanism of the dispenser in order to dispense the base product contained in the cartridge.

xxviii) System according to xiv) to xxvii), comprising a mechanism for homogenizing the first base product, notably a vibrating mechanism.

xxix) Method for applying a cosmetic, makeup and/or care product to human keratin materials, comprising the setting of the dispenser of a dispensing system according to one of the preceding points, depending on the area to be treated, and the dispensing of the product by base products being picked up from the cartridges in the proportions corresponding to the setting of the dispenser.

xxx) Method according to xxix), setting being carried out so as to have the greatest viscosity, application being carried out on skin blemishes.

xxxi) Method according to xxix), setting being carried out so as to have an intermediate viscosity between the end-point viscosities that can be obtained, application being carried out on skin blemishes or in the under-eye area.

xxxii) (third aspect) System for dispensing a product, optionally according to one of i) to xxxi), comprising a dispenser that receives at least two cartridges containing a first base product and a second base product, respectively, the dispenser allowing the delivery of at least these two base products in adjustable proportions in order to form a film, at least one property of which varies depending on the adjustment.

xxxiii) System according to claim xxxii), the property of the film that varies being its flexibility.

xxxiv) System according to claim xxxii), the property of the film that varies being its oily nature.

xxxv) System according to claim xxxii), the property of the film that varies being its tightening nature.

xxxvi) System according to one of xxxii) to xxxv), the two base products being chosen to react with one another to form a film.

xxxvii) System according to xxxvi), the first base product comprising a reactive silicone and the second base product comprising a catalyst that brings about the crosslinking of the reactive silicone.

xxxviii) System according to xxxvii), the reactive silicone comprising a mixture of telechelic polyorganosiloxane bearing a vinyl function at the two chain ends and polyhydrogenosiloxane.

xxxix) System according to xxxvii), the catalyst being platinum based.

xl) System according to xxxii) to xxxix), the first base product comprising a film-forming polymer and the second base product comprising an oily compound that is liquid at room temperature.

xli) System according to xl), the film-forming polymer having a glass transition temperature Tg greater than or equal to 30° C., better still greater than or equal to 60° C.

xlii) System according to xl) or xli), the film-forming polymer being chosen from vinyl, notably acrylic, polymers or copolymers.

xliii) System according to xl), the film-forming polymer being liposoluble.

xliv) System according to xxxii) to xxxv), the first and second base products containing different respective film-forming polymers.

xlv) System according to xliv), the film-forming polymer of the first base product having a glass transition temperature Tg1 and the polymer of the second base product having a glass transition temperature Tg2 different than Tg1, where preferably Tg1>60° C. and Tg2<10° C.

xlvi) System according to xlv), the first base product comprising a polymer or copolymer chosen from methacrylic polymers and copolymers, polyamides, alkyl celluloses, polymers and copolymers of vinylpyrrolidone, and silicone resins.

xlvii) System according to xlv), the second base product comprising a polymer or copolymer chosen from acrylic polymers and copolymers, vinyl polymers and copolymers and polycondensates such as polyesters and polyurethanes.

xlviii) System according to xxxii) to xxxv), the first base product comprising an oily compound with a melting point Mp1>20° C. and the second base product comprising an oily compound with a melting point Mp2<20° C.

xlix) Method for applying a cosmetic, makeup and/or care, product to human keratin materials, with the aid of a dispensing system according to xxxii to xlviii), comprising the setting of the dispenser depending on the area to be treated, and the dispensing of the product by base products being picked up from the cartridges in the proportions corresponding to the setting of the dispenser.

l) (fourth aspect) System for dispensing a cosmetic product, optionally according to any one of the preceding points, comprising a dispenser that receives at least two cartridges that each have a reservoir containing a base product, a first base product containing at least one organic solvent, the cartridge that contains it having a body made of at least one of the thermoplastic materials chosen from the list comprising simple polyolefins, polyvinylchloride (PVC), polyamides and semi-aromatic polyamides, polyphenylene sulfide (PPS), polybismaleimide, polyurethanes, polyesters, polyepoxides, polyether-block-amide, polyacetal, polyetherketone, polyetherimides (PEI), polyimides, polyamide-imide (PAI), FEP (perfluorinated ethylene propylene), PFA (polyfluoroalkoxy), ECTFE (ethylene chloro trifluoro ethylene), and ETFE (ethylene tetrafluoroethylene), and mixtures thereof, and preferably simple polyolefins, polyvinylchloride (PVC), polyamides and semi-aromatic polyamides, polyphenylene sulfide (PPS), polybismaleimide, and mixtures thereof.
li) System according to l), the cartridge that comprises the first base product comprising, besides the body of the cartridge, other components, notably mobile components, exposed to the first base product, at least one of these, notably mobile, components and preferably all of these components being chosen from the said list.
lii) System according to l), the total content of organic solvent(s) in the first base product being greater than or equal to the total water content of the first base product.
liii System according to l) to lii), the total content of organic solvent(s) in the first base product being greater than or equal to 50% relative to all of the solvents.
liv) System according to 1 to liii), the cartridges being identical, except for their content.
lv) System according to l) to liv), at least one of the compositions comprising a perfume.
lvi) System according to l) to lv), the cartridges being received in a removable manner in the dispenser.
lvii) System according to l) to lvi), each product leaving the cartridge through an outlet passage of the cartridge, the outlet passage being defined by a dispensing end piece of the cartridge, said end piece being driven in rotation relative to a body of the cartridge by a drive mechanism of the dispenser in order to dispense the base product contained in the cartridge.
lviii) (fifth aspect) System for dispensing a product, optionally according to any one of points i to lvii), comprising a dispenser that receives at least two cartridges that each have a reservoir containing first and second base products, respectively, the first base product comprising a pigment, the second base product comprising a filler distinct from the pigment of the first base product, the dispenser making it possible to deliver at least these two base products in adjustable proportions.
lix) System according to lviii), the particle size D50 by volume of the pigment and of the filler being between 100 nm and 1 mm.
lx) System according to lviii), the particle size D50 by volume of the pigment ranging from 100 nm to 25 microns, better still from 200 nm to 10 microns.
lxi) System according to lviii to lx), the pigment being chosen from mineral pigments, and preferably hydrophobic modified mineral pigments, notably those of iron oxide or titanium oxide.
lxii) System according to lviii) to lxi), the pigment having a coating comprising at least one lipophilic or hydrophobic compound.
lxiii) System according to lviii) to lxi), the filler being chosen from talc, mica, silica, kaolin, poly-O-alanine powder and polyethylene powder, tetrafluoroethylene polymer powders, lauroyllysine, starch, boron nitride, hollow polymer microspheres such as those of polyvinylidene chloride/acrylonitrile, acrylic acid copolymer microspheres, silicone resin microbeads, polyorganosiloxane elastomer particles, precipitated calcium carbonate, magnesium carbonate, magnesium hydrogen carbonate, hydroxyapatite, barium sulfate, aluminum oxides, polyurethane powders, composite fillers, hollow silica microspheres, and glass or ceramic microcapsules, the particles that are in the form of hollow sphere portions, and mixtures thereof.
lxiv) System according to lviii) to lxiii), the first base product and the second base product comprising an inverse emulsion.
lxv) System according to lviii) to lxiii), the mass content of pigment in the first base product being greater than or equal to 5% and preferably greater than 10%.
lxvi) System according to lviii) to lxv), the mass content of filler in the second base product being greater than or equal to 0.5% and preferably greater than 1%.
lxvii) System according to lviii) to lxvi), comprising a third cartridge with a third base product.
lxviii) System according to lviii) to lxvii), the cartridges being received in a removable manner in the dispenser.
lxix) System according to lviii) to lxviii), each product leaving the cartridge through an outlet passage of the cartridge, the outlet passage being defined by a dispensing end piece of the cartridge, said end piece being driven in rotation relative to a body of the cartridge by a drive mechanism of the dispenser in order to dispense the base product contained in the cartridge.
lxx) Method for applying a cosmetic, makeup and/or care, product to human keratin materials, with the aid of a dispensing system according to lviii) to
lxix), comprising the setting of the dispenser depending on the area to be treated, and the dispensing of the product by base products being picked up from the cartridges in the proportions corresponding to the setting of the dispenser.
lxxi) (sixth aspect) System for dispensing a product, optionally according to any one of points i) to lxx), comprising a dispenser that receives at least two cartridges containing first and second base products, respectively, the first base product comprising, notably in the form of an inverse emulsion, an organic sunscreen and an oil, the second base product comprising an oil, the dispenser making it possible to deliver at least these two base products in adjustable proportions, the concentration of sunscreen in the first base product being greater than that of the second base product, and the concentration of oil in the second base product being greater than that of the first base product.
lxxii) System according to lxxi), the mass content of organic sunscreen in the first base product being greater than or equal to 2%, preferably 4%.
lxxiii) System according to lxxi), the mass content of oil(s) in the second base product being greater than 2%, preferably 4%.
lxxiv) System according to lxxi), the second base product not containing any organic sunscreen.
lxxv) System according to lxxi), the second base product comprising an organic sunscreen.
lxxvi) System according to lxxi), at least one of the first and second base products containing a coloring agent.
lxxvii) System according to lxxvi), the coloring agent being chosen from pigments, notably iron oxides.

lxxviii) System according to lxxvi) or lxxvii), each of the first and second base products comprising a coloring agent.

lxxix) System according to lxxi) to lxxviii), at least one of the first and second base products containing a colorless filler.

lxxx) System according to lxxix), each of the first and second base products comprising a colorless filler.

lxxxi) System according to lxxi) to lxxx), comprising a third cartridge with a third base product.

lxxxii) System according to lxxxi) to lxxx), the cartridges being received in a removable manner in the dispenser.

lxxxiii) System according to lxxxi) to lxxxii), each product leaving the cartridge through an outlet passage of the cartridge, the outlet passage being defined by a dispensing end piece of the cartridge, said end piece being driven in rotation relative to a body of the cartridge by a drive mechanism of the dispenser in order to dispense the base product contained in the cartridge.

lxxxiv) Process for adjusting a system according to lxxxi) to lxxxiii), comprising the adjustment of the dispenser depending on the area to be treated with the product and/or the intensity of the UV radiation.

lxxxv) (seventh aspect) System for dispensing a product, optionally according to any one of the preceding points, comprising a dispenser that receives at least two cartridges that each have a reservoir containing first and second base products, respectively, the first base product comprising at least one of an oil, an interference pigment or a pigment with a metallic tint, the second base product comprising a matting filler, the dispenser making it possible to deliver at least these two base products in adjustable proportions.

lxxxvi) System according to lxxxv), the first base product containing an oil.

lxxxvii) System according to lxxxv) or lxxxvi), the first base product containing an interference pigment.

lxxxviii) System according to lxxxv) to lxxxvii), the first base product containing a pigment with a metallic tint.

lxxxix) System according to lxxxv) to lxxxviii), the particle size D50 by volume of the pigment and of the filler being between 100 nm and 1 mm.

xc) System according to lxxxv) to lxxxix), the filler being chosen from talc, mica, silica, kaolin, poly-Q-alanine powder and polyethylene powder, tetrafluoroethylene polymer powders, lauroyllysine, starch, boron nitride, hollow polymer microspheres such as those of polyvinylidene chloride/acrylonitrile, acrylic acid copolymer microspheres, silicone resin microbeads, polyorganosiloxane elastomer particles, precipitated calcium carbonate, magnesium carbonate, magnesium hydrogen carbonate, hydroxyapatite, barium sulfate, aluminum oxides, polyurethane powders, composite fillers, hollow silica microspheres, and glass or ceramic microcapsules, the particles that are in the form of hollow sphere portions, and mixtures thereof.

xci) System according to lxxxv) to lxxxix), the first base product and the second base product comprising an inverse emulsion.

xcii) System according to lxxxv) to xci), the mass content of filler in the second base product being greater than or equal to 0.5% and preferably greater than or equal to 1%.

xciii) System according to lxxxv) to xcii), comprising a third cartridge with a third base product.

xciv) System according to lxxxv) to xciii), the cartridges being received in a removable manner in the dispenser.

xcv) System according to lxxxv) to xciv), each product leaving the cartridge through an outlet passage of the cartridge, the outlet passage being defined by a dispensing end piece of the cartridge, said end piece being driven in rotation relative to a body of the cartridge by a drive mechanism of the dispenser in order to dispense the base product contained in the cartridge.

xcvi) Method for applying a cosmetic, makeup and/or care, product to human keratin materials, with the aid of a dispensing system according to lxxxv) to xcv), comprising the setting of the dispenser depending on the area to be treated, and the dispensing of the product by base products being picked up from the cartridges in the proportions corresponding to the setting of the dispenser.

xcvii) (eighth aspect) System for dispensing a product, optionally according to any one of the preceding points, comprising a dispenser that receives at least two cartridges that each have a reservoir containing first and second base products, respectively, the first base product comprising a moisturizing agent, the second base product comprising a filler, the dispenser making it possible to deliver at least these two base products in adjustable proportions.

xcviii) System according to xcvii), the moisturizing agent being chosen from polyols, urea and its derivatives, such as notably hydroxyalkyl urea, in particular hydroxyethylurea, hyaluronic acid, glycine, β-alanine, taurine, trimethyl glycine, and mixtures thereof.

xcix) System according to xcvii) to xcviii), the particle size D50 by volume of the filler being between 100 nm and 1 mm.

c) System according to xcvii) to xcix), the filler being chosen from talc, mica, silica, kaolin, poly-β-alanine powder and polyethylene powder, tetrafluoroethylene polymer powders, lauroyllysine, starch, boron nitride, hollow polymer microspheres such as those of polyvinylidene chloride/acrylonitrile, acrylic acid copolymer microspheres, silicone resin microbeads, polyorganosiloxane elastomer particles, precipitated calcium carbonate, magnesium carbonate, magnesium hydrogen carbonate, hydroxyapatite, barium sulfate, aluminum oxides, polyurethane powders, composite fillers, hollow silica microspheres, and glass or ceramic microcapsules, the particles that are in the form of hollow sphere portions, and mixtures thereof.

ci) System according to xcvii) to c), the first base product and the second base product comprising an inverse emulsion.

cii) System according to xcvii) to ci), the mass content of filler in the second base product being greater than or to 0.5% and preferably greater than 1%.

ciii) System according to xcvii) to cii), comprising a third cartridge with a third base product.

civ) System according to xcvii) to ciii), the cartridges being received in a removable manner in the dispenser.

cv) System according to xcvii) to civ), each product leaving the cartridge through an outlet passage of the cartridge, the outlet passage being defined by a dispensing end piece of the cartridge, said end piece being driven in rotation relative to a body of the cartridge by a drive mechanism of the dispenser in order to dispense the base product contained in the cartridge.

cvi) Method for applying a cosmetic, makeup and/or care, product to human keratin materials, with the aid of a dispensing system according to xcvii) to cv), comprising the setting of the dispenser depending on the area to be treated, and the dispensing of the product by base products being picked up from the cartridges in the proportions corresponding to the setting of the dispenser.

cvii) (ninth aspect) System for dispensing a perfumed product, optionally according to any one of the preceding points, comprising a dispenser that receives at least two cartridges containing first and second base products, respectively, the first base product comprising a composition containing at least one alcohol and at least one cellulose derivative, the dispenser making it possible to deliver at least these two base products in adjustable proportions.

cviii) System according to cvii), each base product comprising a composition containing at least one alcohol and at least one cellulose derivative.

cix) System according to cvii) or cviii),the first base product or each base product having a mass concentration of alcohol relative to the other, non-alcoholic compound(s) of at least 80/20, better still 90/10.

cx) System according to cvii) to cix), the first base product or each base product containing at least 50% by mass of ethanol, better still at least 80% of ethanol in its solvent phase.

cxi) System according to cvii) to cx), the first base product or each base product containing at least one odorous compound, preferably chosen from esters, carbonates, acids, anhydrides, aldehydes, alcohols, aliphatic compounds without functions other than alkanes and alkenes, and mixtures thereof cxii) System according to claim cxi), the odorous compound(s) being chosen from hexanal, octanal, nonanal, decanal, undecanal, dodecanal, tridecanal, 2-methyldecanal, 2-methylundecanal, trans-2-hexenal, cis-4-heptanal, 2,6 dimethyl-5-hepten-1-al, E-4-decenal, 10-undecenal, 2-dodecenal, 1,1-dimethoxy-2,2,5-trimethyl-4-hexene, 2-methyl-2-pentenoic acid, (S)-(+)-2-methylbutanoic acid, ethyl formate, cis-3-hexenyl formate, ethyl acetate, butyl acetate, isoamyl acetate, hexyl acetate, 3,5,5-trimethylhexyl acetate, trans-2-hexenyl acetate, cis-3-hexenyl acetate, ethyl propionate, ethyl butyrate, butyl butyrate, isoamyl butyrate, hexyl butyrate, cis-3-hexenyl isobutyrate, ethyl isovalerate, ethyl-2-methyl butyrate, ethyl hexanoate, ethyl 2-methyl pentanoate, 2-propenyl hexanoate, ethyl heptanoate, 2-propenyl heptanoate, ethyl octanoate, methyl 2-nonenoate, ethyl 2-trans-4-cis-decadienoate, methyl 2-octynoate, methyl 2-nonynoate, ethyl 3-octobutanoate, allyl amyl glycolate, Z-3-hexenyl methyl carbonate, 3-octanol; 2,6-dimethyl-2-heptanol, trans-2-hexen-1 ol; 3-hexen-1-ol; 1-octen-3-ol; 9-decen-1-ol; 10-undecen-1-ol; 2-trans-6-cis-nonadien-1-ol; 4-methyl-3-decen-5-ol, myrcene, ocimene, beta-Farnesene, citral, citral diethyl acetate, citronellal, methoxydihydrocitronellal, 2,6,10-trimethyl-9-undecanal, cis-geranic acid, citronellic acid, geranyl ester (formate, acetate, propionate, isobutyrate, isovalerate), neryl acetate, linalyl esters (formate, acetate, propionate, isobutyrate), citronellyl esters (formate, acetate, propionate, isobutyrate, isovalerate, tiglate) and esters of myrcenol, geraniol, nerol, linalool, myrcenol, lavendulol, citronellol, trans,trans-farnesol, trans-nerolidol, tetrahydrogeraniol, tetrahydrolinalool, avendulol, trans,trans-farnesol, trans-nerolidol, tetrahydrogeraniol, tetrahydrolinalool, limonene, terpinene, terpinolene, phellandrene, camphene, 3-carene, menthyl ester (acetate, lactate), alpha-terpinyl esters (acetate), noryl esters (acetate), bornyl esters (acetate), isobornyl esters (acetate), cedryl esters (acetate), 2,4-dimethyl-3-cyclohexene carboxaldehyde, 4-(4-hydroxy-4-methylpentyl)-3-cyclohexene carboxaldehyde, 1-(4-isopropylcyclohexyl)ethanol, 2-methyl-4-(2,2,3-trimethyl-3-cyclopenten-1-yl)butanol, 2-methyl-4-(2,2,3-trimethyl-3-cyclopenten-1-yl)butenol, 3-methyl-5-(2,2,3-trimethyl-3-cyclopenten-1-yl)-4-penten-2-ol, 3,3-dimethyl-5-(2,2,3-trimethyl-3-cyclopenten-1-yl)-4-penten-2-ol, indole, p-cymene, diphenylmethane, benzaldehyde, phenylacetaldehyde, phenylacetaldehyde dimethyl acetal, dihydrocinnamaldehyde, 2-phenylpropanal, cyclamen aldehyde, 2-methyl-3-(4-tert-butyl-phenyl)propanal, cinnamaldehyde, heliotropin, furfuraldehyde, benzyl esters (acetate, propionate, isovalerate), phenethyl esters (acetate, isobutyrate, isovalerate), alpha-trichloromethylbenzyl ester (acetate), cinnamyl acetate, benzoate ester (acetate, hexyl, benzyl), phenylacetate ethyl, phenylacetate geranyl, methyl cinnamate, benzyl cinnamate, phenyl ethyl cinnamate, eugenol acetate, phenylacetic acid, benzyl alcohol, 2-phenyl ethyl alcohol, styrallyl alcohol, 2,2-dimethyl-3-(3-methylphenyl)propanol, cinnamyl alcohol, 3-methyl-5-phenylpentanol, thymol, anethole, isoeugenol, eugenol, anise alcohol, raspberry ketone, ethylmaltol, 2,6-dimethoxyphenol, 2-propylphenol, 2-(methylthio)phenol, ortho-guaiacol, 4-methyl guaiacol, abietic anhydride, citraconic anhydride.

cxiii) System according to cvii) to cxii), the cellulose derivative being chosen from derivatives of cellulose obtained by reacting basified cellulose with propylene oxide or ethylene oxide.

cxiv) System according to cvii) to cxiii), the cellulose derivative being hydroxypropylcellulose.

cxv) System according to cvii) to cxiv), the size of the cellulose derivative being greater than or equal to 10 000, better still between around 850 000 and around 1 150 000.

cxvi) System according to cvii) to cxv), the total mass content of cellulose compound(s) varying between 0.1% and 20%, better still between 0.5% and 5%, the percentage being expressed relative to the mass of the base product.

cxvii) System according to cvii) to cxvi), comprising a third cartridge with a third base product.

cxviii) System according to cvii) to cxvii), the cartridges being received in a removable manner in the dispenser.

cxix) System according to cvii) to cxviii), each product leaving the cartridge through an outlet passage of the cartridge, the outlet passage being defined by a dispensing end piece of the cartridge, said end piece being driven in rotation relative to a body of the cartridge by a drive mechanism of the dispenser in order to dispense the base product contained in the cartridge.

cxx) System according to cvii) to cxix), having an electronic memory for recording, in association with a dispensed product, the respective proportions of each of the base products of this product, in order to be able to automatically dispense this product again later.

cxxi) Method for generating a perfumed product with the aid of a system according to cvii) to cxx), wherein one or more base products contained in respective cartridges of the dispenser is/are selected, and the base products selected are dispensed in chosen quantities.

cxxii) Method according to cxxi), wherein the proportions of the different base products making up the dispensed product are also memorized.

cxxiii) (tenth aspect) System for dispensing a product, optionally according to any one of the preceding points, comprising a dispenser that receives at least two cartridges containing a first base product and a second base product, respectively, the dispenser making it possible to deliver at least these two base products in adjustable proportions, the first base product comprising a volatile solvent and a film-forming polymer, the second base product comprising a nonvolatile oil.

cxxiv) System according to cxxiii), the first base product being in the form of a liquid anhydrous composition.

cxxv) System according to cxxiii) or cxxiv), the second base product being in the form of an anhydrous liquid composition.

cxxvi) System according to cxxiii) to cxxv), the first base product comprising an inverse emulsion.

cxxvii) System according to cxxiii) to cxxvi), the second base product comprising an inverse emulsion.

cxxviii) System according to cxxiii) to cxxvii), the film-forming polymer being hydrophobic.

cxxix) System according to cxxiii), the property of the film that varies being its flexibility.

cxxx) System according to cxxiii), the property of the film that varies being its oily nature.

cxxxi) System according to cxxiii), the property of the film that varies being its tightening nature.

cxxxii) System according to cxxii) to cxxxi), the two base products being chosen to react with one another to form a film.

cxxxiii) System according to cxxxii), the first base product comprising a reactive silicone and the second base product comprising a catalyst that brings about the crosslinking of the reactive silicone.

cxxxiv) System according to cxxxiii), the reactive silicone comprising a mixture of telechelic polyorganosiloxane bearing a vinyl function at the two chain ends and polyhydrogenosiloxane.

cxxxv) System according to cxxxiii), the catalyst being platinum based.

cxxxvi) System according to cxxxiii), the first base product comprising a film-forming polymer and the second base product comprising an oily compound that is liquid at room temperature.

cxxxvii) System according to cxxxvi), the film-forming polymer having a glass transition temperature Tg greater than or equal to 30° C., better still greater than or equal to 60° C.

cxxxviii) System according to cxxxvi) or cxvii), the film-forming polymer being chosen from vinyl, notably acrylic, polymers or copolymers.

cxxxix) System according to cxxxvi) or cxvii), the film-forming polymer being liposoluble.

cx) System according to cxxiii) to cxxviii), the first and second base products containing different respective film-forming polymers.

cxli) System according to claim cxl), the film-forming polymer of the first base product having a glass transition temperature Tg1 and the polymer of the second base product having a glass transition temperature Tg2 different than Tg1, where preferably Tg1>60° C. and Tg2<10° C.

cxlii) System according to claim cxl), the first base product comprising a polymer or copolymer chosen from methacrylic polymers and copolymers, polyamides, alkyl celluloses, polymers and copolymers of vinylpyrrolidone, and silicone resins.

cxliii) System according to claim cxl), the second base product comprising a polymer or copolymer chosen from acrylic polymers and copolymers, vinyl polymers and copolymers and polycondensates such as polyesters and polyurethanes.

cxliv) System according to cxxiii) to cxxviii), the first base product comprising an oily compound with a melting point Mp1>20° C. and the second base product comprising an oily compound with a melting point Mp2<20° C. cxlv) Method for applying a cosmetic, makeup and/or care product to human keratin materials, with the aid of a dispensing system according to cxxiii) to cxliv), comprising the setting of the dispenser depending on the area to be treated, and the dispensing of the product by base products being picked up from the cartridges in the proportions corresponding to the setting of the dispenser.

In the listing above, "according to . . . to . . . " should be understood as meaning according to one of points . . . to . . . ; for example "according to i) to iii)" means according to i), ii) or iii).

The invention claimed is:

1. A system for dispensing a product comprising a dispenser that receives at least two cartridges that each have a reservoir containing first and second base products, respectively, the first base product comprising an organic sunscreen and an oil, the second base product comprising an oil, the dispenser making it possible to deliver at least these two base products in adjustable proportions to vary the sunscreen proportion, the concentration of sunscreen in the first base product being greater than that of the second base product, and the concentration of oil in the second base product being greater than that of the first base product; wherein
at least one of the first and second base products comprises a coloring agent,
the mass content of organic sunscreen in the first base product is greater than or equal to 4%,
the first base product is a water in oil emulsion,
the concentrations of sunscreen in the first and second base product and the concentration of oil in the first and second base product being such that, whatever the proportions of the first and second base product are in the product, the mattness/shines aspect of the product is substantially identical.

2. The system according to claim 1, wherein the mass content of oil in the second base product is greater than 2%.

3. The system according to claim 1, wherein the second base product does not comprise any organic sunscreen.

4. The system according to claim 1, wherein the second base product comprises an organic sunscreen.

5. The system according to claim 1, wherein the coloring agent is selected from pigments.

6. The system according to claim 1, wherein each of the first and second base products comprises a coloring agent.

7. The system according to claim 1, wherein at least one of the first and second base products further comprises a colorless filler.

8. The system according to claim 7, wherein each of the first and second base products comprises a colorless filler.

9. The system according to claim 1, further comprising a third cartridge with a third base product.

10. The system according to claim 1, wherein the cartridges are received in a removable manner in the dispenser.

11. The system according to claim 1, wherein
each product leaves the cartridge through an outlet passage of the cartridge, the outlet passage being defined by a dispensing end piece of the cartridge, said end piece being driven in rotation relative to a body of the cartridge by a drive mechanism of the dispenser in order to dispense the base product contained in the cartridge.

12. A process for adjusting a system according to claim 1, comprising the adjustment of the dispenser depending on the area to be treated with the product and/or the intensity of the UV radiation.

* * * * *